(12) United States Patent
Dreas et al.

(10) Patent No.: US 10,577,365 B2
(45) Date of Patent: Mar. 3, 2020

(54) DERIVATIVES OF QUINOLINE AS INHIBITORS OF DYRK1A AND/OR DYRK1B KINASES

(71) Applicants: Felicitex Therapeutics, Inc., Newton, MA (US); Selvita S.A., Cracow (PL)

(72) Inventors: Agnieszka Dreas, Cracow (PL); Charles-Henry Fabritius, Cracow (PL); Andrzej Dzienia, Czeladz (PL); Anna Buda, Cracow (PL); Michal Galezowski, Cracow (PL); Georgiy Kachkovskyi, Cracow (PL); Urszula Kulesza, Cracow (PL); Katarzyna Kucwaj-Brysz, Cracow (PL); Agnieszka Szamborska-Gbur, Tenczynek (PL); Wojciech Czardybon, Mikolow (PL); Maria Vilenchik, Newton, MA (US); Michael Frid, Medford, MA (US); Alexandra Kuznetsova, Natick, MA (US)

(73) Assignees: Felicitex Therapeutics, Inc., Natick, MA (US); Selvita S.A., Cracow (PL)

( * ) Notice: Subject to any disclaimer, the term of this patent is extended or adjusted under 35 U.S.C. 154(b) by 0 days.

(21) Appl. No.: 15/848,786

(22) Filed: Dec. 20, 2017

(65) Prior Publication Data

US 2018/0179199 A1 Jun. 28, 2018

(30) Foreign Application Priority Data

Dec. 23, 2016 (EP) .................................... 16460096

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
None
See application file for complete search history.

(56) References Cited

U.S. PATENT DOCUMENTS

| 2011/0230500 | A1* | 9/2011 | Keenan | ................ | C07D 403/12 514/255.05 |
| 2015/0018351 | A1 | 1/2015 | Lind et al. | | |
| 2015/0297587 | A1 | 10/2015 | Gelbard et al. | | |

FOREIGN PATENT DOCUMENTS

| WO | 2003/082868 A1 | 10/2003 |
| WO | 2005/085244 A1 | 9/2005 |
| WO | 2005/095400 A1 | 10/2005 |
| WO | 2012/098068 A1 | 7/2012 |
| WO | 2013/026806 A1 | 2/2013 |
| WO | 2016/000615 A1 | 1/2016 |

OTHER PUBLICATIONS

[NoAuthorListed] Compound summary for CID-118641451, PubChem Database; Create Date: Feb. 23, 2016 (Feb. 23, 2016). p. 3.
Aranda, S., et al., "DYRK family of protein kinases: evolutionary relationships, biochemical properties, and functional roles," FASEB, Feb. 2011, v. 25, pp. 449-462.
Becker, W. et al., "Activation, regulation, and inhibition of DYRK1A," FEBS J, 278(2):246-56 2011.
Borst, P., "Cancer drug pan-resistance: pumps, cancer stem cells, quiescence,epithelial to mesenchymal transition, blocked cell death pathways, persisters or what?," Open Biol. May 2012; 2(5): 120066.
Deng and Friedman, "Mirk kinase inhibition blocks the in vivo growth of pancreatic cancer cells," Genes & Cancer, 5(9-10): 337-347, Sep. 2014.
Deng et al., "The Kinase Mirk/Dyrk1B Mediates Cell Survival in Pancreatic Ductal Adenocarcinoma," Cancer Res, 66(8):4149-58, Apr. 15, 2006.
Ewton, D. Z. et al., "Inactivation of Mirk/Dyrk1b Kinase Targets Quiescent Pancreatic Cancer Cells," Mol Cancer Ther, 10(11):2104-14, Aug. 2011.
Extended European Search Report dated Apr. 6, 2017, for EP Application No. 16460096.7 (9 pages).
Ferrer, I., et al., "Constitutive Dyrk1A is abnormally expressed in Alzheimer disease, Down syndrome, Pick disease, and related transgenic models," Neurobiol Dis. Nov. 2005;20(2):392-400.
Friedman, E., "Mirk/Dyrk1B in cancer," J Cell Biochem 102: 274-279, 2007.
International Search Report and Written Opinion for Application No. PCT/US2017/067527, dated Apr. 25, 2018. (18 pages).
Ionescu et al., "DYRK1A Kinase Inhibitors with Emphasis on Cancer," Mini Rev Med Chem, 12(13):1315-29, Sep. 2012.
Keramati, A.R. et al., "A Form of the Metabolic Syndrome Associated with Mutations in DYRK1B," N Engl J Med., 370(20): 1909-1919, May 2014.

(Continued)

*Primary Examiner* — Heidi Reese
(74) *Attorney, Agent, or Firm* — Nutter McClennen & Fish LLP

(57) ABSTRACT

The present invention relates to the compound of formula (I) and salts, stereoisomers, tautomers or N-oxides thereof. The present invention is further concerned with the use of such a compound or salt, stereoisomer, tautomer or N-oxide thereof as medicament and a pharmaceutical composition comprising said compound.

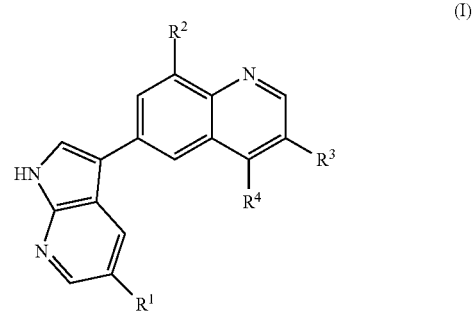

14 Claims, No Drawings

(56) References Cited

OTHER PUBLICATIONS

Khor, B. et al., "The kinase DYRK1A reciprocally regulates the differentiation of Th17 and regulatory T cells," Elife, May 2015;4:e05920. DOI: 10.7554/eLife.05920.
Komarova, N.L. et al., "Effect of cellular quiescence on the success of targeted CML therapy," 2(10): e990.doi:10.1371/journal.pone.0000990 Oct. 2007.
Leder, S. et al., "Cloning and characterization of DYRK1B, a novel member of the DYRK family of protein kinases," Biochem Biophys Res Commun 254, 474-9, Jan. 1999.
Lee, K. et al., "Mirk Protein Kinase is a Mitogen-activated Protein Kinase Substrate That Mediates Survival fo Colon Cancer Cells," Cancer Res 60, 3631-7, Jul. 2000.
Mercer, S.E. at al., "Mirk/Dyrk1b Mediates Cell Survival in Rhabdomyosarcomas," Cancer Res, 66(10):5143-50, May 2006.
Pellegrini, F. P. et al., "Down syndrome, autoimmunity and T regulatory cells," Clin Exp Immunol., 169(3):238-43, May 2012.
Yoshida, K., et al., "Role for DYRK family kinases on regulation of apoptosis," Biochem Pharmacol, 2008, v 76, pp. 1389-1394.

\* cited by examiner

DERIVATIVES OF QUINOLINE AS INHIBITORS OF DYRK1A AND/OR DYRK1B KINASES

FIELD OF THE INVENTION

The present invention relates to substituted 7-azaindole-quinoline compounds and salts, stereoisomers, tautomers or N-oxides thereof. The present invention is further concerned with the use of substituted 7-azaindole-quinoline compounds or salts, stereoisomers, tautomers or N-oxides thereof as medicament and a pharmaceutical composition comprising said compounds.

BACKGROUND OF THE INVENTION

Protein kinases are a class of enzymes capable of transferring phosphate groups form ATP to substrate proteins. Phosphorylation can alter the interactions between proteins, the activity, the localization or degradation of target proteins. As protein kinases are involved in virtually all biochemical pathways, they are regarded as key regulators and implicated in various diseases when mutated or misregulated.

Dual-specificity tyrosine phosphorylation-regulated kinases (DYRK) are a subfamily of protein kinases comprising several isoforms including DYRK1A and DYRK1B. DYRK1A and DYRK1B are known to interact with numerous cytoskeletal, synaptic and nuclear proteins and are believed to play important roles in cell proliferation and apoptosis induction (Yoshida et al., Biochem Pharmacol., 76(11):1389-94, 2008). DYRK1A and DYRK1B share 85% identity at the amino acid level, though expression and functional characteristics differ (Aranda et al., FASEB 25, 449-462; 2011). While DYRK1A is ubiquitously expressed, DYRK1B was found in a limited number of tissues and organs such as testis and skeletal muscle (Leder et al., Biochem Biophys Res Commun 254, 474-9, 1999; Lee et al., Cancer Res 60, 3631-7, 2000). DYRK1A plays a role in cell proliferation and neural differentiation. Transgenic mice overexpressing DYRK1A show learning and memory disabilities. In Down syndrome patients, the gene encoding DYRK1A is present in three copies. It has been observed that trisomy driven overexpression of DYRK1A is associated with early onset Alzheimer's disease. At the gene level, overexpression of DYRK1A is responsible for the deregulation of more than 200 genes and phosphorylation of numerous proteins, including APP, Tau, presenilin and septin-4 which are key proteins in the pathogenesis of Alzheimer's disease (Ferrer et al., Neurobiol Dis 20, 392-400, 2005; EP 2744797).

Moreover, DYRK1A has been implicated in inflammatory as well as autoimmune diseases due to its inhibiting the differentiation of T helper cells. Many autoimmune and other inflammatory diseases are thought to be caused by T regulatory cells ($T_{reg}$ cells), which are responsible for shutting down inflammation processes once they are no longer needed. It is suggested that increased DYRK1A activity inhibits the differentiation of $T_{reg}$ cells thereby failing to stop inflammatory responses (Khor et al., Elife, 22; 4, 2015). Against this background, it is also notable that Down syndrome patients have hypofunctional $T_{reg}$ cells thereby being prone to an increased risk for autoimmune diseases (Pellegrini et al., Clin Exp Immunol., 169(3):238-43, 2012).

As regards cancer, DYRK1A has been implicated in the resistance of cancer cells to pro-apoptotic stimuli and drives several pathways that lead to increased proliferation, migration as well as a reduction of cell death. By consequence, such cancers typically exhibit very aggressive biological characteristics (Ionescu et al., Mini Rev Med Chem, 12(13): 1315-29, 2012).

In contrast to DYRK1A, the gene coding for DYRK1B is located on chromosome 19 (Leder at al., Biochem Biophys Res Commun 254, 474-9, 1999) and is frequently amplified in cancer cells, including pancreatic and ovarian cancer cells (Friedman, J Cell Biochem 102: 274-279, 2007; Deng and Friedman, Genes Cancer, 5(9-10): 337-347, 2014).

DYRK1B has been demonstrated to support the survival of cancer cells (Deng et al., Cancer Res, 66(8):4149-58, 2006; Mercer at al., Cancer Res, 66(10):5143-50, 2006). DYRK1B is overexpressed in approximately 89% of tissue samples of pancreatic ductal adenocarcinomas and 75% of ovarian cancers, as well as in gliomas, leukemias, lung, breast, colon, skin, and other cancers. Levels of DYRK1B are increased 10-fold in some cancer cell populations, especially though not necessarily in quiescent cancer cells, which are known to be comparatively insensitive to anti-cancer therapies, such as chemotherapeutic drugs, targeted drugs, and radiation (Borst, Open Biol 2: 120066, 2012; Komarova and Wodarz, PLoS One 2: e990, 2007). Upon reentry of the cell-cycle, quiescent cancer cells can cause tumor regrowth or recurrence (Ewton et al., Mol Cancer Ther, 10(11):2104-14, 2011). Concerning the underlying mechanism, it was shown that DYRK1B increases expression of antioxidant genes, which results in a decrease in reactive oxygen species and, consequently, an increase in quiescent cell viability (Deng and Friedman, Genes Cancer, 5(9-10): 337-347, 2014). Furthermore, DYRK1B has been shown to play a role in adipogenesis and glucose homeostasis associating its function with metabolic diseases such as the metabolic syndrome (Keramati, N Engl J Med., 370(20): 1909-1919, 2014).

Hence, kinases of the DYRK family are believed to be important targets for the treatment of neurodegenerative, proliferative, inflammatory, autoimmune and metabolic diseases. A feasible approach towards the treatment of said diseases is the use of natural or synthetic kinase inhibitors, several of which have been reported for DYRK1A and DYRK1B.

Regarding natural compounds, the plant-derived polyphenol epigallocatechin gallate (EGCG), the β-carboline alkaloid harmine and its analogues, marine alkaloid leucettamine B and its analogues, and analogues of marine alkaloid meridianin have been identified as DYRK1A inhibitors. Harmine, has been found to inhibit DYRK1B as well. However, EGCG and harmine, and other known DYRK1 inhibitors suffer from lack of selectivity and/or activity thus substantially limiting their value as selective inhibitors. Regarding synthetic compounds, pyridopyrimidine, pyrazolidinedione and benzothiazole or thiazole derivatives have been demonstrated to inhibit DYRK1A. In addition, several small molecules which were originally designed to inhibit other protein kinases, such as purvalanol A, 2-dimethyl-amino-4,5,6,7-tetrabromo-1H-benzimidazole (DMAT) and 4,5,6,7-tetrabromo-1H-benzotriazole (TBB), were described as somewhat efficient in inhibiting DYRK1A activity. However, the limited selectivity and/or activity of said inhibitors remains a significant downside (Becker and Sippl, FEBS J, 278(2):246-56 2011). Furthermore, WO 2012/098068 relates to pyrazolo pyrimidines as inhibitors for DYRK1A and DYRK1B and treatment of proliferative diseases, including cancer, Down syndrome and early onset Alzheimer's disease. However, 7-azaindole-quinoline structures are not described.

WO 2003/082868 relates to 3,5-substituted 7-azaindole derivatives and their use for inhibition of c-Jun N-terminal kinases. WO 2005/085244 relates to 3,5-substituted azaindole derivatives and their use in the inhibition of c-Jun N-terminal kinases.

In view of the above, there is a need for further compounds which inhibit DYRK1A and/or DYRK1B kinase activity in a potent and/or selective manner in order to be capable of treating diseases linked to aberrant expression and/or activity of DYRK1A and/or DYRK1B, and more particularly to increase in expression and/or activity of DYRK1A and/or DYRK1B. In particular, there is a need for compounds which are suitable for the treatment of diseases such as neurodegenerative, proliferative, inflammatory, autoimmune and metabolic diseases.

OBJECTS AND SUMMARY OF THE INVENTION

It is therefore an object of the present invention to provide compounds, which inhibit DYRK1A and/or DYRK1B kinase activity, preferably in a potent and/or selective manner.

It is another object of the present invention to provide compounds, which are capable of treating diseases linked to (increased) DYRK1A and/or DYRK1B expression and/or activity.

It is still another object of the present invention to provide compounds, which are suitable for the treatment of a disease selected from the group consisting of neurodegenerative, proliferative, inflammatory, autoimmune and metabolic diseases involving disregulation of adipogenesis and/or glucose homeostasis.

In particular, it is an object of the present invention to provide compounds, which are suitable for the treatment of cancer, Down syndrome and early onset Alzheimer's disease.

The above objects can be achieved by the compounds of formula (I) as defined herein, and uses thereof.

The inventors of the present invention inter alia surprisingly found that the compounds of formula (I), as defined herein below (see first aspect), inhibit DYRK1A and/or DYRK1B activity. Accordingly, the compounds of formula (I) or a pharmaceutical composition comprising a compound of formula (I), as defined herein below (see second aspect), can be used for the treatment of diseases linked to an (increased) DYRK1A and/or DYRK1B expression and/or activity, in particular neurodegenerative, proliferative, inflammatory, autoimmune and metabolic diseases.

Therefore, in the first aspect, the present invention relates to a compound of formula (I)

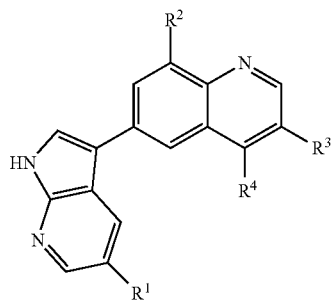

(I)

or a salt, stereoisomer, tautomer or N-oxide thereof, wherein
$R^1$, $R^3$, $R^4$ are independently selected from the group consisting of
(i) H, halogen, CN, $NO_2$, $C_1$-$C_6$-alkyl, $C_2$-$C_6$-alkenyl, $C_2$-$C_6$-alkynyl;
wherein each substitutable carbon atom in the aforementioned moieties is independently unsubstituted or substituted with one or more, same or different substituents $R^7$;
(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$;
(iii) a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;
$R^2$ is selected from the group consisting of H, halogen, CN, $NO_2$, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy and $C_1$-$C_6$-haloalkoxy;
$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;
$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$; and
a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;
$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;

$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;

and wherein n is 0, 1 or 2.

In one embodiment $R^1$ is selected from the group consisting of
(i) H, halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl;
wherein each substitutable carbon atom in the aforementioned moieties is independently unsubstituted or substituted with one or more, same or different substituents $R^7$;
(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$;

preferably $R^1$ is selected from the group consisting of H, halogen, CN, $NO_2$, $C_1$-$C_3$-alkyl, $C_2$-$C_3$-alkenyl, $C_2$-$C_3$-alkynyl and $C(=O)N(R^{6a})(R^{6b})$;

wherein each substitutable carbon atom in the aforementioned moieties is independently unsubstituted or substituted with one or more, same or different substituents $R^7$;

more preferably $R^1$ is selected from the group consisting of H, halogen, CN, $NO_2$, $C_1$-$C_3$-alkyl, $C_2$-$C_3$-alkenyl and $C_2$-$C_3$-alkynyl;

wherein each substitutable carbon atom in the aforementioned moieties is independently unsubstituted or substituted with one or more, same or different substituents $R^7$;

and wherein all other substituents have the meaning as defined above.

In certain embodiments, $R^1$ is as defined above with the proviso that $R^1$ is not chloride or another halogen. In certain embodiments, $R^1$ is not chloride, or another halogen when R2, R3, and R4 are H. In certain embodiments, $R^1$ is selected from the group consisting of H, CN, $NO_2$, $C_1$-$C_3$-alkyl, $C_2$-$C_3$-alkenyl, $C_2$-$C_3$-alkynyl and $C(=O)N(R^{6a})(R^{6b})$;

wherein each substitutable carbon atom in the aforementioned moieties is independently unsubstituted or substituted with one or more, same or different substituents $R^7$.

In another embodiment $R^2$ is selected from the group consisting of H, halogen, CN, $NO_2$, $C_1$-$C_2$-alkyl, vinyl, $C_1$-$C_2$-alkoxy and $C_1$-$C_2$-haloalkoxy;

and wherein all other substituents have the meaning as defined above.

In another embodiment $R^3$ is selected from the group consisting of
(i) H, halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl;
wherein each substitutable carbon atom in the aforementioned moieties is independently unsubstituted or substituted with one or more, same or different substituents $R^7$;
(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$;

preferably $R^3$ is selected from the group consisting of H, halogen, CN, $NO_2$, $N(R^{6a})(R^{6b})$, $N(R^6)C(=O)R^5$;

and wherein all other substituents have the meaning as defined above.

In another embodiment $R^4$ is selected from the group consisting of H, halogen, $N(R^{6a})(R^{6b})$, $C_1$-$C_6$-alkyl, $C_2$-$C_6$-alkenyl, $C_2$-$C_6$-alkynyl, wherein each substitutable carbon atom in the aforementioned moieties is independently unsubstituted or substituted with one or more, same or different $R^7$;

and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

and wherein all other substituents have the meaning as defined above.

In another embodiment $R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$.

In another embodiment $R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$.

In another embodiment R⁸ is selected from the group consisting of $C_1$-$C_3$-alkyl, $C_2$-$C_3$-alkenyl, $C_1$-$C_3$-alkylcarbonyl, $C_2$-$C_3$-alkynyl and $N(R^{6a})(R^{6b})$.

In another embodiment R⁹ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$.

In another embodiment $R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$.

In another embodiment $R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

In another embodiment said compound is selected from the group consisting of 4-chloro-6-{1H-pyrrolo[2,3-b]pyridin-3-yl}quinoline; 6-{1H-pyrrolo[2,3-b]pyridin-3-yl}quinoline; (3S)-1-(6-{1H-pyrrolo[2,3-b]pyridin-3-yl}quinolin-4-yl)piperidin-3-amine; 1-N-(6-{1H-pyrrolo[2,3-b]pyridin-3-yl}quinolin-4-yl)cyclohexane-1,4-diamine; (3S)-1-(6-{1H-pyrrolo[2,3-b]pyridin-3-yl}quinolin-4-yl)pyrrolidin-3-amine; 4-(pyridin-3-yl)-6-{1H-pyrrolo[2,3-b]pyridin-3-yl}quinoline; 4-(pyridin-4-yl)-6-{1H-pyrrolo[2,3-b]pyridin-3-yl}quinoline; 4-phenyl-6-{1H-pyrrolo[2,3-b]pyridin-3-yl}quinoline; {5-ethenyl-1-azabicyclo[2.2.2]octan-2-yl}(6-{1H-pyrrolo[2,3-b]pyridin-3-yl}quinolin-4-yl)methanol; N-(1-methylpiperidin-4-yl)-6-{1H-pyrrolo[2,3-b]pyridin-3-yl}quinolin-4-amine; 8-chloro-6-{1H-pyrrolo[2,3-b]pyridin-3-yl}quinoline hydrochloride; 8-methyl-6-{1H-pyrrolo[2,3-b]pyridin-3-yl}quinoline hydrochloride; 8-fluoro-6-{1H-pyrrolo[2,3-b]pyridin-3-yl}quinoline; 6-{1H-pyrrolo[2,3-b]pyridin-3-yl}-8-(trifluoromethoxy)quinoline; 8-methoxy-6-{1H-pyrrolo[2,3-b]pyridin-3-yl}quinoline; N-(furan-3-ylmethyl)-6-{1H-pyrrolo[2,3-b]pyridin-3-yl}quinolin-3-amine; 8-methyl-4-phenyl-6-{1H-pyrrolo[2,3-b]pyridin-3-yl}quinoline; 8-methyl-4-(pyridin-3-yl)-6-{1H-pyrrolo[2,3-b]pyridin-3-yl}quinoline; 8-fluoro-4-(pyridin-3-yl)-6-{1H-pyrrolo[2,3-b]pyridin-3-yl}quinoline; 3-(4-chloroquinolin-6-yl)-N-methyl-N-(prop-2-en-1-yl)-1H-pyrrolo[2,3-b]pyridine-5-carboxamide; methyl({3-[4-(pent-4-en-1-yl)quinolin-6-yl]-1H-pyrrolo[2,3-b]pyridin-5-yl}methyl)(prop-2-en-1-yl)amine; N-methyl-3-[4-(pyridin-3-yl)quinolin-6-yl]-1H-pyrrolo[2,3-b]pyridine-5-carboxamide; N-methyl-3-[4-(morpholin-4-yl)quinolin-6-yl]-1H-pyrrolo[2,3-b]pyridine-5-carboxamide; 3-(4-chloroquinolin-6-yl)-N-methyl-1H-pyrrolo[2,3-b]pyridine-5-carboxamide; N-methyl-3-(quinolin-6-yl)-1H-pyrrolo[2,3-b]pyridine-5-carboxamide; 3-(8-methoxyquinolin-6-yl)-N-methyl-N-(prop-2-en-1-yl)-1H-pyrrolo[2,3-b]pyridine-5-carboxamide; 3-(8-fluoroquinolin-6-yl)-N-methyl-N-(prop-2-en-1-yl)-1H-pyrrolo[2,3-b]pyridine-5-carboxamide; 3-(8-chloroquinolin-6-yl)-N-methyl-N-(prop-2-en-1-yl)-1H-pyrrolo[2,3-b]pyridine-5-carboxamide; 3-(8-methoxyquinolin-6-yl)-N-methyl-1H-pyrrolo[2,3-b]pyridine-5-carboxamide; 3-(8-fluoroquinolin-6-yl)-N-methyl-1H-pyrrolo[2,3-b]pyridine-5-carboxamide; N-benzyl-3-(8-fluoroquinolin-6-yl)-1H-pyrrolo[2,3-b]pyridine-5-carboxamide; N-benzyl-3-(8-chloroquinolin-6-yl)-1H-pyrrolo[2,3-b]pyridine-5-carboxamide; 3-(8-fluoroquinolin-6-yl)-1H-pyrrolo[2,3-b]pyridine-5-carboxamide; N-(3-aminopropyl)-3-(8-chloroquinolin-6-yl)-1H-pyrrolo[2,3-b]pyridine-5-carboxamide hydrochloride; N-benzyl-3-[8-fluoro-4-(pyridin-3-yl)quinolin-6-yl]-1H-pyrrolo[2,3-b]pyridine-5-carboxamide; N-(3-aminopropyl)-3-[8-fluoro-4-(pyridin-3-yl)quinolin-6-yl]-1H-pyrrolo[2,3-b]pyridine-5-carboxamide hydrochloride; 3-[8-fluoro-4-(pyridin-3-yl)quinolin-6-yl]-N-methyl-N-(prop-2-en-1-yl)-1H-pyrrolo[2,3-b]pyridine-5-carboxamide; 3-[8-fluoro-4-(pyridin-3-yl)quinolin-6-yl]-N-methyl-1H-pyrrolo[2,3-b]pyridine-5-carboxamide; 3-[8-fluoro-4-(2-phenylethyl)quinolin-6-yl]-N-methyl-1H-pyrrolo[2,3-b]pyridine-5-carboxamide; 3-{4-[(3R)-3-aminopiperidin-1-yl]-8-fluoroquinolin-6-yl}-N-methyl-1H-pyrrolo[2,3-b]pyridine-5-carboxamide hydrochloride; N-methyl-3-[8-methyl-4-(pyridin-3-yl)quinolin-6-yl]-1H-pyrrolo[2,3-b]pyridine-5-carboxamide; 3-{4-[(3S)-3-aminopiperidin-1-yl]-8-fluoroquinolin-6-yl}-N-methyl-1H-pyrrolo[2,3-b]pyridine-5-carboxamide hydrochloride; N-methyl-3-[8-fluoro-4-(4-methylpyridin-3-yl)quinolin-6-yl]-1H-pyrrolo[2,3-b]pyridine-5-carboxamide; 3-[8-methoxy-4-(pyridin-3-yl)quinolin-6-yl]-1H-pyrrolo[2,3-b]pyridine-5-carboxamide; N-{3-[8-fluoro-4-(pyridin-3-yl)quinolin-6-yl]-1H-pyrrolo[2,3-b]pyridin-5-yl}acetamide; 3-[8-fluoro-4-(pyridin-3-yl)quinolin-6-yl]-N-(pyridin-3-ylmethyl)-1H-pyrrolo[2,3-b]pyridine-5-carboxamide; 3-{4-[(3R)-3-aminopiperidin-1-yl]-8-fluoroquinolin-6-yl}-N-(pyridin-3-ylmethyl)-1H-pyrrolo[2,3-b]pyridine-5-carboxamide hydrochloride; 3-{4-[(3R)-3-aminopiperidin-1-yl]-8-fluoroquinolin-6-yl}-N-(pyrimidin-5-ylmethyl)-1H-pyrrolo[2,3-b]pyridine-5-carboxamide hydrochloride; benzyl({3-[8-fluoro-4-(pyridin-3-yl)quinolin-6-yl]-1H-pyrrolo[2,3-b]pyridin-5-yl}methyl)amine; (3R)-1-(6-{5-[(benzylamino)methyl]-1H-pyrrolo[2,3-b]pyridin-3-yl}-8-fluoroquinolin-4-yl)piperidin-3-amine; ({3-[8-fluoro-4-(pyridin-3-yl)quinolin-6-yl]-1H-pyrrolo[2,3-b]pyridin-5-yl}methyl)(methyl)(prop-2-en-1-yl)amine; 3-{4-[(3S)-3-aminopiperidin-1-yl]-3-nitroquinolin-6-yl}-N-methyl-1H-pyrrolo[2,3-b]pyridine-5-carboxamide hydrochloride; 3-{3-amino-4-[(3S)-3-aminopiperidin-1-yl]quinolin-6-yl}-N-methyl-1H-pyrrolo[2,3-b]pyridine-5-carboxamide hydrochloride; 3-{4-[(3S)-3-aminopiperidin-1-yl]-3-{[(3-chlorophenyl)methyl]amino}quinolin-6-yl}-N-methyl-1H-pyrrolo[2,3-b]pyridine-5-carboxamide hydrochloride; 3-(3-{[(3-chlorophenyl)methyl]amino}-4-(morpholin-4-yl)quinolin-6-yl)-N-methyl-1H-pyrrolo[2,3-b]pyridine-5-carboxamide; 3-[3-acetamido-4-(morpholin-4-yl)quinolin-6-yl]-N-methyl-1H-pyrrolo[2,3-b]pyridine-5-carboxamide; N-methyl-3-[4-(morpholin-4-yl)-3-[(oxan-4-ylmethyl)amino]quinolin-6-yl]-1H-pyrrolo[2,3-b]pyridine-5-carboxamide; 3-{4-[(4-aminocyclohexyl)amino]-3-nitroquinolin-6-yl}-N-(pyridin-3-ylmethyl)-1H-pyrrolo[2,3-b]pyridine-5-carboxamide hydrochloride; 3-{4-[(4-aminocyclohexyl)amino]-3-[(oxan-4-ylmethyl)amino]quinolin-6-yl}-N-(pyridin-3-ylmethyl)-1H-pyrrolo[2,3-b]pyridine-5-carboxamide hydrochloride; 3-(3-aminoquinolin-6-yl)-N-(pyridin-3-ylmethyl)-1H-pyrrolo[2,3-b]pyridine-5-carboxamide; 3-{3-[(oxan-4-ylmethyl)amino]quinolin-6-yl}-N-(pyridin-3-ylmethyl)-1H-pyrrolo[2,3-b]pyridine-5-carboxamide; 4-[(1-methylpiperidin-4-yl)amino]-6-{1H-pyrrolo[2,3-b]pyridin-3-yl}quinoline-3-carbonitrile; N-methyl-N-(1-methylpiperidin-4-yl)-3-nitro-6-{1H-pyrrolo[2,3-b]pyridin-3-yl}quinolin-4-amine; 1-{4-[(3-amino-6-{1H-pyrrolo[2,3-b]pyridin-3-yl}quinolin-4-yl)amino]piperidin-1-yl}ethan-1-one; N-(3-aminopropyl)-3-(8-fluoroquinolin-6-yl)-1H-pyrrolo[2,3-b]pyridine-5-carboxamide hydrochloride and 3-(3-acetamidoquinolin-6-yl)-N-(pyridin-3-ylmethyl)-1H-pyrrolo[2,3-b]pyridine-5-carboxamide.

In a second aspect, the present invention relates to a pharmaceutical composition comprising a pharmaceutically effective amount of the compound according to formula (I) as defined above, and optionally a pharmaceutically acceptable carrier, diluent or excipient. Put in different words, the present invention relates to the compound according to formula (I) as defined above, or a pharmaceutical composition comprising a pharmaceutically effective amount of the compound according to formula (I) as defined above, for use in medicine.

In a third aspect, the present invention relates to a compound according to formula (I) as defined above, or a pharmaceutical composition comprising a pharmaceutically effective amount of the compound according to formula (I) as defined above, for use in the treatment of neurodegenerative, proliferative, inflammatory, autoimmune and metabolic diseases.

In a fourth aspect, the present invention is concerned with a method for modulating or regulating and preferably inhibiting DYRK1A and/or DYRK1B kinases, wherein said kinases are exposed to at least one compound according to formula (I) as defined above, wherein said method is preferably performed outside the human or animal body.

In a fifth aspect, the present invention relates to the use of a compound according to formula (I) as defined above as DYRK1A and/or DYRK1B modulating and preferably inhibiting agent.

DETAILED DESCRIPTION

In the following, preferred embodiments of the substituents in the above formula (I) are described in further detail.

The following embodiments relate to $R^1$ as defined above in the first aspect.

In embodiment 1(A), $R^1$ is
(i) H, halogen, CN, $NO_2$, $C_1$-$C_6$-alkyl, $C_2$-$C_6$-alkenyl or $C_2$-$C_6$-alkynyl; wherein each substitutable carbon atom in the aforementioned moieties is independently unsubstituted or substituted with one or more, same or different substituents $R^7$; or
(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$ or $N(R^6)S(=O)_nOR^6$.

In preferred embodiment 1(B), $R^1$ is (i) H, halogen, CN, $NO_2$, $C_1$-$C_3$-alkyl, $C_2$-$C_3$-alkenyl or $C_2$-$C_3$-alkynyl, wherein each substitutable carbon atom in the aforementioned moieties is independently unsubstituted or substituted with one or more, same or different substituents $R^7$; or (ii) $C(=O)N(R^{6a})(R^{6b})$.

In a more preferred embodiment 1(C), $R^1$ is (i) H, halogen, CN, $NO_2$, $C_1$-$C_3$-alkyl, $C_2$-$C_3$-alkenyl or $C_2$-$C_3$-alkynyl, wherein each substitutable carbon atom in the aforementioned moieties is independently unsubstituted or substituted with one or more, same or different substituents $R^7$.

In certain embodiments, $R^1$ is as defined above with the proviso that $R^1$ is chloride or another halogen. In certain embodiments, $R^1$ is chloride, or another halogen; when R2, R3, and R4 are H. In certain embodiments, $R^1$ is selected from the group consisting of H, CN, $NO_2$, $C_1$-$C_3$-alkyl, $C_2$-$C_3$-alkenyl, $C_2$-$C_3$-alkynyl and $C(=O)N(R^{6a})(R^{6b})$, wherein each substitutable carbon atom in the aforementioned moieties is independently unsubstituted or substituted with one or more, same or different substituents $R^7$.

The following substituent meanings are relevant in connection with embodiments 1(A), 1(B) and 1(C):
$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and
a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;
$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_n(R^6)$, $N(R^6)S(=O)_nN(R^{6a})(R^{6b})$, $N(R^6)S(=O)_nOR^6$; and
a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;
$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;
$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;
and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;
$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;
$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;
and wherein
n is 0, 1 or 2.
Preferably, the following substituent meanings are relevant in connection with embodiments 1(A), 1(B) and 1(C):
$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^8$ is selected from the group consisting of $C_1$-$C_3$-alkyl, $C_2$-$C_3$-alkenyl, $C_1$-$C_3$-alkylcarbonyl, $C_2$-$C_3$-alkynyl and $N(R^{6a})(R^{6b})$;

$R^9$ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$;

$R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

$R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

More preferably, the following substituent meanings are relevant in connection with embodiments 1(A), 1(B) and 1(C):

$R^5$, $R^6$, $R^{6a}$ and $R^{6b}$ are independently from each other selected from the group consisting of H, $C_1$-$C_5$-alkyl, $C_2$-$C_5$-alkenyl and $C_2$-$C_5$-alkynyl, wherein each substitutable carbon atom in the aforementioned moieties is independently unsubstituted or substituted with one or more, same or different $R^9$;

$R^7$ is $N(R^{6a})(R^{6b})$;

$R^9$ is selected from the group consisting of $N(R^{11a})(R^{11b})$ or a 5- to 6-membered fully unsaturated carbocyclic or heterocyclic ring, wherein said heterocyclic ring comprises one or more, same or different heteroatoms O, N, S;

$R^{11a}$ and $R^{11b}$ are independently selected from the group consisting of H, $C_1$-$C_3$-alkyl, $C_2$-$C_3$-alkenyl and $C_2$-$C_3$-alkynyl.

In a further embodiment 1(D), $R^1$ is H.

In a further embodiment 1(E), $R^1$ is $C(=O)N(R^{6a})(R^{6b})$.

In a further embodiment 1(F), $R^1$ is $C_1$-$C_6$-alkyl, wherein each substitutable carbon atom in said alkyl moiety is independently unsubstituted or substituted with one or more, same or different $R^7$. The formula of this substituent $R^1$ corresponds to formula S9.

The following substituent meanings are relevant in connection with embodiment 1(E) or 1(F):

$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_n(R^6)$, $N(R^6)S(=O)_nN(R^{6a})(R^{6b})$, $N(R^6)S(=O)_nOR^6$; and a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;

$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;

$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$- alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;

and wherein n is 0, 1 or 2.

Preferably, the following substituent meanings are relevant in connection with embodiments 1(E) and 1(F):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^8$ is selected from the group consisting of $C_1$-$C_3$-alkyl, $C_2$-$C_3$-alkenyl, $C_1$-$C_3$-alkylcarbonyl, $C_2$-$C_3$-alkynyl and $N(R^{6a})(R^{6b})$;

$R^9$ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$;

$R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

$R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

More preferably, the following substituent meanings are relevant in connection with embodiment 1(E) or 1(F):

$R^{6a}$, $R^{6b}$ are independently selected from the group consisting of H, $C_1$-$C_6$-alkyl, $C_2$-$C_6$-alkenyl and $C_2$-$C_6$-alkynyl, wherein each substitutable carbon atom in the aforementioned moieties is independently unsubstituted or substituted with one or more, same or different substituents $R^9$;

$R^7$ is $N(R^{6a})(R^{6b})$;

$R^9$ is selected from the group consisting of $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms O, N or S;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl.

In a preferred embodiment 1(E1), $R^1$ is $C(=O)N(R^{6a})(R^{6b})$, wherein $R^{6a}$ is H or $C_1$-$C_5$-alkyl and $R^{6b}$ is H, $C_1$-$C_5$-alkyl, $C_2$-$C_5$-alkenyl or $C_2$-$C_5$-alkynyl, wherein each substitutable carbon atom in the aforementioned moieties is independently unsubstituted or substituted with a substituent selected from $N(R^{11a})(R^{11b})$ and formula S1 as depicted below; wherein $R^{11a}$ and $R^{11b}$ are independently selected from the group consisting of H, $C_1$-$C_3$-alkyl, $C_2$-$C_3$-alkenyl and $C_2$-$C_3$-alkynyl; and wherein $X^1$, $X^2$, $X^3$, $X^4$ and $X^5$ in formula S1 are independently of each other selected from the group consisting of CH and N.

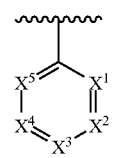

(S1)

In a preferred embodiment 1(F1), $R^1$ is $C_1$-$C_6$-alkyl, wherein each substitutable carbon atom in said alkyl moiety is independently unsubstituted or substituted with $R^7$, wherein $R^7$ is $N(R^{6a})(R^{6b})$, and wherein $R^{6a}$ is H or $C_1$-$C_5$-alkyl and $R^{6b}$ is H, $C_1$-$C_5$-alkyl, $C_2$-$C_5$-alkenyl or $C_2$-$C_5$-alkynyl, wherein each substitutable carbon atom in the aforementioned moieties is independently unsubstituted or substituted with a substituent of formula S2 as depicted below, wherein $X^1$, $X^2$, $X^3$, $X^4$ and $X^5$ in formula S2 are independently of each other selected from the group consisting of CH and N.

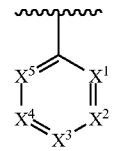

(S2)

In the above substituents S1 and S2 it is preferred that at least 2 of $X^1$, $X^2$, $X^3$, $X^4$ and $X^5$ represent CH.

For S1, it is even more preferred that at least 3 of $X^1$, $X^2$, $X^3$, $X^4$ and $X^5$ represent CH.

For S2, it is even more preferred that $X^1$, $X^2$, $X^3$, $X^4$ and $X^5$ represent CH.

The following embodiments relate to $R^2$ as defined above in the first aspect.

In embodiment 2(A), $R^2$ is H, halogen, CN, $NO_2$, $C_1$-$C_2$-alkyl, vinyl, $C_1$-$C_2$-alkoxy or $C_1$-$C_2$-haloalkoxy.

In a preferred embodiment 2(B), $R^2$ is H, F, Cl, $CH_3$, $OCH_3$ or $OCF_3$.

In a further embodiment 2(C), $R^2$ is H.

In a further embodiment 2(D), $R^2$ is halogen, preferably Cl or F.

15

In a further embodiment 2(E), $R^2$ is $C_1$-$C_6$-alkyl, preferably methyl.

In a further embodiment 2(F), $R^2$ is $C_1$-$C_6$-alkoxy, preferably methoxy.

In a further embodiment 2(G), $R^2$ is $C_1$-$C_6$-haloalkoxy, preferably trifluoromethoxy.

The following embodiments relate to $R^3$ as defined above in the first aspect. In embodiment 3(A), $R^3$ is (i) H, halogen, CN, $NO_2$, $C_1$-$C_6$-alkyl, $C_2$-$C_6$-alkenyl, $C_2$-$C_6$-alkynyl; wherein each substitutable carbon atom in the aforementioned moieties is independently unsubstituted or substituted with one or more, same or different substituents $R^7$;

(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$;

In a preferred embodiment 3(B), $R^3$ is (i) H, halogen, CN or $NO_2$ or (ii) $N(R^{6a})(R^{6b})$ or $N(R^6)C(=O)R^5$.

The following substituent meanings are relevant in connection with embodiments 3(A) and 3(B):

$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$; and a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;

$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;

$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

16 and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;

and wherein n is 0, 1 or 2.

Preferably, the following substituent meanings are relevant in connection with embodiments 3(A) and 3(B):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^8$ is selected from the group consisting of $C_1$-$C_3$-alkyl, $C_2$-$C_3$-alkenyl, $C_1$-$C_3$-alkylcarbonyl, $C_2$-$C_3$-alkynyl and $N(R^{6a})(R^{6b})$;

$R^9$ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$;

$R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

$R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

More preferably, the following substituent meanings are relevant in connection with embodiments 3(A) and 3(B):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$;

$R^7$ is selected from the group consisting of $C_1$-$C_5$-alkyl, $C_2$-$C_5$-alkenyl, $C_2$-$C_5$-alkynyl;

$R^9$ is a 5- to 6-membered saturated or fully unsaturated carbocyclic or heterocyclic ring, wherein said heterocyclic ring comprises one or more heteroatoms O, wherein each substitutable carbon in the aforementioned cyclic moiety is independently unsubstituted or substituted with one or more, same or different substituents $R^{10}$;

$R^{10}$ is halogen.

In a further embodiment 3(C), $R^3$ is H.

In a further embodiment 3(D), $R^3$ is CN.

In a further embodiment 3(E), $R^3$ is $NO_2$.

In a further embodiment 3(F), $R^3$ is $N(R^{6a})(R^{6b})$.

In a further embodiment 3(G), $R^3$ is $N(R^6)C(=O)R^5$.

The following substituent meanings are relevant in connection with embodiments 3(F) and 3(G):

$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and
a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_n R^{11}$;
and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_n R^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;
and wherein
n is 0, 1 or 2.

Preferably, the following substituent meanings are relevant in connection with embodiments 3(F) and 3(G):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and
a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^9$ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$;

$R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

$R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

More preferably, the following substituent meanings are relevant in connection with embodiments 3(F) and 3(G):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$;

$R^9$ is a 5- to 6-membered saturated or fully unsaturated carbocyclic or heterocyclic ring, wherein said heterocyclic ring comprises one or more, same or different heteroatoms O, N or S, wherein each substitutable carbon in the aforementioned cyclic moiety is independently unsubstituted or substituted with one or more, same or different substituents $R^{10}$;

$R^{10}$ is halogen.

In a preferred embodiment 3(F1), $R^1$ is $N(R^{6a})(R^{6b})$, wherein $R^{6a}$ is H and $R^{6b}$ is H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with a substituent selected from formula S3, formula S4 and formula S5 as depicted below; wherein $X^1$, $X^2$ and $X^3$ in formula S3 are independently of each other selected from the group consisting of CH and N; and Y is selected from the group consisting of $CH_2$, O, NH and S;

$X^1$, $X^2$, $X^3$, $X^4$ and $X^5$ formula S4 are independently of each other selected from the group consisting of CH, O, S and NH.

$X^1$, $X^2$, $X^3$, $X^4$ and $X^5$ formula S5 are independently of each other selected from the group consisting of CH and N, wherein each substitutable carbon atom is independently unsubstituted or substituted with one or more, same or different halogen(s).

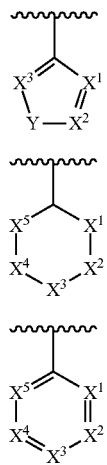

(S3)

(S4)

(S5)

In the above substituents S3, S4 and S5, it is preferred that at least 2 of $X^1$, $X^2$, $X^3$ in S3 or at least 2 of $X^1$, $X^2$, $X^3$, $X^4$ and $X^5$ in S4 or S5 represent CH.

In a preferred embodiment 3(G1), $R^1$ is $N(R^6)C(=O)R^5$, wherein $R^6$ is H and $R^5$ is H, $C_1$-$C_5$-alkyl, $C_2$-$C_5$-alkenyl or $C_2$-$C_5$-alkynyl.

The following embodiments relate to $R^4$ as defined above in the first aspect. In embodiment 4(A), $R^4$ is (i) H, halogen, $C_1$-$C_6$-alkyl, $C_2$-$C_6$-alkenyl, $C_2$-$C_6$-alkynyl, wherein each substitutable carbon atom in the aforementioned moieties is independently unsubstituted or substituted with one or more, same or different $R^7$;

(ii) $N(R^{6a})(R^{6b})$;

(iii) a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^8$.

The following substituent meanings are relevant in connection with embodiment 4(A):

$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)O R^6$, $N(R^6)C(=O)N(R^{6a})(R^{6b})$, $N(R^6)S(=O)_n(R^6)$, $N(R^6)S(=O)_nN(R^{6a})(R^{6b})$, $N(R^6)S(=O)_nOR^6$; and a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;

$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;

$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_n R^{11}$;

and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;

and wherein n is 0, 1 or 2.

Preferably, the following substituent meanings are relevant in connection with embodiment 4(A):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^8$ is selected from the group consisting of $C_1$-$C_3$-alkyl, $C_2$-$C_3$-alkenyl, $C_1$-$C_3$-alkylcarbonyl, $C_2$-$C_3$-alkynyl and $N(R^{6a})(R^{6b})$;

$R^9$ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$.

$R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

$R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

More preferably, the following substituent meanings are relevant in connection with embodiment 4(A):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl and a 5- to 6-membered saturated or fully unsaturated carbocyclic or heterocyclic ring, wherein said heterocyclic ring comprises one or more, same or different heteroatoms selected from O and N, wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^8$ is selected from the group consisting of $C_1$-$C_3$-alkyl, $C_2$-$C_3$-alkenyl and $C_2$-$C_3$-alkynyl;

$R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

$R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

In a further embodiment 4(B), $R^4$ is H.

In a further preferred embodiment 4(C), $R^4$ is halogen.

In a further embodiment 4(D), $R^4$ is $C_1$-$C_6$-alkyl, wherein each substitutable carbon atom in said alkyl moiety is independently unsubstituted or substituted with $R^7$. The formula of this substituent $R^4$ corresponds to formula S9.

In a further embodiment 4(E), $R^4$ is $N(R^{6a})(R^{6b})$.

The following substituent meanings are relevant in connection with embodiments 4(D) and 4(E):

$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_n(R^6)$, $N(R^6)S(=O)_nN(R^{6a})(R^{6b})$, $N(R^6)S(=O)_nOR^6$; and a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;

$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;

$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;
and wherein
n is 0, 1 or 2.

Preferably, the following substituent meanings are relevant in connection with embodiments 4(D) and 4(E):

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^8$ is selected from the group consisting of $C_1$-$C_3$-alkyl, $C_2$-$C_3$-alkenyl, $C_1$-$C_3$-alkylcarbonyl, $C_2$-$C_3$-alkynyl and $N(R^{6a})(R^{6b})$;

$R^9$ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$;

$R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

$R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

More preferably, in embodiments 4(D) and 4(E), as stated above, the substituents $R^{6a}$, $R^{6b}$ and $R^7$ have the following meaning:

$R^5$, $R^6$, $R^{6a}$, $R^{6b}$ are independently selected from the group consisting of H, $C_1$-$C_6$-alkyl, $C_2$-$C_6$-alkenyl and $C_2$-$C_6$-alkynyl and a 3- to 9-membered saturated, partially unsaturated or fully unsaturated carbocyclic or heterocyclic ring, wherein said heterocyclic ring comprises one or more heteroatoms N, and wherein each substitutable carbon or heteroatom in the aforementioned cyclic moieties is independently unsubstituted or substituted with $R^{10}$;

$R^7$ is a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;

$R^8$ is selected from the group consisting of $C_1$-$C_6$-alkyl, $C_1$-$C_6$-haloalkyl, $C_2$-$C_6$-alkenyl and $C_2$-$C_6$-alkynyl;

$R^{10}$ is selected from $C_1$-$C_6$-alkyl, $C_2$-$C_6$-alkenyl, $C_2$-$C_6$-alkynyl, $C_1$-$C_6$-alkylcarbonyl, $NH_2$.

In a preferred embodiment 4(D1), $R^4$ is $C_1$-$C_6$-alkyl, wherein each substitutable carbon atom in said alkyl moiety is independently unsubstituted or substituted with $R^7$, wherein $R^7$ is selected from the group consisting of a 6-membered fully unsaturated carbocyclic and an 8-membered saturated heterobicyclic ring, wherein said heterobicyclic ring comprises one or more, same or different heteroatoms O, N or S, and wherein each substitutable carbon or heteroatom in the aforementioned bicyclic moiety is independently unsubstituted or substituted with $R^8$;

$R^8$ is selected from the group consisting of $C_1$-$C_3$-alkyl, $C_2$-$C_3$-alkenyl and $C_2$-$C_3$-alkynyl.

In embodiment 4(E1), $R^4$ is $N(R^{6a})(R^{6b})$, wherein the substituents $R^{6a}$ is H or $C_1$-$C_5$-alkyl and $R^{6b}$ is selected from the group consisting of H, $C_1$-$C_5$-alkyl, $C_2$-$C_5$-alkenyl, $C_2$-$C_5$-alkynyl and a 6-membered saturated carbocyclic or heterocyclic ring, wherein said heterocyclic ring comprises one or more, same or different heteroatoms selected from O, N or S, wherein each substitutable carbon or heteroatom in the aforementioned cyclic moieties is independently unsubstituted or substituted with one or more, same or different substituents $R^{10}$, wherein $R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $NH_2$.

In a further embodiment 4(F), $R^4$ is $C_2$-$C_6$-alkenyl.

In a further embodiment 4(G), $R^4$ is a 5-membered saturated carbocyclic or heterocyclic ring, wherein said carbocyclic or heterocyclic ring comprises one or more heteroatoms N, and wherein each substitutable carbon atom in the aforementioned cyclic ring is independently unsubstituted or substituted with $NH_2$. The formula of this substituent $R^4$ corresponds to formula S6, wherein $X^1$ is CH or N and $X^2$, $X^3$, $X^4$ and $X^5$ are independently of each other $CH_2$, O, NH, S or $CHNH_2$.

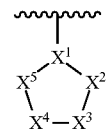

(S6)

In a further embodiment 4(H), $R^4$ is a 6-membered saturated carbocyclic or heterocyclic ring, wherein said heterocyclic ring comprises one or more, same or different heteroatoms selected from O and N, and wherein each substitutable carbon or heteroatom in the aforementioned cyclic moiety is independently unsubstituted or substituted with NH$_2$. The formula of this substituent R$^4$ corresponds to formula S7, wherein X$^1$ is CH or N and X$^2$, X$^3$, X$^4$ and X$^5$ are independently of each other CH$_2$, NH, O, S or CHNH$_2$.

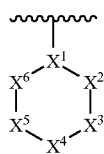

(S7)

In a further embodiment 4(I), R$^4$ is a 6-membered fully unsaturated carbocyclic or heterocyclic ring, wherein said heterocyclic ring comprises one or more heteroatoms N, and wherein each substitutable carbon or heteroatom in the aforementioned cyclic moiety is independently unsubstituted or substituted with CH$_3$. The formula of this substituent R$^4$ corresponds to formula S8, wherein X$^1$, X$^2$, X$^3$, X$^4$ and X$^5$ in formula S5 are independently of each other selected from the group consisting of CH, N and CCH$_3$.

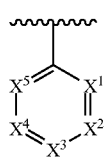

(S8)

In the above substituents S6, S7 and S8 it is preferred that at least 2 of X$^1$, X$^2$, X$^3$, X$^4$, X$^5$ and X$^6$ in S7 or at least 2 of X$^1$, X$^2$, X$^3$, X$^4$ and X$^5$ in S6 or S8 represent CH.

It is to be understood that the above embodiments 1(D)-1(F) regarding R$^1$, 2(C)-2(G) regarding R$^2$, 3(C)-3(G) regarding R$^3$ and 4(B)-4(I) regarding R$^4$, are also disclosed in combination with each other. The following combinations, which are summarized in Table 1 and 2, are preferred. Each of the substituent meanings in Table 1 is furthermore per se, independently of the combination in which it is mentioned, a particularly preferred substituent meaning.

In one embodiment, the combination of R$^1$, R$^2$, R$^3$ and R$^4$ corresponds to any one of lines 1-38 in Table 1 and 2, respectively.

In a preferred embodiment, combinations are preferred wherein R$^1$ corresponds to embodiment 1(D) and R$^2$, R$^3$ and R$^4$ correspond in each case to one line of lines 1-17 in Table 1.

In another preferred embodiment, combinations are preferred wherein R$^1$ corresponds to embodiment 1(E) and R$^2$, R$^3$ and R$^4$ correspond in each case to one line of lines 18-36 in Table 1.

In another preferred embodiment, combinations are preferred wherein R$^1$ corresponds to embodiment 1(F) and R$^2$, R$^3$ and R$^4$ correspond in each case to one line of lines 37 and 38 in Table 1.

In another preferred embodiment, combinations are preferred wherein R$^2$ corresponds to embodiment 2(C) and R$^1$, R$^3$ and R$^4$ correspond in each case to one line of lines 1, 6-11, 14-22 and 30-36 in Table 1.

In another preferred embodiment, combinations are preferred wherein R$^2$ corresponds to embodiment 2(D) and R$^1$, R$^3$ and R$^4$ correspond in each case to one line of lines 2, 12, 24-26 and 37-38 in Table 1.

In another preferred embodiment, combinations are preferred wherein R$^2$ corresponds to embodiment 2(E) and R$^1$, R$^3$ and R$^4$ correspond in each case to one line of lines 3, 13 and 27 in Table 1.

In another preferred embodiment, combinations are preferred wherein R$^2$ corresponds to embodiment 2(F) and R$^1$, R$^3$ and R$^4$ correspond in each case to one line of lines 4 and 23 in Table 1.

In another preferred embodiment, combinations are preferred wherein R$^2$ corresponds to embodiment 2(G) and R$^1$, R$^3$ and R$^4$ correspond to line 5 in Table 1.

In another preferred embodiment, combinations are preferred wherein R$^3$ corresponds to embodiment 3(C) and R$^1$, R$^2$ and R$^4$ correspond in each case to one line of lines 1-13, 18-29 and 37-38 in Table 1.

In another preferred embodiment, combinations are preferred wherein R$^3$ corresponds to embodiment 3(D) and R$^1$, R$^2$ and R$^4$ correspond to line 15 in Table 1.

In another preferred embodiment, combinations are preferred wherein R$^3$ corresponds to embodiment 3(E) and R$^1$, R$^2$ and R$^4$ correspond in each case to one line of lines 16, 32 and 35 in Table 1.

In another preferred embodiment, combinations are preferred wherein R$^3$ corresponds to embodiment 3(F) and R$^1$, R$^2$ and R$^4$ correspond in each case to one line of lines 14, 18, 30, 33 and 36 in Table 1.

In another preferred embodiment, combinations are preferred wherein R$^3$ corresponds to embodiment 3(G) and R$^1$, R$^2$ and R$^4$ correspond in each case to one line of lines 31 and 36 in Table 1.

In another preferred embodiment, combinations are preferred wherein R$^4$ corresponds to embodiment 4(B) and R$^1$, R$^2$ and R$^3$ correspond in each case to one line of lines 1-5, 14, 18, 23, 24, 30 and 31 in Table 1.

In another preferred embodiment, combinations are preferred wherein R$^4$ corresponds to embodiment 4(C) and R$^1$, R$^2$ and R$^3$ correspond in each case to one line of lines 6 and 19 in Table 1.

In another preferred embodiment, combinations are preferred wherein R$^4$ corresponds to embodiment 4(D) and R$^1$, R$^2$ and R$^3$ correspond in each case to one line of lines 10 and 28 in Table 1.

In another preferred embodiment, combinations are preferred wherein R$^4$ corresponds to embodiment 4(E) and R$^1$, R$^2$ and R$^3$ correspond in each case to one line of lines 7, 15-17, 35 and 36 in Table 1.

In another preferred embodiment, combinations are preferred wherein R$^4$ corresponds to embodiment 4(F) and R$^1$, R$^2$ and R$^3$ correspond to line 22 in Table 1.

In another preferred embodiment, combinations are preferred wherein R$^4$ corresponds to embodiment 4(G) and R$^1$, R$^2$ and R$^3$ correspond to line 9 in Table 1.

In another preferred embodiment, combinations are preferred wherein R$^4$ corresponds to embodiment 4(H) and R$^1$, R$^2$ and R$^3$ correspond in each case to one line of lines 8, 21, 26, 29, 32-34 and 38 in Table 1.

In another preferred embodiment, combinations are preferred wherein R$^4$ corresponds to embodiment 4(I) and R$^1$, R$^2$ and R$^3$ correspond in each case to one line of lines 11-13, 20, 25, 27 and 37 in Table 1.

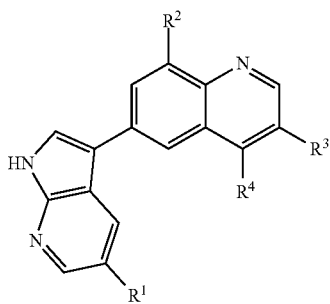

(I)

TABLE 1

| Line | R¹ | R² | R³ | R⁴ |
|---|---|---|---|---|
| 1 | 1(D) | 2(C) | 3(C) | 4(B) |
| 2 | 1(D) | 2(D) | 3(C) | 4(B) |
| 3 | 1(D) | 2(E) | 3(C) | 4(B) |
| 4 | 1(D) | 2(F) | 3(C) | 4(B) |
| 5 | 1(D) | 2(G) | 3(C) | 4(B) |
| 6 | 1(D) | 2(C) | 3(C) | 4(C) |
| 7 | 1(D) | 2(C) | 3(C) | 4(E) |
| 8 | 1(D) | 2(C) | 3(C) | 4(H) |
| 9 | 1(D) | 2(C) | 3(C) | 4(G) |
| 10 | 1(D) | 2(C) | 3(C) | 4(D) |
| 11 | 1(D) | 2(C) | 3(C) | 4(I) |
| 12 | 1(D) | 2(D) | 3(C) | 4(I) |
| 13 | 1(D) | 2(E) | 3(C) | 4(I) |
| 14 | 1(D) | 2(C) | 3(F) | 4(B) |
| 15 | 1(D) | 2(C) | 3(D) | 4(E) |
| 16 | 1(D) | 2(C) | 3(E) | 4(E) |
| 17 | 1(D) | 2(C) | 3(F) | 4(E) |
| 18 | 1(E) | 2(C) | 3(C) | 4(B) |
| 19 | 1(E) | 2(C) | 3(C) | 4(C) |
| 20 | 1(E) | 2(C) | 3(C) | 4(I) |
| 21 | 1(E) | 2(C) | 3(C) | 4(H) |
| 22 | 1(E) | 2(C) | 3(C) | 4(F) |
| 23 | 1(E) | 2(F) | 3(C) | 4(B) |
| 24 | 1(E) | 2(D) | 3(C) | 4(B) |
| 25 | 1(E) | 2(D) | 3(C) | 4(I) |
| 26 | 1(E) | 2(D) | 3(C) | 4(H) |
| 27 | 1(E) | 2(E) | 3(C) | 4(I) |
| 28 | 1(E) | 2(D) | 3(C) | 4(D) |
| 29 | 1(E) | 2(D) | 3(C) | 4(H) |
| 30 | 1(E) | 2(C) | 3(F) | 4(B) |
| 31 | 1(E) | 2(C) | 3(G) | 4(B) |
| 32 | 1(E) | 2(C) | 3(E) | 4(H) |
| 33 | 1(E) | 2(C) | 3(F) | 4(H) |
| 34 | 1(E) | 2(C) | 3(G) | 4(H) |
| 35 | 1(E) | 2(C) | 3(E) | 4(E) |
| 36 | 1(E) | 2(C) | 3(F) | 4(E) |
| 37 | 1(F) | 2(D) | 3(C) | 4(I) |
| 38 | 1(F) | 2(D) | 3(C) | 4(H) |

Further particularly preferred compounds are compiled in Table 2 below. Each of the substituent meanings in Table 2 is furthermore per se, independently of the combination in which it is mentioned, a particularly preferred substituent meaning.

In a preferred embodiment, combinations are preferred wherein $R^1$ corresponds to H and $R^2$, $R^3$ and $R^4$ correspond in each case to one line of lines 1-17 in Table 2.

In another preferred embodiment, combinations are preferred wherein $R^1$ corresponds to $C(=O)N(R^{6a})(R^{6b})$ and $R^2$, $R^3$ and $R^4$ correspond in each case to one line of lines 18-36 in Table 2.

In another preferred embodiment, combinations are preferred wherein $R^1$ corresponds to S9 and $R^2$, $R^3$ and $R^4$ correspond in each case to one line of lines 37 and 38 in Table 2.

In another preferred embodiment, combinations are preferred wherein $R^2$ corresponds to H and $R^1$, $R^3$ and $R^4$ correspond in each case to one line of lines 1, 6-11, 14-22 and 30-36 in Table 2.

In another preferred embodiment, combinations are preferred wherein $R^2$ corresponds to halogen and $R^1$, $R^3$ and $R^4$ correspond in each case to one line of lines 2, 12, 24-26 and 37-38 in Table 2.

In another preferred embodiment, combinations are preferred wherein $R^2$ corresponds to $C_1$-$C_6$-alkyl and $R^1$, $R^3$ and $R^4$ correspond in each case to one line of lines 3, 13 and 27 in Table 2.

In another preferred embodiment, combinations are preferred wherein $R^2$ corresponds to $C_1$-$C_6$-alkoxy and $R^1$, $R^3$ and $R^4$ correspond in each case to one line of lines 4 and 23 in Table 2.

In another preferred embodiment, combinations are preferred wherein $R^2$ corresponds to $C_1$-$C_6$-haloalkoxy and $R^1$, $R^3$ and $R^4$ correspond to line 5 in Table 2.

In another preferred embodiment, combinations are preferred wherein $R^3$ corresponds to H and $R^1$, $R^2$ and $R^4$ correspond in each case to one line of lines 1-13, 18-29 and 37-38 in Table 2.

In another preferred embodiment, combinations are preferred wherein $R^3$ corresponds to CN and $R^1$, $R^2$ and $R^4$ correspond to line 15 in Table 2.

In another preferred embodiment, combinations are preferred wherein $R^3$ corresponds to $NO_2$ and $R^1$, $R^2$ and $R^4$ correspond in each case to one line of lines 16, 32 and 35 in Table 2.

In another preferred embodiment, combinations are preferred wherein $R^3$ corresponds to $N(R^{6a})(R^{6b})$ and $R^1$, $R^2$ and $R^4$ correspond in each case to one line of lines 14, 18, 30, 33 and 36 in Table 2.

In another preferred embodiment, combinations are preferred wherein $R^3$ corresponds to $N(R^6)C(=O)R^5$ and $R^1$, $R^2$ and $R^4$ correspond in each case to one line of lines 31 and 36 in Table 2.

In another preferred embodiment, combinations are preferred wherein $R^4$ corresponds to H and $R^1$, $R^2$ and $R^3$ correspond in each case to one line of lines 1-5, 14, 18, 23, 24, 30 and 31 in Table 2.

In another preferred embodiment, combinations are preferred wherein $R^4$ corresponds to halogen and $R^1$, $R^2$ and $R^3$ correspond in each case to one line of lines 6 and 19 in Table 2.

In another preferred embodiment, combinations are preferred wherein $R^4$ corresponds to S9 and $R^1$, $R^2$ and $R^3$ correspond in each case to one line of lines 10 and 28 in Table 2.

In another preferred embodiment, combinations are preferred wherein $R^4$ corresponds to $N(R^{6a})(R^{6b})$ and $R^1$, $R^2$ and $R^3$ correspond in each case to one line of lines 7, 15-17, 35 and 36 in Table 2.

In another preferred embodiment, combinations are preferred wherein $R^4$ corresponds to $C_2$-$C_6$-alkenyl and $R^1$, $R^2$ and $R^3$ correspond to line 22 in Table 2.

In another preferred embodiment, combinations are preferred wherein $R^4$ corresponds to S6 and $R^1$, $R^2$ and $R^3$ correspond to line 9 in Table 2.

In another preferred embodiment, combinations are preferred wherein $R^4$ corresponds to S7 and $R^1$, $R^2$ and $R^3$ correspond in each case to one line of lines 8, 21, 26, 29, 32-34 and 38 in Table 2.

In another preferred embodiment, combinations are preferred wherein $R^4$ corresponds to S8 and $R^1$, $R^2$ and $R^3$ correspond in each case to one line of lines 11-13, 20, 25, 27 and 37 in Table 2.

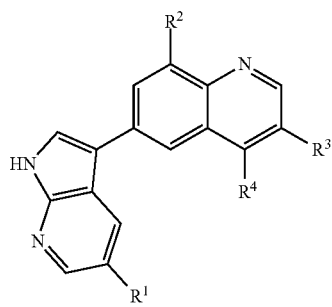

(I)

TABLE 2

| Line | $R^1$ | $R^2$ | $R^3$ | $R^4$ |
|---|---|---|---|---|
| 1 | H | H | H | H |
| 2 | H | halogen | H | H |
| 3 | H | $C_1$-$C_6$-alkyl | H | H |
| 4 | H | $C_1$-$C_6$-alkoxy | H | H |
| 5 | H | $C_1$-$C_6$-haloalkoxy | H | H |
| 6 | H | H | H | halogen |
| 7 | H | H | H | $N(R^{6a})(R^{6b})$ |
| 8 | H | H | H | S7 |
| 9 | H | H | H | S6 |
| 10 | H | H | H | S9 |
| 11 | H | H | H | S8 |
| 12 | H | halogen | H | S8 |
| 13 | H | $C_1$-$C_6$-alkyl | H | S8 |
| 14 | H | H | $N(R^{6a})(R^{6b})$ | H |
| 15 | H | H | CN | $N(R^{6a})(R^{6b})$ |
| 16 | H | H | $NO_2$ | $N(R^{6a})(R^{6b})$ |
| 17 | H | H | $N(R^{6a})(R^{6b})$ | $N(R^{6a})(R^{6b})$ |
| 18 | $C(=O)N(R^{6a})(R^{6b})$ | H | H | H |
| 19 | $C(=O)N(R^{6a})(R^{6b})$ | H | H | halogen |
| 20 | $C(=O)N(R^{6a})(R^{6b})$ | H | H | S8 |
| 21 | $C(=O)N(R^{6a})(R^{6b})$ | H | H | S7 |
| 22 | $C(=O)N(R^{6a})(R^{6b})$ | H | H | $C_2$-$C_6$-alkenyl |
| 23 | $C(=O)N(R^{6a})(R^{6b})$ | $C_1$-$C_6$-alkoxy | H | H |
| 24 | $C(=O)N(R^{6a})(R^{6b})$ | halogen | H | H |
| 25 | $C(=O)N(R^{6a})(R^{6b})$ | halogen | H | S8 |
| 26 | $C(=O)N(R^{6a})(R^{6b})$ | halogen | H | S7 |
| 27 | $C(=O)N(R^{6a})(R^{6b})$ | $C_1$-$C_6$-alkyl | H | S8 |
| 28 | $C(=O)N(R^{6a})(R^{6b})$ | halogen | H | S9 |
| 29 | $C(=O)N(R^{6a})(R^{6b})$ | halogen | H | S7 |
| 30 | $C(=O)N(R^{6a})(R^{6b})$ | H | $N(R^{6a})(R^{6b})$ | H |
| 31 | $C(=O)N(R^{6a})(R^{6b})$ | H | $N(R^6)C(=O)R^5$ | H |
| 32 | $C(=O)N(R^{6a})(R^{6b})$ | H | $NO_2$ | S7 |
| 33 | $C(=O)N(R^{6a})(R^{6b})$ | H | $N(R^{6a})(R^{6b})$ | S7 |
| 34 | $C(=O)N(R^{6a})(R^{6b})$ | H | $N(R^6)C(=O)R^5$ | S7 |
| 35 | $C(=O)N(R^{6a})(R^{6b})$ | H | $NO_2$ | $N(R^{6a})(R^{6b})$ |
| 36 | $C(=O)N(R^{6a})(R^{6b})$ | H | $N(R^{6a})(R^{6b})$ | $N(R^{6a})(R^{6b})$ |
| 37 | S9 | halogen | H | S8 |
| 38 | S9 | halogen | H | S7 |

In Table 2, the following substituent meanings are relevant for $R^1$, $R^2$, $R^3$ and $R^4$.

$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_n(R^6)$, $N(R^6)S(=O)_nN(R^{6a})(R^{6b})$, $N(R^6)S(=O)_nOR^6$; and a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;

$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;

R⁹ is selected from the group consisting of halogen, CN, NO₂, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_n R^{11}$;

and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, NO₂, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_n R^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;

and wherein n is 0, 1 or 2.

S6 is a 5-membered saturated carbocyclic or heterocyclic ring, wherein said carbocyclic or heterocyclic ring comprises one or more heteroatoms N, and wherein each substitutable carbon atom in the aforementioned cyclic ring is independently unsubstituted or substituted with NH₂. The formula of this substituent R⁴ corresponds to formula S6, wherein $X^1$ is CH or N and $X^2$, $X^3$, $X^4$ and $X^5$ are independently of each other CH₂, NH, O, S or CHNH₂.

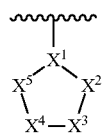

(S6)

S7 is a 6-membered saturated carbocyclic or heterocyclic ring, wherein said heterocyclic ring comprises one or more, same or different heteroatoms selected from O and N, and wherein each substitutable carbon or heteroatom in the aforementioned cyclic moiety is independently unsubstituted or substituted with NH₂. The formula of this substituent R⁴ corresponds to formula S7, wherein $X^1$ is CH or N and $X^2$, $X^3$, $X^4$ and $X^5$ are independently of each other CH₂, NH, O, S or CHNH₂.

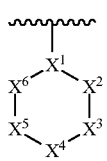

(S7)

S8 is a 6-membered fully unsaturated carbocyclic or heterocyclic ring, wherein said heterocyclic ring comprises one or more heteroatoms N, and wherein each substitutable carbon or heteroatom in the aforementioned cyclic moiety is independently unsubstituted or substituted with CH₃. The formula of this substituent R⁴ corresponds to formula S8, wherein $X^1$, $X^2$, $X^3$, $X^4$ and $X^5$ in formula S5 are independently of each other selected from the group consisting of CH, N and CCH₃.

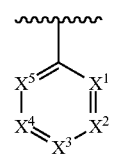

(S8)

S9 is $C_1$-$C_6$-alkyl, wherein each substitutable carbon atom in said alkyl moiety is independently unsubstituted or substituted with one or more, same or different R⁷, wherein R⁷ is as defined above.

In the above substituents S6, S7 and S8 it is preferred that at least 2 of $X^1$, $X^2$, $X^3$, $X^4$, $X^5$ and $X^6$ in S7 or at least 2 of $X^1$, $X^2$, $X^3$, $X^4$ and $X^5$ in S6 or S8 represent CH.

Preferably, in Table 2, the following substituent meanings are relevant for $R^1$, $R^2$, $R^3$ and $R^4$:

$R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$;

R⁷ is selected from the group consisting of halogen, CN, NO₂, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, $OR^6$, $N(R^{6a})(R^{6b})$; and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

R⁸ is selected from the group consisting of $C_1$-$C_3$-alkyl, $C_2$-$C_3$-alkenyl, $C_1$-$C_3$-alkylcarbonyl, $C_2$-$C_3$-alkynyl and $N(R^{6a})(R^{6b})$;

R⁹ is selected from the group consisting of halogen, $C_1$-$C_4$-alkyl, $C_2$-$C_4$-alkenyl, $C_2$-$C_4$-alkynyl, $N(R^{11a})(R^{11b})$ and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$;

R[10] is selected from the group consisting of halogen, $C_1$-$C_3$-alkyl, $C_2$-$C_3$-alkenyl, $C_1$-$C_3$-alkylcarbonyl, $C_2$-$C_3$-alkynyl and $N(R^{11a})(R^{11b})$;

R[11], R[11a] and R[11b] are independently selected from the group consisting of H, $C_1$-$C_3$-alkyl, $C_2$-$C_3$-alkenyl and $C_2$-$C_3$-alkynyl.

S6 is a 5-membered saturated carbocyclic or heterocyclic ring, wherein said carbocyclic or heterocyclic ring comprises one or more heteroatoms N, and wherein each substitutable carbon atom in the aforementioned cyclic ring is independently unsubstituted or substituted with $NH_2$. The formula of this substituent R[4] corresponds to formula S6, wherein $X^1$ is CH or N and $X^2$, $X^3$, $X^4$ and $X^5$ are independently of each other $CH_2$, NH, O, S or $CHNH_2$.

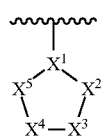

(S6)

S7 is a 6-membered saturated carbocyclic or heterocyclic ring, wherein said heterocyclic ring comprises one or more, same or different heteroatoms selected from O and N, and wherein each substitutable carbon or heteroatom in the aforementioned cyclic moiety is independently unsubstituted or substituted with $NH_2$. The formula of this substituent R[4] corresponds to formula S7, wherein $X^1$ is CH or N and $X^2$, $X^3$, $X^4$ and $X^5$ are independently of each other $CH_2$, NH, O, S or $CHNH_2$.

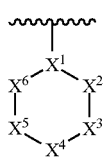

(S7)

S8 is a 6-membered fully unsaturated carbocyclic or heterocyclic ring, wherein said heterocyclic ring comprises one or more heteroatoms N, and wherein each substitutable carbon or heteroatom in the aforementioned cyclic moiety is independently unsubstituted or substituted with $CH_3$. The formula of this substituent R[4] corresponds to formula S8, wherein $X^1$, $X^2$, $X^3$, $X^4$ and $X^5$ in formula S5 are independently of each other selected from the group consisting of CH, N and $CCH_3$.

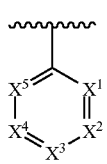

(S8)

S9 is $C_1$-$C_6$-alkyl, wherein each substitutable carbon atom in said alkyl moiety is independently unsubstituted or substituted with one or more, same or different R[7], wherein R[7] is as defined above.

In the above substituents S6, S7 and S8 it is preferred that at least 2 of $X^1$, $X^2$, $X^3$, $X^4$, $X^5$ and $X^6$ in S7 or at least 2 of $X^1$, $X^2$, $X^3$, $X^4$ and $X^5$ in S6 or S8 represent CH.

Even more preferred compounds of the invention are compiled in Table 3 below. Each of the substituent meanings in Table 3 is furthermore per se, independently of the combination in which it is mentioned, a particularly preferred substituent meaning.

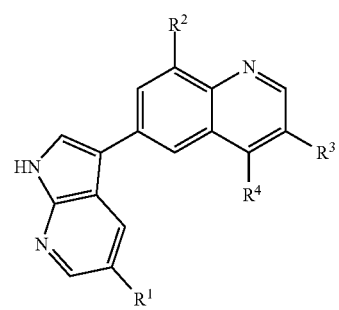

(I)

TABLE 3

| Line | R[1] | R[2] | R[3] | R[4] |
|---|---|---|---|---|
| 1 | 1(D) | 2(C) | 3(C) | 4(B) |
| 2 | 1(D) | 2(D) | 3(C) | 4(B) |
| 3 | 1(D) | 2(E) | 3(C) | 4(B) |
| 4 | 1(D) | 2(F) | 3(C) | 4(B) |
| 5 | 1(D) | 2(G) | 3(C) | 4(B) |
| 6 | 1(D) | 2(C) | 3(C) | 4(C) |
| 7 | 1(D) | 2(C) | 3(C) | 4(E1) |
| 8 | 1(D) | 2(C) | 3(C) | 4(H) |
| 9 | 1(D) | 2(C) | 3(C) | 4(G) |
| 10 | 1(D) | 2(C) | 3(C) | 4(D1) |
| 11 | 1(D) | 2(C) | 3(C) | 4(I) |
| 12 | 1(D) | 2(D) | 3(C) | 4(I) |
| 13 | 1(D) | 2(E) | 3(C) | 4(I) |
| 14 | 1(D) | 2(C) | 3(F1) | 4(B) |
| 15 | 1(D) | 2(C) | 3(D) | 4(E1) |
| 16 | 1(D) | 2(C) | 3(E) | 4(E1) |
| 17 | 1(D) | 2(C) | 3(F1) | 4(E1) |
| 18 | 1(E1) | 2(C) | 3(C) | 4(B) |
| 19 | 1(E1) | 2(C) | 3(C) | 4(C) |
| 20 | 1(E1) | 2(C) | 3(C) | 4(I) |
| 21 | 1(E1) | 2(C) | 3(C) | 4(H) |
| 22 | 1(E1) | 2(C) | 3(C) | 4(F) |
| 23 | 1(E1) | 2(F) | 3(C) | 4(B) |
| 24 | 1(E1) | 2(D) | 3(C) | 4(B) |
| 25 | 1(E1) | 2(D) | 3(C) | 4(I) |
| 26 | 1(E1) | 2(D) | 3(C) | 4(H) |
| 27 | 1(E1) | 2(E) | 3(C) | 4(I) |
| 28 | 1(E1) | 2(D) | 3(C) | 4(D) |
| 29 | 1(E1) | 2(D) | 3(C) | 4(H) |
| 30 | 1(E1) | 2(C) | 3(F1) | 4(B) |
| 31 | 1(E1) | 2(C) | 3(G1) | 4(B) |
| 32 | 1(E1) | 2(C) | 3(E) | 4(H) |
| 33 | 1(E1) | 2(C) | 3(F1) | 4(H) |
| 34 | 1(E1) | 2(C) | 3(G1) | 4(H) |
| 35 | 1(E1) | 2(C) | 3(E) | 4(E1) |
| 36 | 1(E1) | 2(C) | 3(F1) | 4(E1) |
| 37 | 1(F1) | 2(D) | 3(C) | 4(I) |
| 38 | 1(F1) | 2(D) | 3(C) | 4(H) |

In a most preferred embodiment, the compound of the present invention is selected from the group consisting of 4-chloro-6-{1H-pyrrolo[2,3-b]pyridin-3-yl}quinoline; 6-{1H-pyrrolo[2,3-b]pyridin-3-yl}quinoline; (3S)-1-(6-{1H-pyrrolo[2,3-b]pyridin-3-yl}quinoline-4-yl)piperidin-3-amine; 1-N-(6-{1H-pyrrolo[2,3-b]pyridin-3-yl}quinoline-4-yl)cyclohexane-1,4-diamine; (3S)-1-(6-{1H-pyrrolo[2,3-b]

pyridin-3-yl}quinoline-4-yl)pyrrolidin-3-amine; 4-(pyridin-3-yl)-6-{1H-pyrrolo[2,3-b]pyridin-3-yl}quinoline; 4-(pyridin-4-yl)-6-{1H-pyrrolo[2,3-b]pyridin-3-yl}quinoline; 4-phenyl-6-{1H-pyrrolo[2,3-b]pyridin-3-yl}quinoline; {5-ethenyl-1-azabicyclo[2.2.2]octan-2-yl}(6-{1H-pyrrolo[2,3-b]pyridin-3-yl}quinoline-4-yl)methanol; N-(1-methylpiperidin-4-yl)-6-{1H-pyrrolo[2,3-b]pyridin-3-yl}quinoline-4-amine; 8-chloro-6-{1H-pyrrolo[2,3-b]pyridin-3-yl}quinoline hydrochloride; 8-methyl-6-{1H-pyrrolo[2,3-b]pyridin-3-yl}quinoline hydrochloride; 8-fluoro-6-{1H-pyrrolo[2,3-b]pyridin-3-yl}quinoline; 6-{1H-pyrrolo[2,3-b]pyridin-3-yl}-8-(trifluoromethoxy)quinoline; 8-methoxy-6-{1H-pyrrolo[2,3-b]pyridin-3-yl}quinoline; N-(furan-3-ylmethyl)-6-{1H-pyrrolo[2,3-b]pyridin-3-yl}quinoline-3-amine; 8-methyl-4-phenyl-6-{1H-pyrrolo[2,3-b]pyridin-3-yl}quinoline; 8-methyl-4-(pyridin-3-yl)-6-{1H-pyrrolo[2,3-b]pyridin-3-yl}quinoline; 8-fluoro-4-(pyridin-3-yl)-6-{1H-pyrrolo[2,3-b]pyridin-3-yl}quinoline; 3-(4-chloroquinoline-6-yl)-N-methyl-N-(prop-2-en-1-yl)-1H-pyrrolo[2,3-b]pyridine-5-carboxamide; methyl({3-[4-(pent-4-en-1-yl)quinoline-6-yl]-1H-pyrrolo[2,3-b]pyridin-5-yl}methyl)(prop-2-en-1-yl)amine; N-methyl-3-[4-(pyridin-3-yl)quinoline-6-yl]-1H-pyrrolo[2,3-b]pyridine-5-carboxamide; N-methyl-3-[4-(morpholin-4-yl)quinoline-6-yl]-1H-pyrrolo[2,3-b]pyridine-5-carboxamide; 3-(4-chloroquinoline-6-yl)-N-methyl-1H-pyrrolo[2,3-b]pyridine-5-carboxamide; N-methyl-3-(quinoline-6-yl)-1H-pyrrolo[2,3-b]pyridine-5-carboxamide; 3-(8-methoxyquinoline-6-yl)-N-methyl-N-(prop-2-en-1-yl)-1H-pyrrolo[2,3-b]pyridine-5-carboxamide; 3-(8-fluoroquinoline-6-yl)-N-methyl-N-(prop-2-en-1-yl)-1H-pyrrolo[2,3-b]pyridine-5-carboxamide; 3-(8-chloroquinoline-6-yl)-N-methyl-N-(prop-2-en-1-yl)-1H-pyrrolo[2,3-b]pyridine-5-carboxamide; 3-(8-methoxyquinoline-6-yl)-N-methyl-1H-pyrrolo[2,3-b]pyridine-5-carboxamide; 3-(8-fluoroquinoline-6-yl)-N-methyl-1H-pyrrolo[2,3-b]pyridine-5-carboxamide; N-benzyl-3-(8-fluoroquinoline-6-yl)-1H-pyrrolo[2,3-b]pyridine-5-carboxamide; N-benzyl-3-(8-chloroquinoline-6-yl)-1H-pyrrolo[2,3-b]pyridine-5-carboxamide; 3-(8-fluoroquinoline-6-yl)-1H-pyrrolo[2,3-b]pyridine-5-carboxamide; N-(3-aminopropyl)-3-(8-chloroquinoline-6-yl)-1H-pyrrolo[2,3-b]pyridine-5-carboxamide hydrochloride; N-benzyl-3-[8-fluoro-4-(pyridin-3-yl)quinoline-6-yl]-1H-pyrrolo[2,3-b]pyridine-5-carboxamide; N-(3-aminopropyl)-3-[8-fluoro-4-(pyridin-3-yl)quinoline-6-yl]-1H-pyrrolo[2,3-b]pyridine-5-carboxamide hydrochloride; 3-[8-fluoro-4-(pyridin-3-yl)quinoline-6-yl]-N-methyl-N-(prop-2-en-1-yl)-1H-pyrrolo[2,3-b]pyridine-5-carboxamide; 3-[8-fluoro-4-(pyridin-3-yl)quinoline-6-yl]-N-methyl-1H-pyrrolo[2,3-b]pyridine-5-carboxamide; 3-[8-fluoro-4-(2-phenylethyl)quinoline-6-yl]-N-methyl-1H-pyrrolo[2,3-b]pyridine-5-carboxamide; 3-{4-[(3R)-3-aminopiperidin-1-yl]-8-fluoroquinoline-6-yl}-N-methyl-1H-pyrrolo[2,3-b]pyridine-5-carboxamide hydrochloride; N-methyl-3-[8-methyl-4-(pyridin-3-yl)quinoline-6-yl]-1H-pyrrolo[2,3-b]pyridine-5-carboxamide; 3-{4-[(3S)-3-aminopiperidin-1-yl]-8-fluoroquinoline-6-yl}-N-methyl-1H-pyrrolo[2,3-b]pyridine-5-carboxamide hydrochloride; N-methyl-3-[8-fluoro-4-(4-methylpyridin-3-yl)quinoline-6-yl]-1H-pyrrolo[2,3-b]pyridine-5-carboxamide; 3-[8-methoxy-4-(pyridin-3-yl)quinoline-6-yl]-1H-pyrrolo[2,3-b]pyridine-5-carboxamide; N-{3-[8-fluoro-4-(pyridin-3-yl)quinoline-6-yl]-1H-pyrrolo[2,3-b]pyridin-5-yl}acetamide; 3-[8-fluoro-4-(pyridin-3-yl)quinoline-6-yl]-N-(pyridin-3-ylmethyl)-1H-pyrrolo[2,3-b]pyridine-5-carboxamide; 3-{4-[(3R)-3-aminopiperidin-1-yl]-8-fluoroquinoline-6-yl}-N-(pyridin-3-ylmethyl)-1H-pyrrolo[2,3-b]pyridine-5-carboxamide hydrochloride; 3-{4-[(3R)-3-aminopiperidin-1-yl]-8-fluoroquinoline-6-yl}-N-(pyrimidin-5-ylmethyl)-1H-pyrrolo[2,3-b]pyridine-5-carboxamide hydrochloride; benzyl({3-[8-fluoro-4-(pyridin-3-yl)quinoline-6-yl]-1H-pyrrolo[2,3-b]pyridin-5-yl}methyl)amine; (3R)-1-(6-{5-[(benzylamino)methyl]-1H-pyrrolo[2,3-b]pyridin-3-yl}-8-fluoroquinoline-4-yl)piperidin-3-amine; ({3-[8-fluoro-4-(pyridin-3-yl)quinoline-6-yl]-1H-pyrrolo[2,3-b]pyridin-5-yl}methyl)(methyl)(prop-2-en-1-yl)amine; 3-{4-[(3S)-3-aminopiperidin-1-yl]-3-nitroquinoline-6-yl}-N-methyl-1H-pyrrolo[2,3-b]pyridine-5-carboxamide hydrochloride; 3-{3-amino-4-[(3S)-3-aminopiperidin-1-yl]quinoline-6-yl}-N-methyl-1H-pyrrolo[2,3-b]pyridine-5-carboxamide hydrochloride; 3-{4-[(3S)-3-aminopiperidin-1-yl]-3-{[(3-chlorophenyl)methyl]amino}quinoline-6-yl}-N-methyl-1H-pyrrolo[2,3-b]pyridine-5-carboxamide hydrochloride; 3-(3-{[(3-chlorophenyl)methyl]amino}-4-(morpholin-4-yl)quinoline-6-yl)-N-methyl-1H-pyrrolo[2,3-b]pyridine-5-carboxamide; 3-[3-acetamido-4-(morpholin-4-yl)quinoline-6-yl]-N-methyl-1H-pyrrolo[2,3-b]pyridine-5-carboxamide; N-methyl-3-[4-(morpholin-4-yl)-3-[(oxan-4-ylmethyl)amino]quinoline-6-yl]-1H-pyrrolo[2,3-b]pyridine-5-carboxamide; 3-{4-[(4-aminocyclohexyl)amino]-3-nitroquinoline-6-yl}-N-(pyridin-3-ylmethyl)-1H-pyrrolo[2,3-b]pyridine-5-carboxamide hydrochloride; 3-{4-[(4-aminocyclohexyl)amino]-3-[(oxan-4-ylmethyl)amino]quinoline-6-yl}-N-(pyridin-3-ylmethyl)-1H-pyrrolo[2,3-b]pyridine-5-carboxamide hydrochloride; 3-(3-aminoquinoline-6-yl)-N-(pyridin-3-ylmethyl)-1H-pyrrolo[2,3-b]pyridine-5-carboxamide; 3-{3-[(oxan-4-ylmethyl)amino]quinoline-6-yl}-N-(pyridin-3-ylmethyl)-1H-pyrrolo[2,3-b]pyridine-5-carboxamide; 4-[(1-methylpiperidin-4-yl)amino]-6-{1H-pyrrolo[2,3-b]pyridin-3-yl}quinoline-3-carbonitrile; N-methyl-N-(1-methylpiperidin-4-yl)-3-nitro-6-{1H-pyrrolo[2,3-b]pyridin-3-yl}quinoline-4-amine; 1-{4-[(3-amino-6-{1H-pyrrolo[2,3-b]pyridin-3-yl}quinoline-4-yl)amino]piperidin-1-yl}ethan-1-one; N-(3-aminopropyl)-3-(8-fluoroquinoline-6-yl)-1H-pyrrolo[2,3-b]pyridine-5-carboxamide hydrochloride and 3-(3-acetamidoquinoline-6-yl)-N-(pyridin-3-ylmethyl)-1H-pyrrolo[2,3-b]pyridine-5-carboxamide.

In a particularly preferred embodiment, $R^1$ corresponds to embodiment 1(D), wherein the compound of formula (I) is selected from the group consisting of 4-chloro-6-{1H-pyrrolo[2,3-b]pyridin-3-yl}quinoline; 6-{1H-pyrrolo[2,3-b]pyridin-3-yl}quinoline; (3S)-1-(6-{1H-pyrrolo[2,3-b]pyridin-3-yl}quinoline-4-yl)piperidin-3-amine; 1-N-(6-{1H-pyrrolo[2,3-b]pyridin-3-yl}quinoline-4-yl)cyclohexane-1,4-diamine; (3S)-1-(6-{1H-pyrrolo[2,3-b]pyridin-3-yl}quinoline-4-yl)pyrrolidin-3-amine; 4-(pyridin-3-yl)-6-{1H-pyrrolo[2,3-b]pyridin-3-yl}quinoline; 4-(pyridin-4-yl)-6-{1H-pyrrolo[2,3-b]pyridin-3-yl}quinoline; 4-phenyl-6-{1H-pyrrolo[2,3-b]pyridin-3-yl}quinoline; {5-ethenyl-1-azabicyclo[2.2.2]octan-2-yl}(6-{1H-pyrrolo[2,3-b]pyridin-3-yl}quinoline-4-yl)methanol; N-(1-methylpiperidin-4-yl)-6-{1H-pyrrolo[2,3-b]pyridin-3-yl}quinoline-4-amine; 8-chloro-6-{1H-pyrrolo[2,3-b]pyridin-3-yl}quinoline hydrochloride; 8-methyl-6-{1H-pyrrolo[2,3-b]pyridin-3-yl}quinoline hydrochloride; 8-fluoro-6-{1H-pyrrolo[2,3-b]pyridin-3-yl}quinoline; 6-{1H-pyrrolo[2,3-b]pyridin-3-yl}-8-(trifluoromethoxy)quinoline; 8-methoxy-6-{1H-pyrrolo[2,3-b]pyridin-3-yl}quinoline; N-(furan-3-ylmethyl)-6-{1H-pyrrolo[2,3-b]pyridin-3-yl}quinoline-3-amine; 8-methyl-4-phenyl-6-{1H-pyrrolo[2,3-b]pyridin-3-yl}quinoline; 8-methyl-4-(pyridin-3-yl)-6-{1H-pyrrolo[2,3-b]pyridin-3-yl}quinoline; 8-fluoro-4-(pyridin-3-yl)-6-{1H- pyrrolo[2,3-b]pyridin-3-yl}quinoline; 4-[(1-methylpiperidin-4-yl)amino]-6-{1H-pyrrolo[2,3-b]pyridin-3-yl}quinoline-3-carbonitrile; N-methyl-N-(1-methylpiperidin-4-yl)-3-nitro-6-{1H-pyrrolo[2,3-b]pyridin-3-yl}quinoline-4-amine and 1-{4-[(3-amino-6-{1H-pyrrolo[2,3-b]pyridin-3-yl}quinoline-4-yl)amino]piperidin-1-yl}ethan-1-one.

In a particularly preferred embodiment, $R^1$ corresponds to embodiment 1(E), wherein the compound of formula (I) is selected from the group consisting of 3-(4-chloroquinoline-6-yl)-N-methyl-N-(prop-2-en-1-yl)-1H-pyrrolo[2,3-b]pyridine-5-carboxamide; N-methyl-3-[4-(pyridin-3-yl)quinoline-6-yl]-1H-pyrrolo[2,3-b]pyridine-5-carboxamide; N-methyl-3-[4-(morpholin-4-yl)quinoline-6-yl]-1H-pyrrolo[2,3-b]pyridine-5-carboxamide; 3-(4-chloroquinoline-6-yl)-N-methyl-1H-pyrrolo[2,3-b]pyridine-5-carboxamide; N-methyl-3-(quinoline-6-yl)-1H-pyrrolo[2,3-b]pyridine-5-carboxamide; 3-(8-methoxyquinoline-6-yl)-N-methyl-N-(prop-2-en-1-yl)-1H-pyrrolo[2,3-b]pyridine-5-carboxamide; 3-(8-fluoroquinoline-6-yl)-N-methyl-N-(prop-2-en-1-yl)-1H-pyrrolo[2,3-b]pyridine-5-carboxamide; 3-(8-chloroquinoline-6-yl)-N-methyl-N-(prop-2-en-1-yl)-1H-pyrrolo[2,3-b]pyridine-5-carboxamide; 3-(8-methoxyquinoline-6-yl)-N-methyl-1H-pyrrolo[2,3-b]pyridine-5-carboxamide; 3-(8-fluoroquinoline-6-yl)-N-methyl-1H-pyrrolo[2,3-b]pyridine-5-carboxamide; N-benzyl-3-(8-fluoroquinoline-6-yl)-1H-pyrrolo[2,3-b]pyridine-5-carboxamide; N-benzyl-3-(8-chloroquinoline-6-yl)-1H-pyrrolo[2,3-b]pyridine-5-carboxamide; 3-(8-fluoroquinoline-6-yl)-1H-pyrrolo[2,3-b]pyridine-5-carboxamide; N-(3-aminopropyl)-3-(8-chloroquinoline-6-yl)-1H-pyrrolo[2,3-b]pyridine-5-carboxamide hydrochloride; N-(3-aminopropyl)-3-(8-fluoroquinoline-6-yl)-1H-pyrrolo[2,3-b]pyridine-5-carboxamide hydrochloride; N-benzyl-3-[8-fluoro-4-(pyridin-3-yl)quinoline-6-yl]-1H-pyrrolo[2,3-b]pyridine-5-carboxamide; N-(3-aminopropyl)-3-[8-fluoro-4-(pyridin-3-yl)quinoline-6-yl]-1H-pyrrolo[2,3-b]pyridine-5-carboxamide hydrochloride; 3-[8-fluoro-4-(pyridin-3-yl)quinoline-6-yl]-N-methyl-N-(prop-2-en-1-yl)-1H-pyrrolo[2,3-b]pyridine-5-carboxamide; 3-[8-fluoro-4-(pyridin-3-yl)quinoline-6-yl]-N-methyl-1H-pyrrolo[2,3-b]pyridine-5-carboxamide; 3-[8-fluoro-4-(2-phenylethyl)quinoline-6-yl]-N-methyl-1H-pyrrolo[2,3-b]pyridine-5-carboxamide; 3-{4-[(3R)-3-aminopiperidin-1-yl]-8-fluoroquinoline-6-yl}-N-methyl-1H-pyrrolo[2,3-b]pyridine-5-carboxamide hydrochloride; N-methyl-3-[8-methyl-4-(pyridin-3-yl)quinoline-6-yl]-1H-pyrrolo[2,3-b]pyridine-5-carboxamide; 3-{4-[(3S)-3-aminopiperidin-1-yl]-8-fluoroquinoline-6-yl}-N-methyl-1H-pyrrolo[2,3-b]pyridine-5-carboxamide hydrochloride; N-methyl-3-[8-fluoro-4-(4-methylpyridin-3-yl)quinoline-6-yl]-1H-pyrrolo[2,3-b]pyridine-5-carboxamide; 3-[8-methoxy-4-(pyridin-3-yl)quinoline-6-yl]-1H-pyrrolo[2,3-b]pyridine-5-carboxamide; N-{3-[8-fluoro-4-(pyridin-3-yl)quinoline-6-yl]-1H-pyrrolo[2,3-b]pyridin-5-yl}acetamide; 3-[8-fluoro-4-(pyridin-3-yl)quinoline-6-yl]-N-(pyridin-3-ylmethyl)-1H-pyrrolo[2,3-b]pyridine-5-carboxamide; 3-{4-[(3R)-3-aminopiperidin-1-yl]-8-fluoroquinoline-6-yl}-N-(pyridin-3-ylmethyl)-1H-pyrrolo[2,3-b]pyridine-5-carboxamide hydrochloride; 3-{4-[(3R)-3-aminopiperidin-1-yl]-8-fluoroquinoline-6-yl}-N-(pyrimidin-5-ylmethyl)-1H-pyrrolo[2,3-b]pyridine-5-carboxamide hydrochloride; 3-{4-[(3S)-3-aminopiperidin-1-yl]-3-nitroquinoline-6-yl}-N-methyl-1H-pyrrolo[2,3-b]pyridine-5-carboxamide hydrochloride; 3-{3-amino-4-[(3S)-3-aminopiperidin-1-yl]quinoline-6-yl}-N-methyl-1H-pyrrolo[2,3-b]pyridine-5-carboxamide hydrochloride; 3-{4-[(3S)-3-aminopiperidin-1-yl]-3-{[(3-chlorophenyl)methyl]amino}quinoline-6-yl}-N-methyl-1H-pyrrolo[2,3-b]pyridine-5-carboxamide hydrochloride; 3-(3-{[(3-chlorophenyl)methyl]amino}-4-(morpholin-4-yl)quinoline-6-yl)-N-methyl-1H-pyrrolo[2,3-b]pyridine-5-carboxamide; 3-[3-acetamido-4-(morpholin-4-yl)quinoline-6-yl]-N-methyl-1H-pyrrolo[2,3-b]pyridine-5-carboxamide; N-methyl-3-[4-(morpholin-4-yl)-3-[(oxan-4-ylmethyl)amino]quinoline-6-yl]-1H-pyrrolo[2,3-b]pyridine-5-carboxamide; 3-{4-[(4-aminocyclohexyl)amino]-3-nitroquinoline-6-yl}-N-(pyridin-3-ylmethyl)-1H-pyrrolo[2,3-b]pyridine-5-carboxamide hydrochloride; 3-{4-[(4-aminocyclohexyl)amino]-3-[(oxan-4-ylmethyl)amino]quinoline-6-yl}-N-(pyridin-3-ylmethyl)-1H-pyrrolo[2,3-b]pyridine-5-carboxamide hydrochloride; 3-(3-aminoquinoline-6-yl)-N-(pyridin-3-ylmethyl)-1H-pyrrolo[2,3-b]pyridine-5-carboxamide; 3-{3-[(oxan-4-ylmethyl)amino]quinoline-6-yl}-N-(pyridin-3-ylmethyl)-1H-pyrrolo[2,3-b]pyridine-5-carboxamide; 3-(3-acetamidoquinoline-6-yl)-N-(pyridin-3-ylmethyl)-1H-pyrrolo[2,3-b]pyridine-5-carboxamide.

In a particularly preferred embodiment, $R^1$ corresponds to embodiment 1(F), wherein the compound of formula (I) is selected from the group consisting of methyl({3-[4-(pent-4-en-1-yl)quinoline-6-yl]-1H-pyrrolo[2,3-b]pyridin-5-yl}methyl)(prop-2-en-1-yl); benzyl({3-[8-fluoro-4-(pyridin-3-yl)quinoline-6-yl]-1H-pyrrolo[2,3-b]pyridin-5-yl}methyl)amine; (3R)-1-(6-{5-[(benzylamino)methyl]-1H-pyrrolo[2,3-b]pyridin-3-yl}-8-fluoroquinoline-4-yl)piperidin-3-amine and ({3-[8-fluoro-4-(pyridin-3-yl)quinoline-6-yl]-1H-pyrrolo[2,3-b]pyridin-5-yl}methyl)(methyl)(prop-2-en-1-yl)amine.

Definitions

The term "compound(s) of the present invention" is to be understood as equivalent to the term "compound(s) according to the invention", therefore also comprising a salt, stereoisomer, tautomer or N-oxide thereof.

The compounds according to the invention may be amorphous or may exist in one or more different crystalline states (polymorphs) which may have different macroscopic properties such as stability or show different biological properties such as activities. The present invention relates to amorphous and crystalline compounds of formula I, mixtures of different crystalline states of the respective compound of the invention, as well as amorphous or crystalline salts thereof.

Salts of the compounds according to the invention are preferably pharmaceutically acceptable salts, such as those containing counterions present in drug products listed in the US FDA Orange Book database. They can be formed in a customary manner, e.g., by reacting the compound with an acid of the anion in question if the compounds according to the invention have a basic functionality or by reacting acidic compounds according to the invention with a suitable base.

Suitable cationic counterions are in particular the ions of the alkali metals, preferably lithium, sodium and potassium, of the alkaline earth metals, preferably calcium, magnesium and barium, and of the transition metals, preferably manganese, copper, silver, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore the cations of 1,4-piperazine, meglumine, benzathine and lysine.

Suitable acidic counterions are in particular chloride, bromide, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate, furthermore lactate, gluconate, and poly acids such as succinate, oxalate, maleate, fumarate, malate, tartrate and citrate, furthermore sulfonate anions such as besylate (benzenesulfonate), tosylate (p-toluenesulfonate), napsylate (naphthalene-2-sulfonate), mesylate (methanesulfonate), esylate (ethanesulfonate), and ethanedisulfonate. They can be formed by reacting compounds according to the invention that have a basic functionality with an acid of the corresponding anion.

Depending on the substitution pattern, the compounds according to the invention may have one or more centres of chirality, including axial chirality. The invention provides both pure enantiomers or pure diastereomers of the compounds according to the invention, and their mixtures, including racemic mixtures. Suitable compounds according to the invention also include all possible geometrical stereoisomers (cis/trans isomers or E/Z isomers) and mixtures thereof. Cis/trans isomers may be present with respect to, e.g., an alkene, carbon-nitrogen double-bond or amide group.

Tautomers may be formed, if a substituent is present at the compound of formula I, which allows for the formation of tautomers such as keto-enol tautomers, imine-enamine tautomers, amide-imidic acid tautomers or the like.

The term "N-oxide" includes any compound of the present invention which has at least one tertiary nitrogen atom that is oxidized to a N-oxide moiety.

The term "substituted", as used herein, means that a hydrogen atom bonded to a designated atom is replaced with a specified substituent, provided that the substitution results in a stable or chemically feasible compound. Unless otherwise indicated, a substituted atom may have one or more substituents and each substituent is independently selected.

The term "substitutable", when used in reference to a designated atom, means that attached to the atom is a hydrogen, which can be replaced with a suitable substituent.

When it is referred to certain atoms or moieties being substituted with "one or more" substituents, the term "one or more" is intended to cover at least one substituent, e.g. 1 to 10 substituents, preferably 1, 2, 3, 4, or 5 substituents, more preferably 1, 2, or 3 substituents, most preferably 1, or 2 substituents. When neither the term "unsubstituted" nor "substituted" is explicitly mentioned concerning a moiety, said moiety is to be considered as unsubstituted.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine or chlorine.

The term "alkyl" as used herein denotes in each case a straight-chain or branched alkyl group having usually from 1 to 6 carbon atoms, preferably 1 to 5 or 1 to 4 carbon atoms, more preferably 1 to 3 or 1 to 2 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkoxy denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkenyl" as used herein denotes in each case an unsaturated hydrocarbon group having usually 2 to 6, preferably 2 to 4 carbon atoms comprising at least one carbon-carbon double bond in any position, e.g. vinyl (ethenyl), allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like. If geometric isomers are possible with regard to the double bond, the present invention relates to both, the E- and Z-isomers. Preferred alkenyl groups according to the invention are terminal alkenyl groups. The bonding of vinyl is exemplified below.

The term "haloalkenyl" as used herein refers to an alkenyl group as defined above, wherein the hydrogen atoms are partially or totally replaced with halogen atoms.

The term "alkynyl" as used herein denotes in each case an unsaturated hydrocarbon group having usually 2 to 6, preferably 2 to 5 or 2 to 4 carbon atoms, more preferably 2 to 3 carbon atoms, comprising at least one carbon-carbon triple bond in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "alkylcarbonyl" ($C_1$-$C_6$—C(=O)—) refers to a straight-chain or branched alkyl group as defined above, which is bonded via the carbon atom of a carbonyl group (C=O) to the remainder of the molecule.

The term "alkoxy" as used herein denotes in each case a straight-chain or branched alkyl group which is bonded via an oxygen atom and has usually from 1 to 6 carbon atoms, preferably 1 to 2 carbon atoms, more preferably 1 carbon atom. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having from 1 to 6 carbon atoms, preferably 1 to 2 carbon atoms, more preferably 1 carbon atom, wherein the hydrogen atoms of this group are partially or totally replaced with halogen atoms, in particular fluorine atoms. Preferred haloalkoxy moieties include $C_1$-haloalkoxy, in particular $C_1$-fluoroalkoxy, such as trifluoromethoxy and the like.

The term "carbocyclic" includes, unless otherwise indicated, in general a 3- to 9-membered, preferably a 4- to 8-membered or a 5- to 7-membered, more preferably a 5- or 6-membered monocyclic ring comprising 3 to 9, preferably 4 to 8 or 5 to 7, more preferably 5 or 6 carbon atoms. The carbocycle may be saturated, partially unsaturated, or fully unsaturated. Preferably, the term "carbocycle" covers cycloalkyl and cycloalkenyl groups as defined above, for example cyclopropane, cyclobutane, cyclopentane and cyclohexane rings. When it is referred to "fully unsaturated" carbocycles, this term also includes "aromatic" carbocycles or aryls. In certain preferred embodiments, a fully unsaturated carbocycle is an aromatic carbocycle as defined below, preferably a 6-membered aromatic carbocycle. Phenyl is a preferred fully unsaturated carbocycle.

The term "carbobicyclic" includes in general bicyclic 6 to 14-membered, preferably 7- to 12-membered or 8- to 10-membered, more preferably 8- or 9-membered bicyclic rings comprising 6 to 14, preferably 7 to 12 or 8 to 10, more preferably 8 or 9 carbon atoms. The carbobicycle may be saturated, partially unsaturated, or fully unsaturated. Preferably, the term "carbobicycle" covers bicycloalkyl, bicycloalkenyl and bicyclic aromatic groups, for example bicyclohexane (decalin), bicycloheptane (such as norbornane), bicyclooctane (such as bicyclo[2.2.2]octane, bicyclo[3.2.1]octane or bicyclo[4.2.0]octane), bicyclononane (such as bicyclo[3.3.1]nonane or bicyclo[4.3.0]nonane), bicyclodecane (such as bicyclo[4.4.0]decane), bicycloundecane (such as bicyclo[3.3.3]undecane), norbornene, naphthalene and the like. A particularly preferred carbobicycle is norbornane (bicycle[2.2.1]heptane).

The term "heterocyclic" includes, unless otherwise indicated, in general a 3- to 9-membered, preferably a 4- to 8-membered or 5- to 7-membered, more preferably 5- or 6-membered, in particular 6-membered monocyclic ring. The heterocycle may be saturated, partially unsaturated, or fully unsaturated. As used in this context, the term "fully unsaturated" also includes "aromatic". In a preferred embodiment, a fully unsaturated heterocycle is thus an aromatic heterocycle, preferably a 5- or 6-membered aromatic heterocycle comprising one or more, e.g. 1, 2, 3, or 4, preferably 1, 2, or 3 heteroatoms selected from N, O and S as ring members, where S-atoms as ring members may be present as S, SO or $SO_2$. Examples of aromatic heterocycles are provided below in connection with the definition of "hetaryl". "Hetaryls" or "heteroaryls" are covered by the term "heterocycles". The saturated or partially unsaturated heterocycles usually comprise 1, 2, 3, 4 or 5, preferably 1, 2 or 3 heteroatoms selected from N, O and S as ring members, where S-atoms as ring members may be present as S, SO or $SO_2$. Preferably, the S atom will not be present in oxidized form in fully unsaturated compounds. In particular, the following scenarios are covered:

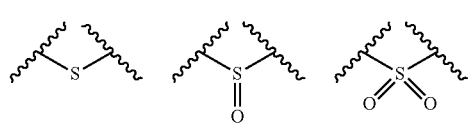

A skilled person is aware that resonance structures of the oxidized forms may be possible.

Saturated heterocycles include, unless otherwise indicated, in general 3- to 9-membered, preferably 4- to 8-membered or 5- to 7-membered, more preferably 5- or 6-membered monocyclic rings comprising 3 to 9, preferably 4 to 8 or 5 to 7, more preferably 5 or 6 atoms comprising at least one heteroatom, such as pyrrolidine, tetrahydrothiophene, tetrahydrofuran, piperidine, tetrahydropyran, dioxane, morpholine or piperazine.

The term "hetaryl" or "heteroaryl" or "aromatic heterocycle" or "aromatic heterocyclic ring" includes monocyclic 5- or 6-membered aromatic heterocycles comprising as ring members 1, 2, 3 or 4 heteroatoms selected from N, O and S, where S-atoms as ring members may be present as S, SO or $SO_2$. Preferably, the S atom will not be present in oxidized form in fully unsaturated compounds. In particular, the following scenarios are covered:

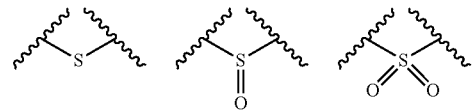

A skilled person is aware that resonance structures of the oxidized forms may be possible. Examples of 5- or 6-membered aromatic heterocycles include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

The term "heterobicyclic" includes in general bicyclic 6 to 14-membered, preferably 7- to 12-membered or 8- to 10-membered, more preferably 8- or 9-membered bicyclic rings comprising as ring members 1, 2, 3 or 4 heteroatoms selected from N, O and S, where S-atoms as ring members may be present as S, SO or $SO_2$. The heterobicycle may be saturated, partially unsaturated, or fully unsaturated. Examples of heterobicycles include benzofuranyl, benzothienyl, indolyl, indazolyl, benzimidazolyl, benzoxathiazolyl, benzoxadiazolyl, benzothiadiazolyl, benzoxazinyl, quinolinyl, isoquinolinyl, purinyl, 1,8-naphthyridyl, pteridyl, pyrido[3,2-d]pyrimidyl, pyridoimidazolyl, triethylenediamine or quinuclidine and the like. Quinuclidine is a preferred heterobicycle. These heterobicyclic groups may be bonded to the remainder of the molecule via any ring atom including the heteroatoms and the carbon atoms. Preferably, the quinuclidine is bonded as follows:

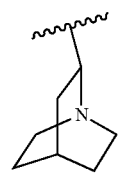 [SMILES: *C1CC2CCN1CC2]

As used in the specification and the claims, the singular forms of "a" and "an" also include the corresponding plurals unless the context clearly dictates otherwise. The same applies for plural forms used herein, which also include the singular forms unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The term "pharmaceutically acceptable excipient" as used herein refers to compounds commonly comprised in pharmaceutical compositions, which are known to the skilled person. Examples of suitable excipients are exemplary listed below. Typically, a pharmaceutically acceptable excipient can be defined as being pharmaceutically inactive.

The term "treatment" is to be understood as also including the option of "prophylaxis". Thus, whenever reference is made herein to a "treatment" or "treating", this is to be understood as "treatment and/or prophylaxis" or "treating and/or preventing".

Description of Pharmaceutical Compositions According to the Present Invention

A pharmaceutical composition according to the present invention may be formulated for oral, buccal, nasal, rectal, topical, transdermal or parenteral application. Oral application may be preferred. Parenteral application can also be preferred and includes intravenous, intraarterial, intratumoral, intrathecal, intravesical, intramuscular or subcutaneous administration. The compound according to formula (I) should be applied in pharmaceutically effective amounts, for example in the amounts as set out herein below.

A pharmaceutical composition of the present invention may also be designated as formulation or dosage form. A compound of formula (I) may also be designated in the following as (pharmaceutically) active agent or active compound.

Pharmaceutical compositions may be solid or liquid dosage forms or may have an intermediate, e.g. gel-like character depending inter alia on the route of administration.

In general, the inventive dosage forms can comprise various pharmaceutically acceptable excipients, which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, aqueous salt solutions, alcohols, oils, preferably vegetable oils, propylene glycol, polyoxyethelene sorbitans, polyethylene-polypropylene block co-polymers such as poloxamer 188 or poloxamer 407, polyethylene glycols such as polyethylene glycol 200, 300, 400, 600, etc., gelatin, lactose, amylose, magnesium stearate, surfactants, perfume oil, fatty acid monoglycerides, diglycerides and triglycerides, polyoxyethylated medium or long chain fatty acids such as ricinoleic acid, and polyoxyethylated fatty acid mono-, di, and triglycerides such as capric or caprilic acids, petroethral fatty acid esters, hydroxymethyl celluloses such as hydroxymethyl, hydroxyethyl, hydroxypropyl, hydroxypropyl acetate succinate, polyvinylpyrrolidone, crosspovidone and the like. The pharmaceutical compositions can be sterile and, if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound.

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavouring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions of the compounds of formula (I) in water-soluble form. Additionally, suspensions of the compounds of formula (I) may be prepared as appropriate oily injection suspensions. Suitable lipophilic solvents or vehicles include fatty oils such as sesame oil, soybean oil, or tocopherols, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Particularly preferred dosage forms are injectable preparations of a compound of formula (I). Thus, sterile injectable aqueous or oleaginous suspensions can for example be formulated according to the known art using suitable dispersing agents, wetting agents and/or suspending agents. A sterile injectable preparation can also be a sterile injectable solution or suspension or an emulsion in a non-toxic parenterally acceptable diluent or solvent. Among the acceptable vehicles and solvents that can be used are water and isotonic sodium chloride solution. Sterile oils are also conventionally used as solvent or suspending medium.

Suppositories for rectal administration of a compound of formula (I) can be prepared by e.g. mixing the compound with a suitable non-irritating excipient such as cocoa butter, synthetic triglycerides and polyethylene glycols which are solid at room temperature but liquid at rectal temperature such that they will melt in the rectum and release the compound according to formula (I) from said suppositories.

For administration by inhalation, the compounds according to the present invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone (crosspovidone), agar, or alginic acid or a salt thereof such as sodium alginate. The oral dosage forms may be formulated to ensure an immediate release of the compound of formula (I) or a sustained release of the compound of formula (I).

A solid dosage form may comprise a film coating. For example, the inventive dosage form may be in the form of a so-called film tablet. A capsule of the invention may be a two-piece hard gelatin capsule, a two-piece hydroxypropylmethylcellulose capsule, a two-piece capsule made of vegetable or plant-based cellulose or a two-piece capsule made of polysaccharide.

The dosage form according to the invention may be formulated for topical application. Suitable pharmaceutical application forms for such an application may be a topical nasal spray, sublingual administration forms and controlled and/or sustained release skin patches. For buccal administration, the compositions may take the form of tablets or lozenges formulated in conventional manner.

The compositions may conveniently be presented in unit dosage forms and may be prepared by any of the methods well known in the art of pharmacy. The methods can include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

As regards human patients, the compound of formula (I) may be administered to a patient in an amount of about 0.001 mg to about 5000 mg per day, preferably of about 0.01 mg to about 100 mg per day, more preferably of about 0.1 mg to about 50 mg per day, which is the effective amount. The phrase "effective amount" means an amount of compound that, when administered to a mammal in need of such treatment, is sufficient to treat or prevent a particular disease or condition.

Furthermore, the pharmaceutical composition may also contain the compound of formula (I) as a prodrug such as an ester or amide thereof. A prodrug is any compound which is converted under physiological conditions or by solvolysis to any of the compounds of the invention. A prodrug may be inactive prior to administration but may be converted to an active compound of the invention in vivo.

Indications, for which the Compounds of the Present Invention May be Used

The compounds according to the present invention are preferably used for the treatment of a disease selected from the group consisting of neurodegenerative, proliferative, inflammatory, autoimmune and metabolic diseases. The proliferative diseases include cancer.

Thus, in one embodiment, the compounds of the present invention are useful for the treatment of cancer, such as cancer of the upper gastrointestinal tract, pancreatic carcinoma, breast cancer, colon cancer, ovarian carcinoma, cervix carcinoma, endometrial cancer, brain tumor, testicular cancer, laryngeal carcinoma, osteocarcinoma, osteosarcoma, prostate cancer, retinoblastoma, liver carcinoma, non small cell lung cancer, small cell lung cancer, neuroblastoma, renal carcinoma, thyroid carcinoma, esophageal cancer, soft tissue sarcoma, skin cancer, osteosarcoma, rhabdomyosarcoma, bladder cancer or metastatic cancer.

In another embodiment, the compounds of the present invention are useful for the treatment of hematopoietic disorders, such as acute myeloid leukemia (AML), Morbus Hodgkin, Non-Hodgkin's lymphoma, hematopoietic disease, acute non-lymphocytic leukemia (ANLL), myeloproliferative disease acute promyelocytic leukemia (APL), acute myelomonocytic leukemia (AMMoL), multiple myeloma, polycythemia vera, lymphoma, acute lymphocytic leukemia (ALL), chronic lymphocytic leukemia (CCL), Wilm's tumor, or Ewing's Sarcoma.

In a preferred embodiment, the compounds of the present invention are useful for the treatment of non small cell lung cancer, small cell lung cancer, ovarian cancer, colon cancer, pancreatic cancer, prostate cancer, breast cancer, and/or hematopoietic disorders, such as acute myeloid leukemia (AML), Morbus Hodgkin, Non-Hodgkin's lymphoma, hematopoietic disease, acute non-lymphocytic leukemia (ANLL), myeloproliferative disease acute promyelocytic leukemia (APL), acute myelomonocytic leukemia (AMMoL), multiple myeloma, polycythemia vera, lymphoma, acute lymphocytic leukemia (ALL), chronic lymphocytic leukemia (CCL), Wilm's tumor, or Ewing's Sarcoma.

Metabolic diseases are diseases caused by an abnormal metabolic process and may either be congenital due to an inherited enzyme abnormality or acquired due to a disease of an endocrine organ or failure of a metabolically important organ such as the liver or the pancreas. The present invention is directed to the compound of formula (I) for use in the treatment of in particular metabolic diseases such as the metabolic syndrome or Diabetes.

Additionally, the compounds of the invention may be used to treat inflammation associated with autoimmune diseases or diseases resulting from inflammation including systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, asthma, bronchitis, acute pancreatitis, chronic pancreatitis, allergies of various taypes or possibly Alzheimer's disease.

The compounds of the present invention may also be used to treat a neurodegenerative diseases including Alzheimer's disease (including early onset Alzheimer's disease), Parkinson's disease, amyotrophic lateral sclerosis, Huntington's disease, senile chorea, Sydenham's chorea, frontotemporal lobar dementia, spinocerebellar ataxia, dementia with Lewy bodies, cerebral ischemia or neurodegenerative disease caused by traumatic injury, glutamate neurotoxicity, hypoxia, peripheral neuropathy, including mononeuropathy, multiple mononeuropathy or polyneuropathy. Examples of peripheral neuropathy may be found in diabetes mellitus, Lyme disease or uremia, peripheral neuropathy caused by a toxic agent, demyelinating disease such as acute or chronic inflammatory polyneuropathy, leukodystrophies, or Guillain-Barré syndrome, multiple mononeuropathy secondary to a collagen vascular disorder (e.g. polyarteritis nodosa, SLE, Sjögren's syndrome), multiple mononeuropathy secondary to sarcoidosis, multiple mononeuropathy secondary to a metabolic disease (e.g. diabetes or amyloidosis), or multiple mononeuropathy secondary to an infectious disease (e.g Lyme disease or HIV infection). A particularly preferred disease is Alzheimer's disease.

The compounds of the present invention may also be used to treat or ameliorate Down syndrome.

In a preferred embodiment relating to the pharmaceutical compositions of the present invention, said pharmaceutical composition comprises said compound as the only pharmaceutically active agent. Alternatively, said pharmaceutical composition comprises at least one further independent pharmaceutically active agent in addition to said compound, wherein said additional active agent is typically used for the intended indication(s) as outlined above.

The present invention is further illustrated by the following examples.

EXAMPLES

Some abbreviations that may appear in this application are defined as follows hereinafter.

| Abbreviation | Meaning |
|---|---|
| AcOH | Acetic acid |
| Boc | tert-Butyloxycarbonyl |
| $Bu_4N^+NO_3^-$ | Tetrabutylammonium nitrate |
| DCE | 1,2-Dimethoxyethane |
| DIPEA | N,N-Diisopropylethylamine |
| DMAP | N,N-Dimethylpyridin-4-amine |
| DMF | N,N-Dimethylformamide |
| $Et_3N$ | Triethylamine |
| $Et_2O$ | Diethyl ether |
| EtOAc | Ethyl acetate |
| EtOH | Ethanol |
| FCC | Flash column chromatography |
| HPLC | High-performance liquid chromatography |
| i-PrOH | Isopropanol |
| $[Ir(OMe)cod]_2$ | (1,5-Cyclooctadiene)(methoxy)iridium(I) dimer |
| MeOH | Methanol |
| $Me_4Phen$ | 3,4,7,8-Tetramethyl-1,10-phenanthroline |
| MeSNa | Sodium 2-mercaptoethanesulfonate |
| NIS | N-Iodosuccimide |
| NaOAc | Sodium acetate |
| $Na(OAc)_3BH$ | Sodium triacetoxyborohydride |
| NaOtBu | Sodium tert-butoxide |
| $Pd(dppf)Cl_2$ | [1,1'-Bis(diphenylphosphino)ferrocene]dichloropalladium(II) |
| $Pd(dppf)Cl_2*CH_2Cl_2$ | [1,1'-Bis(diphenylphosphino)ferrocene]dichloropalladium(II), complex with dichloromethane |
| $Pd(OAc)_2$ | Palladium(II) acetate |
| $Pd(Ph_3P)_4$ | Tetrakis(triphenylphosphine)palladium(0) |
| $PhNTf_2$ | N-Phenyl-bis(trifluoromethanesulfonimide) |
| rt | Room temperature, i.e. 20-25° C. |
| RuPhos | 2-Dicyclohexylphosphino-2',6'-diisopropoxybiphenyl |
| TFAA | Trifluoroacetic anhydride |
| THF | Tetrahydrofurane |
| TsCl | 4-Methylbenzenesulfonyl chloride |
| UPLC | Ultra performance liquid chromatography |
| UPLC-MS | Ultra performance liquid chromatography tandem mass spectrometer |

The compounds of the present invention can be prepared according to the procedures of the following Schemes and Examples, using appropriate materials and are further exemplified by the following specific examples. Analytical data of compounds made according to the following examples are shown in Table 4.

Unless otherwise specified, all starting materials are obtained from commercial suppliers and used without further purifications. Unless otherwise specified, all temperatures are expressed in ° C. and all reactions are conducted at rt. Compounds are purified by either silica chromatography or preparative HPLC.

$^1$H NMR $^1$H NMR is recorded on 400 MHz spectrometers. Chemical shifts (δ) are reported in ppm relative to the residual solvent signal (δ=2.5 ppm for $^1$H NMR in DMSO-d6). $^1$H NMR data are reported as follows: chemical shift (multiplicity, coupling constants and number of hydrogens). Multiplicity is abbreviated as follows: s (singlet), d (doublet), t (triplet), q (quartet), m (multiplet), dd (doublet of doublets), tt (triplet of triplets), td (triplet of doublets) br (broad). NMR, UPLC, HPLC and MS data provided in the examples described below are registered on: NMR: Bruker Avance III HD 400 MHz, probe BBO

HPLC

Method name: Kinetex-BCM

Equipment: HPLC with UV-Vis or DAD detector; column: Kinetex XB C18 4.6×50 mm 2.6 μm; eluents: (A) 0.1% formic acid-water solution, (B) 0.1% formic acid-ACN solution.

Analytical method: Autosampler-injection volume: 1 μL; pump-flow: 0.5 mL/min.

| Time [min] | [%] B |
|---|---|
| 0.0 | 20 |
| 6.7 | 80 |
| 7.5 | 80 |
| 7.8 | 95 |
| 9.5 | 95 |
| 10.0 | 20 |
| 12.0 | 20 |

Column compartment: column temperature: 25° C.; time of analysis: 12 min; detector-DAD.

Method name: Kinetex-ROT

Equipment: HPLC with UV-Vis or DAD detector; column: Kinetex XB C18 4.6×50 mm 2.6 μm; eluents: (A) 0.1% formic acid-water solution, (B) 0.1% formic acid-ACN solution.

Analytical method: Autosampler-injection volume: 1 μL; pump-flow: 0.45 mL/min.

| Time [min] | [%] B |
|---|---|
| 0.0 | 5 |
| 2.0 | 5 |
| 9.5 | 80 |
| 10.5 | 80 |
| 12.0 | 5 |
| 14.0 | 5 |

Column compartment: column temperature: 25° C.; time of analysis: 14 min; detector-DAD.

Method name: BCM-30

Equipment: HPLC with UV-Vis or DAD detector; column: Waters Symmetry C18 3.9×150 mm 5 μm; eluents: (A) 0.1% formic acid-water solution; (B) 0.1% formic acid-ACN solution.

Analytical method: Autosampler-injection volume: 3 μL; pump-flow: 1.2 ml/min.

| Time [min] | [%] B |
|---|---|
| 0.0 | 20 |
| 20.0 | 80 |
| 22.0 | 80 |
| 22.5 | 95 |
| 25.0 | 95 |
| 25.3 | 20 |
| 30.0 | 20 |

Column compartment: column temperature: 25° C.; time of analysis: 30 min; detector: wavelength: 254 nm, maximum absorbance.

Method name: ROT-C18-1

Equipment: HPLC with UV-Vis or DAD detector; column: Waters Symmetry C18 3.9×150 mm 5 μm; eluents: (A) 0.1% formic acid-water solution, (B) 0.1% formic acid-ACN solution.

Analytical method: Autosampler-injection volume: 3 μL; Pump-flow: 1.0 ml/min.

| Time [min] | [%] A | [%] B |
|---|---|---|
| 0.0 | 95 | 5 |
| 5.0 | 95 | 5 |
| 25.0 | 20 | 80 |
| 27.0 | 20 | 80 |
| 28.0 | 95 | 5 |
| 30.0 | 95 | 5 |

Column compartment: column temperature: 25° C.; time of analysis: 30 min; detector: DADwavelength: 254 nm, maximum absorbance.

Shimadzu LC-MS:

Method name: lc-ms1-2-ba

Equipment: Shimadzu UPLC-MS 2020; HPLC with UV-Vis or DAD detector; column: Waters Acquity UPLC HSS C18, 50 mm×2.1 mm×1.8 μm; eluents: (A) 0.1% formic acid in ACN, (B) 0.1% formic acid in water.

Analytical method: Autosampler-injection volume: 1 μL; Pump-flow=0.5 mL/min.

| Time [min] | % B |
|---|---|
| 0.00 | 95 |
| 0.00 | 95 |
| 4.00 | 5 |
| 5.00 | 5 |
| 5.20 | 95 |
| 6.00 | 95 |

Column compartment: column temperature: 25° C.; time of analysis: 6 min; detector: DAD-wavelengths: 254, 230, 270, 280 nm.

MS:

Nebulizer: 40 psi; dry gas: 9 l/min; dry gas temperature: 365° C.; scan: 100-1000 m/z; polarity: positive and/or negative.

Scheme 1.

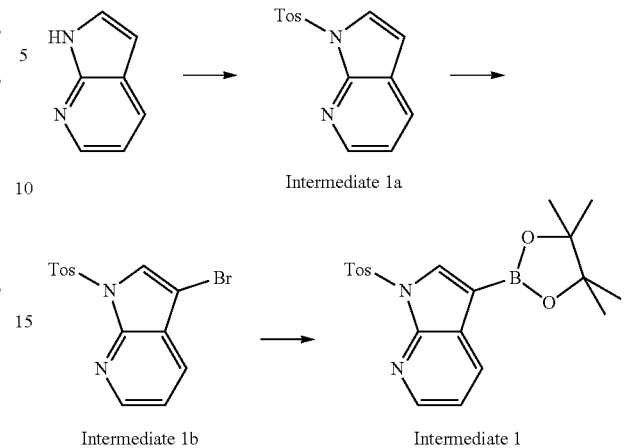

Intermediate 1a (Acc. to WO2013/006634A2)

1-(4-Methylbenzenesulfonyl)-1H-pyrrolo[2,3-b]pyridine

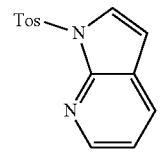

To a stirred solution of 7-azaindole (6.0 g, 50.0 mmol, 1.0 eq.) in THF (20 mL) was added NaH (60% dispersion in mineral oil, 2.2 g, 66.0 mmol, 1.3 eq.) at 0° C. The reaction mixture was allowed to warm to rt and stirred for 30 min. After cooling to 0° C., TsCl (11.6 g, 2.1 mmol, 1.2 eq.) was added to the reaction mixture and it was stirred at rt overnight. The reaction mixture was quenched with water and extracted with EtOAc. The organic layer was washed with brine, dried over $Na_2SO_4$ and evaporated to dryness. The residue was purified by column chromatography (EtOAc gradient in hexane) to give 1-(4-methylbenzenesulfonyl)-1H-pyrrolo[2,3-b]pyridine (Intermediate 1a) as a white solid (12.8 g; yield: 93%; UPLC purity: 100%).

Intermediate 1b (Acc. to WO2013/006634A2)

3-bromo-1-(4-methylbenzenesulfonyl)-1H-pyrrolo[2,3-b]pyridine

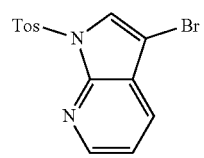

To a solution of 1-(4-methylbenzenesulfonyl)-1H-pyrrolo[2,3-b]pyridine (Intermediate 1a) (12.8 g, 47.0 mmol, 1.0 eq.) in chloroform (40 mL) bromine (2.7 mL, 52.0 mmol, 1.1 eq.) was added via a dropping funnel over 45 min and the reaction mixture was stirred at rt for 48 h. The reaction mixture was quenched with saturated solution of $Na_2SO_3$. The organic layer was dried over $Na_2SO_4$ and evaporated to dryness to afford 3-bromo-1-(4-methylbenzenesulfonyl)-1H-pyrrolo[2,3-b]pyridine (Intermediate 1b) as an off-white solid (15.2 g; yield: 92%; UPLC purity: 87%).

Intermediate 1. General Procedure 1

1-(4-Methylbenzenesulfonyl)-3-(tetramethyl-1,3,2-dioxaborolan-2-yl)-1H-pyrrolo[2,3-b]pyridine

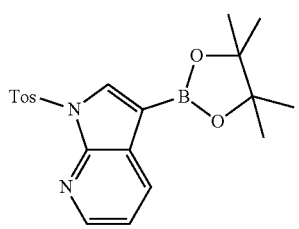

A sealed tube was charged with 3-bromo-1-(4-methylbenzenesulfonyl)-1H-pyrrolo[2,3-b]pyridine (Intermediate 1 b) (4.5 g, 12.8 mmol, 1.0 eq.), bis(pinacolato)diboron (4.9 g, 19.2 mmol, 1.5 eq.), potassium acetate (3.1 g, 31.0 mmol, 2.5 eq.) and 1,4-dioxane (40 mL). The mixture was sonicated under a stream of argon before Pd(dppf)Cl$_2$*CH$_2$Cl$_2$ (0.28 g, 0.38 mmol, 0.03 eq.) was added. The reaction mixture was stirred at 85° C. overnight. Then it was cooled and filtered through a pad of Celite, washed with EtOAc and the filtrate was concentrated. The crude product mixture was dissolved in EtOAc and washed with water, then brine. The organic layer was dried over Na$_2$SO$_4$, filtered and concentrated to give a mixture of boronic ester-1-(4-methylbenzenesulfonyl)-3-(tetramethyl-1,3,2-dioxaborolan-2-yl)-1H-pyrrolo[2,3-b]pyridine (Intermediate 1) and boronic acid-[1-(4-methylbenzenesulfonyl)-1H-pyrrolo[2,3-b]pyridin-3-yl]boronic acid in the ratio 1:1. Both products were not separated and used in consecutive step without further purification.

Scheme 2.

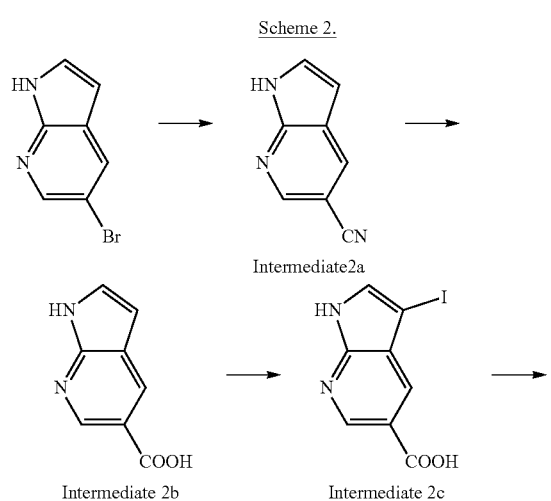

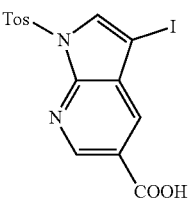

Intermediate 2

Intermediate 2a (Acc. to WO2005/085244A1)

1H-Pyrrolo[2,3-b]pyridine-5-carbonitrile

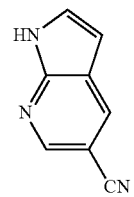

A solution of 5-bromo-1H-pyrrolo[2,3-b]pyridine (5.0 g, 25.0 mmol, 1.0 eq.), Zn(CN)$_2$ (3.6 g, 20.0 mmol, 0.8 eq.) in dry DMF (65 mL) was deoxygenated with a stream of argon for 30 min and then Pd(Ph$_3$P)$_4$ (1.7 g, 1.5 mmol, 0.06 eq.) was added. The reaction mixture was heated at 80° C. for 36 h then quenched with water and extracted with EtOAc. The organic layer was dried over Na$_2$SO$_4$ and evaporated to dryness. The residue was treated with small amount of CH$_2$Cl$_2$ and filtered. The collected precipitate was rinsed with CH$_2$Cl$_2$ and dried on air to give 1H-pyrrolo[2,3-b]pyridine-5-carbonitrile (Intermediate 2a) as a white solid (3.0 g; yield: 83%; UPLC purity: 100%).

Intermediate 2b (Acc. to US20070066641)

1H-Pyrrolo[2,3-b]pyridine-5-carboxylic acid

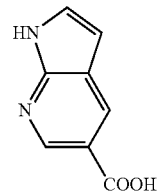 [SMILES: O=C(O)c1cnc2[nH]ccc2c1]

A sealed tube was charged with 1H-pyrrolo[2,3-b]pyridine-5-carbonitrile (Intermediate 2a) (1.5 g, 10.0 mmol, 1.0 eq.), KOH (11.7 g, 209.0 mmol, 21.0 eq.) in a mixture of EtOH/water (1:1) (100 mL). The reaction mixture was heated at 90° C. for 2 days. Then EtOH was evaporated and aqueous layer was diluted with water to the total volume of 100 mL, acidified with concentrated HCl (20 mL) and neutralized with NaOAc. The precipitate was collected by filtration, rinsed thoroughly with water and dried on air to provide 1H-pyrrolo[2,3-b]pyridine-5-carboxylic acid (Intermediate 2b) as a white solid which was used in consecutive step without further purification (UPLC purity: 73%).

Intermediate 2c

3-Iodo-1H-pyrrolo[2,3-b]pyridine-5-carboxylic acid

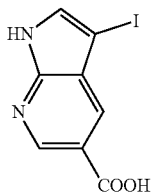

A solution of 1H-pyrrolo[2,3-b]pyridine-5-carboxylic acid (Intermediate 2b) (1.4 g, 8.9 mmol, 1.0 eq.) and NIS (2.0 g, 8.9 mmol, 1.0 eq.) in DMF was stirred at rt overnight. The reaction mixture was quenched with saturated solution of $Na_2SO_3$. The formed precipitate was collected by filtration, rinsed with water and dried to give 3-iodo-1H-pyrrolo[2,3-b]pyridine-5-carboxylic acid (Intermediate 2c) as a pale yellow solid (1.76 g; yield: 69%; UPLC purity: 98%).

Intermediate 2 (Procedure Acc. to WO2012/129338A1)

3-Iodo-1-(4-methylbenzenesulfonyl)-1H-pyrrolo[2,3-b]pyridine-5-carboxylic acid

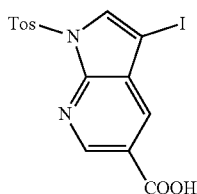

To a stirred solution of 3-iodo-1H-pyrrolo[2,3-b]pyridine-5-carboxylic acid (Intermediate 2c) (6.7 g, 23.0 mmol, 1.0 eq.) in DMF (20 mL) was added NaH (60% dispersion in mineral oil, 1.22 g, 51.0 mmol, 2.2 eq.) at 0° C. The reaction mixture was allowed to warm to rt and then TsCl (5.3 g, 27.8 mmol, 1.2 eq.) was added. After stirring at rt overnight the reaction mixture was diluted with water and acidified with concentrated HCl and then neutralized with NaOAc. The formed precipitate was collected by filtration, rinsed with water and $Et_2O$ and dried on air to perform 3-iodo-1-(4-methylbenzenesulfonyl)-1H-pyrrolo[2,3-b]pyridine-5-carboxylic acid (Intermediate 2) as a solid (8.7 q; yield: 85%; NMR purity: 90%).

Scheme 3.

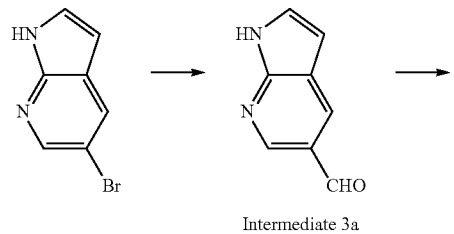

Intermediate 3a

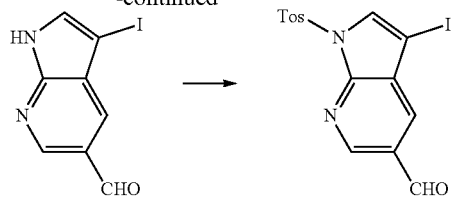

Intermediate 3a

1H-Pyrrolo[2,3-b]pyridine-5-carbaldehyde

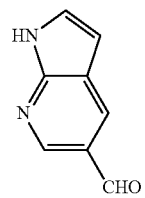

To a solution of 5-bromo-1H-pyrrolo[2,3-b]pyridine (1.0 g, 5.0 mmol, 1.0 eq.) in anhydrous THF (50 mL) at −78° C. under argon was slowly added a solution of 1.6 M n-butyl lithium in hexane (6.7 mL, 10.7 mmol, 2.1 eq.) and the reaction mixture was allowed to stir for next 40 min at −78° C. To the resulting suspension 1 mL of dry DMF was added successively and the reaction mixture stirring was continued at rt overnight. Then the reaction mixture was quenched with saturated solution of $NH_4Cl$; the organic layer was separated and the aqueous phase was extracted with EtOAc. The organic layers were combined, washed with brine, dried over $Na_2SO_4$, filtered and concentrated to afford 1H-pyrrolo[2,3-b]pyridine-5-carbaldehyde (Intermediate 3a) as an yellow solid (1.0 g; yield: 69%; UPLC purity: 98%).

Intermediate 3b

3-Iodo-1H-pyrrolo[2,3-b]pyridine-5-carbaldehyde

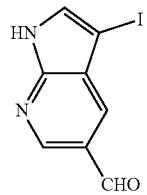

A solution of 1H-pyrrolo[2,3-b]pyridine-5-carbaldehyde (Intermediate 3a) (2.4 g, 16.3 mmol, 1.0 eq.) and NIS (3.7 g, 16.3 mmol, 1.0 eq.) in DMF (25 mL) was stirred at rt overnight. The reaction mixture was diluted with water (50 mL) and a saturated solution of $Na_2SO_3$ (2 mL). The formed precipitate was collected by filtration, rinsed with water and dried to give 3-iodo-1H-pyrrolo[2,3-b]pyridine-5-carbaldehyde (Intermediate 3b) as a solid (4.0 g; yield: 91%; UPLC purity: 100%).

Intermediate 3

3-(Iodo-1-(4-methylbenzenesulfonyl)-1H-pyrrolo[2,3-b]pyridine-5-carbaldehyde

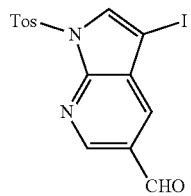

To a stirred solution of 3-iodo-1H-pyrrolo[2,3-b]pyridine-5-carbaldehyde (Intermediate 3b) (4.0 g, 14.9 mmol, 1 eq.) in DMF (60 mL) was added NaH (60% dispersion in mineral oil, 0.7 g, 17.8 mmol, 1.2 eq.) at 0° C. The reaction mixture was allowed to warm to rt and then TsCl (3.1 g, 16.3 mmol, 1.1 eq.) was added. After stirring at rt overnight the reaction mixture was diluted with water (150 mL) and the formed precipitate was collected by filtration, rinsed with water and dried on air to perform 3-iodo-1-(4-methylbenzenesulfonyl)-1H-pyrrolo[2,3-b]pyridine-5-carbaldehyde (Intermediate 3) as a beige solid (5.9 g; yield: 94%; UPLC purity: 98%).

Intermediate 4. General Procedure 2

4-Chloro-6-[1-(4-methylbenzenesulfonyl)-1H-pyrrolo[2,3-b]pyridin-3-yl]quinoline

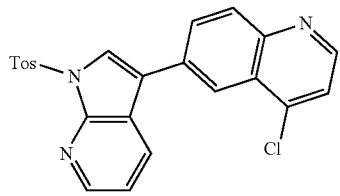

A sealed tube was charged with 1-(4-methylbenzenesulfonyl)-3-(tetramethyl-1,3,2-dioxaborolan-2-yl)-1H-pyrrolo[2,3-b]pyridine (Intermediate 1) (0.45 g, 1.1 mmol, 1.0 eq.), 6-bromo-4-chloroquinoline (0.3 g, 1.1 mmol, 1.0 eq.), potassium carbonate (0.42 g, 3.0 mmol, 2.7 eq.) in a mixture of 1,4-dioxane/water 2/1 (1.5 mL) under argon. The mixture was sonicated under a stream of argon before Pd(PPh$_3$)$_4$ (0.04 g, 0.03 mmol, 0.03 eq.) was added. The reaction mixture was heated at 120° C. under microwave irradiation for 25 min. Then it was cooled and filtered through Celite, washed with EtOAc and the filtrate was concentrated. The crude product mixture was purified by flash column chromatography (EtOAc gradient in hexane followed by MeOH gradient in EtOAc) to provide 4-chloro-6-[1-(4-methylbenzenesulfonyl)-1H-pyrrolo[2,3-b]pyridin-3-yl]quinoline (0.3 g; yield: 61%, UPLC purity: 100%).

Example 1

General Procedure 3

4-Chloro-6-{1H-pyrrolo[2,3-b]pyridin-3-yl}quinoline

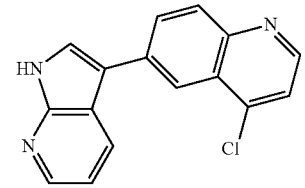 [SMILES: Clc1ccnc2ccc(-c3c[nH]c4ncccc34)cc12]

A solution of 4-chloro-6-[1-(4-methylbenzenesulfonyl)-1H-pyrrolo[2,3-b]pyridin-3-yl]quinoline (Intermediate 4) (0.06 g, 0.14 mmol, 1.0 eq.) and ceasium carbonate (0.18 g, 0.6 mmol, 4.0 eq.) in a mixture of THF/water 2/1 (3 mL) was stirred at rt for 48 h. The reaction mixture was diluted with CH$_2$Cl$_2$ and washed with water. The organic layer was dried over Na$_2$SO$_4$ and concentrated in vacuo. The resulting residue was purified by HPLC to give 4-chloro-6-{1H-pyrrolo[2,3-b]pyridin-3-yl}quinoline (0.025 g; yield: 64%; UPLC purity: 100%).

Intermediate 5

6-[1-(4-Methylbenzenesulfonyl)-1H-pyrrolo[2,3-b]pyridin-3-yl]quinoline

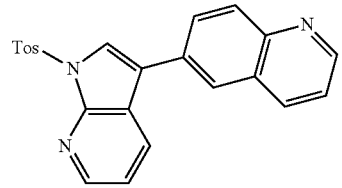

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.16 g, 0.4 mmol, 1.1 eq.), 6-bromoquinoline hydrochloride (0.09 g, 0.4 mmol, 1.0 eq.), K$_2$CO$_3$ (0.2 g, 1.5 mmol, 4.0 eq.), Pd(dppf)$_2$Cl$_2$*CH$_2$Cl$_2$ (0.06 g, 0.07 mmol, 0.2 eq.) in a mixture of 1,4-dioxane/water 3/1 (8 mL). Purification by FCC (EtOAc gradient in hexane) provided 6-[1-(4-methylbenzenesulfonyl)-1H-pyrrolo[2,3-b]pyridin-3-yl]quinoline as a brownish solid (0.07 g; yield: 47%; UPLC purity: 100%).

Example 2

6-{1H-Pyrrolo[2,3-b]pyridin-3-yl}quinoline

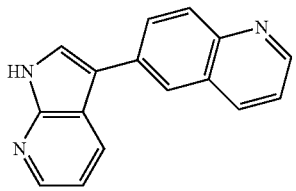 [SMILES: c1cnc2ccc(-c3c[nH]c4ncccc34)cc2c1]

The title compound was prepared according to General Procedure 3 with 6-[1-(4-methylbenzenesulfonyl)-1H-pyrrolo[2,3-b]pyridin-3-yl]quinoline (Intermediate 5) (0.07 g, 0.2 mmol, 1.0 eq.), NaOtBu (0.03 g, 0.4 mmol, 2.0 eq.) dissolved in 1,4-dioxane (2 mL). The reaction mixture was stirred at 80° C. overnight. Purification by FCC (MeOH gradient in CH₂Cl₂) provided 6-{1H-pyrrolo[2,3-b]pyridin-3-yl}quinoline as an yellow solid (0.025 g; yield: 60%; HPLC purity: 97%).

Intermediate 6. General Procedure 4 tert-Butyl N-[(3S)-1-{6-[1-(4-methylbenzenesulfonyl)-1H-pyrrolo[2,3-b]pyridin-3-yl]quinolin-4-yl}piperidin-3-yl]carbamate

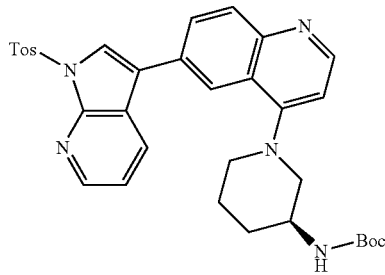

A solution of 4-chloro-6-[1-(4-methylbenzenesulfonyl)-1H-pyrrolo[2,3-b]pyridin-3-yl]quinoline (Intermediate 4) (0.15 g, 0.35 mmol, 1.0 eq.), (S)-3-(Boc-amino)piperidine (0.14 g, 0.7 mmol, 2.0 eq.), DIPEA (0.09 g, 0.7 mmol, 2.0 eq.) in i-PrOH (3 mL) was heated at 140° C. under microwave irradiation for 1.5 h. After cooling to rt, solvent was evaporated and the crude reaction mixture was used in consecutive step without further purification (UPLC purity: 71%).

Intermediate 7 tert-Butyl N-[(3S)-1-(6-{1H-pyrrolo[2,3-b]pyridin-3-yl}quinolin-4-yl)piperidin-3-yl]carbamate

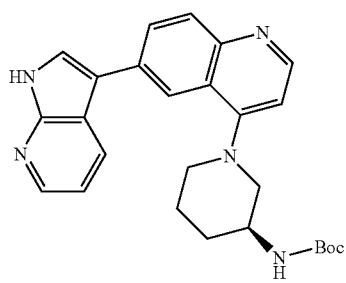 [SMILES: CC(C)(C)OC(=O)N[C@H]1CCCN(c2ccnc3ccc(-c4c[nH]c5ncccc45)cc23)C1]

The title compound was prepared according to General Procedure 3 with tert-butyl N-[(3S)-1-{6-[1-(4-methylbenzenesulfonyl)-1H-pyrrolo[2,3-b]pyridin-3-yl]quinolin-4-yl}piperidin-3-yl]carbamate (Intermediate 6) (0.08 g, 0.14 mmol, 1.0 eq.), NaOtBu (0.02 g, 0.2 mmol, 1.5 eq.) dissolved in 1,4-dioxane (3.5 mL). The reaction mixture was stirred at 80° C. for 5 h. Purification by FCC (MeOH gradient in CH₂Cl₂) provided tert-butyl N-[(3S)-1-(6-{1H-pyrrolo[2,3-b]pyridin-3-yl}quinolin-4-yl)piperidin-3-yl]carbamate (0.02 g; yield: 29%; UPLC purity: 94%).

Example 3

General Procedure 5

(3S)-1-(6-{1H-Pyrrolo[2,3-b]pyridin-3-yl}quinolin-4-yl)piperidin-3-amine

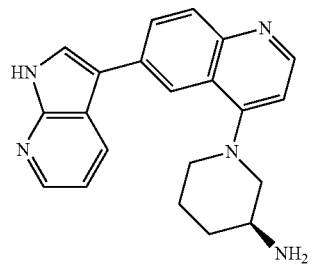 [SMILES: N[C@H]1CCCN(c2ccnc3ccc(-c4c[nH]c5ncccc45)cc23)C1]

To the solution of tert-butyl N-[(3S)-1-(6-{1H-pyrrolo[2,3-b]pyridin-3-yl}quinolin-4-yl)piperidin-3-yl]carbamate (Intermediate 7) (0.02 g, 0.04 mmol, 1.0 eq.) in MeOH (1 mL) 4 M HCl in 1,4-dioxane (3 mL) was added. The reaction mixture was stirred at rt overnight. The precipitate was collected by filtration, washed by Et₂O and dried on air to provide (3S)-1-(6-{1H-pyrrolo[2,3-b]pyridin-3-yl}quinolin-4-yl)piperidin-3-amine as a white powder (0.012 g; yield: 60%; HPLC purity: 95%).

Intermediate 8 trans-1-N-{6-[1-(4-Methylbenzenesulfonyl)-1H-pyrrolo[2,3-b]pyridin-3-yl]quinolin-4-yl}cyclohexane-1,4-diamine

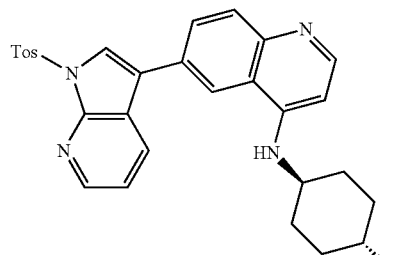

The title compound was prepared according to General Procedure 4 with (4-chloro-6-[1-(4-methylbenzenesulfonyl)-1H-pyrrolo[2,3-b]pyridin-3-yl]quinoline (Intermediate 4) (0.12 g, 0.3 mmol, 1.0 eq.), trans-cyclohexane-1,4-diamine (0.06 g, 0.55 mmol, 4.0 eq.), DIPEA (0.07 g, 0.55 mmol, 4.0 eq.) in i-PrOH (3 mL). The reaction mixture was heated at 170° C. under microwave irradiation for 1 h. The crude reaction mixture was used in consecutive step without further purification.

Example 4 trans-1-N-(6-{1H-Pyrrolo[2,3-b]pyridin-3-yl}quinolin-4-yl)cyclohexane-1,4-diamine

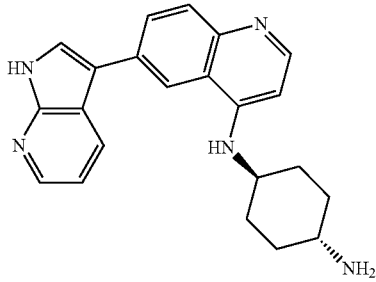 [SMILES: N[C@H]1CC[C@H](Nc2ccnc3ccc(-c4c[nH]c5ncccc45)cc23)CC1]

The title compound was prepared according to General Procedure 3 with trans-1-N-{6-[1-(4-methylbenzenesulfonyl)-1H-pyrrolo[2,3-b]pyridin-3-yl]quinolin-4-yl}cyclohexane-1,4-diamine (Intermediate 8) (0.14 g, 0.3 mmol, 1.0 eq.) and ceasium carbonate (0.36 g, 1.1 mmol, 4.0 eq.) in a mixture of THF/water 2/1 (3 mL). Purification by HPLC afforded trans-1-N-(6-{1H-pyrrolo[2,3-b]pyridin-3-yl}quinolin-4-yl)cyclohexane-1,4-diamine (0.059 g; yield: 62%; HPLC purity: 91%).

Intermediate 9 tert-Butyl N-[(3S)-1-{6-[1-(4-methylbenzenesulfonyl)-1H-pyrrolo[2,3-b]pyridin-3-yl]quinolin-4-yl}pyrrolidin-3-yl]carbamate

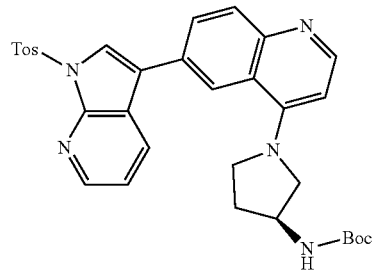

The title compound was prepared according to General Procedure 4 with 4-chloro-6-[1-(4-methylbenzenesulfonyl)-1H-pyrrolo[2,3-b]pyridin-3-yl]quinoline (Intermediate 4) (0.12 g, 1.0 mmol, 1.0 eq.), (S)-3-(Boc-amino)pyrrolidine (0.15 g, 0.8 mmol, 3.0 eq.), DIPEA (0.11 g, 0.8 mmol, 3.0 eq.). The reaction mixture was heated under microwave irradiation at 155° C. for 1 h. The crude product tert-butyl N-[(3S)-1-{6-[1-(4-methylbenzenesulfonyl)-1H-pyrrolo[2,3-b]pyridin-3-yl]quinolin-4-yl}pyrrolidin-3-yl]carbamate was used in consecutive step without further purification.

Intermediate 10 tert-Butyl N-[(3S)-1-(6-{1H-pyrrolo[2,3-b]pyridin-3-yl}quinolin-4-yl)pyrrolidin-3-yl]carbamate

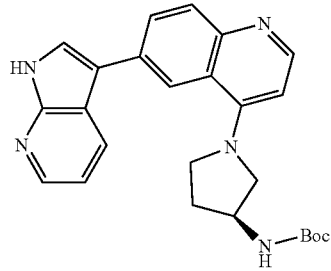 [SMILES: CC(C)(C)OC(=O)N[C@H]1CCN(c2ccnc3ccc(-c4c[nH]c5ncccc45)cc23)C1]

The title compound was prepared according to General Procedure 3 with tert-butyl N-[(3S)-1-{6-[1-(4-methylbenzenesulfonyl)-1H-pyrrolo[2,3-b]pyridin-3-yl]quinolin-4-yl}pyrrolidin-3-yl]carbamate (Intermediate 9) (0.2 g, 0.3 mmol, 1.0 eq.), ceasium carbonate (0.44 g, 1.4 mmol, 4.0 eq.) in a mixture of THF/water 2/1 (3 mL). The crude product tert-butyl N-[(3S)-1-(6-{1H-pyrrolo[2,3-b]pyridin-3-yl}quinolin-4-yl)pyrrolidin-3-yl]carbamate was used in consecutive step without further purification.

Example 5

(3S)-1-(6-{1H-Pyrrolo[2,3-b]pyridin-3-yl}quinolin-4-yl)pyrrolidin-3-amine

The title compound was prepared according to General Procedure 5 with tert-butyl N-[(3S)-1-(6-{1H-pyrrolo[2,3-b]pyridin-3-yl}quinolin-4-yl)pyrrolidin-3-yl]carbamate (Intermediate 10) (0.14 g, 0.3 mmol, 1.0 eq.) in 4 M HCl in 1,4-dioxane (5 mL). The product was purified by HPLC to provide (3S)-1-(6-{1H-pyrrolo[2,3-b]pyridin-3-yl}quinolin-4-yl)pyrrolidin-3-amine (0.08 g; yield: 75%; HPLC purity: 100%).

Intermediate 11

6-[1-(4-Methylbenzenesulfonyl)-1H-pyrrolo[2,3-b]pyridin-3-yl]-4-(pyridin-3-yl)quinoline

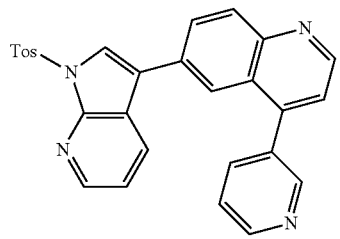

The title compound was prepared according to General Procedure 2 with 4-chloro-6-[1-(4-methylbenzenesulfonyl)-1H-pyrrolo[2,3-b]pyridin-3-yl]quinoline (Intermediate 4) (0.1 g, 0.2 mmol, 1.0 eq.), 3-pyridylboronic acid (0.03 g, 0.25 mmol, 1.1 eq.), K₂CO₃ (0.08 g, 0.6 mmol, 2.7 eq.), Pd(PPh₃)₄ (0.02 g, 0.02 mmol, 0.03 eq.) in a mixture of 1,4-dioxane/water 2/1 (2 mL). The residue was purified by FCC (EtOAc gradient in hexane) to provide 6-[1-(4-methylbenzenesulfonyl)-1H-pyrrolo[2,3-b]pyridin-3-yl]-4-(pyridin-3-yl)quinoline (0.11 g; yield: 64%; UPLC purity: 100%).

Example 6

4-(Pyridin-3-yl)-6-{1H-pyrrolo[2,3-b]pyridin-3-yl}quinoline

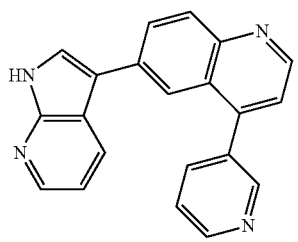 [SMILES: c1cncc(-c2ccnc3ccc(-c4c[nH]c5ncccc45)cc23)c1]

The title compound was prepared according to General Procedure 3 with 6-[1-(4-methylbenzenesulfonyl)-1H-pyrrolo[2,3-b]pyridin-3-yl]-4-(pyridin-3-yl)quinoline (Intermediate 11) (0.07 g, 0.2 mmol, 1.0 eq.), NaOtBu (0.02 g, 0.2 mmol, 1.5 eq.) dissolved in 1,4-dioxane (3.5 mL). The reaction mixture was heated at 80° C. overnight. The crude reaction mixture was purified by flash column chromatography (MeOH gradient in CH₂Cl₂) to give 4-(pyridin-3-yl)-6-{1H-pyrrolo[2,3-b]pyridin-3-yl}quinoline (0.028 g; yield: 60%; UPLC purity: 97%).

Intermediate 12

6-[1-(4-Methylbenzenesulfonyl)-1H-pyrrolo[2,3-b]pyridin-3-yl]-4-(pyridin-4-yl)quinoline

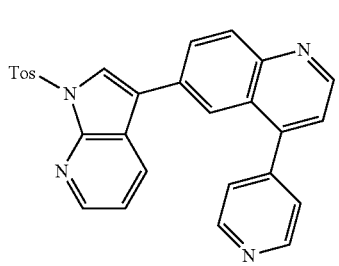

The title compound was prepared according to General Procedure 2 with 4-chloro-6-[1-(4-methylbenzenesulfonyl)-1H-pyrrolo[2,3-b]pyridin-3-yl]quinoline (Intermediate 4) (0.14 g, 0.3 mmol, 1.0 eq.), 4-pyridylboronic acid (0.04 g, 0.3 mmol, 1.0 eq.), K₂CO₃ (0.12 g, 0.8 mmol, 2.7 eq.), Pd(PPh₃)₄ (0.011 g, 0.01 mmol, 0.03 eq.) in a mixture of 1,4-dioxane/water 2/1 (4.5 mL). The residue was purified by FCC (MeOH gradient in CH₂Cl₂; column neutralized with 0.1% Et₃N in CH₂Cl₂, then washed with CH₂Cl₂ before purification) to provide 6-[1-(4-methylbenzenesulfonyl)-1H-pyrrolo[2,3-b]pyridin-3-yl]-4-(pyridin-4-yl)quinoline (0.092 g; yield: 60%; UPLC purity: 95%).

Example 7

4-(Pyridin-4-yl)-6-{1H-pyrrolo[2,3-b]pyridin-3-yl}quinoline

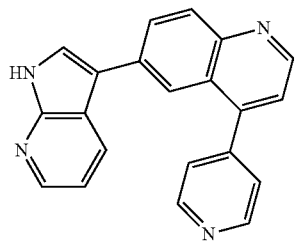 [SMILES: c1cnc2[nH]cc(-c3ccc4nccc(-c5ccncc5)c4c3)c2c1]

The title compound was prepared according to General Procedure 3 with 6-[1-(4-methylbenzenesulfonyl)-1H-pyrrolo[2,3-b]pyridin-3-yl]-4-(pyridin-4-yl)quinoline (Intermediate 12) (0.09 g, 0.2 mmol, 1.0 eq.), NaOtBu (0.027 g, 0.3 mmol, 1.5 eq.) dissolved in 1,4-dioxane (3 mL). The reaction mixture was heated at 80° C. for 3 h. The crude reaction mixture was purified by flash column chromatography (EtOAc gradient in hexane) to give 4-(pyridin-4-yl)-6-{1H-pyrrolo[2,3-b]pyridin-3-yl}quinoline (0.01 g; yield: 16%; HPLC purity: 100%).

Intermediate 13

6-[1-(4-Methylbenzenesulfonyl)-1H-pyrrolo[2,3-b]pyridin-3-yl]-4-phenylquinoline

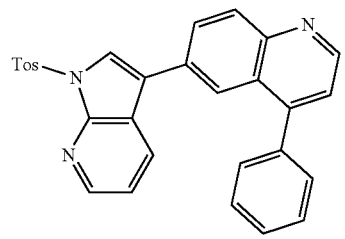

The title compound was prepared according to General Procedure 2 with 4-chloro-6-[1-(4-methylbenzenesulfonyl)-1H-pyrrolo[2,3-b]pyridin-3-yl]quinoline (Intermediate 4) (0.1 g, 0.2 mmol, 1.0 eq.), phenylboronic acid (0.03 g, 0.2 mmol, 1.0 eq.), K₂CO₃ (0.08 g, 0.6 mmol, 2.7 eq.), Pd(PPh₃)₄ (0.008 g, 0.01 mmol, 0.03 eq.) in a mixture of 1,4-dioxane/water 2/1 (4.5 mL). The residue was purified by FCC (MeOH gradient in CH₂Cl₂) to provide 6-[1-(4-methylbenzenesulfonyl)-1H-pyrrolo[2,3-b]pyridin-3-yl]-4-phenyl)quinoline (0.1 g; yield: 95%; UPLC purity: 95%).

Example 8

4-Phenyl-6-{1H-pyrrolo[2,3-b]pyridin-3-yl}quinoline

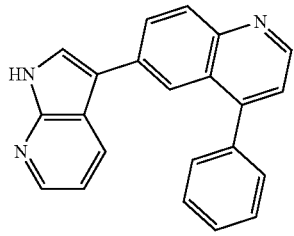 [SMILES: c1ccc(-c2ccnc3ccc(-c4c[nH]c5ncccc45)cc23)cc1]

The title compound was prepared according to General Procedure 3 with 6-[1-(4-methylbenzenesulfonyl)-1H-pyrrolo[2,3-b]pyridin-3-yl]-4-phenylquinoline (Intermediate 13) (0.11 g, 0.2 mmol, 1.0 eq.), NaOtBu (0.027 g, 0.3 mmol, 1.2 eq.) dissolved in 1,4-dioxane (3 mL). The reaction mixture was stirred at rt for 48 h. The crude reaction mixture was purified by flash column chromatography to give 4-phenyl-6-{1H-pyrrolo[2,3-b]pyridin-3-yl}quinoline as an yellow solid (0.055 g; yield: 65%; HPLC purity: 98%).

Intermediate 14

{1H-Pyrrolo[2,3-b]pyridin-3-yl}boronic acid

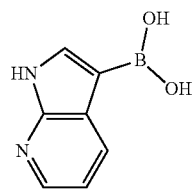 [SMILES: OB(O)c1c[nH]c2ncccc12]

A vacuum dried sealed tube was charged with 7-azaindole (0.12 g, 1.0 mmol, 1.0 eq.), bis(pinacolato)diboron (0.25 g, 1.0 mmol, 1.0 eq.), Me$_4$Phen (0.009 g, 0.05 mmol, 0.04 eq.), [Ir(OMe)cod]$_2$ (0.007 g, 0.01 mmol, 0.01 eq.) in THF (5 mL) in a stream of argon. The reaction mixture was heated at 80° C. overnight and then quenched with MeOH and concentrated. The residue was purified by FCC (EtOAc gradient in hexane) to afford an inseparable mixture of {1H-pyrrolo[2,3-b]pyridin-3-yl}boronic acid and starting material (ratio 4/6) as an yellow oil which was used in consecutive step without further purification.

Intermediate 15

4-[(R)-{5-Ethenyl-1-azabicyclo[2.2.2]octan-2-yl}(hydroxy)methyl]quinolin-6-ol

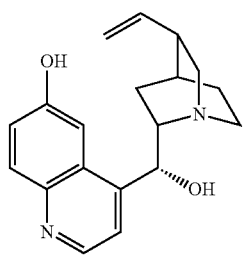 [SMILES: C=CC1CN2CCC1CC2[C@H](O)c1ccnc2ccc(O)cc12]

A suspension of quinine (0.3 g, 1.0 mmol, 1.0 eq.) and MeSNa (0.35 g, 5.0 mmol, 5.0 eq.) in DMF (10 mL) was sparged with argon and heated at 110° C. overnight. After cooling to rt the reaction mixture was diluted with water to 100 mL, acidified with concentrated HCl (1 mL) and then neutralized with NaOAc. The aqueous layer was extracted with EtOAc. Combined organic phase was washed with brine, dried over Na$_2$SO$_4$ and concentrated. The residue was diluted with Et$_2$O and precipitate was collected by filtration. UPLC-MS showed a mixture of a desired product and starting material in ratio 55/45. Aqueous phase was saturated with NaCl and extracted with EtOAc. Again combined organic phase was dried over Na$_2$SO$_4$ and concentrated. The residue was treated with Et$_2$O to afford a white solid which was collected by filtration. UPLC-MS analysis indicated a mixture of product and starting material in ratio 45/55 which was used in consecutive step without further purification.

Intermediate 16

4-[(R)-{5-Ethenyl-1-azabicyclo[2.2.2]octan-2-yl}(hydroxy)methyl]quinolin-6-yl trifluoromethanesulfonate

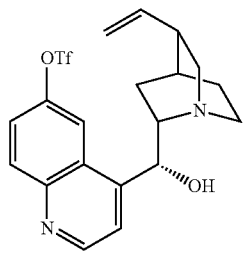 [SMILES: C=CC1CN2CCC1CC2[C@H](O)c1ccnc2ccc(OS(=O)(=O)C(F)(F)F)cc12]

A solution of 4-[(R)-{5-ethenyl-1-azabicyclo[2.2.2]octan-2-yl}(hydroxy)methyl]quinolin-6-ol (Intermediate 15) (0.065 g, 0.2 mmol, 1.0 eq.), pyridine (1 mL), PhNTf$_2$ (0.07 g, 2.1 mmol, 1.0 eq.), DMAP (0.003 g, 0.02 mmol, 0.1 eq.) in DCE (2 mL) was heated at 40° C. overnight. The reaction mixture was diluted with water and organic phase was dried over Na$_2$SO$_4$ and concentrated. The crude product 4-[(R)-{5-ethenyl-1-azabicyclo[2.2.2]octan-2-yl}(hydroxy)methyl]quinolin-6-yl trifluoromethanesulfonate as a brown oil was used in consecutive step without further purification (UPLC purity: 71%).

Example 9

{5-Ethenyl-1-azabicyclo[2.2.2]octan-2-yl}(6-{1H-pyrrolo[2,3-b]pyridin-3-yl}quinolin-4-yl)methanol

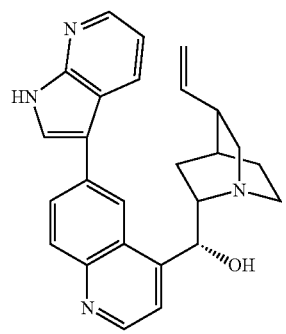 [SMILES: C=CC1CN2CCC1CC2[C@H](O)c1ccnc2ccc(-c3c[nH]c4ncccc34)cc12]

The title compound was prepared according to General Procedure 2 with 4-[R)-{5-ethenyl-1-azabicyclo[2.2.2]octan-2-yl}(hydroxy)methyl]quinolin-6-yl trifluoromethanesulfonate (Intermediate 16) (0.09 g, 0.2 mmol, 1.0 eq.), {1H-pyrrolo[2,3-b]pyridin-3-yl}boronic acid (Intermediate 14) (0.28 g, 1.1 mmol, 5.5 eq.), K₂CO₃ (0.08 g, 0.6 mmol, 3.0 eq.), Pd(dppf)₂Cl₂*CH₂Cl₂ (0.03 g, 0.04 mmol, 0.2 eq.) in a mixture of 1,4-dioxane/water 3/1 (4 mL). HPLC purification afforded {5-ethenyl-1-azabicyclo[2.2.2]octan-2-yl}(6-{1H-pyrrolo[2,3-b]pyridin-3-yl}quinolin-4-yl)methanol as a brownish solid (0.007 g; yield: 8%; HPLC purity: 87%).

Intermediate 17

6-Bromo-N-(1-methylpiperidin-4-yl)quinoline-4-amine

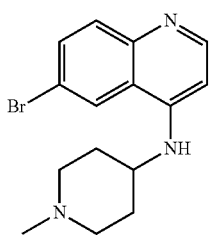 [SMILES: CN1CCC(Nc2ccnc3ccc(Br)cc23)CC1]

The title compound was prepared according to General Procedure 4 with 6-bromo-4-chloroquinoline (0.4 g, 1.6 mmol, 1.0 eq.), 1-methyl-4-piperidylamine (0.75 g, 6.6 mmol, 4.0 eq.), DIPEA (0.85 g, 6.6 mmol, 4.0 eq.) in i-PrOH (4 mL). The reaction mixture was heated at 150° C. under microwave irradiation for 16 h and then heating was continued in an oil bath for 48 h at 120° C. The crude reaction mixture was purified by FCC to provide 6-bromo-N-(1-methylpiperidin-4-yl)quinoline-4-amine (0.36 g; yield: 68%; UPLC purity: 95%).

Intermediate 18

6-[1-(4-Methylbenzenesulfonyl)-1H-pyrrolo[2,3-b]pyridine-3-yl]-N-(1-methylpiperidin-4-yl)quinolin-4-amine

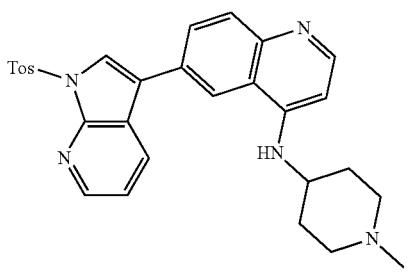

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.47 g, 1.5 mmol, 2.0 eq.), 6-bromo-N-(1-methylpiperidin-4-yl)quinolin-4-amine (Intermediate 17) (0.25 g, 0.7 mmol, 1.0 eq.), K₂CO₃ (0.2 g, 1.5 mmol, 2.0 eq.), Pd(dppf)₂Cl₂*CH₂Cl₂ (0.06 g, 0.07 mmol, 0.1 eq.) in a mixture of 1,4-dioxane/water 2/1 (4.5 mL) and heated at 80° C. for 3 h. The residue was purified by FCC (MeOH gradient in CH₂Cl₂) to provide 6-[1-(4-methylbenzenesulfonyl)-1H-pyrrolo[2,3-b]pyridin-3-yl]-N-(1-methylpiperidin-4-yl)quinolin-4-amine (0.06 g; yield: 14%; UPLC purity: 94%).

Example 10

N-(1-Methylpiperidin-4-yl)-6-{1H-pyrrolo[2,3-b]pyridin-3-yl}quinolin-4-amine

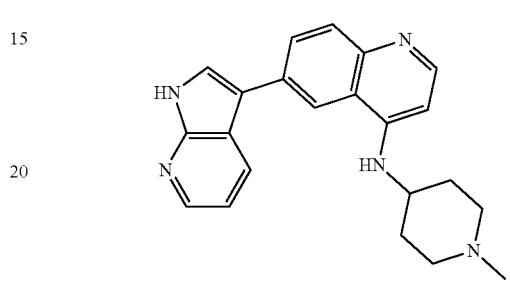

The title compound was prepared according to General Procedure 3 with 6-[1-(4-methylbenzenesulfonyl)-1H-pyrrolo[2,3-b]pyridin-3-yl]-N-(1-methylpiperidin-4-yl)quinolin-4-amine (Intermediate 18) (0.06 g, 0.12 mmol, 1.0 eq.), NaOtBu (0.05 g, 0.2 mmol, 1.5 eq.) dissolved in 1,4-dioxane (2.0 mL). The reaction mixture was stirred at rt for 12 h. The crude reaction mixture was purified by flash column chromatography to give N-(1-methylpiperidin-4-yl)-6-{1H-pyrrolo[2,3-b]pyridin-3-yl}quinolin-4-amine as an yellow solid (0.009 g; yield: 21%; HPLC purity: 92%).

Intermediate 19

8-Chloro-6-[1-(4-methylbenzenesulfonyl)-1H-pyrrolo[2,3-b]pyridine-3-yl]quinoline

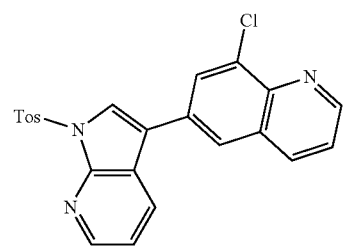

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.18 g, 0.4 mmol, 1.0 eq.), 6-bromo-8-chloroquinoline (0.1 g, 0.4 mmol, 1.1 eq.), K₂CO₃ (0.15 g, 1.0 mmol, 2.7 eq.), Pd(PPh₃)₄ (0.01 g, 0.01 mmol, 0.03 eq.) in a mixture of 1,4-dioxane/water 2/1 (1.5 mL). The reaction mixture was heated at 80° C. for 3 h. The residue was purified by FCC (EtOAc gradient in hexane) to provide 8-chloro-6-[1-(4-methylbenzenesulfonyl)-1H-pyrrolo[2,3-b]pyridin-3-yl]quinoline as a white solid (0.04 g; yield: 23%; UPLC purity: 98%).

Example 11

8-Chloro-6-{1H-pyrrolo[2,3-b]pyridin-3-yl}quinoline hydrochloride

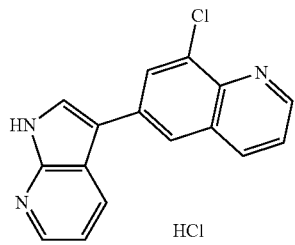 [SMILES: Clc1cc(-c2c[nH]c3ncccc23)cc2cccnc12 ; Cl]

The title compound was prepared according to General Procedure 3 with 8-chloro-6-[1-(4-methylbenzenesulfonyl)-1H-pyrrolo[2,3-b]pyridin-3-yl]quinoline (Intermediate 19) (0.04 g, 0.1 mmol, 1.0 eq.), ceasium carbonate (0.12 g, 0.4 mmol, 4.0 eq.) in a THF (1 mL). The reaction mixture was heated at reflux for 48 h. Obtained product was purified by HPLC and converted into HCl salt via dissolution of the product in MeOH (1 mL) and adding 4 M HCl in 1,4-dioxane. The precipitate was collected by filtration to provide 8-chloro-6-{1H-pyrrolo[2,3-b]pyridin-3-yl}quinoline hydrochloride as an yellow solid (0.004 g; yield: 13%; HPLC purity: 96%).

Intermediate 20

8-Methyl-6-[1-(4-methylbenzenesulfonyl)-1H-pyrrolo[2,3-b]pyridin-3-yl]quinoline

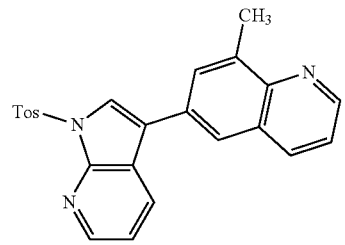

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.3 g, 0.7 mmol, 1.1 eq.), 6-bromo-8-methylquinoline (0.12 g, 0.7 mmol, 1.0 eq.), $K_2CO_3$ (0.25 g, 1.8 mmol, 2.7 eq.), $Pd(PPh_3)_4$ (0.06 g, 0.005 mmol, 0.03 eq.) in a mixture of 1,4-dioxane/water 2/1 (6 mL). The residue was purified by FCC (EtOAc gradient in hexane) to provide 8-methyl-6-[1-(4-methylbenzenesulfonyl)-1H-pyrrolo[2,3-b]pyridin-3-yl]quinoline as a white solid (0.12 g; yield: 43%; UPLC purity: 88%).

Example 12

8-Methyl-6-{1H-pyrrolo[2,3-b]pyridin-3-yl}quinoline hydrochloride

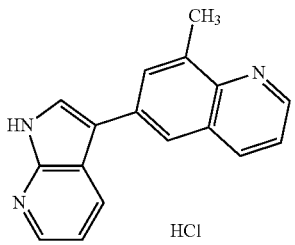 [SMILES: Cc1cc(-c2c[nH]c3ncccc23)cc2cccnc12 ; Cl]

The title compound was prepared according to General Procedure 3 with 8-methyl-6-[1-(4-methylbenzenesulfonyl)-1H-pyrrolo[2,3-b]pyridin-3-yl]quinoline (Intermediate 20) (0.12 g, 0.3 mmol, 1.0 eq.), NaOtBu (0.04 g, 0.4 mmol, 1.5 eq.) dissolved in 1,4-dioxane (3.5 mL). The reaction mixture was heated at 80° C. overnight. Obtained product was purified by FCC and converted into HCl salt via dissolution of product in MeOH (1 mL) and adding 4 M HCl in 1,4-dioxane (4 mL). The precipitate was collected by filtration to provide 8-methyl-6-{1H-pyrrolo[2,3-b]pyridin-3-yl}quinoline hydrochloride as a white solid (0.01 g; yield: 13%; HPLC purity: 97%).

Intermediate 21

8-Fluoro-6-[1-(4-methylbenzenesulfonyl)-1H-pyrrolo[2,3-b]pyridin-3-yl]quinoline

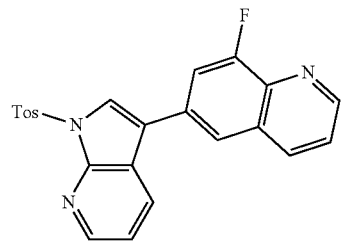

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.3 g, 0.7 mmol, 1.0 eq.), 6-bromo-8-fluoroquinoline (0.17 g, 0.7 mmol, 1.0 eq.), $K_2CO_3$ (0.28 g, 2.0 mmol, 2.7 eq.), $Pd(PPh_3)_4$ (0.03 g, 0.02 mmol, 0.03 eq.) in a mixture of 1,4-dioxane/water 2/1 (7.5 mL). The residue was purified by FCC (EtOAc gradient in hexane) to provide 8-fluoro-6-[1-(4-methylbenzenesulfonyl)-1H-pyrrolo[2,3-b]pyridin-3-yl]quinoline as a white solid (0.14 g; yield: 45%; UPLC purity: 96%).

Example 13

8-Fluoro-6-{1H-pyrrolo[2,3-b]pyridin-3-yl}quinoline

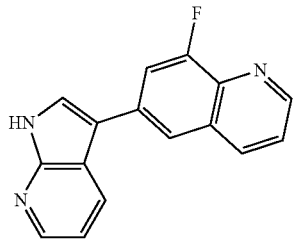 [SMILES: Fc1cc(-c2c[nH]c3ncccc23)cc2cccnc12]

The title compound was prepared according to General Procedure 3 with 8-fluoro-6-[1-(4-methylbenzenesulfonyl)-1H-pyrrolo[2,3-b]pyridin-3-yl]quinoline (Intermediate 21) (0.08 g, 0.2 mmol, 1.0 eq.), NaOtBu (0.03 g, 0.3 mmol, 1.5 eq.) dissolved in 1,4-dioxane (3.0 mL). Purification by FCC (EtOAc gradient in hexane) provided 8-fluoro-6-{1H-pyrrolo[2,3-b]pyridin-3-yl}quinoline as a white solid (0.02 g; yield: 36%; HPLC purity: 100%).

Example 14

6-{1H-Pyrrolo[2,3-b]pyridin-3-yl}-8-(trifluoromethoxy)quinoline

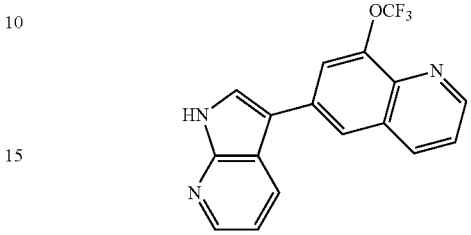

The title compound was prepared according to General Procedure 3 with 6-[1-(4-methylbenzenesulfonyl)-1H-pyrrolo[2,3-b]pyridin-3-yl]-8-(trifluoromethoxy)quinoline (Intermediate 22) (0.06 g, 0.1 mmol, 1.0 eq.), NaOtBu (0.02 g, 0.2 mmol, 1.5 eq.) dissolved in 1,4-dioxane (3 mL). Purification by FCC (EtOAc gradient in hexane) provided 6-{1H-pyrrolo[2,3-b]pyridin-3-yl}-8-(trifluoromethoxy)quinoline as a white solid (0.05 g; yield: 11%; HPLC purity: 96%).

Intermediate 22

6-[1-(4-Methylbenzenesulfonyl)-1H-pyrrolo[2,3-b]pyridin-3-yl]-8-(trifluoromethoxy)quinoline

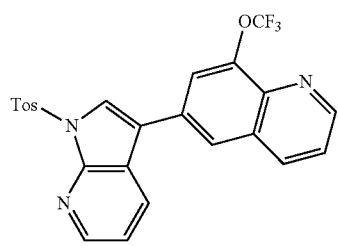

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.1 g, 0.3 mmol, 1.0 eq.), 6-bromo-8-trifluoromethoxyquinoline (0.07 g, 0.3 mmol, 1.0 eq.), $K_2CO_3$ (0.09 g, 0.7 mmol, 2.7 eq.), $Pd(PPh_3)_4$ (0.08 g, 0.01 mmol, 0.03 eq.) in a mixture of 1,4-dioxane/water 2/1 (7.5 mL). The residue was purified by FCC (EtOAc gradient in hexane) to provide 6-[1-(4-methylbenzenesulfonyl)-1H-pyrrolo[2,3-b]pyridin-3-yl]-8-(trifluoromethoxy)quinoline as a white solid (0.06 g; yield: 55%; UPLC purity: 99%).

Intermediate 23

8-Methoxy-6-[1-(4-methylbenzenesulfonyl)-1H-pyrrolo[2,3-b]pyridin-3-yl]quinoline

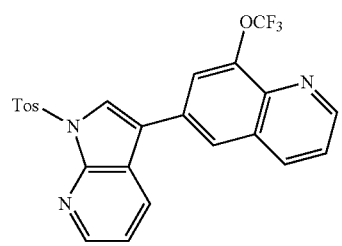

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.17 g, 0.4 mmol, 1.0 eq.), 6-bromo-8-methoxyquinoline (0.08 g, 0.4 mmol, 1.0 eq.), $K_2CO_3$ (0.16 g, 1.1 mmol, 2.7 eq.), $Pd(dppf)_2Cl_2*CH_2Cl_2$ (0.01 g, 0.01 mmol, 0.03 eq.) in a mixture of 1,4-dioxane/water 2/1 (4.5 mL). The residue was purified by FCC (EtOAc gradient in hexane; column neutralized with 0.1% $Et_3N$ in $CH_2Cl_2$ then washed with $CH_2Cl_2$ before purification) to provide 8-methoxy-6-[1-(4-methylbenzenesulfonyl)-1H-pyrrolo[2,3-b]pyridin-3-yl]quinoline as a dark orange solid (0.13 g; yield: 70%; UPLC purity: 99%).

Example 15

8-Methoxy-6-{1H-pyrrolo[2,3-b]pyridin-3-yl}quinoline

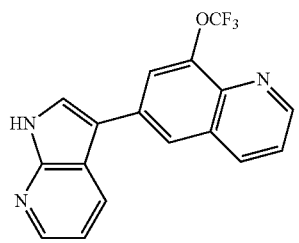 [SMILES: FC(F)(F)Oc1cc(-c2c[nH]c3ncccc23)cc2cccnc12]

The title compound was prepared according to General Procedure 3 with 8-methoxy-6-[1-(4-methylbenzenesulfonyl)-1H-pyrrolo[2,3-b]pyridin-3-yl]quinoline (Intermediate 23) (0.13 g, 0.3 mmol, 1.0 eq.), NaOtBu (0.05 g, 0.5 mmol, 1.7 eq.) dissolved in 1,4-dioxane (3 mL). Purification by FCC (EtOAc gradient in hexane; column neutralized with 0.1% Et$_3$N in CH$_2$Cl$_2$ then washed with CH$_2$Cl$_2$ before purification) provided 8-methoxy-6-{1H-pyrrolo[2,3-b]pyridin-3-yl}quinoline as an yellow solid (0.03 g; yield: 31%; HPLC purity: 98%).

Intermediate 24

6-(tetramethyl-1,3,2-dioxaborolan-2-yl)quinolin-3-amine; (3-aminoquinolin-6-yl)boronic acid

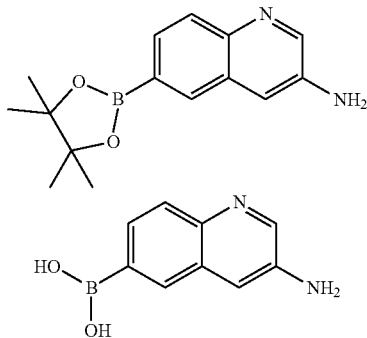

The title compound was prepared according to General Procedure 1 with 6-bromoquinoline-3-amine (0.3 g, 1.3 mmol, 1.0 eq.), bis(pinacolato)diboron (0.4 g, 1.5 mmol, 1.1 eq.), potassium acetate (0.26 g, 2.7 mmol, 2.0 eq.), Pd(dppf)$_2$Cl$_2$*CH$_2$Cl$_2$ (0.05 g, 0.07 mmol, 0.05 eq.) and 1,4-dioxane (2 mL). The reaction mixture was heated at 80° C. for 5 h. The residue was purified by FCC (EtOAc gradient in hexane) to provide an inseparable mixture of products 1:1 boronic ester/acid-6-(tetramethyl-1,3,2-dioxaborolan-2-yl)quinolin-3-amine/(3-aminoquinolin-6-yl)boronic acid which were used in consecutive step without separation (UPLC purity: 77%).

Intermediate 25

6-[1-(4-Methylbenzenesulfonyl)-1H-pyrrolo[2,3-b]pyridin-3-yl]quinolin-3-amine

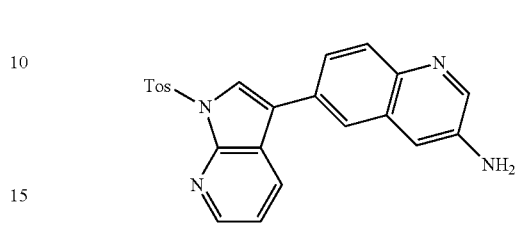

The title compound was prepared according to General Procedure 2 with 3-bromo-1-(4-methylbenzenesulfonyl)-1H-pyrrolo[2,3-b]pyridine (Intermediate 1b) (0.26 g, 0.7 mmol, 1.0 eq.), 6-(tetramethyl-1,3,2-dioxaborolan-2-yl)quinolin-3-amine/(3-aminoquinolin-6-yl)boronic acid (Intermediate 24) (0.26 g, 0.9 mmol, 1.3 eq.), K$_2$CO$_3$ (0.2 g, 1.4 mmol, 2.0 eq.), Pd(dppf)$_2$Cl$_2$*CH$_2$Cl$_2$ (0.12 g, 0.15 mmol, 0.2 eq.) in a mixture of 1,4-dioxane/water 2/1 (6 mL). The residue was purified by FCC (EtOAc gradient in hexane) to provide 6-[1-(4-methylbenzenesulfonyl)-1H-pyrrolo[2,3-b]pyridin-3-yl]quinolin-3-amine (0.16 g; yield: 53%; UPLC purity: 72%).

Intermediate 26. General Procedure 6

N-(Furan-3-ylmethyl)-6-[1-(4-methylbenzenesulfonyl)-1H-pyrrolo[2,3-b]pyridin-3-yl]quinolin-3-amine

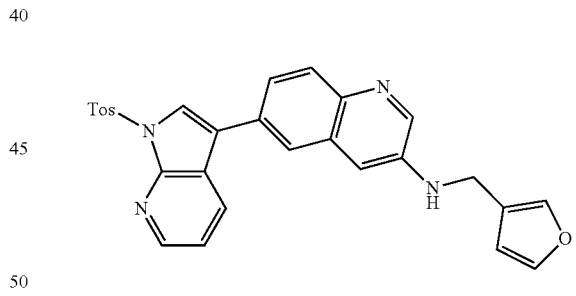

A solution of 6-[1-(4-methylbenzenesulfonyl)-1H-pyrrolo[2,3-b]pyridin-3-yl]quinolin-3-amine (Intermediate 25) (0.16 g, 0.4 mmol, 1.0 eq.), furan-3-carbaldehyde (0.09 g, 1.0 mmol, 2.5 eq.), catalytic amount of AcOH (0.2 mL) in MeOH (2 mL) was stirred at rt for 30 min. Then sodium cyanoborohydride (0.05 g, 0.8 mmol, 2.0 eq.) was added and stirring was continued overnight. The reaction mixture was diluted with water and EtOAc. The aqueous layer was extracted with EtOAc and the combined organic layers were dried over Na$_2$SO$_4$, filtered and concentrated. The residue was purified by FCC (EtOAc gradient in hexane) to provide N-(furan-3-ylmethyl)-6-[1-(4-methylbenzenesulfonyl)-1H-pyrrolo[2,3-b]pyridin-3-yl]quinolin-3-amine (0.06 g; yield: 25%; UPLC purity: 97%).

Example 16

N-(Furan-3-ylmethyl)-6-{1H-pyrrolo[2,3-b]pyridin-3-yl}quinolin-3-amine

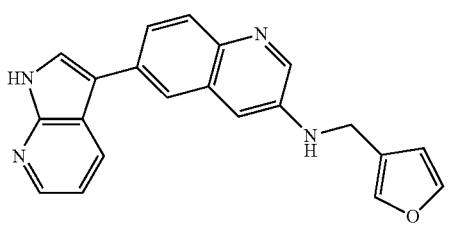 [SMILES: c1cnc2[nH]cc(-c3ccc4ncc(NCc5ccoc5)cc4c3)c2c1]

The title compound was prepared according to General Procedure 3 with N-(furan-3-ylmethyl)-6-[1-(4-methylbenzenesulfonyl)-1H-pyrrolo[2,3-b]pyridin-3-yl]quinolin-3-amine (Intermediate 26) (0.06 g, 0.1 mmol, 1.0 eq.), NaOtBu (0.02 g, 0.2 mmol, 1.5 eq.) dissolved in 1,4-dioxane (2 mL). The reaction mixture was stirred at rt overnight. Purification by FCC (EtOAc gradient in hexane) provided N-(furan-3-ylmethyl)-6-{1H-pyrrolo[2,3-b]pyridin-3-yl}quinolin-3-amine as a beige solid (0.01 g; yield: 33%; HPLC purity: 95%).

Intermediate 27

4-Chloro-8-methyl-6-[1-(4-methylbenzenesulfonyl)-1H-pyrrolo[2,3-b]pyridin-3-yl]quinoline

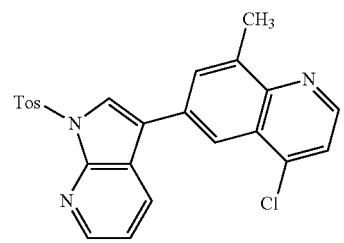

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (0.5 g, 1.3 mmol, 1.1 eq.), 6-bromo-4-chloro-8-methylquinoline (0.3 g, 1.2 mmol, 1.0 eq.), $K_2CO_3$ (0.4 g, 3.2 mmol, 2.7 eq.), Pd(PPh$_3$)$_4$ (0.1 g, 0.1 mmol, 0.03 eq.) in a mixture of 1,4-dioxane/water 2/1 (10 mL). The residue was purified by FCC (EtOAc gradient in hexane) to provide 4-chloro-8-methyl-6-[1-(4-methylbenzenesulfonyl)-1H-pyrrolo[2,3-b]pyridin-3-yl]quinoline (0.12 g; yield: 22%; UPLC purity: 96%).

Intermediate 28

8-Methyl-6-[1-(4-methylbenzenesulfonyl)-1H-pyrrolo[2,3-b]pyridin-3-yl]-4-phenylquinoline

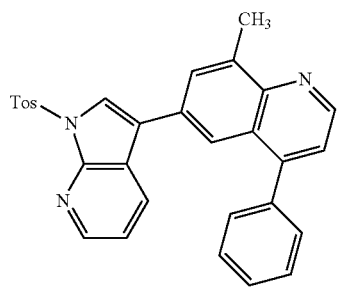

The title compound was prepared according to General Procedure 6 with 4-chloro-8-methyl-6-[1-(4-methylbenzenesulfonyl)-1H-pyrrolo[2,3-b]pyridin-3-yl]quinoline (Intermediate 27) (0.11 g, 0.3 mmol, 1.0 eq.), phenylboronic acid (0.03 g, 0.3 mmol, 1.0 eq.), $K_2CO_3$ (0.1 g, 0.7 mmol, 2.7 eq.), Pd(PPh$_3$)$_4$ (0.02 g, 0.02 mmol, 0.03 eq.) in a mixture of 1,4-dioxane/water 2/1 (3 mL). The residue was purified by FCC (EtOAc gradient in hexane) to provide 8-methyl-6-[1-(4-methylbenzenesulfonyl)-1H-pyrrolo[2,3-b]pyridin-3-yl]-4-phenylquinoline (0.12 g; yield: 97%; UPLC purity: 100%).

Example 17

8-Methyl-4-phenyl-6-{1H-pyrrolo[2,3-b]pyridin-3-yl}quinoline

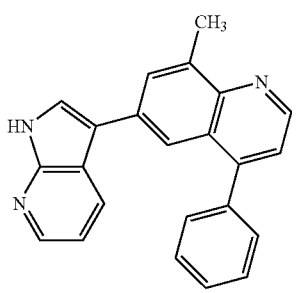 [SMILES: Cc1cc(-c2c[nH]c3ncccc23)cc2c(-c3ccccc3)ccnc12]

The title compound was prepared according to General Procedure 3 with 8-methyl-6-[1-(4-methylbenzenesulfonyl)-1H-pyrrolo[2,3-b]pyridin-3-yl]-4-phenylquinoline (Intermediate 28) (0.12 g, 0.3 mmol, 1.0 eq.), NaOtBu (0.04 g, 0.4 mmol, 1.5 eq.) dissolved in 1,4-dioxane (3.5 mL). The reaction mixture was stirred at rt overnight. Purification by FCC (EtOAc gradient in hexane; column neutralized with 0.1% Et$_3$N in CH$_2$Cl$_2$ then washed with CH$_2$Cl$_2$ before purification) provided 8-methyl-4-phenyl-6-{1H-pyrrolo[2,3-b]pyridin-3-yl}quinoline (0.05 g; yield: 58%; HPLC purity: 100%).

Intermediate 29

8-Methyl-6-[1-(4-methylbenzenesulfonyl)-1H-pyrrolo[2,3-b]pyridin-3-yl]-4-(pyridin-3-yl)quinoline

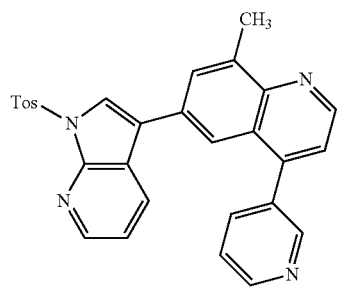

The title compound was prepared according to General Procedure 2 with 4-chloro-8-methyl-6-[1-(4-methylbenzenesulfonyl)-1H-pyrrolo[2,3-b]pyridin-3-yl]quinoline (Intermediate 27) (0.13 g, 0.3 mmol, 1.0 eq.), 3-pyridyl boronic acid (0.05 g, 0.4 mmol, 1.5 eq.), $K_2CO_3$ (0.08 g, 0.6 mmol, 2.0 eq.), Pd(dppf$_2$)Cl$_2$ (0.04 g, 0.1 mmol, 0.2 eq.) in a mixture of 1,4-dioxane/water 2/1 (2 mL). After work up crude 8-methyl-6-[1-(4-methylbenzenesulfonyl)-1H-pyrrolo[2,3-b]pyridin-3-yl]-4-(pyridin-3-yl)quinoline was used in consecutive step without further purification (UPLC purity: 89%).

Example 18

8-Methyl-4-(pyridin-3-yl)-6-{1H-pyrrolo[2,3-b]pyridin-3-yl}quinoline

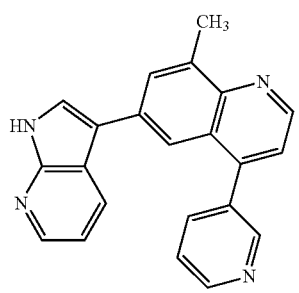 [SMILES: Cc1cc(-c2c[nH]c3ncccc23)cc2c(-c3cccnc3)ccnc12]

The title compound was prepared according to General Procedure 3 with 8-methyl-6-[1-(4-methylbenzenesulfonyl)-1H-pyrrolo[2,3-b]pyridin-3-yl]-4-(pyridin-3-yl)quinoline (Intermediate 29) (0.13 g, 0.3 mmol, 1.0 eq.), NaOtBu (0.04 g, 0.4 mmol, 1.5 eq.) dissolved in 1,4-dioxane (3.5 mL). The reaction mixture was stirred at rt for 3 h. Purification by FCC (MeOH gradient in CH$_2$Cl$_2$; column neutralized with 0.1% Et$_3$N in CH$_2$Cl$_2$ then washed with CH$_2$Cl$_2$ before purification) provided 8-methyl-4-(pyridin-3-yl)-6-{1H-pyrrolo[2,3-b]pyridin-3-yl}quinoline (0.02 g; yield: 14%; HPLC purity: 94%).

Intermediate 30

4-Chloro-8-fluoro-6-[1-(4-methylbenzenesulfonyl)-1H-pyrrolo[2,3-b]pyridin-3-yl]quinoline

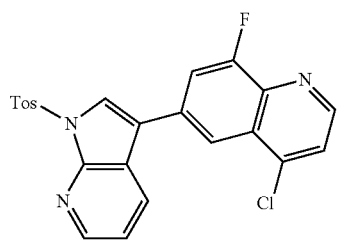

The title compound was prepared according to General Procedure 2 with 1-(4-methylbenzenesulfonyl)-3-(tetramethyl-1,3,2-dioxaborolan-2-yl)-1H-pyrrolo[2,3-b]pyridine (Intermediate 1) (1.0 g, 2.5 mmol, 1.2 eq.), 6-bromo-4-chloro-8-fluoroquinoline (0.5 g, 2.1 mmol, 1.0 eq.), $K_2CO_3$ (0.8 g, 6.3 mmol, 3.0 eq.), Pd(dppf$_2$)Cl$_2$*CH$_2$Cl$_2$ (0.3 g, 0.4 mmol, 0.2 eq.) in a mixture of 1,4-dioxane/water 2/1 (4 mL). The reaction mixture was stirred at 80° C. for 4 h. Purification by FCC (EtOAc gradient in hexane; column neutralized with 0.1% Et$_3$N in CH$_2$Cl$_2$ then washed with CH$_2$Cl$_2$ before purification) provided 4-chloro-8-fluoro-6-[1-(4-methylbenzenesulfonyl)-1H-pyrrolo[2,3-b]pyridin-3-yl]quinoline (0.29 g; yield: 31%; UPLC purity: 66%).

Intermediate 31

8-Fluoro-6-[1-(4-methylbenzenesulfonyl)-1H-pyrrolo[2,3-b]pyridin-3-yl]-4-(pyridin-3-yl)quinoline

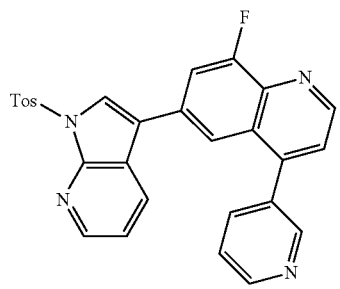

The title compound was prepared according to General Procedure 2 with 4-chloro-8-fluoro-6-[1-(4-methylbenzenesulfonyl)-1H-pyrrolo[2,3-b]pyridin-3-yl]quinoline (Intermediate 30) (0.18 g, 0.4 mmol, 1.0 eq.), 3-pyridyl boronic acid (0.06 g, 0.5 mmol, 1.2 eq.), $K_2CO_3$ (0.16 g, 1.2 mmol, 3.0 eq.), Pd(PPh$_3$)$_4$ (0.02 g, 0.02 mmol, 0.05 eq.) in a mixture of 1,4-dioxane/water 2/1 (3 mL). After work up the residue was purify by FCC (MeOH gradient in CH$_2$Cl$_2$; column neutralized with 0.1% Et$_3$N in CH$_2$Cl$_2$ then washed with CH$_2$Cl$_2$ before purification) to provide 8-fluoro-6-[1-(4-methylbenzenesulfonyl)-1H-pyrrolo[2,3-b]pyridin-3-yl]-4-(pyridin-3-yl)quinoline (0.17 g; yield: 73%; UPLC purity: 94%).

Example 19

8-Fluoro-4-(pyridin-3-yl)-6-{1H-pyrrolo[2,3-b]pyridin-3-yl}quinoline

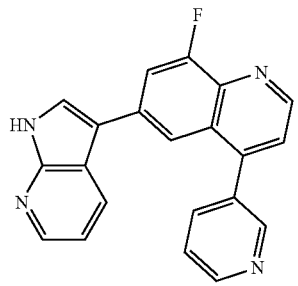 [SMILES: Fc1cc(-c2c[nH]c3ncccc23)cc2c(-c3cccnc3)ccnc12]

The title compound was prepared according to General Procedure 3 with 8-fluoro-6-[1-(4-methylbenzenesulfonyl)-1H-pyrrolo[2,3-b]pyridin-3-yl]-4-(pyridin-3-yl)quinoline (Intermediate 31) (0.17 g, 0.3 mmol, 1.0 eq.), NaOtBu (0.07 g, 0.7 mmol, 2.0 eq.) dissolved in 1,4-dioxane (10 mL). The reaction mixture was stirred at rt overnight. Purification by FCC (MeOH gradient in $CH_2Cl_2$; column neutralized with 0.1% $Et_3N$ in $CH_2Cl_2$ then washed with $CH_2Cl_2$ before purification) provided 8-fluoro-4-(pyridin-3-yl)-6-{1H-pyrrolo[2,3-b]pyridin-3-yl}quinoline (0.07 g; yield: 59%; HPLC purity: 98%).

Intermediate 32. General Procedure 7

3-Iodo-N-methyl-1-(4-methylbenzenesulfonyl)-N-(prop-2-en-1-yl)-1H-pyrrolo[2,3-b]pyridine-5-carboxamide

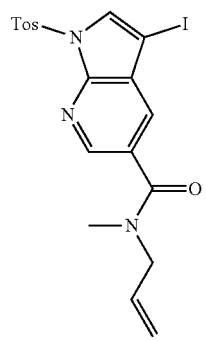

The 3-iodo-1-(4-methylbenzenesulfonyl)-1H-pyrrolo[2,3-b]pyridine-5-carboxylic acid (Intermediate 2) (1.0 g, 2.3 mmol, 1.0 eq.) was refluxed in $SOCl_2$ (5 mL) for 1 h. The resulted turbid solution was concentrated. The obtained solid was suspended in $CH_3CN$ (10 mL) and N-methylallyl amine (0.5 g, 6.8 mmol, 3.0 eq.) was added carefully. The reaction mixture was stirred at rt for 3 days and after that time concentrated to dryness. The residue was dissolved in EtOAc and washed with water. The organic layer was dried over $Na_2SO_4$ and concentrated. Purification by FCC (EtOAc gradient in hexane) provided 3-iodo-N-methyl-1-(4-methylbenzenesulfonyl)-N-(prop-2-en-1-yl)-1H-pyrrolo[2,3-b]pyridine-5-carboxamide as a light brown foam (0.63 g; yield: 56%; UPLC purity: 99%).

Intermediate 33

(4-Chloroquinolin-6-yl)boronic acid

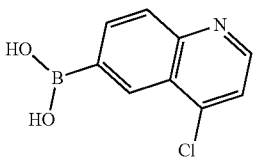

The title compound was prepared according to General Procedure 1 with 4-chloro-6-bromoquinoline (2.0 g, 8.3 mmol, 1.0 eq.), bis(pinacolato)diboron (2.3 g, 9.1 mmol, 1.1 eq.), potassium acetate (1.61 g, 16.5 mmol, 2.0 eq.), $Pd(dppf)_2Cl_2$ (0.3 g, 0.4 mmol, 0.05 eq.) and 1,4-dioxane (10 mL). The reaction mixture was heated at 80° C. overnight. The product (4-chloroquinolin-6-yl)boronic acid was used in consecutive step without further purification (UPLC purity: 78%).

Intermediate 34

3-(4-Chloroquinolin-6-yl)-N-methyl-1-(4-methylbenzenesulfonyl)-N-(prop-2-en-1-yl)-1H-pyrrolo[2,3-b]pyridine-5-carboxamide

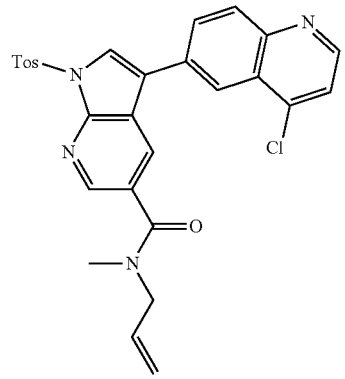

The title compound was prepared according to General Procedure 2 with 3-iodo-N-methyl-1-(4-methylbenzenesulfonyl)-N-(prop-2-en-1-yl)-1H-pyrrolo[2,3-b]pyridine-5-carboxamide (Intermediate 32) (0.4 g, 0.8 mmol, 1.0 eq.), (4-chloroquinolin-6-yl)boronic acid (Intermediate 33) (0.3 g, 1.1 mmol, 1.3 eq.), $K_2CO_3$ (0.22 g, 1.6 mmol, 2.0 eq.), $Pd(dppf)_2Cl_2*CH_2Cl_2$ (0.13 g, 0.02 mmol, 0.2 eq.) in a mixture of 1,4-dioxane/water 2/1 (6 mL). After work up the residue was purify by FCC (EtOAC) to provide 3-(4-chloroquinolin-6-yl)-N-methyl-1-(4-methylbenzenesulfonyl)-N-(prop-2-en-1-yl)-1H-pyrrolo[2,3-b]pyridine-5-carboxamide (0.28 g; yield: 66%; UPLC purity: 99%).

Example 20

3-(4-Chloroquinolin-6-yl)-N-methyl-N-(prop-2-en-1-yl)-1H-pyrrolo[2,3-b]pyridine-5-carboxamide

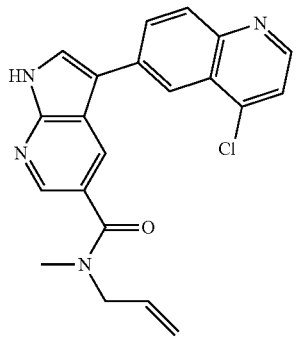 [SMILES: C=CCN(C)C(=O)c1cnc2[nH]cc(-c3ccc4nccc(Cl)c4c3)c2c1]

The title compound was prepared according to General Procedure 3 with 3-(4-chloroquinolin-6-yl)-N-methyl-1-(4-methylbenzenesulfonyl)-N-(prop-2-en-1-yl)-1H-pyrrolo[2,3-b]pyridine-5-carboxamide (Intermediate 34) (0.05 g, 0.09 mmol, 1.0 eq.), NaOtBu (0.014 g, 0.14 mmol, 1.5 eq.) dissolved in 1,4-dioxane (2 mL). The reaction mixture was stirred at rt for 4 h. Purification by FCC (MeOH gradient in CH$_2$Cl$_2$) provided 3-(4-chloroquinolin-6-yl)-N-methyl-N-(prop-2-en-1-yl)-1H-pyrrolo[2,3-b]pyridine-5-carboxamide (0.013 g; yield: 37%; HPLC purity: 91%).

Intermediate 35

3-(4-Chloroquinolin-6-yl)-1-(4-methylbenzenesulfonyl)-1H-pyrrolo[2,3-b]pyridine-5-carbaldehyde

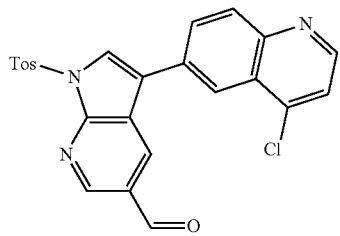

The title compound was prepared according to General Procedure 2 with 3-iodo-1-(4-methylbenzenesulfonyl)-1H-pyrrolo[2,3-b]pyridine-5-carbaldehyde (Intermediate 3) (0.8 g, 1.9 mmol, 1.0 eq.), (4-chloroquinolin-6-yl)boronic acid (Intermediate 33) (0.6 g, 2.1 mmol, 1.1 eq.), K$_2$CO$_3$ (0.77 g, 5.6 mmol, 3.0 eq.), Pd(dppf)$_2$Cl$_2$*CH$_2$Cl$_2$ (0.3 g, 0.4 mmol, 0.2 eq.) in a mixture of 1,4-dioxane/water 2/1 (16 mL). Purification by FCC (EtOAc gradient in hexane) provided 3-(4-chloroquinolin-6-yl)-1-(4-methylbenzenesulfonyl)-1H-pyrrolo[2,3-b]pyridine-5-carbaldehyde (0.53 g; yield: 62%; UPLC purity: 93%).

Intermediate 36. General Procedure 8

3-[4-(Pent-4-en-1-yl)quinolin-6-yl]-1H-pyrrolo[2,3-b]pyridine-5-carbaldehyde

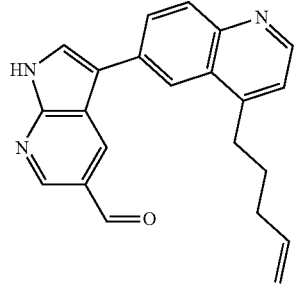 [SMILES: C=CCCCc1ccnc2ccc(-c3c[nH]c4ncc(C=O)cc34)cc12]

3-(4-Chloroquinolin-6-yl)-1-(4-methylbenzenesulfonyl)-1H-pyrrolo[2,3-b]pyridine-5-carbaldehyde (Intermediate 35) (0.2 g, 0.4 mmol, 1.0 eq.), potassium trifluoro(pent-4-en-1-yl)borate (0.1 g, 0.6 mmol, 1.5 eq.), Pd(OAc)$_2$ (0.002 g, 0.01 mmol, 0.02 eq.), RuPhos (0.08 g, 0.02 mmol, 0.04 eq.), and K$_2$CO$_3$ (0.18 g, 1.3 mmol, 3.0 eq.) in a mixture of toluene (5 mL) and water (0.5 mL) were placed in a sealed tube and the flask was evacuated and purged with argon twice. The reaction mixture was heated at 80° C. overnight. After cooling to rt solvents were evaporated. The crude reaction mixture was purified by FCC (EtOAc gradient in hexane) to provide 3-[4-(pent-4-en-1-yl)quinolin-6-yl]-1H-pyrrolo[2,3-b]pyridine-5-carbaldehyde as an yellow solid (0.058 g; yield: 36%; UPLC purity: 100%).

Example 21

Methyl({3-[4-(pent-4-en-1-yl)quinolin-6-yl]-1H-pyrrolo[2,3-b]pyridin-5-yl}methyl)(prop-2-en-1-yl)amine

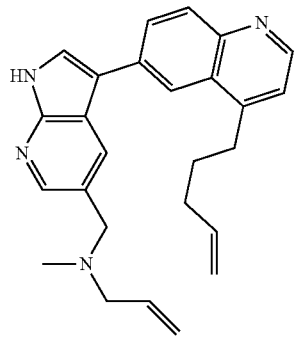 [SMILES: C=CCCCc1ccnc2ccc(-c3c[nH]c4ncc(CN(C)CC=C)cc34)cc12]

The title compound was prepared according to General Procedure 6 with 3-[4-(pent-4-en-1-yl)quinolin-6-yl]-1H-pyrrolo[2,3-b]pyridine-5-carbaldehyde (Intermediate 36) (0.05 g, 0.15 mmol, 1.0 eq.), N-methylallyl amine (0.02 g, 0.3 mmol, 2.0 eq.), Na(OAc)$_3$BH (0.08 g, 0.4 mmol, 2.5 eq.) in CH$_2$Cl$_2$ (5 mL). The reaction mixture was stirred at rt overnight and then diluted with water and EtOAc. The aqueous layer was extracted with EtOAc and the combined organic layers were dried over Na$_2$SO$_4$, filtered and concentrated. The residue was purified by FCC (EtOAc gradient in hexane) to provide methyl({3-[4-(pent-4-en-1-yl)quinolin-6-yl]-1H-pyrrolo[2,3-b]pyridin-5-yl}methyl)(prop-2-en-1-yl)amine (0.06 g; yield: 25%; HPLC purity: 98%).

Intermediate 37

3-Iodo-N-methyl-1-(4-methylbenzenesulfonyl)-1H-pyrrolo[2,3-b]pyridine-5-carboxamide

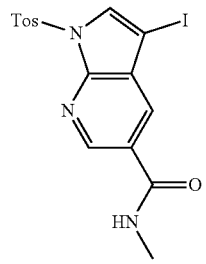

The title compound was prepared according to General Procedure 7 with 3-iodo-1-(4-methylbenzenesulfonyl)-1H-pyrrolo[2,3-b]pyridine-5-carboxylic acid (Intermediate 2) (2.0 g, 4.5 mmol, 1.0 eq.) and SOCl$_2$ (15 mL). Then methyl amine 40% aqueous solution (3 mL) was added and the reaction mixture was stirred at rt for 1 h, then diluted with water and aqueous solution of NaHCO$_3$. The precipitate was collected by filtration, rinsed with water and dried on air to give 3-iodo-N-methyl-1-(4-methylbenzenesulfonyl)-1H-pyrrolo[2,3-b]pyridine-5-carboxamide as a solid (1.7 g; yield: 83%; UPLC purity: 100%).

Intermediate 38

3-(4-Chloroquinolin-6-yl)-N-methyl-1-(4-methylbenzenesulfonyl)-1H-pyrrolo[2,3-b]pyridine-5-carboxamide

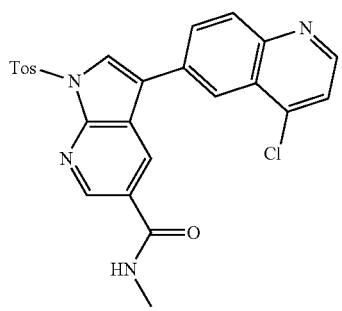

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.18 g, 0.4 mmol, 1.0 eq.), (4-chloroquinolin-6-yl)boronic acid (Intermediate 33) (0.13 g, 0.44 mmol, 1.1 eq.), K$_2$CO$_3$ (0.16 g, 1.2 mmol, 3.0 eq.), Pd(dppf)$_2$Cl$_2$*CH$_2$Cl$_2$ (0.06 g, 0.08 mmol, 0.2 eq.) in a mixture of 1,4-dioxane/water 2/1 (16 mL). Purification by FCC (MeOH gradient in CH$_2$Cl$_2$) provided 3-(4-chloroquinolin-6-yl)-N-methyl-1-(4-methylbenzenesulfonyl)-1H-pyrrolo[2,3-b]pyridine-5-carboxamide as a light brown foam (0.13 g; yield: 69%; UPLC purity: 93%).

Intermediate 39

N-Methyl-1-(4-methylbenzenesulfonyl)-3-[4-(pyridin-3-yl)quinolin-6-yl]-1H-pyrrolo[2,3-b]pyridine-5-carboxamide

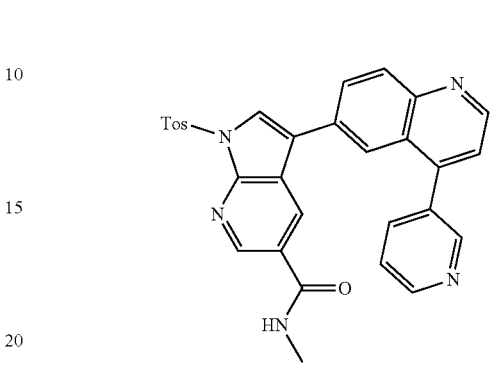

The title compound was prepared according to General Procedure 2 with 3-(4-chloroquinolin-6-yl)-N-methyl-1-(4-methylbenzenesulfonyl)-1H-pyrrolo[2,3-b]pyridine-5-carboxamide (Intermediate 38) (0.13 g, 0.3 mmol, 1.0 eq.), 3-pyridyl boronic acid (0.03 g, 0.3 mmol, 1.0 eq.), K$_2$CO$_3$ (0.11 g, 0.8 mmol, 3.0 eq.), Pd(PPh$_3$)$_4$ (0.02 g, 0.01 mmol, 0.05 eq.) in a mixture of 1,4-dioxane/water 2/1 (4 mL). After work up the residue was purify by FCC (MeOH gradient in CH$_2$Cl$_2$) to provide N-methyl-1-(4-methylbenzenesulfonyl)-3-[4-(pyridin-3-yl)quinolin-6-yl]-1H-pyrrolo[2,3-b]pyridine-5-carboxamide (0.07 g; yield: 48%; UPLC purity: 95%).

Example 22

N-Methyl-3-[4-(pyridin-3-yl)quinolin-6-yl]-1H-pyrrolo[2,3-b]pyridine-5-carboxamide

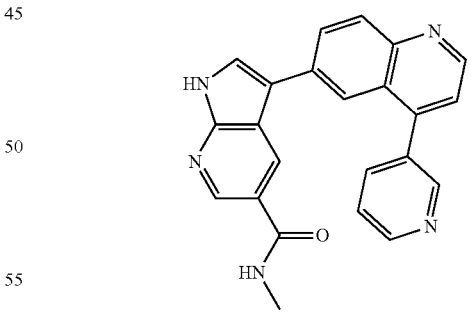

The title compound was prepared according to General Procedure 3 with N-methyl-1-(4-methylbenzenesulfonyl)-3-[4-(pyridin-3-yl)quinolin-6-yl]-1H-pyrrolo[2,3-b]pyridine-5-carboxamide (Intermediate 39) (0.07 g, 0.01 mmol, 1.0 eq.), NaOtBu (0.03 g, 0.3 mmol, 2.3 eq.) in 1,4-dioxane (5 mL). The reaction mixture was stirred at 80° C. for 3 h. Purification by HPLC provided N-methyl-3-[4-(pyridin-3-yl)quinolin-6-yl]-1H-pyrrolo[2,3-b]pyridine-5-carboxamide (0.013 g; yield: 26%; HPLC purity: 96%).

Intermediate 40

6-Bromo-4-(morpholin-4-yl)quinoline

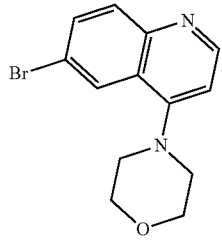 [SMILES: Brc1ccc2nccc(N3CCOCC3)c2c1]

The title compound was prepared according to General Procedure 4 with 6-bromo-4-chloro)quinoline (3.0 g, 12.4 mmol, 1.0 eq.), morpholine (3.0 g, 34.5 mmol, 3.0 eq.), DIPEA (4.56 g, 35.3 mmol, 3.0 eq.) in i-PrOH (30 mL). The reaction mixture was stirred at 80° C. overnight and then additional 3.0 eq. of morpholine were added and heating was continued at 100° C. for next 48 h. The reaction mixture was diluted with $CH_2Cl_2$ and water and aqueous layer was washed with $CH_2Cl_2$. The combined organic layers were washed with brine, dried under $Na_2SO_4$ and concentrated to give 6-bromo-4-(morpholin-4-yl)quinoline as a light brown solid (UPLC purity: 99%).

Intermediate 41

[4-(Morpholin-4-yl)quinolin-6-yl]boronic acid

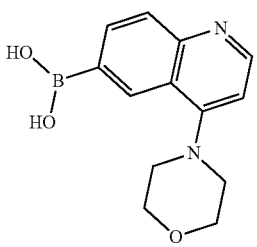 [SMILES: OB(O)c1ccc2nccc(N3CCOCC3)c2c1]

The title compound was prepared according to General Procedure 1 with 6-bromo-4-(morpholin-4-yl)quinoline (Intermediate 40) (3.7 g, 12.5 mmol, 1.0 eq.), bis(pinacolato)diboron (4.76 g, 18.7 mmol, 1.5 eq.), $K_3PO_4$ (3.7 g, 37.5 mmol, 1.4 eq.), $Pd(dppf)_2Cl_2*CH_2Cl_2$ (0.4 g, 0.5 mmol, 0.04 eq.) and 1,4-dioxane (20 mL). The reaction mixture was stirred at 80° C. for 3 h, then additional 2.0 eq. of bis(pinacolato)diboron and 0.08 eq. of $Pd(dppf)_2Cl_2*CH_2Cl_2$ were added and heating was continued at 80° C. for next 12 h. The reaction mixture was diluted with EtOAC and filtered through a pad of Celite. After concentration the residue was purified by FCC (EtOAc gradient in hexane) to provide [4-(morpholin-4-yl)quinolin-6-yl]boronic acid as a beige solid (2.43 g; yield: 74%; UPLC purity: 75%).

Intermediate 42

N-methyl-1-(4-methylbenzenesulfonyl)-3-[4-(morpholin-4-yl)quinolin-6-yl]-1H-pyrrolo[2,3-b]pyridine-5-carboxamide

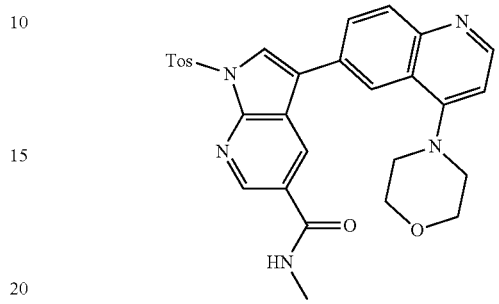

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.7 g, 1.5 mmol, 1.0 eq.), [4-(morpholin-4-yl)quinolin-6-yl]boronic acid (Intermediate 41) (0.7 g, 2.7 mmol, 1.7 eq.), $K_2CO_3$ (0.4 g, 3.1 mmol, 2.0 eq.), $Pd(dppf)_2Cl_2*CH_2Cl_2$ (0.12 g, 0.15 mmol, 0.1 eq.) in a mixture of 1,4-dioxane/water 2/1 (12 mL). After work up the residue was purify by FCC (EtOAc gradient in hexane) to provide N-methyl-1-(4-methylbenzenesulfonyl)-3-[4-(morpholin-4-yl)quinolin-6-yl]-1H-pyrrolo[2,3-b]pyridine-5-carboxamide (1.4 g; yield: 83%; UPLC purity: 99%).

Example 23

N-Methyl-3-[4-(morpholin-4-yl)quinolin-6-yl]-1H-pyrrolo[2,3-b]pyridine-5-carboxamide

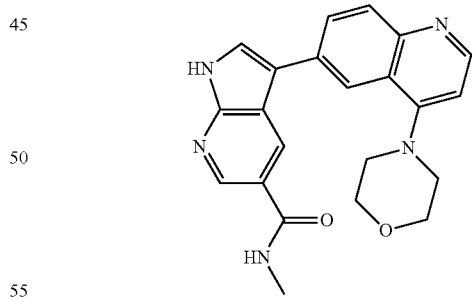

The title compound was prepared according to General Procedure 3 with N-methyl-1-(4-methylbenzenesulfonyl)-3-[4-(morpholin-4-yl)quinolin-6-yl]-1H-pyrrolo[2,3-b]pyridine-5-carboxamide (Intermediate 42) (0.99 g, 1.7 mmol, 1.0 eq.), NaOtBu (0.34 g, 3.5 mmol, 2.0 eq.) dissolved in 1,4-dioxane (20 mL). The reaction mixture was stirred at rt for 3 days. Purification by FCC (MeOH gradient in $CH_2Cl_2$) provided N-methyl-3-[4-(morpholin-4-yl)quinolin-6-yl]-1H-pyrrolo[2,3-b]pyridine-5-carboxamide (0.6 g; yield: 79%; HPLC purity: 99%).

Example 24

3-(4-Chloroquinolin-6-yl)-N-methyl-1H-pyrrolo[2,3-b]pyridine-5-carboxamide

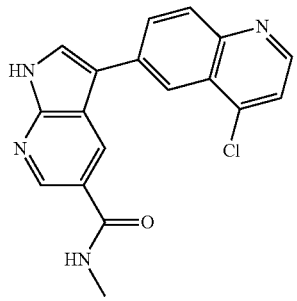 [SMILES: CNC(=O)c1cnc2[nH]cc(-c3ccc4nccc(Cl)c4c3)c2c1]

The title compound was prepared according to General Procedure 3 with 3-(4-chloroquinolin-6-yl)-N-methyl-1-(4-methylbenzenesulfonyl)-1H-pyrrolo[2,3-b]pyridine-5-carboxamide (Intermediate 38) (0.12 g, 0.2 mmol, 1.0 eq.), NaOtBu (0.05 g, 0.5 mmol, 2.0 eq.) in 1,4-dioxane (5 mL). The reaction mixture was stirred at rt overnight. Purification by FCC (MeOH gradient in $CH_2Cl_2$) provided 3-(4-chloroquinolin-6-yl)-N-methyl-1H-pyrrolo[2,3-b]pyridine-5-carboxamide (0.03 g; yield: 39%; HPLC purity: 98%).

Intermediate 43

(Quinolin-6-yl)boronic acid

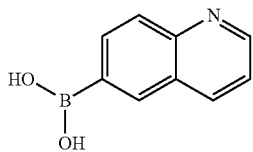 [SMILES: OB(O)c1ccc2ncccc2c1]

The title compound was prepared according to General Procedure 1 with 6-bromoquinoline hydrochloride (0.2 g, 0.8 mmol, 1.0 eq.), bis(pinacolato)diboron (0.21 g, 0.9 mmol, 1.1 eq.), potassium acetate (0.23 g, 2.3 mmol, 3.0 eq.), Pd(dppf)$_2$Cl$_2$*CH$_2$Cl$_2$ (0.03 g, 0.04 mmol, 0.05 eq.) and 1,4-dioxane (3 mL). The reaction mixture was stirred at 80° C. for 3 h. The crude product was used in consecutive step without further purification (UPLC purity: 71%).

Intermediate 44

N-methyl-1-(4-methylbenzenesulfonyl)-3-(quinolin-6-yl)-1H-pyrrolo[2,3-b]pyridine-5-carboxamide

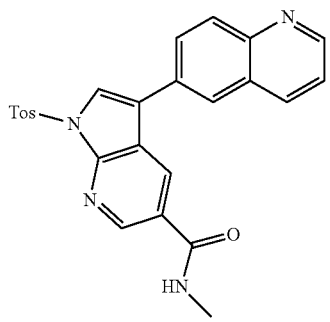

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.15 g, 0.3 mmol, 1.0 eq.), (quinolin-6-yl)boronic acid (Intermediate 43) (0.14 g, 0.4 mmol, 1.3 eq.), K$_2$CO$_3$ (0.09 g, 0.7 mmol, 2.0 eq.), Pd(dppf)$_2$Cl$_2$*CH$_2$Cl$_2$ (0.03 g, 0.03 mmol, 0.1 eq.) in a mixture of 1,4-dioxane/water 3/1 (4 mL). After work up the residue was purified by FCC (EtOAc gradient in hexane) to provide N-methyl-1-(4-methylbenzenesulfonyl)-3-(quinolin-6-yl)-1H-pyrrolo[2,3-b]pyridine-5-carboxamide (0.13 g; yield: 87%; UPLC purity: 97%).

Example 25

N-Methyl-3-(quinolin-6-yl)-1H-pyrrolo[2,3-b]pyridine-5-carboxamide

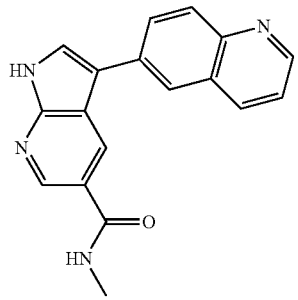 [SMILES: CNC(=O)c1cnc2[nH]cc(-c3ccc4ncccc4c3)c2c1]

The title compound was prepared according to General Procedure 3 with N-methyl-1-(4-methylbenzenesulfonyl)-3-(quinolin-6-yl)-1H-pyrrolo[2,3-b]pyridine-5-carboxamide (Intermediate 44) (0.15 g, 0.32 mmol, 1.0 eq.), NaOtBu (0.13 g, 0.48 mmol, 1.5 eq.) dissolved in 1,4-dioxane (3 mL). The reaction mixture was stirred at rt for 2 h. Purification by FCC (MeOH gradient in $CH_2Cl_2$) provided N-methyl-3-(quinolin-6-yl)-1H-pyrrolo[2,3-]pyridine-5-carboxamide (0.07 g; yield: 66%; HPLC purity: 99%).

Intermediate 45

(8-Methoxyquinolin-6-yl)boronic acid

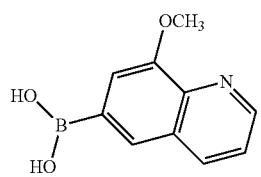 [SMILES: COc1cc(B(O)O)cc2cccnc12]

The title compound was prepared according to General Procedure 1 with 6-chloro-8-methoxyquinoline (0.16 g, 0.8 mmol, 1.0 eq.), bis(pinacolato)diboron (0.23 g, 0.9 mmol, 1.1 eq.), potassium acetate (0.16 g, 1.6 mmol, 2.0 eq.), Pd(dppf)$_2$Cl$_2$*CH$_2$Cl$_2$ (0.03 g, 0.04 mmol, 0.05 eq.) and 1,4-dioxane (2 mL). The reaction mixture was stirred at 80° C. for 5 h. Purification by FCC (EtOAc gradient in hexane) provided (8-methoxyquinolin-6-yl)boronic acid (0.16 g; yield: 69%; UPLC purity: 69%).

Intermediate 46

3-(8-Methoxyquinolin-6-yl)-N-methyl-1-(4-methyl-benzenesulfonyl)-N-(prop-2-en-1-yl)-1H-pyrrolo[2,3-b]pyridine-5-carboxamide

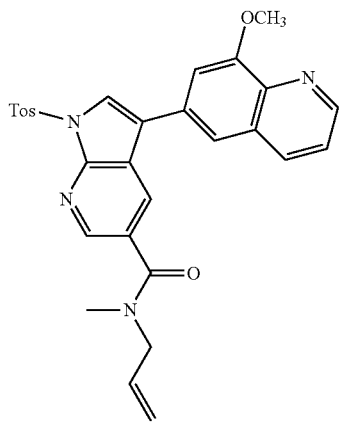

The title compound was prepared according to General Procedure 2 with 3-iodo-N-methyl-1-(4-methylbenzenesulfonyl)-N-(prop-2-en-1-yl)-1H-pyrrolo[2,3-b]pyridine-5-carboxamide (Intermediate 32) (0.15 g, 0.3 mmol, 1.0 eq.), (8-methoxyquinolin-6-yl)boronic acid (Intermediate 45) (0.1 g, 0.4 mmol, 1.3 eq.), $K_2CO_3$ (0.08 g, 0.6 mmol, 2.0 eq.), Pd(dppf)$_2$Cl$_2$*CH$_2$Cl$_2$ (0.05 g, 0.06 mmol, 0.2 eq.) in a mixture of 1,4-dioxane/water 2/1 (6 mL). After work up the residue was purified by FCC (EtOAc gradient in hexane) to provide 3-(8-methoxyquinolin-6-yl)-N-methyl-1-(4-methyl-benzenesulfonyl)-N-(prop-2-en-1-yl)-1H-pyrrolo[2,3-b]pyridine-5-carboxamide (0.06 g; yield: 36%; UPLC purity: 99%).

Example 26

3-(8-Methoxyquinolin-6-yl)-N-methyl-N-(prop-2-en-1-yl)-1H-pyrrolo[2,3-b]pyridine-5-carboxamide

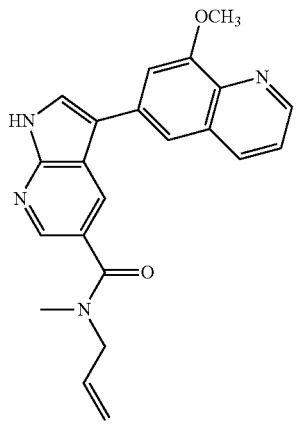 [SMILES: C=CCN(C)C(=O)c1cnc2[nH]cc(-c3cc(OC)c4ncccc4c3)c2c1]

The title compound was prepared according to General Procedure 3 with 3-(8-methoxyquinolin-6-yl)-N-methyl-1-(4-methylbenzenesulfonyl)-N-(prop-2-en-1-yl)-1H-pyrrolo[2,3-b]pyridine-5-carboxamide (Intermediate 46) (0.06 g, 0.11 mmol, 1.0 eq.), NaOtBu (0.015 g, 0.17 mmol, 1.5 eq.) dissolved in 1,4-dioxane (2 mL). The reaction mixture was stirred at rt for 2 h. Purification by FCC (MeOH gradient in CH$_2$Cl$_2$) provided 3-(8-methoxyquinolin-6-yl)-N-methyl-N-(prop-2-en-1-yl)-1H-pyrrolo[2,3-b]pyridine-5-carboxamide (0.04 g; yield: 10%; HPLC purity: 90%).

Intermediate 47

(8-Fluoroquinolin-6-yl)boronic acid

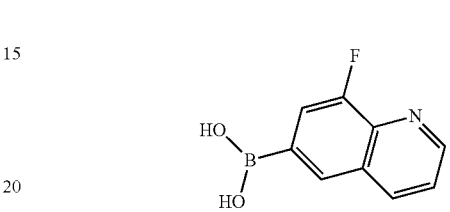

The title compound was prepared according to General Procedure 1 with 6-chloro-8-fluoroquinoline (0.81 g, 3.6 mmol, 1.0 eq.), bis(pinacolato)diboron (1.0 g, 3.9 mmol, 1.1 eq.), potassium acetate (0.7 g, 7.2 mmol, 2.0 eq.), Pd(dppf)$_2$Cl$_2$*CH$_2$Cl$_2$ (0.13 g, 0.2 mmol, 0.05 eq.) and 1,4-dioxane (18 mL). The reaction mixture was stirred at 80° C. for 5 h. Obtained (8-fluoroquinolin-6-yl)boronic acid was used in consecutive step without further purification (UPLC purity: 92%).

Intermediate 48

3-(8-Fluoroquinolin-6-yl)-N-methyl-1-(4-methylbenzenesulfonyl)-N-(prop-2-en-1-yl)-1H-pyrrolo[2,3-b]pyridine-5-carboxamide

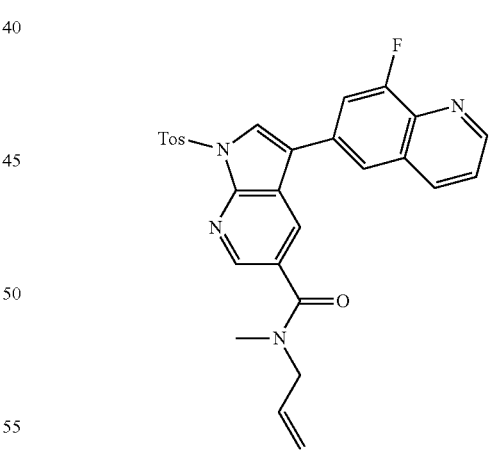

The title compound was prepared according to General Procedure 2 with 3-iodo-N-methyl-1-(4-methylbenzenesulfonyl)-N-(prop-2-en-1-yl)-1H-pyrrolo[2,3-b]pyridine-5-carboxamide (Intermediate 32) (0.2 g, 0.4 mmol, 1.0 eq.), (8-fluoroquinolin-6-yl)boronic acid (Intermediate 47) (0.2 g, 0.4 mmol, 1.3 eq.), $K_2CO_3$ (0.11 g, 0.8 mmol, 2.0 eq.), Pd(dppf)$_2$Cl$_2$*CH$_2$Cl$_2$ (0.08 g; 0.01 mmol; 0.2 eq.) in a mixture of 1,4-dioxane/water 2/1 (3 mL). After work up the residue was purify by FCC (EtOAc gradient in hexane) to provide 3-(8-fluoroquinolin-6-yl)-N-methyl-1-(4-methylbenzenesulfonyl)-N-(prop-2-en-1-yl)-1H-pyrrolo[2,3-b]pyridine-5-carboxamide (0.11 g; yield: 50%; UPLC purity: 94%).

Example 27

3-(8-Fluoroquinolin-6-yl)-N-methyl-N-(prop-2-en-1-yl)-1H-pyrrolo[2,3-b]pyridine-5-carboxamide

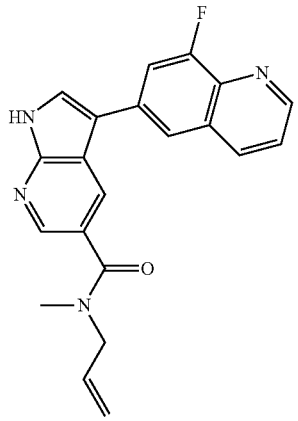

The title compound was prepared according to General Procedure 3 with 3-(8-fluoroquinolin-6-yl)-N-methyl-1-(4-methylbenzenesulfonyl)-N-(prop-2-en-1-yl)-1H-pyrrolo[2,3-b]pyridine-5-carboxamide (Intermediate 48) (0.11 g, 0.2 mmol, 1.0 eq.), NaOtBu (0.09 g, 0.3 mmol, 1.5 eq.) dissolved in 1,4-dioxane (4 mL). The reaction mixture was stirred at rt for 2 h. Purification by FCC (MeOH gradient in CH$_2$Cl$_2$) provided 3-(8-fluoroquinolin-6-yl)-N-methyl-N-(prop-2-en-1-yl)-1H-pyrrolo[2,3-b]pyridine-5-carboxamide (0.045 g; yield: 57%; HPLC purity: 98%).

Intermediate 49

(8-Chloroquinolin-6-yl)boronic acid

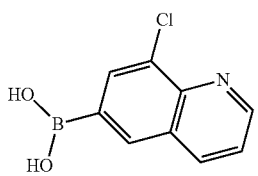

The title compound was prepared according to General Procedure 1 with 6-bromo-8-chloroquinoline (0.59 g, 2.4 mmol, 1.0 eq.), bis(pinacolato)diboron (0.6 g, 2.4 mmol, 1.0 eq.), potassium acetate (0.48 g, 4.9 mmol, 2.0 eq.), Pd(dppf)$_2$Cl$_2$*CH$_2$Cl$_2$ (0.09 g, 0.1 mmol, 0.05 eq.) and 1,4-dioxane (10 mL). The reaction mixture was stirred at 80° C. for 5 h. Obtained (8-chloroquinolin-6-yl)boronic acid was used in consecutive step without further purification (UPLC purity: 92%).

Intermediate 50

3-(8-Chloroquinolin-6-yl)-N-methyl-1-(4-methylbenzenesulfonyl)-N-(prop-2-en-1-yl)-1H-pyrrolo[2,3-b]pyridine-5-carboxamide

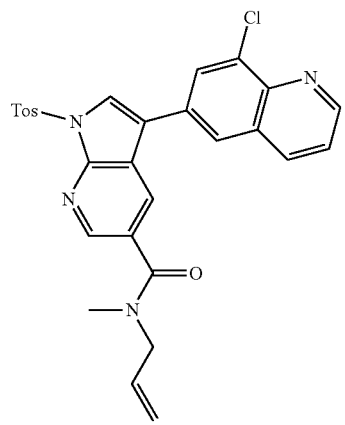

The title compound was prepared according to General Procedure 2 with 3-iodo-N-methyl-1-(4-methylbenzenesulfonyl)-N-(prop-2-en-1-yl)-1H-pyrrolo[2,3-b]pyridine-5-carboxamide (Intermediate 32) (0.15 g, 0.3 mmol, 1.0 eq.), (8-chloroquinolin-6-yl)boronic acid (Intermediate 49) (0.1 g, 0.4 mmol, 1.2 eq.), K$_2$CO$_3$ (0.12 g, 0.9 mmol, 3.0 eq.), Pd(dppf)$_2$Cl$_2$*CH$_2$Cl$_2$ (0.05 g, 0.06 mmol, 0.2 eq.) in a mixture of 1,4-dioxane/water 2/1 (3 mL). The reaction mixture was stirred at 80° C. for 3 h. After work up the residue was purified by FCC (EtOAc gradient in hexane) to provide 3-(8-chloroquinolin-6-yl)-N-methyl-1-(4-methylbenzenesulfonyl)-N-(prop-2-en-1-yl)-1H-pyrrolo[2,3-b]pyridine-5-carboxamide as a light yellow foam (0.11 g; yield: 67%; UPLC purity: 98%).

Example 28

3-(8-Chloroquinolin-6-yl)-N-methyl-N-(prop-2-en-1-yl)-1H-pyrrolo[2,3-b]pyridine-5-carboxamide

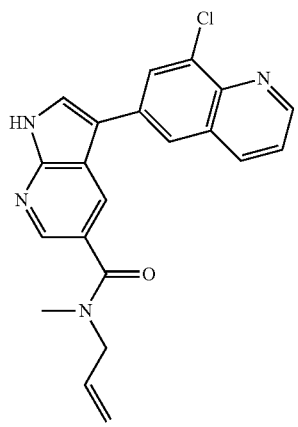 [SMILES: C=CCN(C)C(=O)c1cnc2[nH]cc(-c3cc(F)c4ncccc4c3)c2c1]

The title compound was prepared according to General Procedure 3 with 3-(8-chloroquinolin-6-yl)-N-methyl-1-(4- methylbenzenesulfonyl)-N-(prop-2-en-1-yl)-1H-pyrrolo[2,3-b]pyridine-5-carboxamide (Intermediate 50) (0.1 g, 0.2 mmol, 1.0 eq.), NaOtBu (0.04 g, 0.4 mmol, 2.0 eq.) in 1,4-dioxane (4 mL). The reaction mixture was stirred at rt overnight. Purification by FCC (MeOH gradient in CH$_2$Cl$_2$) provided 3-(8-chloroquinolin-6-yl)-N-methyl-N-(prop-2-en-1-yl)-1H-pyrrolo[2,3-b]pyridine-5-carboxamide (0.013 g; yield: 18%; HPLC purity: 97%).

Intermediate 51

3-(8-Methoxyquinolin-6-yl)-N-methyl-1-(4-methylbenzenesulfonyl)-1H-pyrrolo[2,3-b]pyridine-5-carboxamide

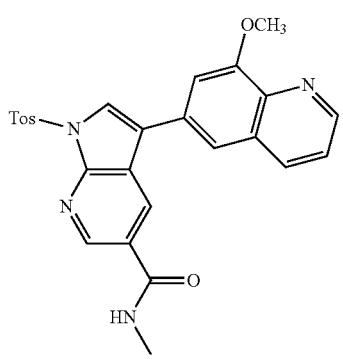

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.15 g, 0.3 mmol, 1.0 eq.), (8-methoxyquinolin-6-yl)boronic acid (Intermediate 45) (0.1 g, 0.4 mmol, 1.3 eq.), K$_2$CO$_3$ (0.09 g, 0.7 mmol, 2.0 eq.), Pd(dppf)$_2$Cl$_2$*CH$_2$Cl$_2$ (0.05 g, 0.07 mmol, 0.2 eq.) in a mixture of 1,4-dioxane/water 2/1 (3 mL). The reaction mixture was stirred at 80° C. for 3 h. Purification by FCC (MeOH gradient in CH$_2$Cl$_2$) provided 3-(8-methoxyquinolin-6-yl)-N-methyl-1-(4-methylbenzenesulfonyl)-1H-pyrrolo[2,3-b]pyridine-5-carboxamide (0.07 g; yield: 42%; UPLC purity: 100%).

Example 29

3-(8-Methoxyquinolin-6-yl)-N-methyl-1H-pyrrolo[2,3-b]pyridine-5-carboxamide

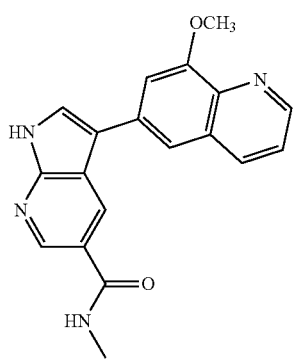 [SMILES: CNC(=O)c1cnc2[nH]cc(-c3cc(OC)c4ncccc4c3)c2c1]

The title compound was prepared according to General Procedure 3 with 3-(8-methoxyquinolin-6-yl)-N-methyl-1-(4-methylbenzenesulfonyl)-1H-pyrrolo[2,3-b]pyridine-5-carboxamide (Intermediate 51) (0.07 g, 0.1 mmol, 1.0 eq.), NaOtBu (0.02 g, 0.2 mmol, 1.5 eq.) in 1,4-dioxane (2 mL). The reaction mixture was stirred at rt for 2 h. Purification by FCC (MeOH gradient in CH$_2$Cl$_2$) provided 3-(8-methoxyquinolin-6-yl)-N-methyl-1H-pyrrolo[2,3-b]pyridine-5-carboxamide (0.007 g; yield: 15%; HPLC purity: 86%).

Intermediate 52

3-(8-Fluoroquinolin-6-yl)-N-methyl-1-(4-methylbenzenesulfonyl)-1H-pyrrolo[2,3-b]pyridine-5-carboxamide

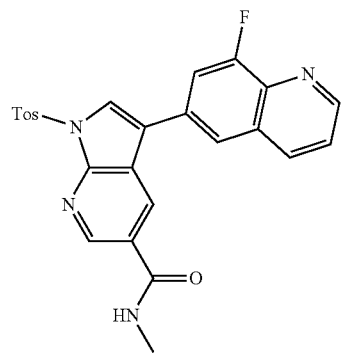

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.17 g, 0.4 mmol, 1.0 eq.), (8-fluoroquinolin-6-yl)boronic acid (Intermediate 47) (0.1 g, 0.4 mmol, 1.3 eq.), K$_2$CO$_3$ (0.1 g, 0.7 mmol, 2.0 eq.), Pd(dppf)$_2$Cl$_2$*CH$_2$Cl$_2$ (0.05 g, 0.07 mmol, 0.2 eq.) in a mixture of 1,4-dioxane/water 2/1 (3 mL). The reaction mixture was stirred at 80° C. for 3 h. Purification by FCC (MeOH gradient in CH$_2$Cl$_2$) provided 3-(8-fluoroquinolin-6-yl)-N-methyl-1-(4-methylbenzenesulfonyl)-1H-pyrrolo[2,3-b]pyridine-5-carboxamide (0.05 g; yield: 37%; UPLC purity: 95%).

Example 30

3-(8-Fluoroquinolin-6-yl)-N-methyl-1H-pyrrolo[2,3-b]pyridine-5-carboxamide

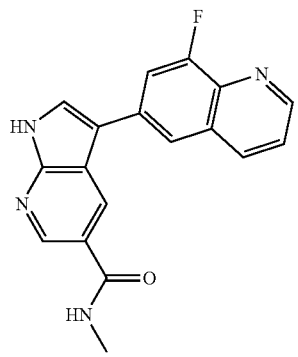 [SMILES: CNC(=O)c1cnc2[nH]cc(-c3cc(F)c4ncccc4c3)c2c1]

The title compound was prepared according to General Procedure 3 with 3-(8-fluoroquinolin-6-yl)-N-methyl-1-(4-methylbenzenesulfonyl)-1H-pyrrolo[2,3-b]pyridine-5-carboxamide (Intermediate 52) (0.06 g, 0.1 mmol, 1.0 eq.), NaOtBu (0.02 g, 0.2 mmol, 1.5 eq.) dissolved in 1,4-dioxane (2 mL). The reaction mixture was stirred at rt for 2 h. Purification by FCC (MeOH gradient in CH$_2$Cl$_2$) provided 3-(8-fluoroquinolin-6-yl)-N-methyl-1H-pyrrolo[2,3-b]pyridine-5-carboxamide (0.004 g; yield: 10%; HPLC purity: 97%).

Intermediate 53. General Procedure 9

N-Benzyl-3-iodo-1-(4-methylbenzenesulfonyl)-1H-pyrrolo[2,3-b]pyridine-5-carboxamide

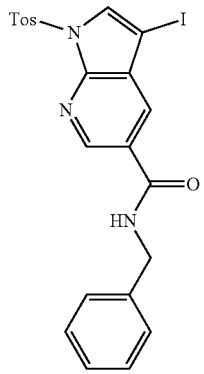

A solution of 3-iodo-1-(4-methylbenzenesulfonyl)-1H-pyrrolo[2,3-b]pyridine-5-carboxylic acid (Intermediate 2) (1.0 g, 2.3 mmol, 1.0 eq.), benzylamine (0.3 g, 2.7 mmol, 1.2 eq.), DIPEA (0.9 g, 6.8 mmol, 3.0 eq.) in a mixture of $CH_2Cl_2$ (20 mL) and DMF (4 mL) was stirred for 10 min at rt. After that time 1-propanephosphonic acid cyclic anhydride (1.1 g, 3.4 mmol, 1.5 eq.) was added and stirring was continued overnight. The reaction mixture was quenched with water and aqueous layer was extracted with $CH_2Cl_2$. The combined organic layers were dried over $Na_2SO_4$, filtered and concentrated. The crude reaction mixture was purified by FCC (EtOAc gradient in hexane) to provide N-benzyl-3-iodo-1-(4-methylbenzenesulfonyl)-1H-pyrrolo[2,3-b]pyridine-5-carboxamide (0.4 g, yield: 37%; UPLC purity: 92%).

Intermediate 54

N-Benzyl-3-(8-fluoroquinolin-6-yl)-1-(4-methylbenzenesulfonyl)-1H-pyrrolo[2,3-b]pyridine-5-carboxamide

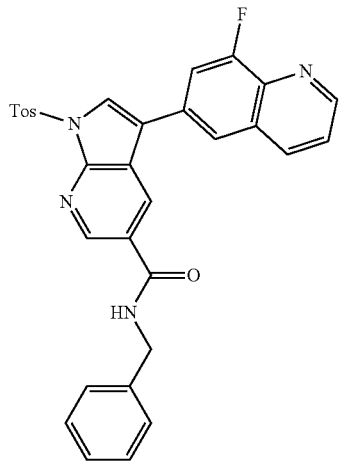

The title compound was prepared according to General Procedure 2 with N-benzyl-3-iodo-1-(4-methylbenzenesulfonyl)-1H-pyrrolo[2,3-b]pyridine-5-carboxamide (Intermediate 53) (0.18 g, 0.3 mmol, 1.0 eq.), (8-fluoroquinolin-6-yl)boronic acid (Intermediate 47) (0.1 g, 0.4 mmol, 1.3 eq.), $K_2CO_3$ (0.1 g, 0.7 mmol, 2.0 eq.), $Pd(dppf)_2Cl_2*CH_2Cl_2$ (0.05 g, 0.07 mmol, 0.2 eq.) in a mixture of 1,4-dioxane/water 2/1 (3 mL). The reaction mixture was stirred at 80° C. for 3 h. Purification by FCC (MeOH gradient in $CH_2Cl_2$) provided N-benzyl-3-(8-fluoroquinolin-6-yl)-1-(4-methylbenzenesulfonyl)-1H-pyrrolo[2,3-b]pyridine-5-carboxamide (0.13 g; yield: 70%; UPLC purity: 94%).

Example 31

N-Benzyl-3-(8-fluoroquinolin-6-yl)-1H-pyrrolo[2,3-b]pyridine-5-carboxamide

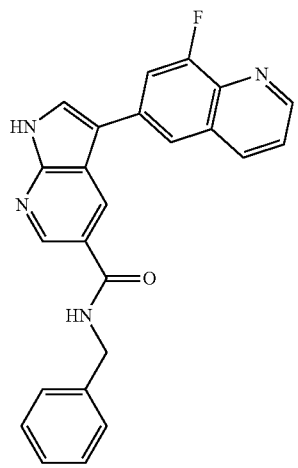 [SMILES: O=C(NCc1ccccc1)c1cnc2[nH]cc(-c3cc(F)c4ncccc4c3)c2c1]

The title compound was prepared according to General Procedure 3 with N-benzyl-3-(8-fluoroquinolin-6-yl)-1-(4-methylbenzenesulfonyl)-1H-pyrrolo[2,3-b]pyridine-5-carboxamide (Intermediate 54) (0.13 g, 0.2 mmol, 1.0 eq.), NaOtBu (0.1 g, 0.4 mmol, 1.5 eq.) dissolved in 1,4-dioxane (5 mL). The reaction mixture was stirred at rt for 2 h. Purification by FCC (MeOH gradient in $CH_2Cl_2$) provided N-benzyl-3-(8-fluoroquinolin-6-yl)-1H-pyrrolo[2,3-b]pyridine-5-carboxamide (0.03 g; yield: 36%; HPLC purity: 96%).

Intermediate 55

N-Benzyl-3-(8-chloroquinolin-6-yl)-1-(4-methylbenzenesulfonyl)-1H-pyrrolo[2,3-b]pyridine-5-carboxamide

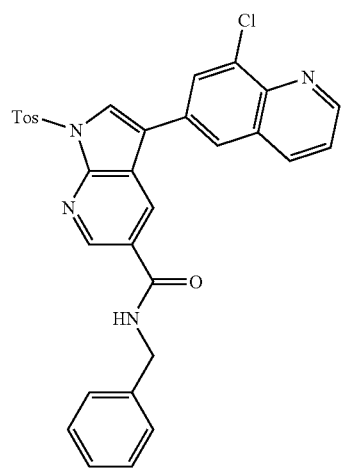

The title compound was prepared according to General Procedure 2 with N-benzyl-3-iodo-1-(4-methylbenzenesulfonyl)-1H-pyrrolo[2,3-b]pyridine-5-carboxamide (Intermediate 53) (0.2 g, 0.4 mmol, 1.0 eq.), (8-chloroquinolin-6-yl)boronic acid (Intermediate 49) (0.13 g, 0.4 mmol, 1.2 eq.), K₂CO₃ (0.16 g, 1.1 mmol, 3.0 eq.), Pd(dppf)₂Cl₂*CH₂Cl₂ (0.06 g, 0.08 mmol, 0.2 eq.) in a mixture of 1,4-dioxane/water 3/1 (4 mL). The reaction mixture was stirred at 80° C. for 3 h. Purification by FCC (EtOAc gradient in hexane) provided N-benzyl-3-(8-chloroquinolin-6-yl)-1-(4-methylbenzenesulfonyl)-1H-pyrrolo[2,3-b]pyridine-5-carboxamide as a brownish solid (0.17 g; yield: 80%; UPLC purity: 98%).

Example 32

N-Benzyl-3-(8-chloroquinolin-6-yl)-1H-pyrrolo[2,3-b]pyridine-5-carboxamide

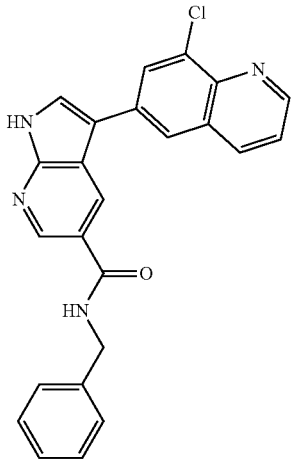 [SMILES: O=C(NCc1ccccc1)c1cnc2[nH]cc(-c3cc(Cl)c4ncccc4c3)c2c1]

The title compound was prepared according to General Procedure 3 with N-benzyl-3-(8-chloroquinolin-6-yl)-1-(4-methylbenzenesulfonyl)-1H-pyrrolo[2,3-b]pyridine-5-carboxamide (Intermediate 55) (0.16 g, 0.3 mmol, 1.0 eq.), NaOtBu (0.05 g, 0.5 mmol, 2.0 eq.) dissolved in 1,4-dioxane (5 mL). The reaction mixture was stirred at 80° C. for 14 h. Purification by FCC (MeOH gradient in CH₂Cl₂) provided N-benzyl-3-(8-chloroquinolin-6-yl)-1H-pyrrolo[2,3-b]pyridine-5-carboxamide (0.02 g; yield: 18%; HPLC purity: 100%).

Intermediate 56

3-Iodo-1-(4-methylbenzenesulfonyl)-1H-pyrrolo[2,3-b]pyridine-5-carboxamide

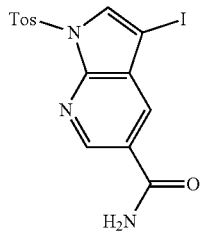

The title compound was prepared according to General Procedure 7 with 3-iodo-1-(4-methylbenzenesulfonyl)-1H-pyrrolo[2,3-b]pyridine-5-carboxylic acid (Intermediate 2) (2.5 g, 5.6 mmol, 1.0 eq.) and SOCl₂ (40 mL). Then NH₄OH (2 mL) was added and the reaction mixture stirred at rt for 48 h. The reaction mixture was diluted with water and aqueous solution of NaHCO₃. The precipitate was collected by filtration, rinsed with water and dried on air to give 3-iodo-1-(4-methylbenzenesulfonyl)-1H-pyrrolo[2,3-b]pyridine-5-carboxamide as a solid (0.5 g; yield: 71%; UPLC purity: 99%).

Intermediate 57

3-(8-Fluoroquinolin-6-yl)-1-(4-methylbenzenesulfonyl)-1H-pyrrolo[2,3-b]pyridine-5-carboxamide

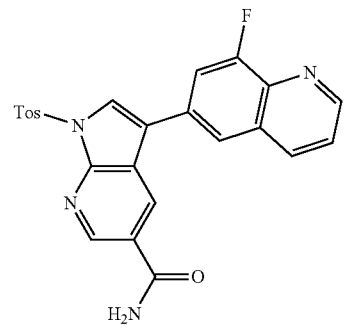

The title compound was prepared according to General Procedure 2 with 3-iodo-1-(4-methylbenzenesulfonyl)-1H-pyrrolo[2,3-b]pyridine-5-carboxamide (Intermediate 56), (0.78 g, 1.8 mmol, 1.0 eq.), (8-fluoroquinolin-6-yl)boronic acid (Intermediate 47) (0.7 g, 2.6 mmol, 1.5 eq.), K₂CO₃ (0.5 g, 3.5 mmol, 2.0 eq.), Pd(dppf)₂Cl₂*CH₂Cl₂ (0.13 g, 0.03 mmol, 0.1 eq.) in a mixture of 1,4-dioxane/water 2/1 (12 mL). The reaction mixture was stirred at 80° C. for 3 h. Purification by FCC (MeOH gradient in CH₂Cl₂) provided 3-(8-fluoroquinolin-6-yl)-1-(4-methylbenzenesulfonyl)-1H-pyrrolo[2,3-b]pyridine-5-carboxamide (0.19 g; yield: 24%; UPLC purity: 98%).

Example 33

3-(8-Fluoroquinolin-6-yl)-1H-pyrrolo[2,3-b]pyridine-5-carboxamide

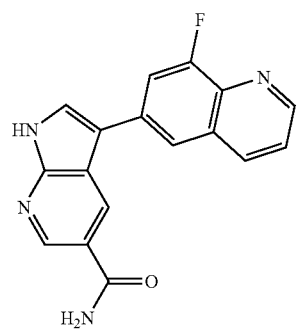 [SMILES: NC(=O)c1cnc2[nH]cc(-c3cc(F)c4ncccc4c3)c2c1]

The title compound was prepared according to General Procedure 3 with 3-(8-fluoroquinolin-6-yl)-1-(4-methylbenzenesulfonyl)-1H-pyrrolo[2,3-b]pyridine-5-carboxamide (Intermediate 57) (0.19 g, 0.4 mmol, 1.0 eq.), NaOtBu (0.17 g, 0.6 mmol, 1.5 eq.) dissolved in 1,4-dioxane (8 mL). The reaction mixture was stirred at rt for 2 h. Purification by FCC (MeOH gradient in CH₂Cl₂) provided 3-(8-fluoroquinolin-6-yl)-1H-pyrrolo[2,3-b]pyridine-5-carboxamide as a beige solid (0.06 g; yield: 57%; HPLC purity: 95%).

Intermediate 58 tert-Butyl N-(3-{[3-iodo-1-(4-methylbenzenesulfonyl)-1H-pyrrolo[2,3-b]pyridin-5-yl]formamido}propyl)carbamate

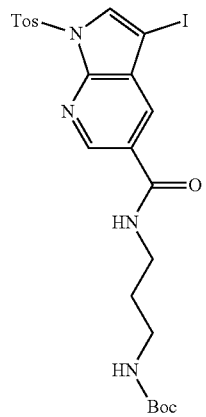

The title compound was prepared according to General Procedure 9 with 3-iodo-1-(4-methylbenzenesulfonyl)-1H-pyrrolo[2,3-b]pyridine-5-carboxylic acid (Intermediate 2) (1.0 g, 2.3 mmol, 1.0 eq.), n-Boc-1,3-diaminopropane (0.5 g, 2.7 mmol, 1.2 eq.), DIPEA (0.9 g, 6.8 mmol, 3.0 eq.) and 1-propanephosphonic acid cyclic anhydride (1.1 g, 3.4 mmol, 1.5 eq.) in CH$_2$Cl$_2$ (20 mL). Purification by FCC (EtOAc gradient in hexane) provided tert-butyl N-(3-{[3-iodo-1-(4-methylbenzenesulfonyl)-1H-pyrrolo[2,3-b]pyridin-5-yl]formamido}propyl)carbamate (0.7 g, yield: 53%; UPLC purity: 100%).

Intermediate 59 tert-Butyl N-(3-{[3-(8-chloroquinolin-6-yl)-1-(4-methylbenzenesulfonyl)-1H-pyrrolo[2,3-b]pyridin-5-yl]formamido}propyl)carbamate

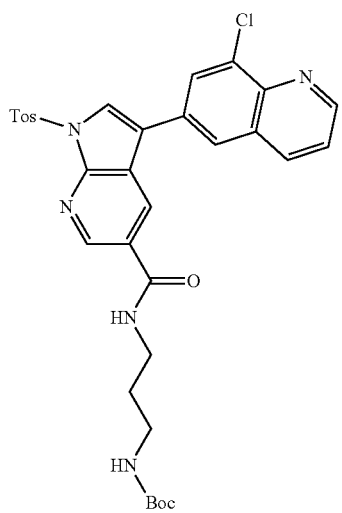

The title compound was prepared according to General Procedure 2 with tert-butyl N-(3-{[3-iodo-1-(4-methylbenzenesulfonyl)-1H-pyrrolo[2,3-b]pyridin-5-yl]formamido}propyl)carbamate (Intermediate 58), (0.3 g, 0.5 mmol, 1.0 eq.), (8-chloroquinolin-6-yl)boronic acid (Intermediate 49) (0.19 g, 0.6 mmol, 1.3 eq.), K$_2$CO$_3$ (0.14 g, 1.0 mmol, 2.0 eq.), Pd(dppf)$_2$Cl$_2$*CH$_2$Cl$_2$ (0.07 g, 0.1 mmol, 0.2 eq.) in a mixture of 1,4-dioxane/water 3/1 (4 mL). The reaction mixture was heated at 80° C. for 3 h. Purification by FCC (EtOAc gradient in hexane) provided tert-butyl N-(3-{[3-(8-chloroquinolin-6-yl)-1-(4-methylbenzenesulfonyl)-1H-pyrrolo[2,3-b]pyridin-5-yl]formamido}propyl)carbamate as a light beige solid (0.23 g; yield: 74%; UPLC purity: 96%).

Intermediate 60 tert-Butyl N-(3-{[3-(8-chloroquinolin-6-yl)-1H-pyrrolo[2,3-b]pyridin-5-yl]formamido}propyl)carbamate

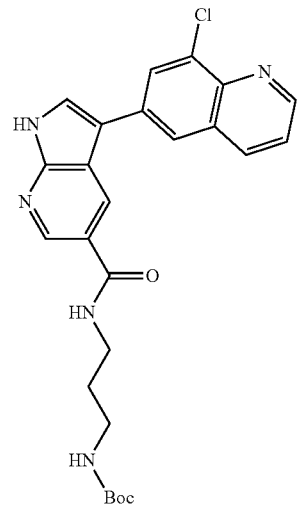 [SMILES: CC(C)(C)OC(=O)NCCCNC(=O)c1cnc2[nH]cc(-c3cc(Cl)c4ncccc4c3)c2c1]

The title compound was prepared according to General Procedure 3 with tert-butyl N-(3-{[3-(8-chloroquinolin-6-yl)-1-(4-methylbenzenesulfonyl)-1H-pyrrolo[2,3-b]pyridin-5-yl]formamido}propyl)carbamate (Intermediate 59) (0.2 g, 0.4 mmol, 1.0 eq.), KOH (0.04 g, 0.7 mmol, 1.5 eq.) dissolved in THF (15 mL). The reaction mixture was stirred at 50° C. for 4 h. The precipitate was collected by filtration to provide tert-butyl N-(3-{[3-(8-chloroquinolin-6-yl)-1H-pyrrolo[2,3-b]pyridin-5-yl]formamido}propyl)carbamate as an yellowish solid (0.07 g; yield: 33%; UPLC purity: 98%).

Example 34

N-(3-Aminopropyl)-3-(8-chloroquinolin-6-yl)-1H-pyrrolo[2,3-b]pyridine-5-carboxamide hydrochloride

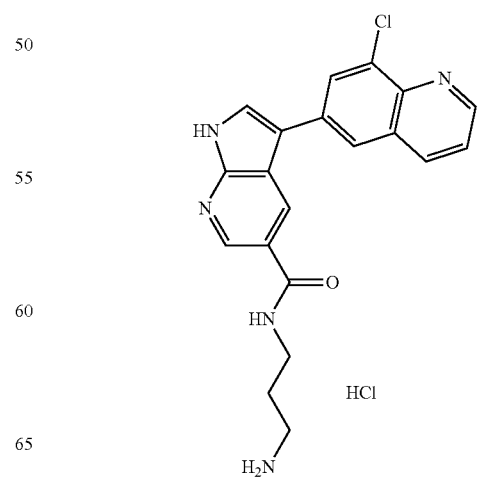

The title compound was prepared according to General Procedure 5 with tert-butyl N-(3-{[3-(8-chloroquinolin-6-yl)-1H-pyrrolo[2,3-b]pyridin-5-yl]formamido}propyl)carbamate (Intermediate 59) (0.06 g, 0.1 mmol, 1.0 eq.) in MeOH (0.5 mL) and 4 M HCl in 1,4-dioxane (2 mL). The yellow solid was collected by filtration to provide N-(3-aminopropyl)-3-(8-chloroquinolin-6-yl)-1H-pyrrolo[2,3-b]pyridine-5-carboxamide hydrochloride (0.033 g; yield: 70%; HPLC purity: 98%).

Intermediate 61 tert-Butyl N-(3-{[3-(8-fluoroquinolin-6-yl)-1-(4-methylbenzenesulfonyl)-1H-pyrrolo[2,3-b]pyridin-5-yl]formamido}propyl)carbamate

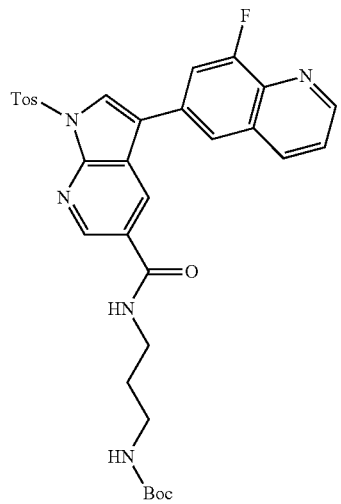

The title compound was prepared according to General Procedure 2 with tert-butyl N-(3-{[3-iodo-1-(4-methylbenzenesulfonyl)-1H-pyrrolo[2,3-b]pyridin-5-yl]formamido}propyl)carbamate (Intermediate 58) (0.3 g, 0.5 mmol, 1.0 eq.), (8-fluoroquinolin-6-yl)boronic acid (Intermediate 47) (0.18 g, 0.6 mmol, 1.3 eq.), K₂CO₃ (0.14 g, 1.0 mmol, 2.0 eq.), Pd(dppf)₂Cl₂*CH₂Cl₂ (0.07 g, 0.1 mmol, 0.2 eq.) in a mixture of 1,4-dioxane/water 3/1 (4 mL). The reaction mixture was heated at 80° C. for 3 h. Purification by FCC (EtOAc gradient in hexane) provided tert-butyl N-(3-{[3-(8-fluoroquinolin-6-yl)-1-(4-methylbenzenesulfonyl)-1H-pyrrolo[2,3-b]pyridin-5-yl]formamido}propyl)carbamate as a light beige solid (0.25 g; yield: 81%; UPLC purity: 97%).

Intermediate 62 tert-Butyl N-(3-{[3-(8-fluoroquinolin-6-yl)-1H-pyrrolo[2,3-b]pyridin-5-yl]formamido}propyl)carbamate

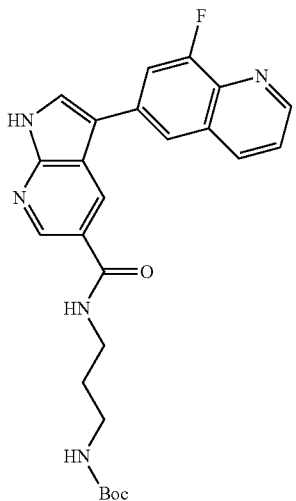 [SMILES: CC(C)(C)OC(=O)NCCCNC(=O)c1cnc2[nH]cc(-c3cc(F)c4ncccc4c3)c2c1]

The title compound was prepared according to General Procedure 3 with tert-butyl N-(3-{[3-(8-fluoroquinolin-6-yl)-1-(4-methylbenzenesulfonyl)-1H-pyrrolo[2,3-b]pyridin-5-yl]formamido}propyl)carbamate (Intermediate 61) (0.15 g, 0.2 mmol, 1.0 eq.), NaOtBu (0.1 g, 0.36 mmol, 2.9 eq.) dissolved in 1,4-dioxane (6 mL). The reaction mixture was stirred at rt for 2 h. Purification by FCC (MeOH gradient in CH₂Cl₂) provided tert-butyl N-(3-{[3-(8-fluoroquinolin-6-yl)-1H-pyrrolo[2,3-b]pyridin-5-yl]formamido}propyl)carbamate (0.06 g; yield: 57%; UPLC purity: 95%).

Example 35

N-(3-Aminopropyl)-3-(8-fluoroquinolin-6-yl)-1H-pyrrolo[2,3-b]pyridine-5-carboxamide hydrochloride

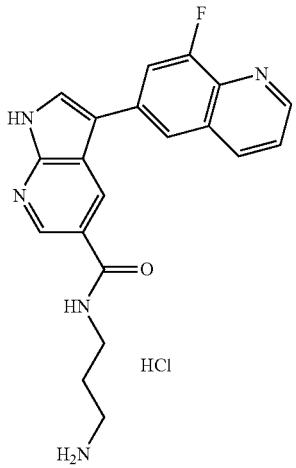 [SMILES: NCCCNC(=O)c1cnc2[nH]cc(-c3cc(F)c4ncccc4c3)c2c1 ; Cl]

The title compound was prepared according to General Procedure 5 with tert-butyl N-(3-{[3-(8-fluoroquinolin-6-yl)-1H-pyrrolo[2,3-b]pyridin-5-yl]formamido}propyl)carbamate (Intermediate 62) (0.06 g, 0.01 mmol, 1.0 eq.) in THF (1 mL) and 2 M HCl in Et₂O (3 mL). The precipitate was collected by filtration to provide N-(3-aminopropyl)-3-(8-fluoroquinolin-6-yl)-1H-pyrrolo[2,3-b]pyridine-5-carboxamide hydrochloride (0.024 g; yield: 63%; HPLC purity: 95%).

Intermediate 63

(4-Chloro-8-fluoroquinolin-6-yl)boronic acid

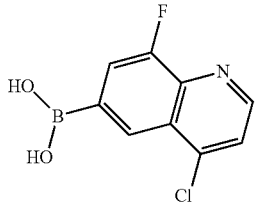 [SMILES: OB(O)c1cc(F)c2nccc(Cl)c2c1]

The title compound was prepared according to General Procedure 1 with 6-bromo-4-chloro-8-fluoroquinoline (0.9 g, 3.5 mmol, 1.0 eq.), bis(pinacolato)diboron (0.9 g, 3.5 mmol, 1.0 eq.), potassium acetate (0.7 g, 7.0 mmol, 2.0 eq.), Pd(dppf)₂Cl₂*CH₂Cl₂ (0.13 g, 0.2 mmol, 0.05 eq.) and 1,4-dioxane (10 mL). The reaction mixture was heated at 80° C. for 5 h. Obtained (4-chloro-8-fluoroquinolin-6-yl)boronic acid was used in consecutive step without further purification (UPLC purity: 64%).

Intermediate 64

N-Benzyl-3-(4-chloro-8-fluoroquinolin-6-yl)-1-(4-methylbenzenesulfonyl)-1H-pyrrolo[2,3-b]pyridine-5-carboxamide

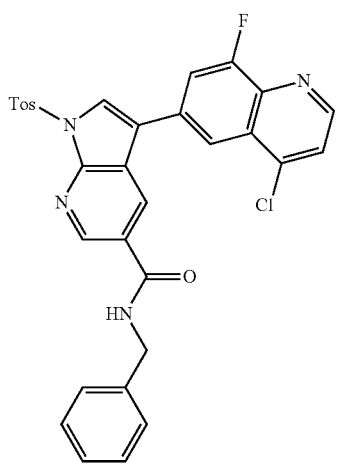

The title compound was prepared according to General Procedure 2 with N-benzyl-3-iodo-1-(4-methylbenzenesulfonyl)-1H-pyrrolo[2,3-b]pyridine-5-carboxamide (Intermediate 53) (0.17 g, 0.3 mmol, 1.0 eq.), (4-chloro-8-fluoroquinolin-6-yl)boronic acid (Intermediate 63) (0.15 g, 0.5 mmol, 1.5 eq.), K₂CO₃ (0.09 g, 0.6 mmol, 2.0 eq.), Pd(dppf)₂Cl₂*CH₂Cl₂ (0.05 g, 0.06 mmol, 0.2 eq.) in a mixture of 1,4-dioxane/water 2/1 (6 mL). The reaction mixture was stirred at 80° C. for 3 h. Purification by FCC (MeOH gradient in CH₂Cl₂) provided N-benzyl-3-(4-chloro-8-fluoroquinolin-6-yl)-1-(4-methylbenzenesulfonyl)-1H-pyrrolo[2,3-b]pyridine-5-carboxamide (0.78 g; yield: 41%; UPLC purity: 96%).

Intermediate 65

N-Benzyl-3-[8-fluoro-4-(pyridin-3-yl)quinolin-6-yl]-1-(4-methylbenzenesulfonyl)-1H-pyrrolo[2,3-b]pyridine-5-carboxamide

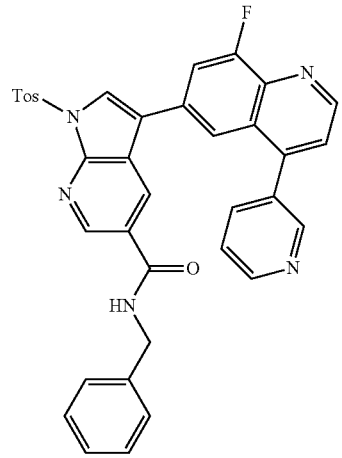

The title compound was prepared according to General Procedure 2 with N-benzyl-3-(4-chloro-8-fluoroquinolin-6-yl)-1-(4-methylbenzenesulfonyl)-1H-pyrrolo[2,3-b]pyridine-5-carboxamide (Intermediate 64) (0.08 g, 0.1 mmol, 1.0 eq.), 3-pyridyl boronic acid (0.02 g, 0.2 mmol, 1.5 eq.), K₂CO₃ (0.04 g, 0.3 mmol, 2.0 eq.), Pd(PPh₃)₄ (0.03 g, 0.03 mmol, 0.2 eq.) in a mixture of 1,4-dioxane/water 2/1 (3 mL). The crude product-N-benzyl-3-[8-fluoro-4-(pyridin-3-yl)quinolin-6-yl]-1-(4-methylbenzenesulfonyl)-1H-pyrrolo[2,3-b]pyridine-5-carboxamide was used in used in consecutive step without further purification (UPLC purity: 64%).

Example 36

N-Benzyl-3-[8-fluoro-4-(pyridin-3-yl)quinolin-6-yl]-1H-pyrrolo[2,3-b]pyridine-5-carboxamide

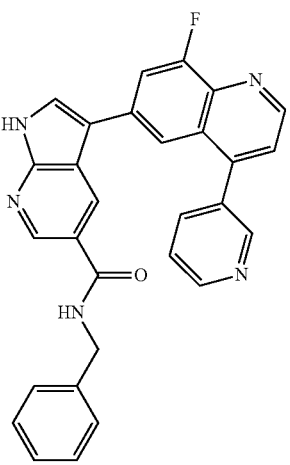 [SMILES: O=C(NCc1ccccc1)c1cnc2[nH]cc(-c3cc(F)c4nccc(-c5cccnc5)c4c3)c2c1]

The title compound was prepared according to General Procedure 3 with N-benzyl-3-[8-fluoro-4-(pyridin-3-yl)quinolin-6-yl]-1-(4-methylbenzenesulfonyl)-1H-pyrrolo[2,3-b]pyridine-5-carboxamide (Intermediate 65) (0.09 g, 0.2 mmol, 1.0 eq.), NaOtBu (0.06 g, 0.2 mmol, 1.5 eq.) dissolved in 1,4-dioxane (6 mL). The reaction mixture was stirred at rt for 1.5 h. Purification by FCC (MeOH gradient in CH₂Cl₂) provided N-benzyl-3-[8-fluoro-4-(pyridin-3-yl)quinolin-6-yl]-1H-pyrrolo[2,3-b]pyridine-5-carboxamide (0.02 g; yield: 43%; HPLC purity: 92%).

Intermediate 66 tert-Butyl N-(3-{[3-(4-chloro-8-fluoroquinolin-6-yl)-1-(4-methylbenzenesulfonyl)-1H-pyrrolo[2,3-b]pyridin-5-yl]formamido}propyl)carbamate

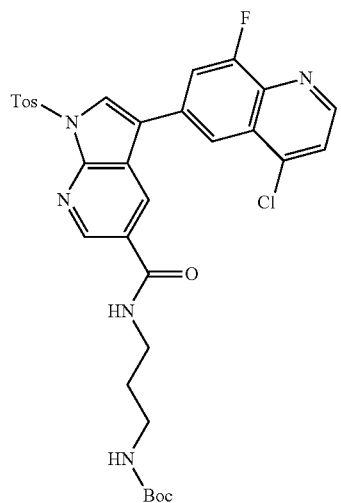

The title compound was prepared according to General Procedure 2 with tert-butyl N-(3-{[3-iodo-1-(4-methylbenzenesulfonyl)-1H-pyrrolo[2,3-b]pyridin-5-yl]formamido}propyl)carbamate (Intermediate 58) (0.18 g, 0.3 mmol, 1.0 eq.), (4-chloro-8-fluoroquinolin-6-yl)boronic acid (Intermediate 63) (0.12 g, 0.4 mmol, 1.3 eq.), K₂CO₃ (0.08 g, 0.6 mmol, 2.0 eq.), Pd(dppf)₂Cl₂*CH₂Cl₂ (0.05 g, 0.06 mmol, 0.2 eq.) in a mixture of 1,4-dioxane/water 2/1 (6 mL). The reaction mixture was heated at 80° C. for 3 h. Purification by FCC (EtOAc gradient in hexane) provided tert-butyl N-(3-{[3-(4-chloro-8-fluoroquinolin-6-yl)-1-(4-methylbenzenesulfonyl)-1H-pyrrolo[2,3-b]pyridin-5-yl]formamido}propyl)carbamate (0.1 g; yield: 51%; UPLC purity: 97%).

Intermediate 67 tert-Butyl N-[3-({3-[8-fluoro-4-(pyridin-3-yl)quinolin-6-yl]-1-(4-methylbenzenesulfonyl)-1H-pyrrolo[2,3-b]pyridin-5-yl}formamido)propyl]carbamate

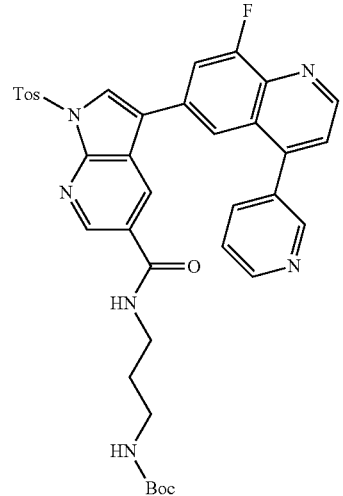

The title compound was prepared according to General Procedure 2 with tert-butyl N-(3-{[3-(4-chloro-8-fluoroquinolin-6-yl)-1-(4-methylbenzenesulfonyl)-1H-pyrrolo[2,3-b]pyridin-5-yl]formamido}propyl)carbamate (Intermediate 66) (0.1 g, 0.1 mmol, 1.0 eq.), 3-pyridyl boronic acid (0.02 g, 0.2 mmol, 1.1 eq.), K₂CO₃ (0.06 g, 0.4 mmol, 2.7 eq.), Pd(dppf)₂Cl₂*CH₂Cl₂ (0.01 g, 0.01 mmol, 0.03 eq.) in a mixture of 1,4-dioxane/water 2/1 (3 mL). After 25 min of microwave irradiation, UPLC-MS showed traces of the starting material (Intermediate 66) and additional portions of 3-pyridyl boronic acid (0.02 g, 0.2 mmol, 1.1 eq.), and Pd(dppf)₂Cl₂*CH₂Cl₂ (0.01 g, 0.01 mmol, 0.03 eq.) were added. Stirring was continued for next 25 min at 120° C. UPLC-MS showed a formation of a mixture of products: tert-butyl N-[3-({3-[8-fluoro-4-(pyridin-3-yl)quinolin-6-yl]-1-(4-methylbenzenesulfonyl)-1H-pyrrolo[2,3-b]pyridin-5-yl}formamido)propyl]carbamate and tert-butyl N-[3-({3-[8-fluoro-4-(pyridin-3-yl)quinolin-6-yl]-1H-pyrrolo[2,3-b]pyridin-5-yl}formamido)propyl]carbamate which was used in consecutive step without separation.

Intermediate 68 tert-Butyl N-[3-({3-[8-fluoro-4-(pyridin-3-yl)quinolin-6-yl]-1H-pyrrolo[2,3-b]pyridin-5-yl}formamido)propyl]carbamate

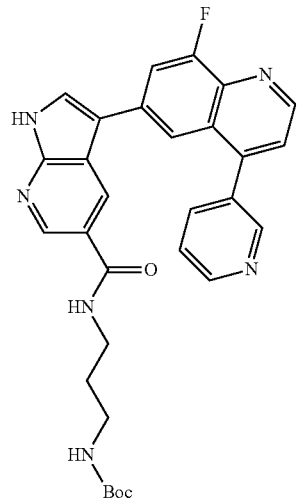 [SMILES: CC(C)(C)OC(=O)NCCCNC(=O)c1cnc2[nH]cc(-c3cc(F)c4nccc(-c5cccnc5)c4c3)c2c1]

The title compound was prepared according to General Procedure 3 with tert-butyl N-[3-({3-[8-fluoro-4-(pyridin-3-yl)quinolin-6-yl]-1-(4-methylbenzenesulfonyl)-1H-pyrrolo[2,3-b]pyridin-5-yl}formamido)propyl]carbamate (Intermediate 67) (0.1 g, 0.2 mmol, 1.0 eq.), NaOtBu (0.02 g, 0.2 mmol, 1.5 eq.) dissolved in 1,4-dioxane (3 mL). The reaction mixture was stirred at rt for 3 h. Purification by FCC (MeOH gradient in CH$_2$Cl$_2$) provided tert-butyl N-[3-({3-[8-fluoro-4-(pyridin-3-yl)quinolin-6-yl]-1H-pyrrolo[2,3-b]pyridin-5-yl}formamido)propyl]carbamate (0.035 g; yield: 42%; UPLC purity: 99%).

Example 37

N-(3-Aminopropyl)-3-[8-fluoro-4-(pyridin-3-yl)quinolin-6-yl]-1H-pyrrolo[2,3-b]pyridine-5-carboxamide hydrochloride

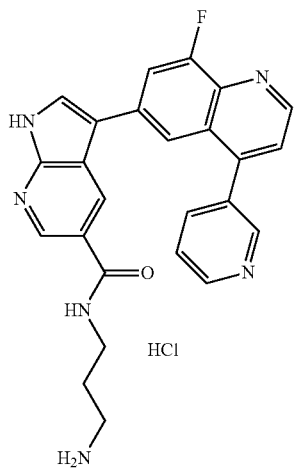 [SMILES: NCCCNC(=O)c1cnc2[nH]cc(-c3cc(F)c4nccc(-c5cccnc5)c4c3)c2c1 ; Cl]

The title compound was prepared according to General Procedure 5 with tert-butyl N-[3-({3-[8-fluoro-4-(pyridin-3-yl)quinolin-6-yl]-1H-pyrrolo[2,3-b]pyridin-5-yl}formamido)propyl]carbamate (Intermediate 68) (0.035 g, 0.006 mmol, 1.0 eq.) in MeOH (0.5 mL) and 2 M HCl in Et$_2$O (3 mL) (3 mL). The yellow solid was collected by filtration to provide N-(3-aminopropyl)-3-[8-fluoro-4-(pyridin-3-yl)quinolin-6-yl]-1H-pyrrolo[2,3-b]pyridine-5-carboxamide hydrochloride (0.02 g; yield: 69%; HPLC purity: 98%).

Intermediate 69

3-(4-Chloro-8-fluoroquinolin-6-yl)-N-methyl-1-(4-methylbenzenesulfonyl)-N-(prop-2-en-1-yl)-1H-pyrrolo[2,3-b]pyridine-5-carboxamide

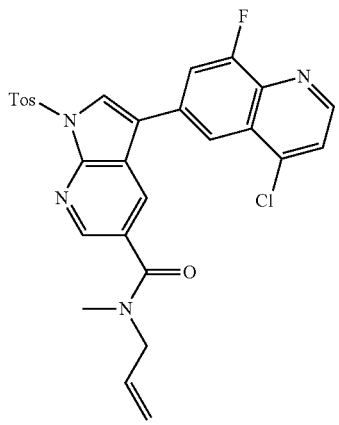

The title compound was prepared according to General Procedure 2 with 3-iodo-N-methyl-1-(4-methylbenzenesulfonyl)-N-(prop-2-en-1-yl)-1H-pyrrolo[2,3-b]pyridine-5-carboxamide (Intermediate 32) (0.2 g, 0.4 mmol, 1.0 eq.), (4-chloro-8-fluoroquinolin-6-yl)boronic acid (Intermediate 63) (0.16 g, 0.5 mmol, 1.3 eq.), K$_2$CO$_3$ (0.11 g, 0.8 mmol, 2.0 eq.), Pd(dppf)$_2$Cl$_2$*CH$_2$Cl$_2$ (0.06 g, 0.08 mmol, 0.2 eq.) in a mixture of 1,4-dioxane/water 2/1 (6 mL). The reaction mixture was stirred at 80° C. for 3 h. Purification by FCC (EtOAc gradient in hexane) provided 3-(4-chloro-8-fluoroquinolin-6-yl)-N-methyl-1-(4-methylbenzenesulfonyl)-N-(prop-2-en-1-yl)-1H-pyrrolo[2,3-b]pyridine-5-carboxamide (0.15 g; yield: 67%; UPLC purity: 93%).

Intermediate 70

3-[8-Fluoro-4-(pyridin-3-yl)quinolin-6-yl]-N-methyl-1-(4-methylbenzenesulfonyl)-N-(prop-2-en-1-yl)-1H-pyrrolo[2,3-b]pyridine-5-carboxamide

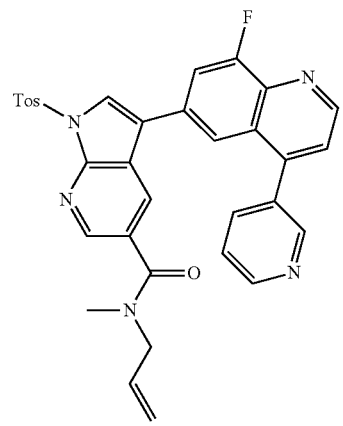

The title compound was prepared according to General Procedure 2 with 3-(4-chloro-8-fluoroquinolin-6-yl)-N-methyl-1-(4-methylbenzenesulfonyl)-N-(prop-2-en-1-yl)-1H-pyrrolo[2,3-b]pyridine-5-carboxamide (Intermediate 69) (0.15 g, 0.3 mmol, 1.0 eq.), 3-pyridyl boronic acid (0.04 g, 0.4 mmol, 1.3 eq.), K$_2$CO$_3$ (0.1 g, 0.7 mmol, 2.7 eq.), Pd(dppf)$_2$Cl$_2$*CH$_2$Cl$_2$ (0.02 g, 0.02 mmol, 0.3 eq.) in a mixture of 1,4-dioxane/water 2/1 (4 mL). The reaction mixture was stirred at 125° C. for 25 min. Purification by FCC (EtOAc gradient in hexane) afforded 3-[8-fluoro-4-(pyridin-3-yl)quinolin-6-yl]-N-methyl-1-(4-methylbenzenesulfonyl)-N-(prop-2-en-1-yl)-1H-pyrrolo[2,3-b]pyridine-5-carboxamide (0.08 g; yield: 53%; UPLC purity: 99%).

Example 38

3-[8-Fluoro-4-(pyridin-3-yl)quinolin-6-yl]-N-methyl-N-(prop-2-en-1-yl)-1H-pyrrolo[2,3-b]pyridine-5-carboxamide

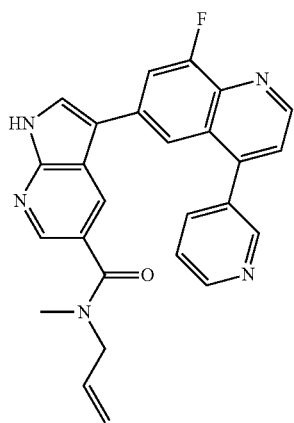 [SMILES: C=CCN(C)C(=O)c1cnc2[nH]cc(-c3cc(F)c4nccc(-c5cccnc5)c4c3)c2c1]

The title compound was prepared according to General Procedure 3 with 3-[8-fluoro-4-(pyridin-3-yl)quinolin-6-yl]-N-methyl-1-(4-methylbenzenesulfonyl)-N-(prop-2-en-1-yl)-1H-pyrrolo[2,3-b]pyridine-5-carboxamide (Intermediate 70) (0.09 g, 0.2 mmol, 1.0 eq.), KOH (0.01 g, 0.2 mmol, 1.5 eq.) dissolved in THF (3 mL). The reaction mixture was stirred at 50° C. for 3 h. Purification by FCC (MeOH gradient in CH$_2$Cl$_2$) afforded 3-[8-fluoro-4-(pyridin-3-yl)quinolin-6-yl]-N-methyl-N-(prop-2-en-1-yl)-1H-pyrrolo[2,3-b]pyridine-5-carboxamide (0.01 g; yield: 20%; HPLC purity: 99%).

Intermediate 71

3-(4-Chloro-8-fluoroquinolin-6-yl)-N-methyl-1-(4-methylbenzenesulfonyl)-1H-pyrrolo[2,3-b]pyridine-5-carboxamide

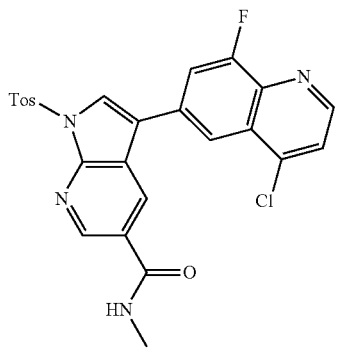

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (1.5 g, 3.3 mmol, 1.0 eq.), (4-chloro-8-fluoroquinolin-6-yl)boronic acid (Intermediate 63) (1.3 g, 4.3 mmol, 1.3 eq.), K$_2$CO$_3$ (0.9 g, 6.6 mmol, 2.0 eq.), Pd(dppf)$_2$Cl$_2$*CH$_2$Cl$_2$ (0.5 g, 0.7 mmol, 0.2 eq.) in a mixture of 1,4-dioxane/water 2/1 (18 mL). The reaction mixture was stirred at 80° C. for 3 h. Purification by FCC (EtOAc gradient in hexane) afforded 3-(4-chloro-8-fluoroquinolin-6-yl)-N-methyl-1-(4-methylbenzenesulfonyl)-1H-pyrrolo[2,3-b]pyridine-5-carboxamide (1.1 g; yield: 66%; UPLC purity: 88%).

Intermediate 72

3-[8-Fluoro-4-(pyridin-3-yl)quinolin-6-yl]-N-methyl-1-(4-methylbenzenesulfonyl)-1H-pyrrolo[2,3-b]pyridine-5-carboxamide

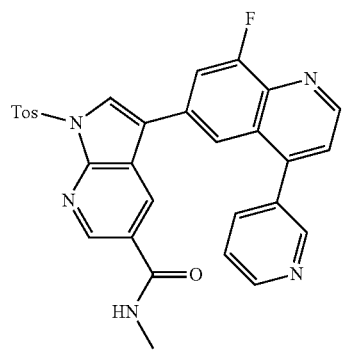

The title compound was prepared according to General Procedure 2 with 3-(4-chloro-8-fluoroquinolin-6-yl)-N-methyl-1-(4-methylbenzenesulfonyl)-1H-pyrrolo[2,3-b]pyridine-5-carboxamide (Intermediate 71) (1.1 g, 1.1 mmol, 1.0 eq.), 3-pyridyl boronic acid (0.28 g, 1.2 mmol, 1.1 eq.), K$_2$CO$_3$ (0.8 g, 2.9 mmol, 2.7 eq.), Pd(dppf)$_2$Cl$_2$*CH$_2$Cl$_2$ (0.14 g, 0.09 mmol, 0.3 eq.) in a mixture of 1,4-dioxane/water 2/1 (22 mL). The reaction mixture was stirred at 120° C. for 25 min. Purification by FCC (MeOH gradient in CH$_2$Cl$_2$) afforded 3-[8-fluoro-4-(pyridin-3-yl)quinolin-6-yl]-N-methyl-1-(4-methylbenzenesulfonyl)-1H-pyrrolo[2,3-b]pyridine-5-carboxamide (1.2 g; yield: 46%; UPLC purity: 88%).

Example 39

3-[8-Fluoro-4-(pyridin-3-yl)quinolin-6-yl]-N-methyl-1H-pyrrolo[2,3-b]pyridine-5-carboxamide

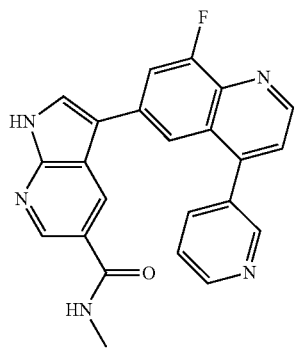 [SMILES: CNC(=O)c1cnc2[nH]cc(-c3cc(F)c4nccc(-c5cccnc5)c4c3)c2c1]

The title compound was prepared according to General Procedure 3 with 3-[8-fluoro-4-(pyridin-3-yl)quinolin-6-yl]-N-methyl-1-(4-methylbenzenesulfonyl)-1H-pyrrolo[2,3-b]pyridine-5-carboxamide (Intermediate 72) (0.5 g, 0.9 mmol, 1.0 eq.), NaOtBu (0.13 g, 1.4 mmol, 1.5 eq.) dissolved in 1,4-dioxane (8 mL). The reaction mixture was stirred at rt for 5 h. UPLC-MS showed 40% of starting material. Additional portion of NaOtBu (0.06 g, 0.7 mmol, 0.75 eq.) was added and stirring was continued overnight. Purification by FCC (MeOH gradient in $CH_2Cl_2$; column neutralized with 0.1% $Et_3N$ in $CH_2Cl_2$ then washed with $CH_2Cl_2$ before purification) provided 3-[8-fluoro-4-(pyridin-3-yl)quinolin-6-yl]-N-methyl-1H-pyrrolo[2,3-b]pyridine-5-carboxamide (0.14 g; yield: 39%; HPLC purity: 99%).

Intermediate 73

3-[8-Fluoro-4-(2-phenylethyl)quinolin-6-yl]-N-methyl-1-(4-methylbenzenesulfonyl)-1H-pyrrolo[2,3-b]pyridine-5-carboxamide

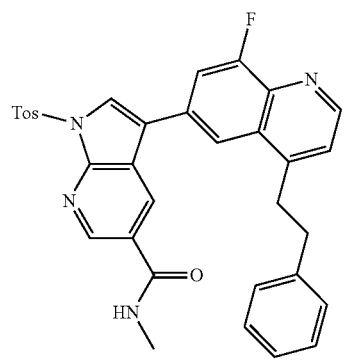

The title compound was prepared according to General Procedure 8 with 3-(4-chloro-8-fluoroquinolin-6-yl)-N-methyl-1-(4-methylbenzenesulfonyl)-1H-pyrrolo[2,3-b]pyridine-5-carboxamide (Intermediate 71) (0.1 g, 0.2 mmol, 1.0 eq.), potassium phenethyltrifluoroborate (0.09 g, 0.4 mmol, 2.0 eq.), $Pd(OAc)_2$ (0.001 g, 0.01 mmol, 0.03 eq.), RuPhos (0.006 g, 0.01 mmol, 0.06 eq.), and $K_2CO_3$ (0.08 g, 0.6 mmol, 3.0 eq.) in a mixture of toluene (3 mL) and water (0.3 mL). After 23 h of heating UPLC-MS showed 54% of starting material. Additional amount of potassium phenethyltrifluoroborate (0.09 g, 0.4 mmol, 2.0 eq.), $Pd(OAc)_2$ (0.03 eq.), RuPhos (0.06 eq.) in a mixture of toluene (2 mL) and water (0.2 mL) were added and heating was continued for 20 h. UPLC-MS showed 31% of starting material. Additional heating for 24 h resulted in 68% of product in UPLC-MS analysis. Purification by FCC (EtOAc gradient in hexane) gave 3-[8-fluoro-4-(2-phenylethyl)quinolin-6-yl]-N-methyl-1-(4-methylbenzenesulfonyl)-1H-pyrrolo[2,3-b]pyridine-5-carboxamide as a beige solid (0.05 g; yield: 42%; UPLC purity: 94%).

Example 40

3-[8-Fluoro-4-(2-phenylethyl)quinolin-6-yl]-N-methyl-1H-pyrrolo[2,3-b]pyridine-5-carboxamide

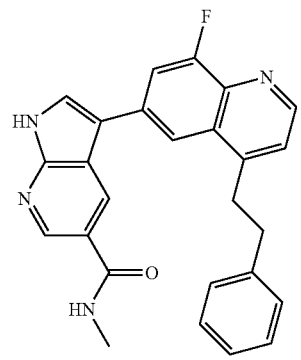 [SMILES: CNC(=O)c1cnc2[nH]cc(-c3cc(F)c4nccc(CCc5ccccc5)c4c3)c2c1]

The title compound was prepared according to General Procedure 3 with 3-[8-fluoro-4-(2-phenylethyl)quinolin-6-yl]-N-methyl-1-(4-methylbenzenesulfonyl)-1H-pyrrolo[2,3-b]pyridine-5-carboxamide (Intermediate 73) (0.05 g, 0.09 mmol, 1.0 eq.), NaOtBu (0.01 g, 0.2 mmol, 2.0 eq.) dissolved in 1,4-dioxane (2 mL). The reaction mixture was stirred at 80° C. for 1.5 h. Purification by FCC (MeOH gradient in $CH_2Cl_2$) provided 3-[8-fluoro-4-(2-phenylethyl)quinolin-6-yl]-N-methyl-1H-pyrrolo[2,3-b]pyridine-5-carboxamide as a beige solid (0.015 g; yield: 41%; HPLC purity: 94%).

Intermediate 74 tert-Butyl N-[(3R)-1-{8-fluoro-6-[1-(4-methylbenzenesulfonyl)-5-(methylcarbamoyl)-1H-pyrrolo[2,3-b]pyridin-3-yl]quinolin-4-yl}piperidin-3-yl]carbamate

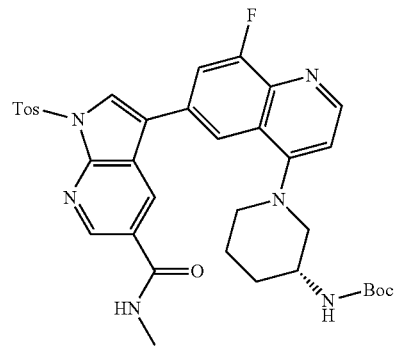

The title compound was prepared according to General Procedure 4 with 3-(4-chloro-8-fluoroquinolin-6-yl)-N-methyl-1-(4-methylbenzenesulfonyl)-1H-pyrrolo[2,3-b]pyridine-5-carboxamide (Intermediate 71) (0.13 g, 0.3 mmol, 1.0 eq.), (R)-3-(Boc-amino)piperidine (0.1 g, 0.5 mmol, 2.0 eq.), DIPEA (0.07 g, 0.5 mmol, 2 eq.) in i-PrOH (3 mL). The reaction mixture was stirred at 110° C. for 5 days. Purification by FCC (MeOH gradient in $CH_2Cl_2$) afforded tert-butyl N-[(3R)-1-{8-fluoro-6-[1-(4-methylbenzenesulfonyl)-5-(methylcarbamoyl)-1H-pyrrolo[2,3-b]pyridin-3-yl]quinolin-4-yl}piperidin-3-yl]carbamate (0.05 g; yield: 29%; UPLC purity: 97%).

Intermediate 75 tert-Butyl N-[(3R)-1-{8-fluoro-6-[5-(methylcarbamoyl)-1H-pyrrolo[2,3-b]pyridin-3-yl]quinolin-4-yl}piperidin-3-yl]carbamate

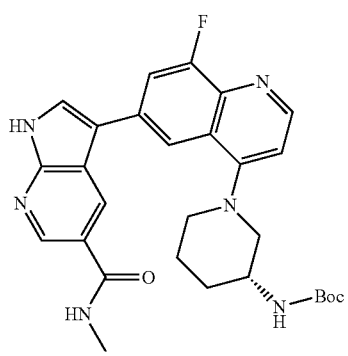 [SMILES: CNC(=O)c1cnc2[nH]cc(-c3cc(F)c4nccc(N5CCC[C@@H](NC(=O)OC(C)(C)C)C5)c4c3)c2c1]

The title compound was prepared according to General Procedure 3 with tert-butyl N-[(3R)-1-{8-fluoro-6-[1-(4-methylbenzenesulfonyl)-5-(methylcarbamoyl)-1H-pyrrolo[2,3-b]pyridin-3-yl]quinolin-4-yl}piperidin-3-yl]carbamate (Intermediate 74) (0.05 g, 0.07 mmol, 1.0 eq.), KOH (0.006 g, 0.1 mmol, 1.5 eq.) dissolved in THF (3 mL). The reaction mixture was stirred at 50° C. for 3 h. After work-up the residue was used in consecutive step without further purification.

Example 41

3-{4-[(3R)-3-Aminopiperidin-1-yl]-8-fluoroquinolin-6-yl}-N-methyl-1H-pyrrolo[2,3-b]pyridine-5-carboxamide hydrochloride

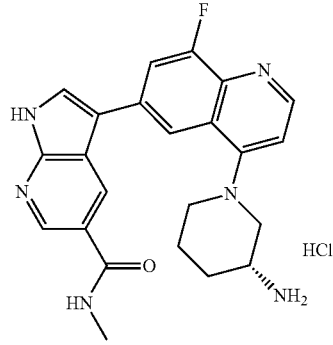 [SMILES: CNC(=O)c1cnc2[nH]cc(-c3cc(F)c4nccc(N5CCC[C@@H](N)C5)c4c3)c2c1 ; Cl]

The title compound was prepared according to General Procedure 5 with tert-butyl N-[(3R)-1-{8-fluoro-6-[5-(methylcarbamoyl)-1H-pyrrolo[2,3-b]pyridin-3-yl]quinolin-4-yl}piperidin-3-yl]carbamate (Intermediate 75) (0.02 g, 0.03 mmol, 1.0 eq.) in MeOH (0.5 mL) and 2 M HCl in Et$_2$O (2 mL). HPLC purification of collected precipitate provided 3-{4-[(3R)-3-aminopiperidin-1-yl]-8-fluoroquinolin-6-yl}-N-methyl-1H-pyrrolo[2,3-b]pyridine-5-carboxamide hydrochloride (0.009 g; yield: 56%; HPLC purity: 100%).

Intermediate 76

(4-Chloro-8-methylquinolin-6-yl)boronic acid; 4-Chloro-8-methyl-6-(tetramethyl-1,3,2-dioxaborolan-2-yl)quinoline

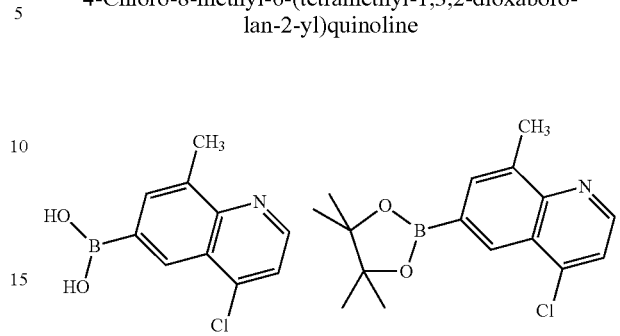

The title compound was prepared according to General Procedure 1 with 6-bromo-4-chloro-8-methylquinoline (0.5 g, 2.0 mmol, 1.0 eq.), bis(pinacolato)diboron (0.5 g, 2.0 mmol, 1.0 eq.), potassium acetate (0.47 g, 5.0 mmol, 2.5 eq.), Pd(dppf)$_2$Cl$_2$*CH$_2$Cl$_2$ (0.08 g, 0.01 mmol, 0.05 eq.) and 1,4-dioxane (5 mL). The reaction mixture was stirred at 80° C. for 4 h. Obtained mixture of (4-chloro-8-methylquinolin-6-yl)boronic acid and 4-chloro-8-methyl-6-(tetramethyl-1,3,2-dioxaborolan-2-yl)quinoline in the ratio 1:1 was used in consecutive step without further purification.

Intermediate 77

3-(4-Chloro-8-methylquinolin-6-yl)-N-methyl-1-(4-methylbenzenesulfonyl)-1H-pyrrolo[2,3-b]pyridine-5-carboxamide

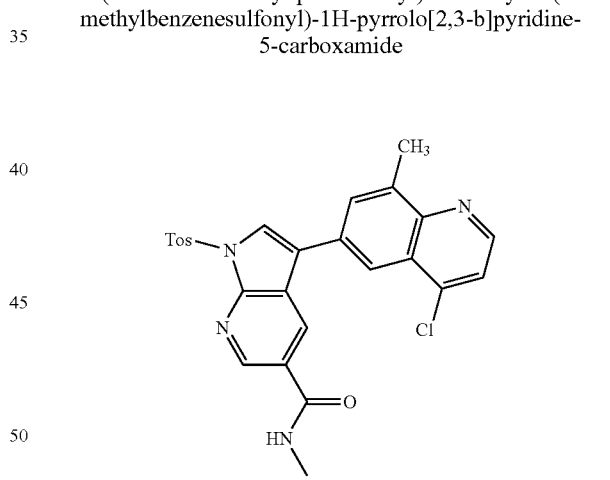

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.2 g, 0.4 mmol, 1.0 eq.), (4-chloro-8-methylquinolin-6-yl)boronic acid and 4-chloro-8-methyl-6-(tetramethyl-1,3,2-dioxaborolan-2-yl)quinoline (Intermediate 76) (0.15 g, 0.5 mmol, 1.1 eq.), K$_2$CO$_3$ (0.1 g, 0.9 mmol, 2.0 eq.), Pd(dppf)$_2$Cl$_2$ (0.05 g, 0.1 mmol, 0.2 eq.) in a mixture of 1,4-dioxane/water 2/1 (6 mL). The reaction mixture was stirred at 80° C. for 3 h. Purification by FCC (EtOAc gradient in hexane) afforded 3-(4-chloro-8-methylquinolin-6-yl)-N-methyl-1-(4-methylbenzenesulfonyl)-1H-pyrrolo[2,3-b]pyridine-5-carboxamide (0.076 g; yield: 34%; UPLC purity: 90%).

Intermediate 78

N-Methyl-3-[8-methyl-4-(pyridin-3-yl)quinolin-6-yl]-1-(4-methylbenzenesulfonyl)-1H-pyrrolo[2,3-b]pyridine-5-carboxamide

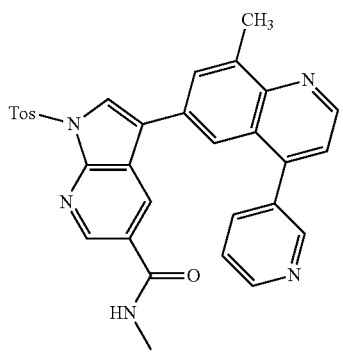

The title compound was prepared according to General Procedure 2 with 3-(4-chloro-8-methylquinolin-6-yl)-N-methyl-1-(4-methylbenzenesulfonyl)-1H-pyrrolo[2,3-b]pyridine-5-carboxamide (Intermediate 77) (0.07 g, 0.1 mmol, 1.0 eq.), 3-pyridyl boronic acid (0.028 g, 0.2 mmol, 1.5 eq.), $K_2CO_3$ (0.04 g, 0.3 mmol, 2.0 eq.), Pd(dppf)$_2$Cl$_2$ (0.006 g, 0.08 mmol, 0.05 eq.) in a mixture of 1,4-dioxane/water 2/1 (5 mL). The reaction mixture was irradiated in microwave at 120° C. for 40 min. UPLC-MS from crude reaction mixture showed a mixture of products: N-methyl-3-[8-methyl-4-(pyridin-3-yl)quinolin-6-yl]-1-(4-methylbenzenesulfonyl)-1H-pyrrolo[2,3-b]pyridine-5-carboxamide and unprotected analog N-methyl-3-[8-methyl-4-(pyridin-3-yl)quinolin-6-yl]-1H-pyrrolo[2,3-b]pyridine-5-carboxamide which were used in consecutive step without further purification.

Example 42

N-Methyl-3-[8-methyl-4-(pyridin-3-yl)quinolin-6-yl]-1H-pyrrolo[2,3-b]pyridine-5-carboxamide

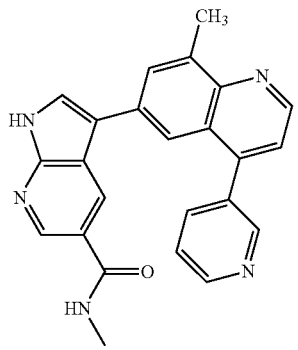 [SMILES: CNC(=O)c1cnc2[nH]cc(-c3cc(C)c4nccc(-c5cccnc5)c4c3)c2c1]

The title compound was prepared according to General Procedure 3 with a mixture of N-methyl-3-[8-methyl-4-(pyridin-3-yl)quinolin-6-yl]-1-(4-methylbenzenesulfonyl)-1H-pyrrolo[2,3-b]pyridine-5-carboxamide and N-methyl-3-[8-methyl-4-(pyridin-3-yl)quinolin-6-yl]-1H-pyrrolo[2,3-b]pyridine-5-carboxamide (Intermediate 78) (0.07 g, 0.1 mmol, 1.0 eq.), NaOtBu (0.018 g, 0.2 mmol, 1.5 eq.) dissolved in 1,4-dioxane (2 mL). The reaction mixture was stirred at rt for 3 h. Purification by FCC (MeOH gradient in $CH_2Cl_2$) provided N-methyl-3-[8-methyl-4-(pyridin-3-yl)quinolin-6-yl]-1H-pyrrolo[2,3-b]pyridine-5-carboxamide as an yellowish solid (0.01 g; yield: 20%; HPLC purity: 98%).

Intermediate 79 tert-Butyl N-[(3S)-1-(6-bromo-8-fluoroquinolin-4-yl)piperidin-3-yl]carbamate

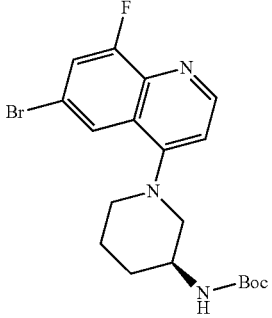 [SMILES: CC(C)(C)OC(=O)N[C@H]1CCCN(c2ccnc3c(F)cc(Br)cc23)C1]

A solution of 6-bromo-4-chloro-8-fluoroquinoline (0.3 g, 1.1 mmol, 1.0 eq.) and (S)-3-(Boc-amino)piperidine (0.6 g, 2.9 mmol, 2.5 eq.) in $CH_3CN$ (5 mL) was heated at 80° C. overnight. The reaction mixture was concentrated and the residue was purified by FCC (EtOAc gradient in hexane) to afford tert-butyl N-[(3S)-1-(6-bromo-8-fluoroquinolin-4-yl)piperidin-3-yl]carbamate (0.2 g, yield: 43%; UPLC purity: 96%).

Intermediate 80

{4-[(3S)-3-{[(Tert-butoxy)carbonyl]amino}piperidin-1-yl]-8-fluoroquinolin-6-yl}boronic acid

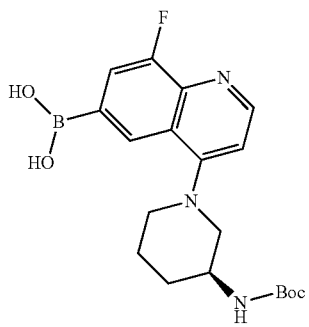 [SMILES: CC(C)(C)OC(=O)N[C@H]1CCCN(c2ccnc3c(F)cc(B(O)O)cc23)C1]

The title compound was prepared according to General Procedure 1 with tert-butyl N-[(3S)-1-(6-bromo-8-fluoroquinolin-4-yl)piperidin-3-yl]carbamate (Intermediate 79) (0.2 g, 0.5 mmol, 1.0 eq.), bis(pinacolato)diboron (0.2 g, 0.7 mmol, 1.5 eq.), potassium acetate (0.1 g, 1.2 mmol, 2.5 eq.), Pd(dppf)$_2$Cl$_2$*$CH_2Cl_2$ (0.02 g, 0.02 mmol, 0.05 eq.) and 1,4-dioxane (10 mL). The reaction mixture was stirred at 80° C. for 5 h. Obtained {4-[(3S)-3-{[(tert-butoxy)carbonyl]

amino}piperidin-1-yl]-8-fluoroquinolin-6-yl}boronic acid was used in consecutive step without further purification (UPLC purity: 84%).

Intermediate 81 tert-Butyl N-[(3S)-1-{8-fluoro-6-[1-(4-methylbenzenesulfonyl)-5-(methylcarbamoyl)-1H-pyrrolo[2,3-b]pyridin-3-yl]quinolin-4-yl}piperidin-3-yl]carbamate

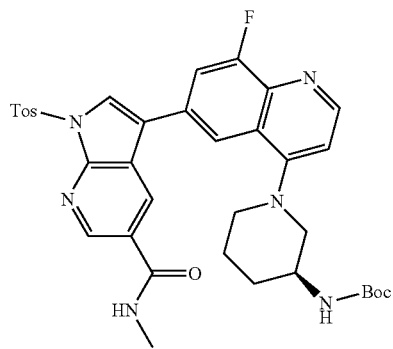

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.15 g, 0.3 mmol, 1.0 eq.), {4-[(3S)-3-{[(tert-butoxy)carbonyl]amino}piperidin-1-yl]-8-fluoroquinolin-6-yl}boronic acid (Intermediate 80) (0.2 g, 0.4 mmol, 1.3 eq.), $K_2CO_3$ (0.09 g, 0.7 mmol, 2.0 eq.), Pd(dppf)$_2$Cl$_2$*CH$_2$Cl$_2$ (0.05 g, 0.07 mmol, 0.2 eq.) in a mixture of 1,4-dioxane/water 2/1 (6 mL). The reaction mixture was stirred at 80° C. for 3 h. Purification by FCC (MeOH gradient in CH$_2$Cl$_2$) afforded tert-butyl N-[(3S)-1-{8-fluoro-6-[1-(4-methylbenzenesulfonyl)-5-(methylcarbamoyl)-1H-pyrrolo[2,3-b]pyridin-3-yl]quinolin-4-yl}piperidin-3-yl]carbamate (0.13 g; yield: 58%; UPLC purity: 96%).

Intermediate 82 tert-Butyl N-[(3S)-1-{8-fluoro-6-[5-(methylcarbamoyl)-1H-pyrrolo[2,3-b]pyridin-3-yl]quinolin-4-yl}piperidin-3-yl]carbamate

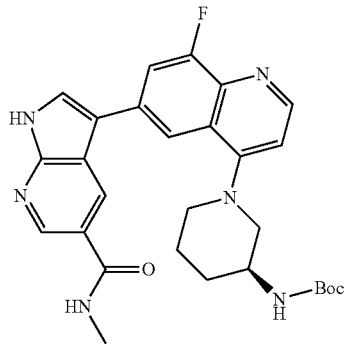 [SMILES: CNC(=O)c1cnc2[nH]cc(-c3cc(F)c4nccc(N5CCC[C@H](NC(=O)OC(C)(C)C)C5)c4c3)c2c1]

The title compound was prepared according to General Procedure 3 with tert-butyl N-[(3S)-1-{8-fluoro-6-[1-(4-methylbenzenesulfonyl)-5-(methylcarbamoyl)-1H-pyrrolo[2,3-b]pyridin-3-yl]quinolin-4-yl}piperidin-3-yl]carbamate (Intermediate 81) (0.13 g, 0.2 mmol, 1.0 eq.), NaOtBu (0.08 g, 0.3 mmol, 1.5 eq.) dissolved in 1,4-dioxane (6 mL). The reaction mixture was stirred at rt overnight. Purification by FCC (MeOH gradient in CH$_2$Cl$_2$) provided tert-butyl N-[(3S)-1-{8-fluoro-6-[5-(methylcarbamoyl)-1H-pyrrolo[2,3-b]pyridin-3-yl]quinolin-4-yl}piperidin-3-yl]carbamate as a beige solid (0.04 g; yield: 40%; UPLC purity: 94%).

Example 43

3-{4-[(3S)-3-Aminopiperidin-1-yl]-8-fluoroquinolin-6-yl}-N-methyl-1H-pyrrolo[2,3-b]pyridine-5-carboxamide hydrochloride

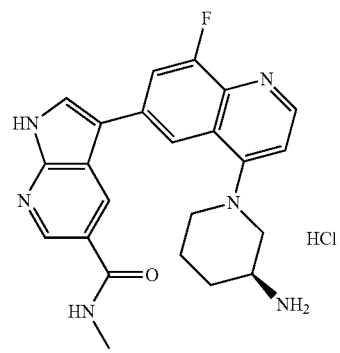 [SMILES: CNC(=O)c1cnc2[nH]cc(-c3cc(F)c4nccc(N5CCC[C@H](N)C5)c4c3)c2c1 ; Cl]

The title compound was prepared according to General Procedure 5 with tert-butyl N-[(3S)-1-{8-fluoro-6-[5-(methylcarbamoyl)-1H-pyrrolo[2,3-b]pyridin-3-yl]quinolin-4-yl}piperidin-3-yl]carbamate (Intermediate 82) (0.04 g, 0.08 mmol, 1.0 eq.) in MeOH (1 mL) and 2 M HCl in Et$_2$O (3 mL). Yellow precipitate was collected by filtration to provide 3-{4-[(3S)-3-aminopiperid in-1-yl]-8-fluoroquinolin-6-yl}-N-methyl-1H-pyrrolo[2,3-b]pyridine-5-carboxamide hydrochloride (0.03 g; yield: 98%; HPLC purity: 94%).

Example 44

N-Methyl-3-[8-fluoro-4-(4-methylpyridin-3-yl)quinolin-6-yl]-1H-pyrrolo[2,3-b]pyridine-5-carboxamide

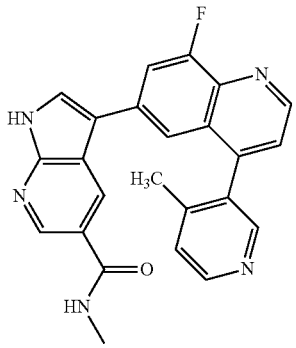 [SMILES: CNC(=O)c1cnc2[nH]cc(-c3cc(F)c4nccc(-c5cnccc5C)c4c3)c2c1]

The title compound was prepared according to General Procedure 2 with 3-(4-chloro-8-fluoroquinolin-6-yl)-N-methyl-1-(4-methylbenzenesulfonyl)-1H-pyrrolo[2,3-b]

pyridine-5-carboxamide (Intermediate 71) (0.07 g, 0.14 mmol, 1.0 eq.), 4-methylpyridine-3-boronic acid (0.03 g, 0.2 mmol, 1.5 eq.), K$_2$CO$_3$ (0.04 g, 0.3 mmol, 2.0 eq.), Pd(PPh$_3$)$_4$ (0.03 g, 0.03 mmol, 0.2 eq.) in a mixture of 1,4-dioxane/water 2/1 (3 mL). The reaction mixture was stirred at 120° C. for 25 min. Purification by FCC (MeOH gradient in CH$_2$Cl$_2$) afforded N-methyl-3-[8-fluoro-4-(4-methylpyridin-3-yl)quinolin-6-yl]-1H-pyrrolo[2,3-b]pyridine-5-carboxamide (0.009 g; yield: 11%; HPLC purity: 96%).

Intermediate 83

6-Chloro-8-methoxy-4-(pyridin-3-yl)quinoline

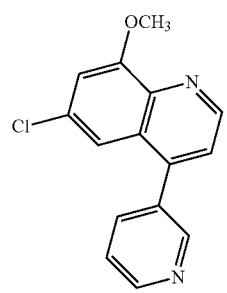 [SMILES: COc1cc(Cl)cc2c(-c3cccnc3)ccnc12]

The title compound was prepared according to General Procedure 2 with 4-bromo-6-chloro-8-methoxyquinoline (0.2 g, 0.7 mmol, 1.0 eq.), 3-pyridylboronic acid (0.1 g, 0.8 mmol, 1.1 eq.), K$_2$CO$_3$ (0.2 g, 1.5 mmol, 2.0 eq.), Pd(dppf)$_2$Cl$_2$ (0.03 g, 0.15 mmol, 0.05 eq.) in a mixture of 1,4-dioxane/water 2/1 (6 mL). The reaction mixture was stirred at 80° C. overnight. Purification by FCC (MeOH gradient in CH$_2$Cl$_2$) afforded 6-chloro-8-methoxy-4-(pyridin-3-yl)quinoline (0.16 g; yield: 78%; UPLC purity: 100%).

Intermediate 84

[8-Methoxy-4-(pyridin-3-yl)quinolin-6-yl]boronic acid

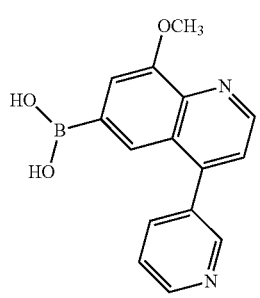 [SMILES: COc1cc(B(O)O)cc2c(-c3cccnc3)ccnc12]

The title compound was prepared according to General Procedure 1 with 6-chloro-8-methoxy-4-(pyridin-3-yl)quinoline (Intermediate 83) (0.16 g, 0.6 mmol, 1.0 eq.), bis(pinacolato)diboron (0.16 g, 0.6 mmol, 1.1 eq.), potassium acetate (0.11 g, 1.2 mmol, 2.0 eq.), Pd(dppf)$_2$Cl$_2$*CH$_2$Cl$_2$ (0.04 g, 0.06 mmol, 0.1 eq.) and 1,4-dioxane (2 mL). After 5 h of heating at 80° C. UPLC-MS showed 60% of starting material. Additional portion of catalyst (0.1 eg) and bis(pinacolato)diboron (0.5 eq.) was added and heating was continued for next 8 h. After work-up obtained [8-methoxy-4-(pyridin-3-yl)quinolin-6-yl]boronic acid was used in consecutive step without further purification (UPLC purity: 71%).

Intermediate 85

3-[8-Methoxy-4-(pyridin-3-yl)quinolin-6-yl]-1-(4-methylbenzenesulfonyl)-1H-pyrrolo[2,3-b]pyridine-5-carboxamide

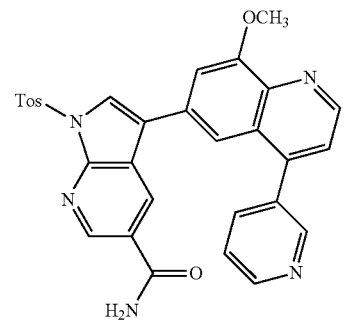

The title compound was prepared according to General Procedure 2 with 3-iodo-1-(4-methylbenzenesulfonyl)-1H-pyrrolo[2,3-b]pyridine-5-carboxamide (Intermediate 56) (0.2 g, 0.5 mmol, 1.0 eq.), [8-methoxy-4-(pyridin-3-yl)quinolin-6-yl]boronic acid (Intermediate 84) (0.25 g, 0.7 mmol, 1.5 eq.), K$_2$CO$_3$ (0.13 g, 0.9 mmol, 2.0 eq.), Pd(dppf)$_2$Cl$_2$*CH$_2$Cl$_2$ (0.04 g, 0.05 mmol, 0.1 eq.) in a mixture of 1,4-dioxane/water 2/1 (6 mL). The reaction mixture was stirred at 80° C. for 3 h. Purification by FCC (MeOH gradient in CH$_2$Cl$_2$) provided 3-[8-methoxy-4-(pyridin-3-yl)quinolin-6-yl]-1-(4-methylbenzenesulfonyl)-1H-pyrrolo[2,3-b]pyridine-5-carboxamide (0.12 g; yield: 47%; UPLC purity: 96%).

Example 45

3-[8-Methoxy-4-(pyridin-3-yl)quinolin-6-yl]-1H-pyrrolo[2,3-b]pyridine-5-carboxamide

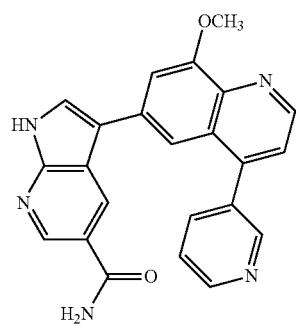 [SMILES: COc1cc(-c2c[nH]c3ncc(C(N)=O)cc23)cc2c(-c3cccnc3)ccnc12]

The title compound was prepared according to General Procedure 3 with 3-[8-methoxy-4-(pyridin-3-yl)quinolin-6-yl]-1-(4-methylbenzenesulfonyl)-1H-pyrrolo[2,3-b]pyridine-5-carboxamide (Intermediate 85) (0.04 g, 0.07 mmol, 1.0 eq.), NaOtBu (0.04 g, 0.1 mmol, 2.5 eq.) dissolved in 1,4-dioxane (4 mL). The reaction mixture was stirred at rt for 4 h. Purification by FCC (MeOH gradient in CH$_2$Cl$_2$) provided 3-[8-methoxy-4-(pyridin-3-yl)quinolin-6-yl]-1H-pyrrolo[2,3-b]pyridine-5-carboxamide as an yellow solid (0.015 g; yield: 52%; HPLC purity: 99%).

Intermediate 86 (Acc. to PCT 2009/111278)

3-Bromo-1-(4-methylbenzenesulfonyl)-5-nitro-1H-pyrrolo[2,3-b]pyridine

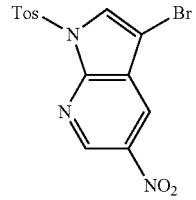

Tetrabutylammonium nitrate (7.3 g, 23.9 mmol, 1.5 eq.) was dissolved in dry CH$_2$Cl$_2$ (10 mL) and the solution was cooled to 0° C. Then trifluoroacetic anhydride was added and the reaction mixture was stirred at 0° C. for 20 min. In another flask a solution of 3-bromo-1-(4-methylbenzenesulfonyl)-1H-pyrrolo[2,3-b]pyridine (Intermediate 1b) (5.6 g, 15.9 mmol, 1.0 eq.) in CH$_2$Cl$_2$ (15 mL) was cooled to 0° C. To this solution was transferred precooled mixture of Bu$_4$N$^+$ NO$_3^-$, TFAA in CH$_2$Cl$_2$. The reaction mixture was stirred at rt overnight and then quenched with water. The organic layer was extracted with CH$_2$Cl$_2$. The combined organic layers were dried over Na$_2$SO$_4$, filtered and concentrated. The residue was dissolved in Et$_2$O/CH$_2$Cl$_2$ (9:1), sonicated for 15 min. The precipitate was collected by filtration, rinsed with Et$_2$O and dried on air to provide 3-bromo-1-(4-methylbenzenesulfonyl)-5-nitro-1H-pyrrolo[2,3-b]pyridine (4.14 g; yield: 65%; UPLC purity: 98%).

Intermediate 87

3-Bromo-1-(4-methylbenzenesulfonyl)-1H-pyrrolo[2,3-b]pyridin-5-amine

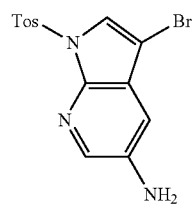

To a solution of 3-bromo-1-(4-methylbenzenesulfonyl)-5-nitro-1H-pyrrolo[2,3-b]pyridine (Intermediate 86) (0.5 g, 1.2 mmol, 1.0 eq.) and Raney-nickel (1 g) in EtOH (15 mL) hydrazine monohydrate was added dropwise (0.25 g, 5.1 mmol, 4.0 eq.). The reaction mixture was stirred at rt for 1 h and then filtered through a pad of Celite. The filtrate was dried over Na$_2$SO$_4$ and concentrated. Purification by FCC (EtOAc gradient in hexane) afforded 3-bromo-1-(4-methylbenzenesulfonyl)-1H-pyrrolo[2,3-b]pyridin-5-amine (0.22 g; yield: 58%; UPLC purity: 79%).

Intermediate 88

N-[3-Bromo-1-(4-methylbenzenesulfonyl)-1H-pyrrolo[2,3-b]pyridin-5-yl]acetamide

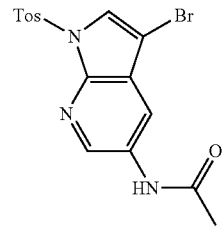

A solution of 3-bromo-1-(4-methylbenzenesulfonyl)-1H-pyrrolo[2,3-b]pyridin-5-amine (Intermediate 87) (0.23 g, 0.6 mmol, 1.0 eq.) and Et$_3$N (0.6 g, 6.3 mmol, 10.0 eq.) in CH$_2$Cl$_2$ (3 mL) was cooled to 0° C. Then acetyl chloride (0.15 g, 1.9 mmol, 3.0 eq.) was added dropwise and the reaction mixture was stirred at rt overnight. The reaction mixture was concentrated and the residue was dissolved in EtOAc and washed with saturated solution of NaHCO$_3$. The organic layer was dried over MgSO$_4$, filtered and concentrated to provide N-[3-bromo-1-(4-methylbenzenesulfonyl)-1H-pyrrolo[2,3-b]pyridin-5-yl]acetamide (0.25 g; yield: 98%; UPLC purity: 81%).

Intermediate 89

N-[3-(4-Chloro-8-fluoroquinolin-6-yl)-1-(4-methylbenzenesulfonyl)-1H-pyrrolo[2,3-b]pyridin-5-yl]acetamide

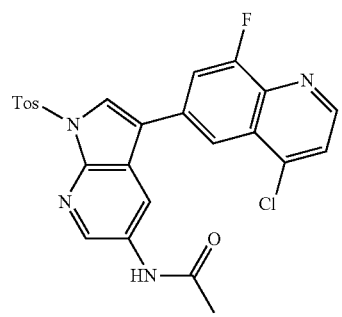

The title compound was prepared according to General Procedure 2 with N-[3-bromo-1-(4-methylbenzenesulfonyl)-1H-pyrrolo[2,3-b]pyridin-5-yl]acetamide (Intermediate 88) (0.25 g, 0.6 mmol, 1.0 eq.), (4-chloro-8-fluoroquinolin-6-yl)boronic acid (Intermediate 63) (0.22 g, 0.7 mmol, 1.3 eq.), K$_2$CO$_3$ (0.15 g, 1.1 mmol, 2.0 eq.), Pd(dppf)$_2$Cl$_2$*CH$_2$Cl$_2$ (0.09 g, 0.11 mmol, 0.2 eq.) in a mixture of 1,4-dioxane/water 2/1 (6 mL). The reaction mixture was stirred at 80° C. for 3 h. Purification by FCC (MeOH gradient in CH$_2$Cl$_2$) provided N-[3-(4-chloro-8-fluoroquinolin-6-yl)-1-(4-methylbenzenesulfonyl)-1H-pyrrolo[2,3-b]pyridin-5-yl]acetamide (0.09 g; yield: 32%; UPLC purity: 82%).

Intermediate 90

N-{3-[8-Fluoro-4-(pyridin-3-yl)quinolin-6-yl]-1-(4-methylbenzenesulfonyl)-1H-pyrrolo[2,3-b]pyridin-5-yl}acetamide

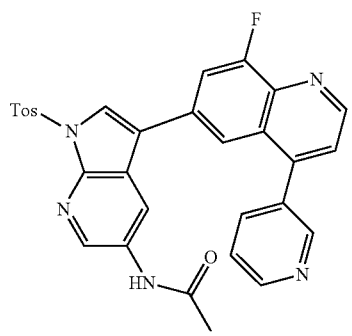

The title compound was prepared according to General Procedure 2 with N-[3-(4-chloro-8-fluoroquinolin-6-yl)-1-(4-methylbenzenesulfonyl)-1H-pyrrolo[2,3-b]pyridin-5-yl]acetamide (Intermediate 89) (0.09 g, 0.2 mmol, 1.0 eq.), 3-pyridylboronic acid (0.02 g, 0.2 mmol, 1.5 eq.), $K_2CO_3$ (0.06 g, 0.5 mmol, 2.7 eq.), Pd(dppf)$_2$Cl$_2$*CH$_2$Cl$_2$ (0.01 g, 0.01 mmol, 0.03 eq.) in a mixture of 1,4-dioxane/water 2/1 (3 mL). The reaction mixture was stirred at 80° C. for 5 h. Purification by FCC (MeOH gradient in CH$_2$Cl$_2$) provided N-{3-[8-fluoro-4-(pyridin-3-yl)quinolin-6-yl]-1-(4-methylbenzenesulfonyl)-1H-pyrrolo[2,3-b]pyridin-5-yl}acetamide (0.06 g; yield: 68%; UPLC purity: 97%).

Example 46

N-{3-[8-Fluoro-4-(pyridin-3-yl)quinolin-6-yl]-1H-pyrrolo[2,3-b]pyridin-5-yl}acetamide

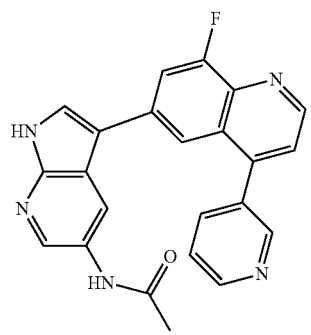 [SMILES: CC(=O)Nc1cnc2[nH]cc(-c3cc(F)c4nccc(-c5cccnc5)c4c3)c2c1]

The title compound was prepared according to General Procedure 3 with N-{3-[8-fluoro-4-(pyridin-3-yl)quinolin-6-yl]-1-(4-methylbenzenesulfonyl)-1H-pyrrolo[2,3-b]pyridin-5-yl}acetamide (Intermediate 90) (0.06 g, 0.1 mmol, 1.0 eq.), NaOtBu (0.02 g, 0.2 mmol, 1.5 eq.) dissolved in 1,4-dioxane (3 mL). The reaction mixture was stirred at rt overnight. Purification by FCC (MeOH gradient in CH$_2$Cl$_2$; column neutralized with 0.1% Et$_3$N in CH$_2$Cl$_2$ then washed with CH$_2$Cl$_2$ before purification) provided N-{3-[8-fluoro-4-(pyridin-3-yl)quinolin-6-yl]-1H-pyrrolo[2,3-b]pyridin-5-yl}acetamide as an yellow solid (0.022 g; yield: 47%; HPLC purity: 95%).

Intermediate 91

3-Iodo-1-(4-methylbenzenesulfonyl)-N-(pyridin-3-ylmethyl)-1H-pyrrolo[2,3-b]pyridine-5-carboxamide

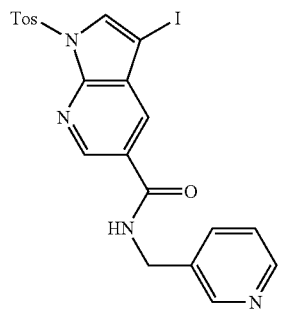

The title compound was prepared according to General Procedure 7 with 3-iodo-1-(4-methylbenzenesulfonyl)-1H-pyrrolo[2,3-b]pyridine-5-carboxylic acid (Intermediate 2) (1.0 g, 2.3 mmol, 1.0 eq.) in SOCl$_2$ (8 mL). After evaporation of SOCl$_2$ to the obtained residue dissolved in CH$_3$CN (10 mL) 3-(aminomethyl)pyridine (0.5 g, 4.5 mmol, 2.0 eq.) and Et$_3$N (0.7 g, 6.8 mmol, 3.0 eq.) were added. The reaction mixture was stirred at rt overnight. Purification by FCC (EtOAc gradient in hexane) provided 3-iodo-1-(4-methylbenzenesulfonyl)-N-(pyridin-3-ylmethyl)-1H-pyrrolo[2,3-b]pyridine-5-carboxamide (0.9 g; yield: 75%; UPLC purity: 100%).

Intermediate 92

3-(4-Chloro-8-fluoroquinolin-6-yl)-1-(4-methylbenzenesulfonyl)-N-(pyridin-3-ylmethyl)-1H-pyrrolo[2,3-b]pyridine-5-carboxamide

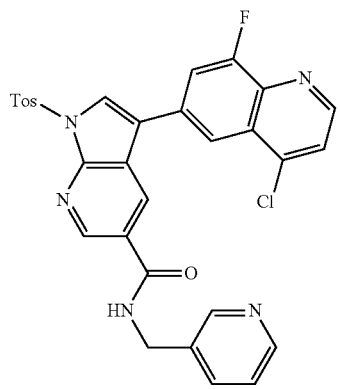

The title compound was prepared according to General Procedure 2 with 3-iodo-1-(4-methylbenzenesulfonyl)-N-(pyridin-3-ylmethyl)-1H-pyrrolo[2,3-b]pyridine-5-carboxamide (Intermediate 91) (0.2 g, 0.4 mmol, 1.0 eq.), (4-chloro-8-fluoroquinolin-6-yl)boronic acid (Intermediate 63) (0.15 g, 0.5 mmol, 1.3 eq.), K$_2$CO$_3$ (0.1 g, 0.8 mmol, 2.0 eq.), Pd(dppf)$_2$Cl$_2$*CH$_2$Cl$_2$ (0.06 g, 0.08 mmol, 0.2 eq.) in a mixture of 1,4-dioxane/water 2/1 (6 mL). The reaction mixture was heated at 80° C. for 3 h. Purification by FCC (MeOH gradient in CH$_2$Cl$_2$) provided 3-(4-chloro-8-fluoroquinolin-6-yl)-1-(4-methylbenzenesulfonyl)-N-(pyridin-3-ylmethyl)-1H-pyrrolo[2,3-b]pyridine-5-carboxamide (0.16 g; yield: 75%; UPLC purity: 84%).

Example 47

3-[8-Fluoro-4-(pyridin-3-yl)quinolin-6-yl]-N-(pyridin-3-ylmethyl)-1H-pyrrolo[2,3-b]pyridine-5-carboxamide

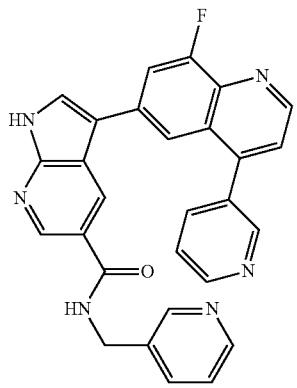 [SMILES: O=C(NCc1cccnc1)c1cnc2[nH]cc(-c3cc(F)c4nccc(-c5cccnc5)c4c3)c2c1]

The title compound was prepared according to General Procedure 2 with 3-(4-chloro-8-fluoroquinolin-6-yl)-1-(4-methylbenzenesulfonyl)-N-(pyridin-3-ylmethyl)-1H-pyrrolo[2,3-b]pyridine-5-carboxamide (Intermediate 92) (0.16 g, 0.3 mmol, 1.0 eq.), 3-pyridylboronic acid (0.04 g, 0.4 mmol, 1.3 eq.), $K_2CO_3$ (0.1 g, 0.7 mmol, 2.7 eq.), Pd(dppf)$_2$Cl$_2$*CH$_2$Cl$_2$ (0.02 g, 0.02 mmol, 0.3 eq.) in a mixture of 1,4-dioxane/water 2/1 (6 mL). The reaction mixture was stirred at 120° C. for 25 min. After Suzuki coupling UPLC-MS showed as the major compound-unprotected product. Purification by FCC (MeOH gradient in CH$_2$Cl$_2$) afforded 3-[8-fluoro-4-(pyridin-3-yl)quinolin-6-yl]-N-(pyridin-3-ylmethyl)-1H-pyrrolo[2,3-b]pyridine-5-carboxamide (0.009 g; yield: 7%; HPLC purity: 91%).

Intermediate 93 tert-Butyl N-[(3R)-1-(6-bromo-8-fluoroquinolin-4-yl)piperidin-3-yl]carbamate

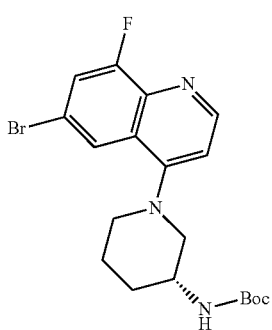 [SMILES: CC(C)(C)OC(=O)N[C@@H]1CCCN(c2ccnc3c(F)cc(Br)cc23)C1]

The title compound was prepared according to General Procedure 4 with 6-bromo-4-chloro-8-fluoroquinoline (2.0 g, 7.7 mmol, 1.0 eq.), (R)-3-(Boc-amino)piperidine (3.8 g, 19.2 mmol, 2.5 eq.) in CH$_3$CN (30 mL). The reaction mixture was heated at 80° C. for 3 days. Purification by FCC provided tert-butyl N-[(3R)-1-(6-bromo-8-fluoroquinolin-4-yl)piperidin-3-yl]carbamate (1.2 g; yield: 37%; UPLC purity: 100%).

Intermediate 94

{4-[(3R)-3-{[(tert-Butoxy)carbonyl]amino}piperidin-1-yl]-8-fluoroquinolin-6-yl}boronic acid

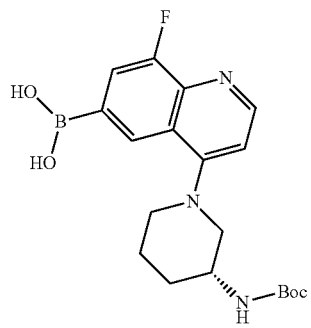 [SMILES: CC(C)(C)OC(=O)N[C@@H]1CCCN(c2ccnc3c(F)cc(B(O)O)cc23)C1]

The title compound was prepared according to General Procedure 1 with tert-butyl N-[(3R)-1-(6-bromo-8-fluoroquinolin-4-yl)piperidin-3-yl]carbamate (Intermediate 93) (1.22 g, 2.9 mmol, 1.0 eq.), bis(pinacolato)diboron (0.7 g, 2.9 mmol, 1.0 eq.), potassium acetate (0.6 g, 5.7 mmol, 2.0 eq.), Pd(dppf)$_2$Cl$_2$*CH$_2$Cl$_2$ (0.1 g, 0.1 mmol, 0.05 eq.) and 1,4-dioxane (15 mL). The reaction mixture was stirred at 80° C. for 5 h. Obtained {4-[(3R)-3-{[(tert-butoxy)carbonyl]amino}piperidin-1-yl]-8-fluoroquinolin-6-yl}boronic acid was used in consecutive step without further purification (UPLC purity: 98%).

Intermediate 95 tert-Butyl N-[(3R)-1-{8-fluoro-6-[1-(4-methylbenzenesulfonyl)-5-[(pyridin-3-ylmethyl)carbamoyl]-1H-pyrrolo[2,3-b]pyridin-3-yl]quinolin-4-yl}piperidin-3-yl]carbamate

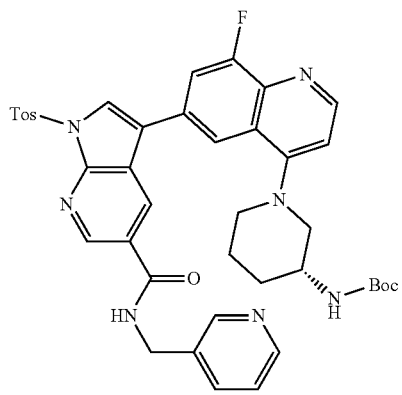

The title compound was prepared according to General Procedure 2 with 3-iodo-1-(4-methylbenzenesulfonyl)-N-(pyridin-3-ylmethyl)-1H-pyrrolo[2,3-b]pyridine-5-carboxamide (Intermediate 91) (0.25 g, 0.5 mmol, 1.0 eq.), {4-[(3R)-3-{[(tert-butoxy)carbonyl]amino}piperidin-1-yl]-8-fluoroquinolin-6-yl}boronic acid (Intermediate 94) (0.2 g, 0.5 mmol, 1.1 eq.), $K_2CO_3$ (0.13 g, 0.9 mmol, 2.0 eq.), Pd(dppf)₂Cl₂*CH₂Cl₂ (0.06 g, 0.07 mmol, 0.2 eq.) in a mixture of 1,4-dioxane/water 2/1 (6 mL). The reaction mixture was stirred at 80° C. for 3 h. The crude product-tert-butyl N-[(3R)-1-{8-fluoro-6-[1-(4-methylbenzenesulfonyl)-5-[(pyridin-3-ylmethyl)carbamoyl]-1H-pyrrolo[2,3-b]pyridin-3-yl]quinolin-4-yl}piperidin-3-yl]carbamate was used in consecutive step without further purification (UPLC purity: 98%).

Intermediate 96 tert-Butyl N-[(3R)-1-(8-fluoro-6-{5-[(pyridin-3-ylmethyl)carbamoyl]-1H-pyrrolo[2,3-b]pyridin-3-yl}quinolin-4-yl)piperidin-3-yl]carbamate

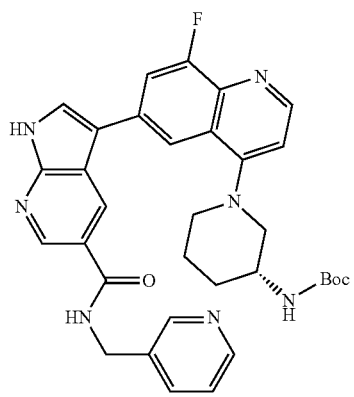 [SMILES: CC(C)(C)OC(=O)N[C@@H]1CCCN(c2ccnc3c(F)cc(-c4c[nH]c5ncc(C(=O)NCc6cccnc6)cc45)cc23)C1]

The title compound was prepared according to General Procedure 3 with tert-butyl N-[(3R)-1-{8-fluoro-6-[1-(4-methylbenzenesulfonyl)-5-(methylcarbamoyl)-1H-pyrrolo[2,3-b]pyridin-3-yl]quinolin-4-yl}piperidin-3-yl]carbamate (Intermediate 95) (0.35 g, 0.6 mmol, 1.0 eq.), NaOtBu (0.07 g, 0.1 mmol, 1.5 eq.) dissolved in 1,4-dioxane (5 mL). The reaction mixture was stirred at rt overnight. UPLC-MS showed presence of starting material. Additional portion of NaOtBu (1.5 eq.) was added and the reaction mixture was heated at 50° C. for 2 h. Purification by FCC (MeOH gradient in CH₂Cl₂) provided tert-butyl N-[(3R)-1-(8-fluoro-6-{5-[(pyridin-3-ylmethyl)carbamoyl]-1H-pyrrolo[2,3-b]pyridin-3-yl}quinolin-4-yl)piperidin-3-yl]carbamate as a beige solid (0.04 g; yield: 14%; UPLC purity: 97%).

Example 48

3-{4-[(3R)-3-Aminopiperidin-1-yl]-8-fluoroquinolin-6-yl}-N-(pyridin-3-ylmethyl)-1H-pyrrolo[2,3-b]pyridine-5-carboxamide hydrochloride

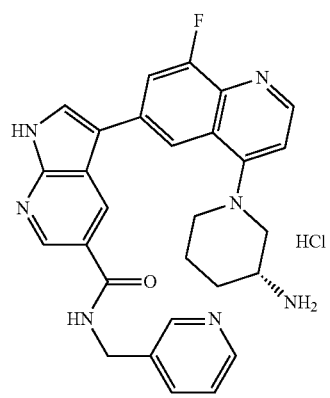 [SMILES: N[C@@H]1CCCN(c2ccnc3c(F)cc(-c4c[nH]c5ncc(C(=O)NCc6cccnc6)cc45)cc23)C1 ; Cl]

The title compound was prepared according to General Procedure 5 with tert-butyl N-[(3R)-1-(8-fluoro-6-{5-[(pyridin-3-ylmethyl)carbamoyl]-1H-pyrrolo[2,3-b]pyridin-3-yl}quinolin-4-yl)piperidin-3-yl]carbamate (Intermediate 96) (0.04 g, 0.07 mmol, 1.0 eq.) in MeOH (1 mL) and 2 M HCl in Et₂O (3 mL). The yellow precipitate was collected by filtration to provide 3-{4-[(3R)-3-aminopiperidin-1-yl]-8-fluoroquinolin-6-yl}-N-(pyridin-3-ylmethyl)-1H-pyrrolo[2,3-b]pyridine-5-carboxamide hydrochloride (0.003 g; yield: 9%; HPLC purity: 96%).

Intermediate 97

3-Iodo-1-(4-methylbenzenesulfonyl)-N-(pyrimidin-5-ylmethyl)-1H-pyrrolo[2,3-b]pyridine-5-carboxamide

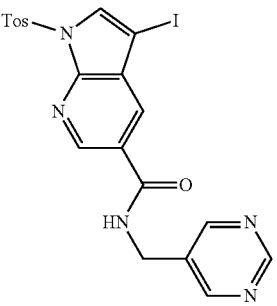

The title compound was prepared according to General Procedure 7 with 3-iodo-1-(4-methylbenzenesulfonyl)-1H-pyrrolo[2,3-b]pyridine-5-carboxylic acid (Intermediate 2) (0.5 g, 1.1 mmol, 1.0 eq.) in SOCl₂ (5 mL). After evaporation of SOCl₂ to the obtained residue dissolved in CH₃CN (10 mL) 3-(aminomethyl)pyrimidine (0.2 g, 2.3 mmol, 2.0 eq.) and Et₃N (0.2 g, 2.3 mmol, 2.0 eq.) were added. The reaction mixture was stirred at rt overnight. Purification by FCC (MeOH gradient in CH₂Cl₂) provided 3-iodo-1-(4-methylbenzenesulfonyl)-N-(pyrimidin-5-ylmethyl)-1H-pyrrolo[2,3-b]pyridine-5-carboxamide (0.34 g; yield: 57%; UPLC purity: 98%).

Intermediate 98 tert-Butyl N-[(3R)-1-{8-fluoro-6-[1-(4-methylbenzenesulfonyl)-5-[(pyrimidin-5-ylmethyl)carbamoyl]-1H-pyrrolo[2,3-b]pyridin-3-yl]quinolin-4-yl}piperidin-3-yl]carbamate

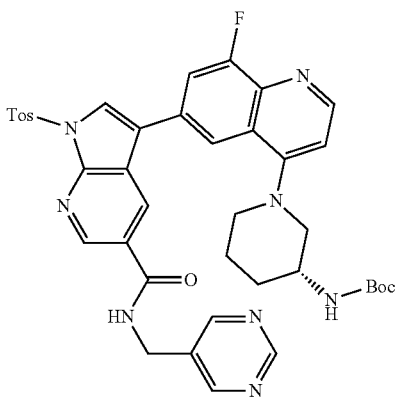

The title compound was prepared according to General Procedure 2 with 3-iodo-1-(4-methylbenzenesulfonyl)-N-(pyrimidin-5-ylmethyl)-1H-pyrrolo[2,3-b]pyridine-5-carboxamide (Intermediate 97) (0.34 g, 0.6 mmol, 1.0 eq.), {4-[(3R)-3-{[(tert-butoxy)carbonyl]amino}piperidin-1-yl]-8-fluoroquinolin-6-yl}boronic acid (Intermediate 94) (0.3 g, 0.7 mmol, 1.1 eq.), K$_2$CO$_3$ (0.18 g, 1.3 mmol, 2.0 eq.), Pd(dppf)$_2$Cl$_2$*CH$_2$Cl$_2$ (0.08 g, 0.1 mmol, 0.2 eq.) in a mixture of 1,4-dioxane/water 2/1 (6 mL). The reaction mixture was stirred at 80° C. for 3 h. Purification by FCC (MeOH gradient in CH$_2$Cl$_2$) afforded tert-butyl N-[(3R)-1-{8-fluoro-6-[1-(4-methylbenzenesulfonyl)-5-[(pyrimidin-5-ylmethyl)carbamoyl]-1H-pyrrolo[2,3-b]pyridin-3-yl]quinolin-4-yl}piperidin-3-yl]carbamate as a brownish solid (0.22 g; yield: 46%; UPLC purity: 93%).

Intermediate 99 tert-Butyl N-[(3R)-1-(8-fluoro-6-{5-[(pyrimidin-5-ylmethyl)carbamoyl]-1H-pyrrolo[2,3-b]pyridin-3-yl}quinolin-4-yl)piperidin-3-yl]carbamate

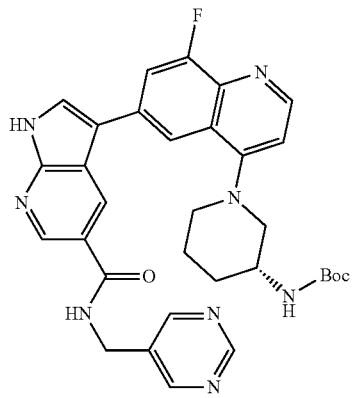 [SMILES: CC(C)(C)OC(=O)N[C@@H]1CCCN(c2ccnc3c(F)cc(-c4c[nH]c5ncc(C(=O)NCc6cncnc6)cc45)cc23)C1]

The title compound was prepared according to General Procedure 3 with tert-butyl N-[(3R)-1-{8-fluoro-6-[1-(4-methylbenzenesulfonyl)-5-[(pyrimidin-5-ylmethyl)carbamoyl]-1H-pyrrolo[2,3-b]pyridin-3-yl]quinolin-4-yl}piperidin-3-yl]carbamate (Intermediate 98) (0.3 g, 0.3 mmol, 1.0 eq.), NaOtBu (0.06 g, 0.6 mmol, 2.0 eq.) dissolved in 1,4-dioxane (5 mL). The reaction mixture was stirred at rt overnight. Purification by FCC (MeOH gradient in CH$_2$Cl$_2$) provided tert-butyl N-[(3R)-1-(8-fluoro-6-{5-[(pyrimidin-5-ylmethyl)carbamoyl]-1H-pyrrolo[2,3-b]pyridin-3-yl}quinolin-4-yl)piperidin-3-yl]carbamate (0.03 g; yield: 17%; UPLC purity: 91%).

Example 49

3-{4-[(3R)-3-Aminopiperidin-1-yl]-8-fluoroquinolin-6-yl}-N-(pyrimidin-5-ylmethyl)-1H-pyrrolo[2,3-b]pyridine-5-carboxamide hydrochloride

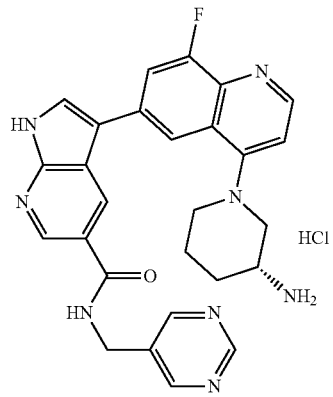 [SMILES: N[C@@H]1CCCN(c2ccnc3c(F)cc(-c4c[nH]c5ncc(C(=O)NCc6cncnc6)cc45)cc23)C1 ; Cl]

The title compound was prepared according to General Procedure 5 with tert-butyl N-[(3R)-1-(8-fluoro-6-{5-[(pyrimidin-5-ylmethyl)carbamoyl]-1H-pyrrolo[2,3-b]pyridin-3-yl}quinolin-4-yl)piperidin-3-yl]carbamate (Intermediate 99) (0.03 g, 0.04 mmol, 1.0 eq.) in MeOH (1 mL) and 2 M HCl in Et$_2$O (3 mL). Yellow precipitate was collected by filtration and additionally purified by HPLC to provide 3-{4-[(3R)-3-aminopiperidin-1-yl]-8-fluoroquinolin-6-yl}-N-(pyrimidin-5-ylmethyl)-1H-pyrrolo[2,3-b]pyridine-5-carboxamide hydrochloride (0.01 g; yield: 42%; HPLC purity: 98%).

Intermediate 100

3-(4-Chloro-8-fluoroquinolin-6-yl)-1-(4-methylbenzenesulfonyl)-1H-pyrrolo[2,3-b]pyridine-5-carbaldehyde

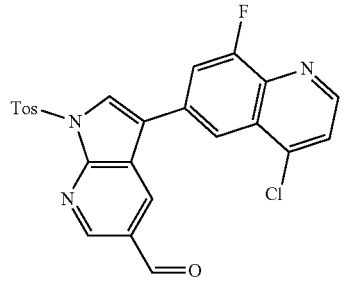

The title compound was prepared according to General Procedure 2 with 3-iodo-1-(4-methylbenzenesulfonyl)-1H-pyrrolo[2,3-b]pyridine-5-carbaldehyde (Intermediate 3) (0.3 g, 0.7 mmol, 1.0 eq.), (4-chloro-8-fluoroquinolin-6-yl)boronic acid (Intermediate 63) (0.2 g, 0.7 mmol, 1.0 eq.), K$_2$CO$_3$ (0.3 g, 2.2 mmol, 3.0 eq.), Pd(dppf)$_2$Cl$_2$*CH$_2$Cl$_2$ (0.1 g, 0.04 mmol, 0.2 eq.) in a mixture of 1,4-dioxane/water 3/1 (6 mL). Purification by FCC (EtOAc gradient in hexane) provided 3-(4-chloro-8-fluoroquinolin-6-yl)-1-(4-methylbenzenesulfonyl)-1H-pyrrolo[2,3-b]pyridine-5-carbaldehyde (0.04 g; yield: 13%; UPLC purity: 85%).

Intermediate 101

3-[8-Fluoro-4-(pyridin-3-yl)quinolin-6-yl]-1-(4-methylbenzenesulfonyl)-1H-pyrrolo[2,3-b]pyridine-5-carbaldehyde

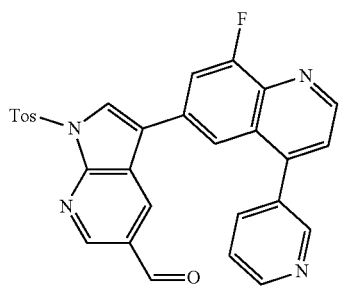

The title compound was prepared according to General Procedure 2 with 3-(4-chloro-8-fluoroquinolin-6-yl)-1-(4-methylbenzenesulfonyl)-1H-pyrrolo[2,3-b]pyridine-5-carbaldehyde (Intermediate 100) (0.1 g, 0.2 mmol, 1.0 eq.), 3-pyridineboronic acid (0.03 g, 0.2 mmol, 1.2 eq.), $K_2CO_3$ (0.08 g, 0.6 mmol, 3.0 eq.), $Pd(PPh_3)_4$ (0.01 g, 0.01 mmol, 0.05 eq.) in a mixture of 1,4-dioxane/water 2/1 (3 mL). The residue was purified by FCC (EtOAc gradient in hexane) to provide 3-[8-fluoro-4-(pyridin-3-yl)quinolin-6-yl]-1-(4-methylbenzenesulfonyl)-1H-pyrrolo[2,3-b]pyridine-5-carbaldehyde as an yellowish solid (0.04 g; yield: 42%; UPLC purity: 75%).

Intermediate 102

Benzyl({3-[8-fluoro-4-(pyridin-3-yl)quinolin-6-yl]-1-(4-methylbenzenesulfonyl)-1H-pyrrolo[2,3-b]pyridin-5-yl}methyl)amine

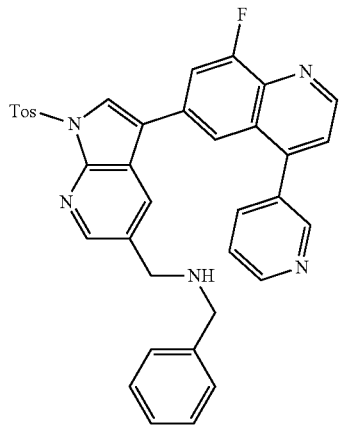

The title compound was prepared according to General Procedure 6 with 3-[8-fluoro-4-(pyridin-3-yl)quinolin-6-yl]-1-(4-methylbenzenesulfonyl)-1H-pyrrolo[2,3-b]pyridine-5-carbaldehyde (Intermediate 101) (0.04 g, 0.09 mmol, 1.0 eq.), benzyl amine (0.02 g, 0.2 mmol, 1.5 eq.), and Na(OAc)$_3$BH (0.04 g, 0.2 mmol, 2.0 eq.). The reaction mixture was stirred at rt for 3 days, then diluted with water and the aqueous layer was extracted with $CH_2Cl_2$. The combined organic layers were dried over $Na_2SO_4$, filtered and concentrated. The crude product-benzyl({3-[8-fluoro-4-(pyridin-3-yl)quinolin-6-yl]-1-(4-methylbenzenesulfonyl)-1H-pyrrolo[2,3-b]pyridin-5-yl}methyl)amine was used in consecutive step without further purification (UPLC purity: 98%).

Example 50

Benzyl({3-[8-fluoro-4-(pyridin-3-yl)quinolin-6-yl]-1H-pyrrolo[2,3-b]pyridin-5-yl}methyl)amine

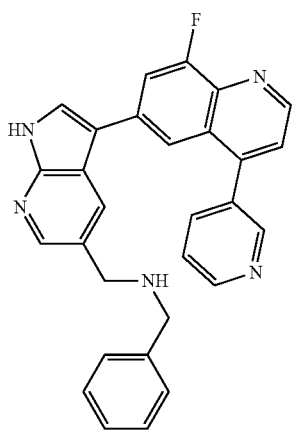 [SMILES: Fc1cc(-c2c[nH]c3ncc(CNCc4ccccc4)cc23)cc2c(-c3cccnc3)ccnc12]

The title compound was prepared according to General Procedure 3 with benzyl({3-[8-fluoro-4-(pyridin-3-yl)quinolin-6-yl]-1-(4-methylbenzenesulfonyl)-1H-pyrrolo[2,3-b]pyridin-5-yl}methyl)amine (Intermediate 102) (0.06 g, 0.1 mmol, 1.0 eq.), NaOtBu (0.02 g, 0.2 mmol, 2.0 eq.) dissolved in 1,4-dioxane (3 mL). The reaction mixture was stirred at 80° C. for 3 h. Purification by FCC (MeOH gradient in $CH_2Cl_2$) provided benzyl({3-[8-fluoro-4-(pyridin-3-yl)quinolin-6-yl]-1H-pyrrolo[2,3-b]pyridin-5-yl}methyl)amine (0.015 g; yield: 34%; HPLC purity: 99%).

Intermediate 103 tert-Butyl N-[(3R)-1-{8-fluoro-6-[5-formyl-1-(4-methylbenzenesulfonyl)-1H-pyrrolo[2,3-b]pyridin-3-yl]quinolin-4-yl}piperidin-3-yl]carbamate

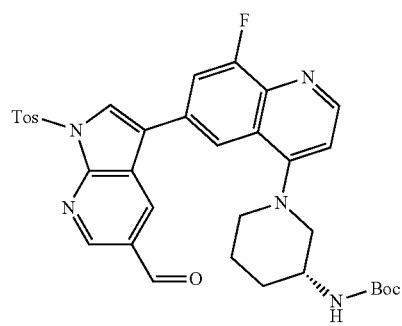

The title compound was prepared according to General Procedure 2 with 3-iodo-1-(4-methylbenzenesulfonyl)-1H-pyrrolo[2,3-b]pyridine-5-carbaldehyde (Intermediate 3) (0.4 g, 0.9 mmol, 1.0 eq.), {4-[(3R)-3-{[(tert-butoxy)carbonyl]amino}piperidin-1-yl]-8-fluoroquinolin-6-yl}boronic acid (Intermediate 94) (0.6 g, 1.2 mmol, 1.3 eq.), K₂CO₃ (0.2 g, 1.9 mmol, 2.0 eq.), Pd(dppf)₂Cl₂*CH₂Cl₂ (0.15 g, 0.2 mmol, 0.2 eq.) in a mixture of 1,4-dioxane/water 2/1 (6 mL). Purification by FCC (MeOH gradient in CH₂Cl₂) provided tert-butyl N-[(3R)-1-{8-fluoro-6-[5-formyl-1-(4-methylbenzenesulfonyl)-1H-pyrrolo[2,3-b]pyridin-3-yl]quinolin-4-yl}piperidin-3-yl]carbamate (0.56 g; yield: 93%; UPLC purity: 87%).

Intermediate 104 tert-Butyl N-[(3R)-1-(6-{5-[(benzylamino)methyl]-1-(4-methylbenzenesulfonyl)-1H-pyrrolo[2,3-b]pyridin-3-yl}-8-fluoroquinolin-4-yl)piperidin-3-yl]carbamate

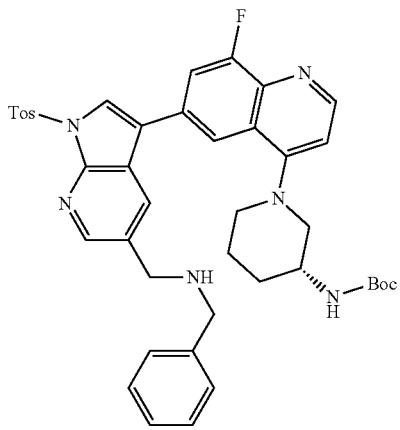

The title compound was prepared according to General Procedure 6 with tert-butyl N-[(3R)-1-{8-fluoro-6-[5-formyl-1-(4-methylbenzenesulfonyl)-1H-pyrrolo[2,3-b]pyridin-3-yl]quinolin-4-yl}piperidin-3-yl]carbamate (Intermediate 103) (0.28 g, 0.4 mmol, 1.0 eq.), benzyl amine (0.07 g, 0.6 mmol, 1.5 eq.), and Na(OAc)₃BH (0.2 g, 0.9 mmol, 2.0 eq.). The reaction mixture was stirred at rt overnight. UPLC-MS showed presence of starting material and additional portion of benzyl amine (0.07 g, 0.6 mmol, 1.5 eq.) and Na(OAc)₃BH (0.2 g, 0.9 mmol, 2.0 eq.) was added. The reaction mixture was stirred at rt for 5 days. Purification by FCC (MeOH gradient in CH₂Cl₂) afforded tert-butyl N-[(3R)-1-(6-{5-[(benzylamino)methyl]-1-(4-methylbenzenesulfonyl)-1H-pyrrolo[2,3-b]pyridin-3-yl}-8-fluoroquinolin-4-yl)piperidin-3-yl]carbamate (0.096 g; yield: 30%; UPLC purity: 82%).

Intermediate 105 tert-Butyl N-[(3R)-1-(6-{5-[(benzylamino)methyl]-1H-pyrrolo[2,3-b]pyridin-3-yl}-8-fluoroquinolin-4-yl)piperidin-3-yl]carbamate

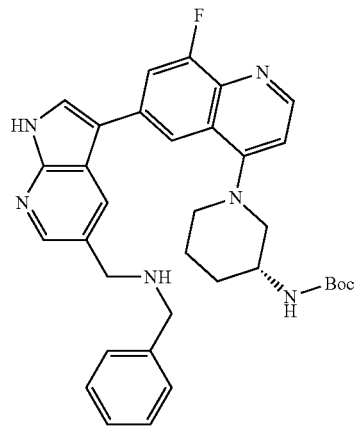 [SMILES: CC(C)(C)OC(=O)N[C@@H]1CCCN(c2ccnc3c(F)cc(-c4c[nH]c5ncc(CNCc6ccccc6)cc45)cc23)C1]

The title compound was prepared according to General Procedure 3 with tert-butyl N-[(3R)-1-(6-{5-[(benzylamino)methyl]-1-(4-methylbenzenesulfonyl)-1H-pyrrolo[2,3-b]pyridin-3-yl}-8-fluoroquinolin-4-yl)piperidin-3-yl]carbamate (Intermediate 104) (0.096 g, 0.1 mmol, 1.0 eq.), NaOtBu (0.02 g, 0.2 mmol, 1.5 eq.) dissolved in 1,4-dioxane (3 mL). The reaction mixture was stirred at rt overnight. Purification by FCC (MeOH gradient in CH₂Cl₂) provided tert-butyl N-[(3R)-1-(6-{5-[(benzylamino)methyl]-1H-pyrrolo[2,3-b]pyridin-3-yl}-8-fluoroquinolin-4-yl)piperidin-3-yl]carbamate (0.03 g; yield: 39%; UPLC purity: 91%).

Example 51

(3R)-1-(6-{5-[(Benzylamino)methyl]-1H-pyrrolo[2,3-b]pyridin-3-yl}-8-fluoroquinolin-4-yl)piperidin-3-amine

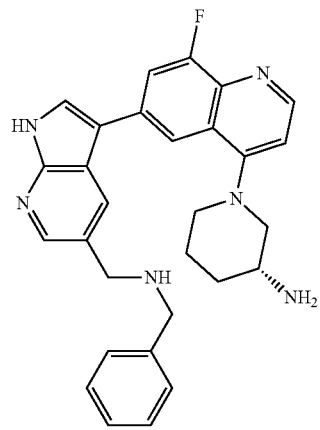 [SMILES: N[C@@H]1CCCN(c2ccnc3c(F)cc(-c4c[nH]c5ncc(CNCc6ccccc6)cc45)cc23)C1]

The title compound was prepared according to General Procedure 5 with tert-butyl N-[(3R)-1-(6-{5-[(benzylamino)methyl]-1H-pyrrolo[2,3-b]pyridin-3-yl}-8-fluoroquinolin-4-yl)piperidin-3-yl]carbamate (Intermediate 105) (0.03 g, 0.05 mmol, 1.0 eq.) in MeOH (0.5 mL) and 2 M HCl in Et₂O (2 mL). The precipitate was collected by filtration and dissolved in water and 2 M solution of NaOH. The product-(3R)-1-(6-{5-[(benzylamino)methyl]-1H-pyrrolo[2,3-b]pyridin-3-yl}-8-fluoroquinolin-4-yl)piperidin-3-amine was again gathered by filtration and dried on air (0.01 g; yield: 40%; HPLC purity: 91%).

Intermediate 106

{[3-Iodo-1-(4-methylbenzenesulfonyl)-1H-pyrrolo[2,3-b]pyridin-5-yl]methyl}(methyl)(prop-2-en-1-yl)amine

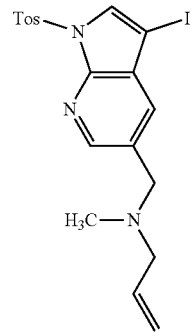

The title compound was prepared according to General Procedure 6 with 3-iodo-1-(4-methylbenzenesulfonyl)-1H-pyrrolo[2,3-b]pyridine-5-carbaldehyde (Intermediate 3) (2.2 g, 5.2 mmol, 1.0 eq.), N-methylallyl amine (0.7 g, 10.4 mmol, 2.0 eq.), Na(OAc)$_3$BH (2.7 g, 12.9 mmol, 2.5 eq.) in CH$_2$Cl$_2$ (110 mL). The reaction mixture was stirred at rt overnight. Purification by FCC (EtOAc gradient in hexane) provided {[3-iodo-1-(4-methylbenzenesulfonyl)-1H-pyrrolo[2,3-b]pyridin-5-yl]methyl}(methyl)(prop-2-en-1-yl)amine as a white solid (1.4 g; yield: 55%; HPLC purity: 99%).

Intermediate 107

{[3-(4-Chloro-8-fluoroquinolin-6-yl)-1-(4-methyl-benzenesulfonyl)-1H-pyrrolo[2,3-b]pyridin-5-yl]methyl}(methyl)(prop-2-en-1-yl)amine

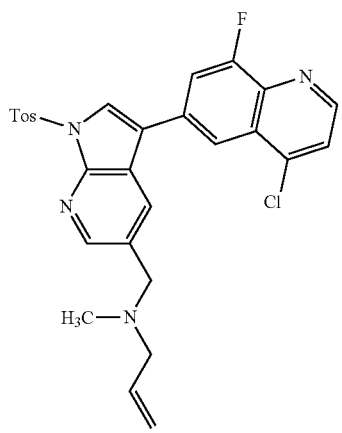

The title compound was prepared according to General Procedure 2 with {[3-iodo-1-(4-methylbenzenesulfonyl)-1H-pyrrolo[2,3-b]pyridin-5-yl]methyl}(methyl)(prop-2-en-1-yl)amine (Intermediate 106) (0.17 g, 0.4 mmol, 1.0 eq.), (4-chloro-8-fluoroquinolin-6-yl)boronic acid (Intermediate 63) (0.14 g, 0.5 mmol, 1.3 eq.), K$_2$CO$_3$ (0.1 g, 0.7 mmol, 2.0 eq.), Pd(dppf)$_2$Cl$_2$*CH$_2$Cl$_2$ (0.06 g, 0.07 mmol, 0.2 eq.) in a mixture of 1,4-dioxane/water 3/1 (6 mL). Purification by FCC (EtOAc gradient in hexane) provided {[3-(4-chloro-8-fluoroquinolin-6-yl)-1-(4-methylbenzenesulfonyl)-1H-pyrrolo[2,3-b]pyridin-5-yl]methyl}(methyl)(prop-2-en-1-yl)amine (0.1 g; yield: 53%; UPLC purity: 98%).

Intermediate 108

({3-[8-Fluoro-4-(pyridin-3-yl)quinolin-6-yl]-1-(4-methylbenzenesulfonyl)-1H-pyrrolo[2,3-b]pyridin-5-yl}methyl)(methyl)(prop-2-en-1-yl)amine

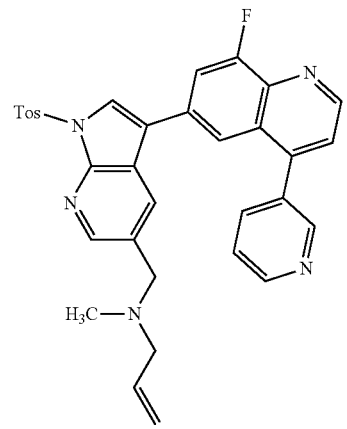

The title compound was prepared according to General Procedure 2 with {[3-(4-chloro-8-fluoroquinolin-6-yl)-1-(4-methylbenzenesulfonyl)-1H-pyrrolo[2,3-b]pyridin-5-yl]methyl}(methyl)(prop-2-en-1-yl)amine (Intermediate 107) (0.1 g, 0.2 mmol, 1.0 eq.), 3-pyridylboronic acid (0.03 g, 0.2 mmol, 1.3 eq.), K$_2$CO$_3$ (0.07 g, 0.5 mmol, 2.7 eq.), Pd(dppf)$_2$Cl$_2$*CH$_2$Cl$_2$ (0.01 g, 0.02 mmol, 0.03 eq.) in a mixture of 1,4-dioxane/water 2/1 (3 mL). The residue was purified by FCC (MeOH gradient in CH$_2$Cl$_2$) to provide ({3-[8-fluoro-4-(pyridin-3-yl)quinolin-6-yl]-1-(4-methylbenzenesulfonyl)-1H-pyrrolo[2,3-b]pyridin-5-yl}methyl)(methyl)(prop-2-en-1-yl)amine (0.06 g; yield: 54%; UPLC purity: 100%).

Example 52

({3-[8-Fluoro-4-(pyridin-3-yl)quinolin-6-yl]-1H-pyrrolo[2,3-b]pyridin-5-yl}methyl)(methyl)(prop-2-en-1-yl)amine

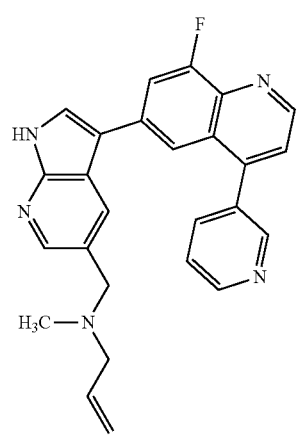 [SMILES: C=CCN(C)Cc1cnc2[nH]cc(-c3cc(F)c4nccc(-c5cccnc5)c4c3)c2c1]

The title compound was prepared according to General Procedure 3 with ({3-[8-fluoro-4-(pyridin-3-yl)quinolin-6-yl]-1-(4-methylbenzenesulfonyl)-1H-pyrrolo[2,3-b]pyridin-5-yl}methyl)(methyl)(prop-2-en-1-yl)amine (Intermediate 108) (0.06 g, 0.1 mmol, 1.0 eq.), KOH (0.008 g, 0.2 mmol, 1.5 eq.) dissolved in THF (3 mL). The reaction mixture was stirred at 50° C. for 3 h then at rt overnight. Purification by FCC (MeOH gradient in CH₂Cl₂) afforded ({3-[8-fluoro-4-(pyridin-3-yl)quinolin-6-yl]-1H-pyrrolo[2,3-b]pyridin-5-yl}methyl)(methyl)(prop-2-en-1-yl)amine (0.026 g; yield: 60%; HPLC purity: 95%).

Intermediate 109 tert-Butyl N-[(3S)-1-(6-bromo-3-nitroquinolin-4-yl)piperidin-3-yl]carbamate

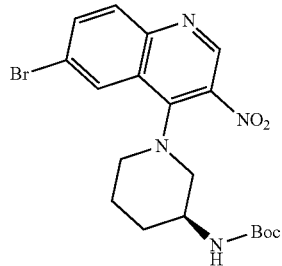 [SMILES: CC(C)(C)OC(=O)N[C@H]1CCCN(c2c([N+](=O)[O-])cnc3ccc(Br)cc23)C1]

The title compound was prepared according to General Procedure 4 with 6-bromo-4-chloro-3-nitroquinoline (0.1 g, 0.4 mmol, 1.0 eq.), (S)-3-(Boc-amino)pyrrolidine (0.07 g, 0.4 mmol, 1.0 eq.), DIPEA (0.09 g, 0.7 mmol, 2.0 eq.) in i-PrOH (2 mL). The reaction mixture was stirred at rt for 1 h and solvent was evaporated. The crude product tert-butyl N-[(3S)-1-(6-bromo-3-nitroquinolin-4-yl)piperidin-3-yl]carbamate was used in consecutive step without further purification (UPLC purity: 92%).

Intermediate 110

{4-[(3S)-3-{[(tert-Butoxy)carbonyl]amino}piperidin-1-yl]-3-nitroquinolin-6-yl}boronic acid

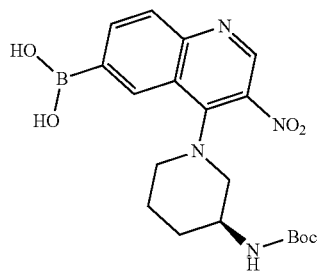 [SMILES: CC(C)(C)OC(=O)N[C@H]1CCCN(c2c([N+](=O)[O-])cnc3ccc(B(O)O)cc23)C1]

The title compound was prepared according to General Procedure 1 with tert-butyl N-[(3S)-1-(6-bromo-3-nitroquinolin-4-yl)piperidin-3-yl]carbamate (Intermediate 109) (0.2 g, 0.4 mmol, 1.0 eq.), bis(pinacolato)diboron (0.1 g, 0.4 mmol, 1.2 eq.), potassium acetate (0.07 g, 0.7 mmol, 2.0 eq.), Pd(dppf)₂Cl₂*CH₂Cl₂ (0.02 g, 0.02 mmol, 0.05 eq.) and 1,4-dioxane (5 mL). The reaction mixture was stirred at 80° C. for 7 h. Obtained {4-[(3S)-3-{[(tert-butoxy)carbonyl]amino}piperidin-1-yl]-3-nitroquinolin-6-yl}boronic acid was used in consecutive step without further purification (UPLC purity: 63%).

Intermediate 111 tert-Butyl N-[(3S)-1-{6-[1-(4-methylbenzenesulfonyl)-5-(methylcarbamoyl)-1H-pyrrolo[2,3-b]pyridin-3-yl]-3-nitroquinolin-4-yl}piperidin-3-yl]carbamate

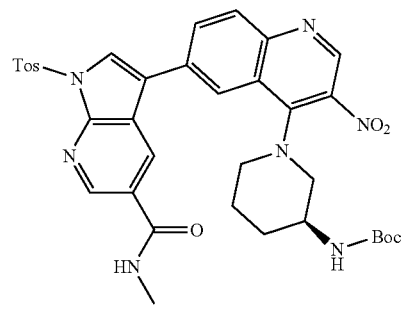

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.2 g, 0.4 mmol, 1.0 eq.), {4-[(3S)-3-{[(tert-butoxy)carbonyl]amino}piperidin-1-yl]-3-nitroquinolin-6-yl}boronic acid (Intermediate 110) (0.3 g, 0.7 mmol, 1.5 eq.), K₂CO₃ (0.12 g, 0.9 mmol, 2.0 eq.), Pd(dppf)₂Cl₂*CH₂Cl₂ (0.04 g, 0.04 mmol, 0.1 eq.) in a mixture of 1,4-dioxane/water 2/1 (6 mL). The reaction mixture was stirred at 80° C. for 3 h. Purification by FCC (MeOH gradient in CH₂Cl₂) afforded tert-butyl N-[(3S)-1-{6-[1-(4-methylbenzenesulfonyl)-5-(methylcarbamoyl)-1H-pyrrolo[2,3-b]pyridin-3-yl]-3-nitroquinolin-4-yl}piperidin-3-yl]carbamate (0.17 g; yield: 55%; UPLC purity: 100%).

Intermediate 112 tert-Butyl N-[(3S)-1-{6-[5-(methylcarbamoyl)-1H-pyrrolo[2,3-b]pyridin-3-yl]-3-nitroquinolin-4-yl}piperidin-3-yl]carbamate

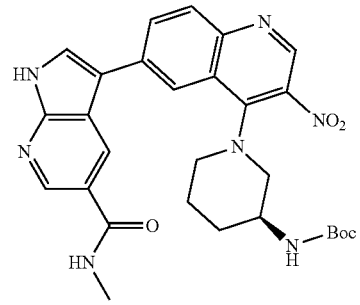

The title compound was prepared according to General Procedure 3 with tert-butyl N-[(3S)-1-{6-[1-(4-methylbenzenesulfonyl)-5-(methylcarbamoyl)-1H-pyrrolo[2,3-b]pyridin-3-yl]-3-nitroquinolin-4-yl}piperidin-3-yl]carbamate (Intermediate 111) (0.07 g, 0.1 mmol, 1.0 eq.), NaOtBu (0.04 g, 0.1 mmol, 1.5 eq.) dissolved in 1,4-dioxane (3 mL). The reaction mixture was stirred at rt for 2 h. Purification by FCC (MeOH gradient in CH$_2$Cl$_2$) provided tert-butyl N-[(3S)-1-{6-[5-(methylcarbamoyl)-1H-pyrrolo[2,3-b]pyridin-3-yl]-3-nitroquinolin-4-yl}piperidin-3-yl]carbamate (0.03 g; yield: 60%; UPLC purity: 93%).

Example 53

3-{4-[(3S)-3-Aminopiperidin-1-yl]-3-nitroquinolin-6-yl}-N-methyl-1H-pyrrolo[2,3-b]pyridine-5-carboxamide hydrochloride

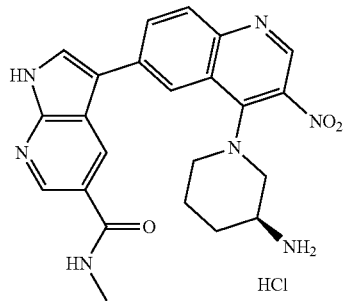 [SMILES: CNC(=O)c1cnc2[nH]cc(-c3ccc4ncc([N+](=O)[O-])c(N5CCC[C@H](N)C5)c4c3)c2c1 ; Cl]

The title compound was prepared according to General Procedure 5 with tert-butyl N-[(3S)-1-{6-[5-(methylcarbamoyl)-1H-pyrrolo[2,3-b]pyridin-3-yl]-3-nitroquinolin-4-yl}piperidin-3-yl]carbamate (Intermediate 112) (0.03 g, 0.06 mmol, 1.0 eq.) in MeOH (0.5 mL) and 2 M HCl in Et$_2$O (2 mL). The precipitate was collected by filtration to provide 3-{4-[(3S)-3-aminopiperidin-1-yl]-3-nitroquinolin-6-yl}-N-methyl-1H-pyrrolo[2,3-b]pyridine-5-carboxamide hydrochloride (0.02 g; yield: 95%; HPLC purity: 91%).

Intermediate 113. General Procedure 10 tert-Butyl N-[(3S)-1-{3-amino-6-[1-(4-methylbenzenesulfonyl)-5-(methylcarbamoyl)-1H-pyrrolo[2,3-b]pyridin-3-yl]quinolin-4-yl}piperidin-3-yl]carbamate

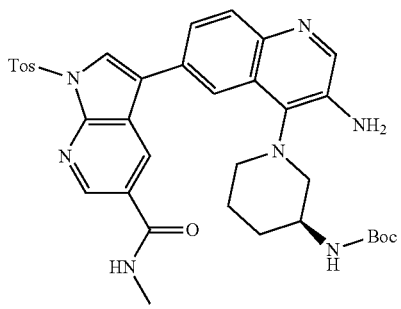

A solution of tert-butyl N-[(3S)-1-{6-[1-(4-methylbenzenesulfonyl)-5-(methylcarbamoyl)-1H-pyrrolo[2,3-b]pyridin-3-yl]-3-nitroquinolin-4-yl}piperidin-3-yl]carbamate (Intermediate 111) (0.07 g, 0.1 mmol, 1.0 eq.) and Raney-Nickel (0.5 g) in THF (3 mL) was stirred at rt for 4 h under balloon with hydrogen. The reaction mixture was filtered through a pad of Celite and the filtrate was concentrated. The tert-butyl N-[(3S)-1-{3-amino-6-[1-(4-methylbenzenesulfonyl)-5-(methylcarbamoyl)-1H-pyrrolo[2,3-b]pyridin-3-yl]quinolin-4-yl}piperidin-3-yl]carbamate was used in consecutive step without further purification (UPLC purity: 100%).

Intermediate 114 tert-Butyl N-[(3S)-1-{3-amino-6-[5-(methylcarbamoyl)-1H-pyrrolo[2,3-b]pyridin-3-yl]quinolin-4-yl}piperidin-3-yl]carbamate

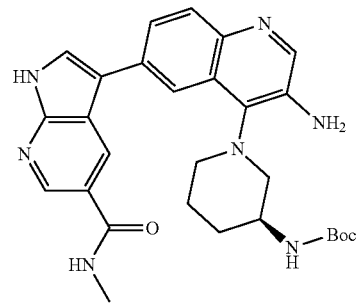 [SMILES: CNC(=O)c1cnc2[nH]cc(-c3ccc4ncc(N)c(N5CCC[C@H](NC(=O)OC(C)(C)C)C5)c4c3)c2c1]

The title compound was prepared according to General Procedure 3 with tert-butyl N-[(3S)-1-{3-amino-6-[1-(4-methylbenzenesulfonyl)-5-(methylcarbamoyl)-1H-pyrrolo[2,3-b]pyridin-3-yl]quinolin-4-yl}piperidin-3-yl]carbamate (Intermediate 113) (0.05 g, 0.07 mmol, 1.0 eq.), NaOtBu (0.03 g, 0.1 mmol, 1.5 eq.) dissolved in 1,4-dioxane (3 mL). The reaction mixture was stirred at rt for 2 h. Purification by FCC (MeOH gradient in CH$_2$Cl$_2$) provided tert-butyl N-[(3S)-1-{3-amino-6-[5-(methylcarbamoyl)-1H-pyrrolo[2,3-b]pyridin-3-yl]quinolin-4-yl}piperidin-3-yl]carbamate (0.04 g; yield: 64%; UPLC purity: 99%).

Example 54

3-{3-Amino-4-[(3S)-3-aminopiperidin-1-yl]quinolin-6-yl}-N-methyl-1H-pyrrolo[2,3-b]pyridine-5-carboxamide hydrochloride

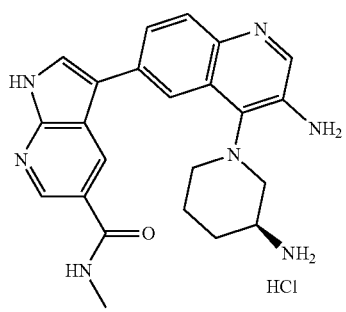 [SMILES: CNC(=O)c1cnc2[nH]cc(-c3ccc4ncc(N)c(N5CCC[C@H](N)C5)c4c3)c2c1 ; Cl]

The title compound was prepared according to General Procedure 5 with tert-butyl N-[(3S)-1-{3-amino-6-[5-(methylcarbamoyl)-1H-pyrrolo[2,3-b]pyridin-3-yl]quinolin-4-yl}piperidin-3-yl]carbamate (Intermediate 114) (0.04 g, 0.08 mmol, 1.0 eq.) in MeOH (0.5 mL) and 2 M HCl in Et$_2$O (3 mL). The precipitate was collected by filtration to provide 3-{3-amino-4-[(3S)-3-aminopiperidin-1-yl]quinolin-6-yl}-

N-methyl-1H-pyrrolo[2,3-b]pyridine-5-carboxamide hydrochloride (0.02 g; yield: 98%; HPLC purity: 98%).

Intermediate 115 tert-Butyl N-[(3S)-1-(3-{[(3-chlorophenyl)methyl]amino}-6-[1-(4-methylbenzenesulfonyl)-5-(methylcarbamoyl)-1H-pyrrolo[2,3-b]pyridin-3-yl]quinolin-4-yl)piperidin-3-yl]carbamate

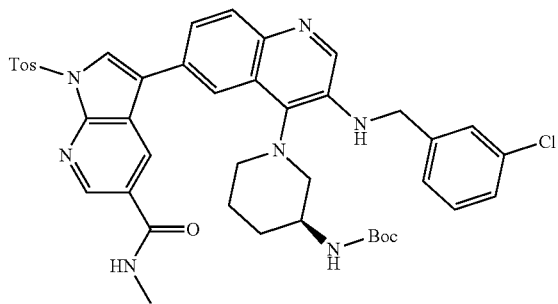

The title compound was prepared according to General Procedure 6 with tert-butyl N-[(3S)-1-{3-amino-6-[1-(4-methylbenzenesulfonyl)-5-(methylcarbamoyl)-1H-pyrrolo[2,3-b]pyridin-3-yl]quinolin-4-yl}piperidin-3-yl]carbamate (Intermediate 113) (0.12 g, 0.2 mmol, 1.0 eq.), 3-chlorobenzaldehyde (0.06 g, 0.4 mmol, 2.5 eq.), AcOH (1 mL), sodium cyanoborohydride (0.02 g, 0.4 mmol, 2.0 eq.) in MeOH (6 mL). The reaction mixture was stirred at rt overnight. Purification by FCC provided tert-butyl N-[(3S)-1-(3-{[(3-chlorophenyl)methyl]amino}-6-[1-(4-methylbenzenesulfonyl)-5-(methylcarbamoyl)-1H-pyrrolo[2,3-b]pyridin-3-yl]quinolin-4-yl)piperidin-3-yl]carbamate (0.08 g; yield: 56%; UPLC purity: 100%).

Intermediate 116 tert-Butyl N-[(3S)-1-(3-{[(3-chlorophenyl)methyl]amino}-6-[5-(methylcarbamoyl)-1H-pyrrolo[2,3-b]pyridin-3-yl]quinolin-4-yl)piperidin-3-yl]carbamate

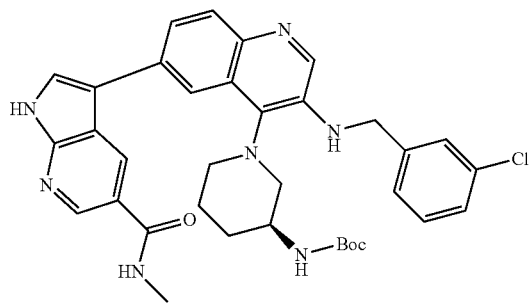 [SMILES: CNC(=O)c1cnc2[nH]cc(-c3ccc4ncc(NCc5cccc(Cl)c5)c(N5CCC[C@H](NC(=O)OC(C)(C)C)C5)c4c3)c2c1]

The title compound was prepared according to General Procedure 3 with tert-butyl N-[(3S)-1-(3-{[(3-chlorophenyl)methyl]amino}-6-[1-(4-methylbenzenesulfonyl)-5-(methylcarbamoyl)-1H-pyrrolo[2,3-b]pyridin-3-yl]quinolin-4-yl)piperidin-3-yl]carbamate (Intermediate 115) (0.08 g, 0.1 mmol, 1.0 eq.), NaOtBu (0.04 g, 0.1 mmol, 1.5 eq.) dissolved in 1,4-dioxane (4 mL). The reaction mixture was stirred at rt for 2 h. Purification by FCC (MeOH gradient in CH$_2$Cl$_2$) afforded tert-butyl N-[(3S)-1-(3-{[(3-chlorophenyl)methyl]amino}-6-[5-(methylcarbamoyl)-1H-pyrrolo[2,3-b]pyridin-3-yl]quinolin-4-yl)piperidin-3-yl]carbamate (0.01 g; yield: 16%; UPLC purity: 99%).

Example 55

3-{4-[(3S)-3-Aminopiperidin-1-yl]-3-{[(3-chlorophenyl)methyl]amino}quinolin-6-yl}-N-methyl-1H-pyrrolo[2,3-b]pyridine-5-carboxamide hydrochloride

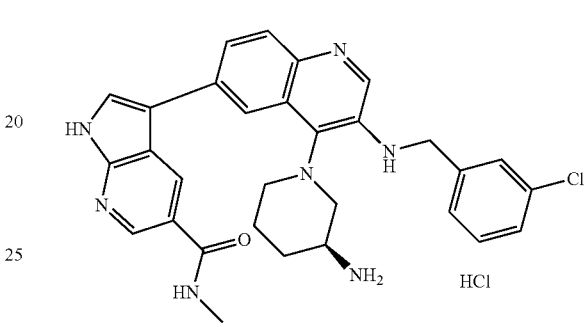

The title compound was prepared according to General Procedure 5 with tert-butyl N-[(3S)-1-(3-{[(3-chlorophenyl)methyl]amino}-6-[5-(methylcarbamoyl)-1H-pyrrolo[2,3-b]pyridin-3-yl]quinolin-4-yl)piperidin-3-yl]carbamate (Intermediate 116) (0.01 g, 0.02 mmol, 1.0 eq.) in MeOH (0.2 mL) and 2 M HCl in Et$_2$O (1.5 mL). The precipitate was collected by filtration to provide 3-{4-[(3S)-3-aminopiperidin-1-yl]-3-{[(3-chlorophenyl)methyl]amino}quinolin-6-yl}-N-methyl-1H-pyrrolo[2,3-b]pyridine-5-carboxamide hydrochloride (0.008 g; yield: 99%; HPLC purity: 95%).

Intermediate 117

6-Bromo-4-(morpholin-4-yl)-3-nitroquinoline

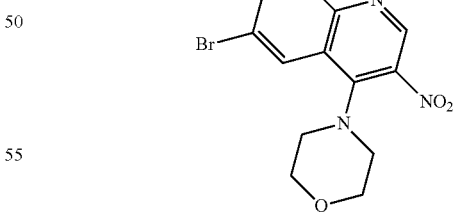

The title compound was prepared according to General Procedure 4 with 6-bromo-4-chloro-3-nitroquinoline (0.1 g, 0.4 mmol, 1.0 eq.), morpholine (0.17 g, 0.9 mmol, 1.0 eq.), DIPEA (0.22 g, 1.7 mmol, 2.0 eq.) in i-PrOH (3 mL). The reaction mixture was stirred at rt for 1.5 h and then concentrated. Purification by FCC (MeOH gradient in CH$_2$Cl$_2$) afforded 6-bromo-4-(morpholin-4-yl)-3-nitroquinoline (0.3 g, yield: 91%; UPLC purity: 98%).

141

Intermediate 118

[4-(Morpholin-4-yl)-3-nitroquinolin-6-yl]boronic acid

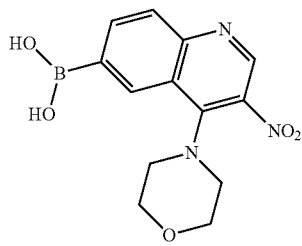 [SMILES: O=[N+]([O-])c1cnc2ccc(B(O)O)cc2c1N1CCOCC1]

The title compound was prepared according to General Procedure 1 with 6-bromo-4-(morpholin-4-yl)-3-nitroquinoline (Intermediate 117) (0.3 g, 0.8 mmol, 1.0 eq.), bis(pinacolato)diboron (0.3 g, 1.2 mmol, 1.5 eq.), potassium acetate (0.16 g, 1.6 mmol, 2.0 eq.), Pd(dppf)$_2$Cl$_2$*CH$_2$Cl$_2$ (0.06 g, 0.08 mmol, 0.1 eq.) and 1,4-dioxane (6 mL). The reaction mixture was stirred at 80° C. for 8 h. Obtained [4-(morpholin-4-yl)-3-nitroquinolin-6-yl]boronic acid was used in consecutive step without further purification (UPLC purity: 87%).

Intermediate 119

N-Methyl-1-(4-methylbenzenesulfonyl)-3-[4-(morpholin-4-yl)-3-nitroquinolin-6-yl]-1H-pyrrolo[2,3-b]pyridine-5-carboxamide

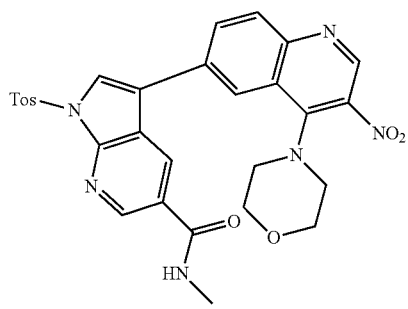

The title compound was prepared according to General Procedure 2 with 3-iodo-N-methyl-1-(4-methylbenzenesulfonyl)-1H-pyrrolo[2,3-b]pyridine-5-carboxamide (Intermediate 37) (0.4 g, 0.9 mmol, 1.0 eq.), [4-(morpholin-4-yl)-3-nitroquinolin-6-yl]boronic acid (Intermediate 118) (0.5 g, 1.3 mmol, 1.5 eq.), K$_2$CO$_3$ (0.24 g, 1.7 mmol, 2.0 eq.), Pd(dppf)$_2$Cl$_2$*CH$_2$Cl$_2$ (0.07 g, 0.09 mmol, 0.1 eq.) in a mixture of 1,4-dioxane/water 2/1 (12 mL). Purification by FCC (MeOH gradient in CH$_2$Cl$_2$) provided N-methyl-1-(4-methylbenzenesulfonyl)-3-[4-(morpholin-4-yl)-3-nitroquinolin-6-yl]-1H-pyrrolo[2,3-b]pyridine-5-carboxamide (0.32 g; yield: 63%; UPLC purity: 99%).

142

Intermediate 120

3-[3-Amino-4-(morpholin-4-yl)quinolin-6-yl]-N-methyl-1-(4-methylbenzenesulfonyl)-1H-pyrrolo[2,3-b]pyridine-5-carboxamide

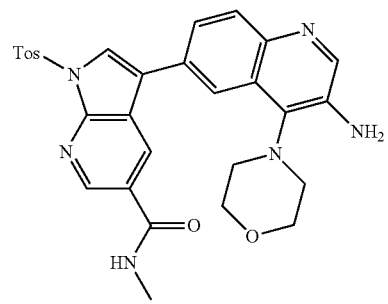

The title compound was prepared according to General Procedure 10 with N-methyl-1-(4-methylbenzenesulfonyl)-3-[4-(morpholin-4-yl)-3-nitroquinolin-6-yl]-1H-pyrrolo[2,3-b]pyridine-5-carboxamide (Intermediate 119) (0.32 g, 0.6 mmol, 1.0 eq.) and Raney-Nickel (1 g) in THF (3 mL) under balloon with hydrogen. The reaction mixture was stirred at rt for 2 h and then filtered through a pad of Celite and the filtrate was concentrated. The 3-[3-amino-4-(morpholin-4-yl)quinolin-6-yl]-N-methyl-1-(4-methylbenzenesulfonyl)-1H-pyrrolo[2,3-b]pyridine-5-carboxamide was used in consecutive step without further purification (UPLC purity: 99%).

Intermediate 121

3-(3-{[(3-Chlorophenyl)methyl]amino}-4-(morpholin-4-yl)quinolin-6-yl)-N-methyl-1-(4-methylbenzenesulfonyl)-1H-pyrrolo[2,3-b]pyridine-5-carboxamide

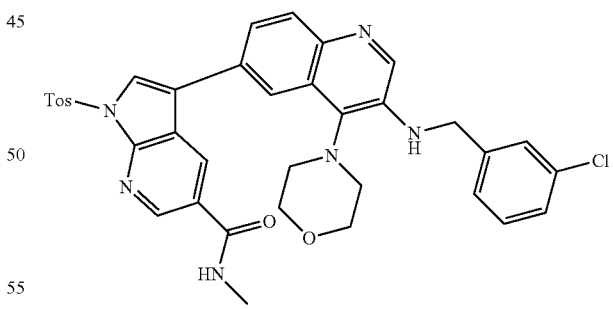

The title compound was prepared according to General Procedure 6 with 3-[3-amino-4-(morpholin-4-yl)quinolin-6-yl]-N-methyl-1-(4-methylbenzenesulfonyl)-1H-pyrrolo[2,3-b]pyridine-5-carboxamide (Intermediate 120) (0.10 g, 0.2 mmol, 1.0 eq.), 3-chlorobenzaldehyde (0.06 g, 0.4 mmol, 2.5 eq.), AcOH (0.5 mL), sodium cyanoborohydride (0.02 g, 0.4 mmol, 2.0 eq.) in MeOH (4 mL). The reaction mixture was stirred at rt overnight. Purification by FCC (MeOH gradient in CH$_2$Cl$_2$) provided 3-(3-{[(3-chlorophenyl)methyl]amino}-4-(morpholin-4-yl)quinolin-6-yl)-N-

Example 56

3-(3-{[(3-Chlorophenyl)methyl]amino}-4-(morpholin-4-yl)quinolin-6-yl)-N-methyl-1H-pyrrolo[2,3-b]pyridine-5-carboxamide

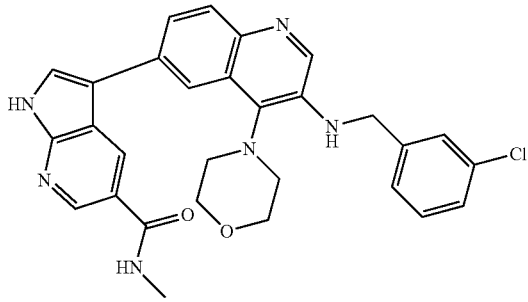 [SMILES: CNC(=O)c1cnc2[nH]cc(-c3ccc4ncc(NCc5cccc(Cl)c5)c(N5CCOCC5)c4c3)c2c1]

The title compound was prepared according to General Procedure 3 with 3-(3-{[(3-chlorophenyl)methyl]amino}-4-(morpholin-4-yl)quinolin-6-yl)-N-methyl-1-(4-methyl benzenesulfonyl)-1H-pyrrolo[2,3-b]pyridine-5-carboxamide (Intermediate 121) (0.07 g, 0.1 mmol, 1.0 eq.), NaOtBu (0.04 g, 0.1 mmol, 1.5 eq.) dissolved in 1,4-dioxane (4 mL). The reaction mixture was stirred at rt for 2 h. Purification by FCC (MeOH gradient in CH$_2$Cl$_2$) afforded 3-(3-{[(3-chlorophenyl)methyl]amino}-4-(morpholin-4-yl)quinolin-6-yl)-N-methyl-1H-pyrrolo[2,3-b]pyridine-5-carboxamide (0.02 g; yield: 43%; HPLC purity: 99%).

Intermediate 122

3-[3-Acetamido-4-(morpholin-4-yl)quinolin-6-yl]-N-methyl-1-(4-methylbenzenesulfonyl)-1H-pyrrolo[2,3-b]pyridine-5-carboxamide

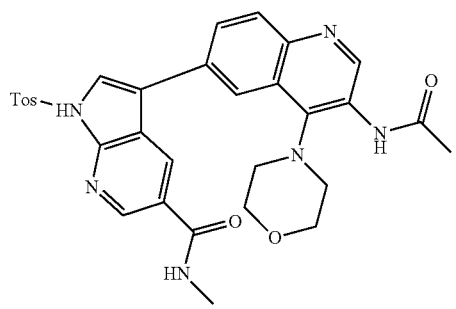

A solution of 3-[3-amino-4-(morpholin-4-yl)quinolin-6-yl]-N-methyl-1-(4-methylbenzenesulfonyl)-1H-pyrrolo[2,3-b]pyridine-5-carboxamide (Intermediate 120) (0.08 g, 0.1 mmol, 1.0 eq.), Et$_3$N (0.14 g, 1.4 mmol, 10.0 eq.) in CH$_2$Cl$_2$ (3 mL) was cooled to 0° C. and then acetyl chloride (0.03 g, 0.4 mmol, 3.0 eq.) was added dropwise. The reaction mixture was stirred at rt overnight and then concentrated. The residue was dissolved in EtOAc and extracted with saturated solution of NaHCO$_3$. Organic layer was dried over MgSO$_4$, filtrated and concentrated. The crude reaction mixture was purified by FCC (MeOH gradient in CH$_2$Cl$_2$) to afford 3-[3-acetamido-4-(morpholin-4-yl)quinolin-6-yl]-N-methyl-1-(4-methylbenzenesulfonyl)-1H-pyrrolo[2,3-b]pyridine-5-carboxamide (0.02 g; yield: 30%; UPLC purity: 97%).

Example 57

3-[3-Acetamido-4-(morpholin-4-yl)quinolin-6-yl]-N-methyl-1H-pyrrolo[2,3-b]pyridine-5-carboxamide

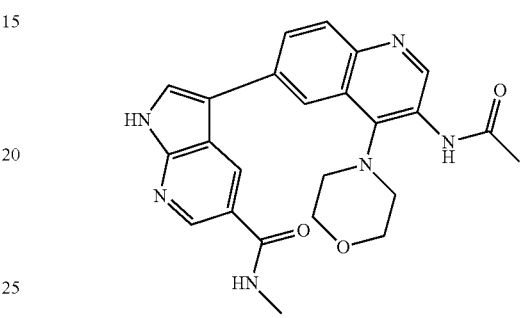

The title compound was prepared according to General Procedure 3 with 3-[3-acetamido-4-(morpholin-4-yl)quinolin-6-yl]-N-methyl-1-(4-methylbenzenesulfonyl)-1H-pyrrolo[2,3-b]pyridine-5-carboxamide (Intermediate 122) (0.02 g, 0.04 mmol, 1.0 eq.), NaOtBu (0.06 g, 0.06 mmol, 1.5 eq.) dissolved in 1,4-dioxane (2 mL). The reaction mixture was stirred at rt for 7 h. Purification by FCC (MeOH gradient in CH$_2$Cl$_2$; column neutralized with 0.1% Et$_3$N in CH$_2$Cl$_2$ then washed with CH$_2$Cl$_2$ before purification) afforded 3-[3-acetamido-4-(morpholin-4-yl)quinolin-6-yl]-N-methyl-1H-pyrrolo[2,3-b]pyridine-5-carboxamide (0.008 g; yield: 45%; HPLC purity: 92%).

Intermediate 123

N-Methyl-1-(4-methylbenzenesulfonyl)-3-[4-(morpholin-4-yl)-3-[(oxan-4-ylmethyl)amino]quinolin-6-yl]-1H-pyrrolo[2,3-b]pyridine-5-carboxamide

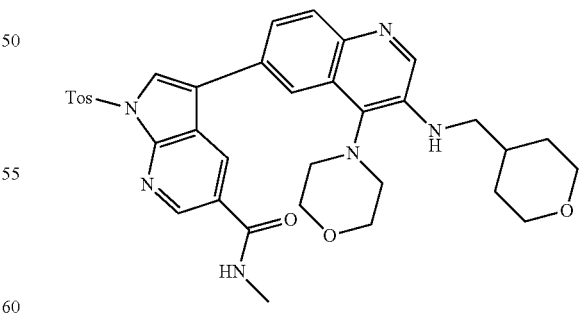

The title compound was prepared according to General Procedure 6 with 3-[3-amino-4-(morpholin-4-yl)quinolin-6-yl]-N-methyl-1-(4-methylbenzenesulfonyl)-1H-pyrrolo[2,3-b]pyridine-5-carboxamide (Intermediate 120) (0.08 g, 0.1 mmol, 1.0 eq.), tetrahydropyran-4-carbaldehyde (0.04 g, 0.4 mmol, 2.5 eq.), AcOH (0.5 mL), sodium cyanoborohydride (0.02 g, 0.3 mmol, 2.0 eq.) in MeOH (2 mL). The reaction mixture was stirred at rt overnight. Purification by FCC (MeOH gradient in CH$_2$Cl$_2$) provided N-methyl-N-(4-methylbenzenesulfonyl)-3-[4-(morpholin-4-yl)-3-[(oxan-4-ylmethyl)amino]quinolin-6-yl]-1H-pyrrolo[2,3-b]pyridine-5-carboxamide (0.07 g; yield: 69%; UPLC purity: 99%).

Example 58

N-Methyl-3-[4-(morpholin-4-yl)-3-[(oxan-4-ylmethyl)amino]quinolin-6-yl]-1H-pyrrolo[2,3-b]pyridine-5-carboxamide

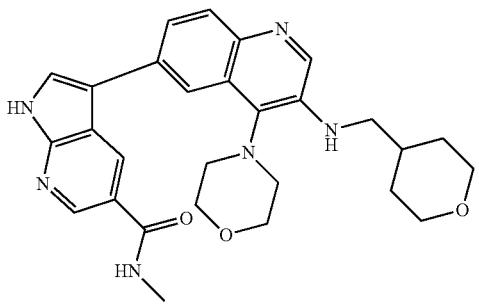 [SMILES: CNC(=O)c1cnc2[nH]cc(-c3ccc4ncc(NCC5CCOCC5)c(N5CCOCC5)c4c3)c2c1]

The title compound was prepared according to General Procedure 3 with N-methyl-1-(4-methylbenzenesulfonyl)-3-[4-(morpholin-4-yl)-3-[(oxan-4-ylmethyl)amino]quinolin-6-yl]-1H-pyrrolo[2,3-b]pyridine-5-carboxamide (Intermediate 123) (0.07 g, 0.1 mmol, 1.0 eq.), NaOtBu (0.01 g, 0.15 mmol, 1.5 eq.) dissolved in 1,4-dioxane (3 mL). The reaction mixture was stirred at rt overnight. HPLC purification afforded N-methyl-3-[4-(morpholin-4-yl)-3-[(oxan-4-ylmethyl)amino]quinolin-6-yl]-1H-pyrrolo[2,3-b]pyridine-5-carboxamide (0.005 g; yield: 10%; HPLC purity: 95%).

Intermediate 124 tert-Butyl N-{4-[(6-bromo-3-nitroquinolin-4-yl)amino]cyclohexyl}carbamate

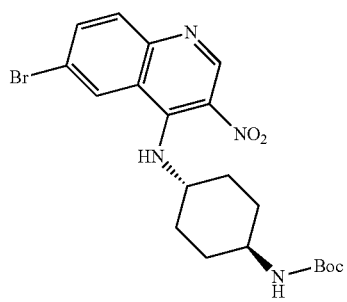 [SMILES: CC(C)(C)OC(=O)N[C@H]1CC[C@H](Nc2c([N+](=O)[O-])cnc3ccc(Br)cc23)CC1]

The title compound was prepared according to General Procedure 4 with 6-bromo-4-chloro-3-nitroquinoline (0.4 g, 1.4 mmol, 1.0 eq.), trans-N-Boc-1,4-cyclohexanediamine (0.36 g, 1.7 mmol, 1.2 eq.), DIPEA (0.54 g, 4.2 mmol, 3.0 eq.) in i-PrOH (2 mL). The reaction mixture was stirred at rt for 2 h and then solvent was evaporated. Purification by FCC (EtOAc gradient in hexane) afforded tert-butyl N-{4-[(6-bromo-3-nitroquinolin-4-yl)amino]cyclohexyl}carbamate (0.6 g; yield: 95%; UPLC purity: 99%).

Intermediate 125 tert-Butyl N-(4-{[3-nitro-6-(tetramethyl-1,3,2-dioxaborolan-2-yl)quinolin-4-yl]amino}cyclohexyl)carbamate

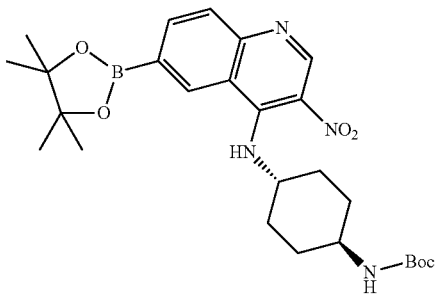 [SMILES: CC(C)(C)OC(=O)N[C@H]1CC[C@H](Nc2c([N+](=O)[O-])cnc3ccc(B4OC(C)(C)C(C)(C)O4)cc23)CC1]

The title compound was prepared according to General Procedure 1 with tert-butyl N-{4-[(6-bromo-3-nitroquinolin-4-yl)amino]cyclohexyl}carbamate (Intermediate 124) (0.8 g, 2.0 mmol, 1.0 eq.), bis(pinacolato)diboron (0.4 g, 2.0 mmol, 1.0 eq.), potassium acetate (0.4 g, 4.0 mmol, 2.5 eq.), Pd(dppf)$_2$Cl$_2$*CH$_2$Cl$_2$ (0.07 g, 0.08 mmol, 0.05 eq.) and 1,4-dioxane (10 mL). The reaction mixture was stirred at 80° C. for 5 h. Obtained tert-butyl N-(4-{[3-nitro-6-(tetramethyl-1,3,2-dioxaborolan-2-yl)quinolin-4-yl]amino}cyclohexyl)carbamate was used in consecutive step without further purification (UPLC purity: 46%).

Intermediate 126 tert-Butyl N-[4-({6-[1-(4-methylbenzenesulfonyl)-5-[(pyridin-3-ylmethyl)carbamoyl]-1H-pyrrolo[2,3-b]pyridin-3-yl]-3-nitroquinolin-4-yl}amino)cyclohexyl]carbamate

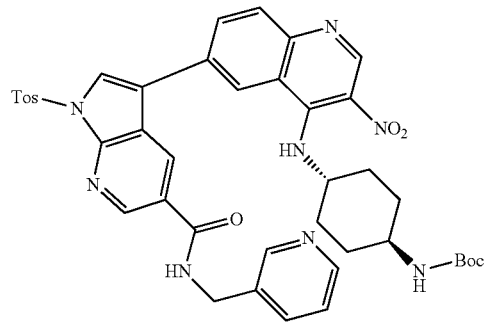

The title compound was prepared according to General Procedure 2 with 3-iodo-1-(4-methylbenzenesulfonyl)-N-(pyridin-3-ylmethyl)-1H-pyrrolo[2,3-b]pyridine-5-carboxamide (Intermediate 91) (0.2 g, 0.4 mmol, 1.0 eq.), tert-butyl N-(4-{[3-nitro-6-(tetramethyl-1,3,2-dioxaborolan-2-yl)quinolin-4-yl]amino}cyclohexyl)carbamate (Intermediate 125) (0.2 g, 0.4 mmol, 1.0 eq.), K$_2$CO$_3$ (0.1 g, 1.0 mmol, 2.0 eq.), Pd(dppf)$_2$Cl$_2$*CH$_2$Cl$_2$ (0.05 g, 0.05 mmol, 0.15 eq.) in a mixture of 1,4-dioxane/water 2/1 (6 mL). The reaction mixture was stirred at 80° C. for 3 h. Purification by FCC (MeOH gradient in CH₂Cl₂) afforded tert-butyl N-[4-({6-[1-(4-methylbenzenesulfonyl)-5-[(pyridin-3-ylmethyl)carbamoyl]-1H-pyrrolo[2,3-b]pyridin-3-yl]-3-nitroquinolin-4-yl}amino)cyclohexyl]carbamate as an yellow solid (0.24 g; yield: 87%; UPLC purity: 99%).

Intermediate 127 tert-Butyl N-{4-[(3-nitro-6-{5-[(pyridin-3-ylmethyl)carbamoyl]-1H-pyrrolo[2,3-b]pyridin-3-yl}quinolin-4-yl)amino]cyclohexyl}carbamate

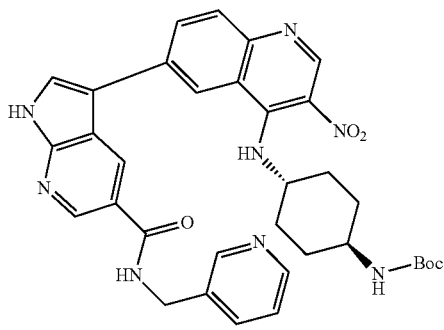 [SMILES: CC(C)(C)OC(=O)N[C@H]1CC[C@H](Nc2c([N+](=O)[O-])cnc3ccc(-c4c[nH]c5ncc(C(=O)NCc6cccnc6)cc45)cc23)CC1]

The title compound was prepared according to General Procedure 3 with tert-butyl N-[4-({6-[1-(4-methylbenzenesulfonyl)-5-[(pyridin-3-ylmethyl)carbamoyl]-1H-pyrrolo[2,3-b]pyridin-3-yl]-3-nitroquinolin-4-yl}amino)cyclohexyl]carbamate (Intermediate 126) (0.24 g, 0.3 mmol, 1.0 eq.), NaOtBu (0.04 g, 0.4 mmol, 1.5 eq.) dissolved in 1,4-dioxane (5 mL). The reaction mixture was stirred at rt overnight. After work up tert-butyl N-{4-[(3-nitro-6-{5-[(pyridin-3-ylmethyl)carbamoyl]-1H-pyrrolo[2,3-b]pyridin-3-yl}quinolin-4-yl)amino]cyclohexyl}carbamate (yellow solid) was used in consecutive step without further purification (UPLC purity: 99%).

Example 59

3-{4-[(4-Aminocyclohexyl)amino]-3-nitroquinolin-6-yl}-N-(pyridin-3-ylmethyl)-1H-pyrrolo[2,3-b]pyridine-5-carboxamide hydrochloride

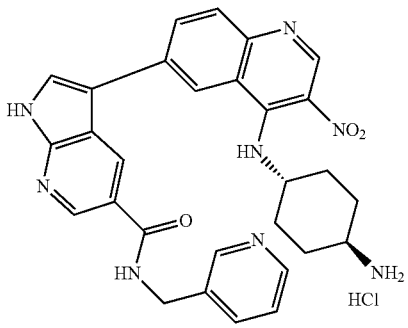 [SMILES: N[C@H]1CC[C@H](Nc2c([N+](=O)[O-])cnc3ccc(-c4c[nH]c5ncc(C(=O)NCc6cccnc6)cc45)cc23)CC1 ; Cl]

The title compound was prepared according to General Procedure 5 with tert-butyl N-{4-[(3-nitro-6-{5-[(pyridin-3-ylmethyl)carbamoyl]-1H-pyrrolo[2,3-b]pyridin-3-yl}quinolin-4-yl)amino]cyclohexyl}carbamate (Intermediate 127) (0.1 g, 0.01 mmol, 1.0 eq.) in MeOH (1 mL) and 2 M HCl in Et₂O (6 mL). The reaction mixture was stirred at rt overnight. The precipitate was collected by filtration to provide 3-{4-[(4-aminocyclohexyl)amino]-3-nitroquinolin-6-yl}-N-(pyridin-3-ylmethyl)-1H-pyrrolo[2,3-b]pyridine-5-carboxamide hydrochloride (0.008 g; yield: 99%; HPLC purity: 87%).

Intermediate 128 tert-Butyl N-[4-({3-amino-6-[1-(4-methylbenzenesulfonyl)-5-[(pyridin-3-ylmethyl)carbamoyl]-1H-pyrrolo[2,3-b]pyridin-3-yl]quinolin-4-yl}amino)cyclohexyl]carbamate

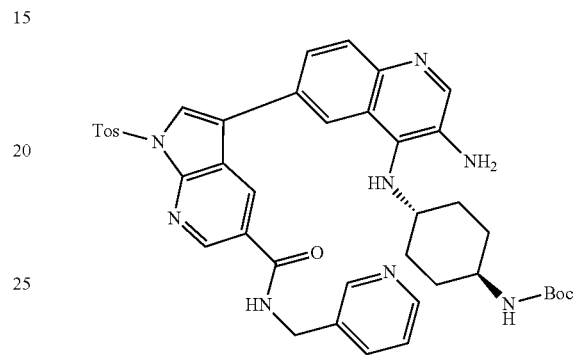

The title compound was prepared according to General Procedure 10 with tert-butyl N-[4-({6-[1-(4-methylbenzenesulfonyl)-5-[(pyridin-3-ylmethyl)carbamoyl]-1H-pyrrolo[2,3-b]pyridin-3-yl]-3-nitroquinolin-4-yl}amino)cyclohexyl]carbamate (Intermediate 126) (0.49 g, 0.6 mmol, 1.0 eq.) and Raney-Nickel (1 g) in THF (12 mL) under balloon with hydrogen. Purification by FCC (EtOAc gradient in hexane) provided tert-butyl N-[4-({3-amino-6-[1-(4-methylbenzenesulfonyl)-5-[(pyridin-3-ylmethyl)carbamoyl]-1H-pyrrolo[2,3-b]pyridin-3-yl]quinolin-4-yl}amino)cyclohexyl]carbamate (0.17 g, yield: 36%; UPLC purity: 99%).

Intermediate 129 tert-Butyl N-[4-({6-[1-(4-methylbenzenesulfonyl)-5-[(pyridin-3-ylmethyl)carbamoyl]-1H-pyrrolo[2,3-b]pyridin-3-yl]-3-[(oxan-4-ylmethyl)amino]quinolin-4-yl}amino)cyclohexyl]carbamate

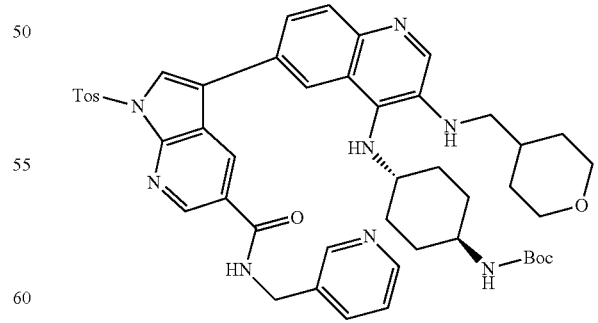

The title compound was prepared according to General Procedure 6 with tert-butyl N-[4-({3-amino-6-[1-(4-methylbenzenesulfonyl)-5-[(pyridin-3-ylmethyl)carbamoyl]-1H-pyrrolo[2,3-b]pyridin-3-yl]quinolin-4-yl}amino)cyclohexyl]carbamate (Intermediate 128) (0.17 g, 0.2 mmol, 1.0 eq.), tetrahydropyran-4-carbaldehyde (0.06 g, 0.6 mmol, 2.5 eq.), AcOH (0.5 mL), sodium cyanoborohydride (0.03 g, 0.4 mmol, 2.0 eq.) in MeOH (6 mL). The reaction mixture was stirred at rt overnight. tert-Butyl N-[4-({6-[1-(4-methylbenzenesulfonyl)-5-[(pyridin-3-ylmethyl)carbamoyl]-1H-pyrrolo[2,3-b]pyridin-3-yl]-3-[(oxan-4-ylmethyl)amino]quinolin-4-yl}amino)cyclohexyl]carbamate was used in consecutive step without further purification (UPLC purity: 99%).

Intermediate 130 tert-Butyl N-[4-({3-[(oxan-4-ylmethyl)amino]-6-{5-[(pyridin-3-ylmethyl)carbamoyl]-1H-pyrrolo[2,3-b]pyridin-3-yl}quinolin-4-yl}amino)cyclohexyl]carbamate

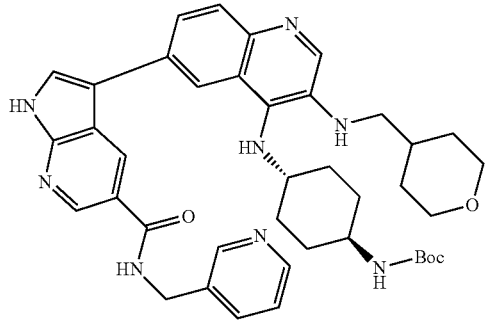 [SMILES: CC(C)(C)OC(=O)N[C@H]1CC[C@H](Nc2c(NCC3CCOCC3)cnc3ccc(-c4c[nH]c5ncc(C(=O)NCc6cccnc6)cc45)cc23)CC1]

The title compound was prepared according to General Procedure 3 with tert-butyl N-[4-({6-[1-(4-methylbenzenesulfonyl)-5-[(pyridin-3-ylmethyl)carbamoyl]-1H-pyrrolo[2,3-b]pyridin-3-yl]-3-[(oxan-4-ylmethyl)amino]quinolin-4-yl}amino)cyclohexyl]carbamate (Intermediate 129) (0.12 g, 0.1 mmol, 1.0 eq.), NaOtBu (0.06 g, 0.6 mmol, 4.0 eq.) dissolved in 1,4-dioxane (8 mL). The reaction mixture was stirred at rt overnight. Purification by FCC (EtOAc gradient in hexane) afforded tert-butyl N-[4-({3-[(oxan-4-ylmethyl)amino]-6-{5-[(pyridin-3-ylmethyl)carbamoyl]-1H-pyrrolo[2,3-b]pyridin-3-yl}quinolin-4-yl}amino)cyclohexyl]carbamate (0.04 g; yield: 39%; UPLC purity: 100%).

Example 60

3-{4-[(4-Aminocyclohexyl)amino]-3-[(oxan-4-ylmethyl)amino]quinolin-6-yl}-N-(pyridin-3-ylmethyl)-1H-pyrrolo[2,3-b]pyridine-5-carboxamide hydrochloride

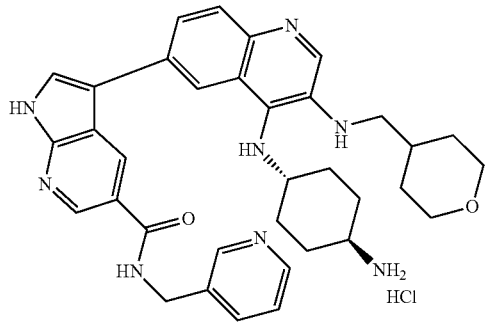 [SMILES: N[C@H]1CC[C@H](Nc2c(NCC3CCOCC3)cnc3ccc(-c4c[nH]c5ncc(C(=O)NCc6cccnc6)cc45)cc23)CC1 ; Cl]

The title compound was prepared according to General Procedure 5 with tert-butyl N-[4-({3-[(oxan-4-ylmethyl)amino]-6-{5-[(pyridin-3-ylmethyl)carbamoyl]-1H-pyrrolo[2,3-b]pyridin-3-yl}quinolin-4-yl}amino)cyclohexyl]carbamate (Intermediate 130) (0.04 g, 0.05 mmol, 1.0 eq.) in MeOH (0.5 mL) and 2 M HCl in Et₂O (3 mL). The reaction mixture was stirred at rt overnight. The precipitate was collected by filtration to provide 3-{4-[(4-aminocyclohexyl)amino]-3-[(oxan-4-ylmethyl)amino]quinolin-6-yl}-N-(pyridin-3-ylmethyl)-1H-pyrrolo[2,3-b]pyridine-5-carboxamide hydrochloride as an yellow solid (0.03 g; yield: 85%; HPLC purity: 90%).

Intermediate 131

3-(3-Aminoquinolin-6-yl)-1-(4-methylbenzenesulfonyl)-N-(pyridin-3-ylmethyl)-1H-pyrrolo[2,3-b]pyridine-5-carboxamide

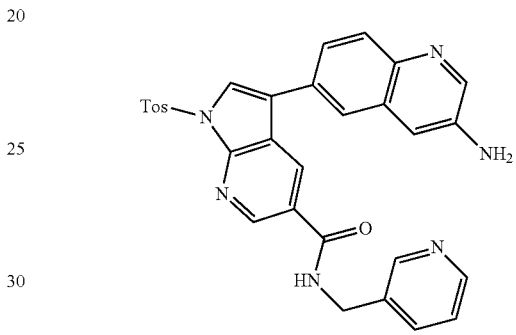

The title compound was prepared according to General Procedure 2 with 3-iodo-1-(4-methylbenzenesulfonyl)-N-(pyridin-3-ylmethyl)-1H-pyrrolo[2,3-b]pyridine-5-carboxamide (Intermediate 91) (0.27 g, 0.02 mmol, 1.0 eq.), 6-(tetramethyl-1,3,2-dioxaborolan-2-yl)quinolin-3-amine (Intermediate 24) (0.14 g, 0.5 mmol, 1.0 eq.), K₂CO₃ (0.14 g, 1.0 mmol, 2.0 eq.), Pd(dppf)₂Cl₂*CH₂Cl₂ (0.06 g, 0.07 mmol, 0.15 eq.) in a mixture of 1,4-dioxane/water 2/1 (6 mL). The reaction mixture was stirred at 80° C. for 3 h. Purification by FCC (MeOH gradient in CH₂Cl₂) afforded 3-(3-aminoquinolin-6-yl)-1-(4-methylbenzenesulfonyl)-N-(pyridin-3-ylmethyl)-1H-pyrrolo[2,3-b]pyridine-5-carboxamide as an yellow solid (0.18 g; yield: 65%; UPLC purity: 97%).

Example 61

3-(3-Aminoquinolin-6-yl)-N-(pyridin-3-ylmethyl)-1H-pyrrolo[2,3-b]pyridine-5-carboxamide

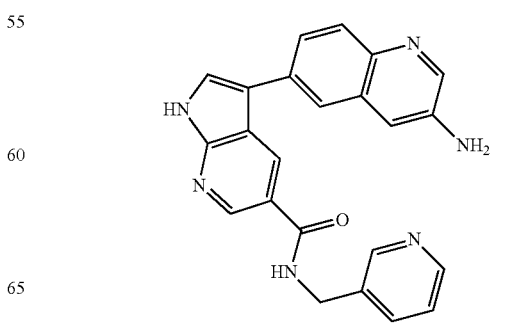

The title compound was prepared according to General Procedure 3 with 3-(3-aminoquinolin-6-yl)-1-(4-methylbenzenesulfonyl)-N-(pyridin-3-ylmethyl)-1H-pyrrolo[2,3-b]pyridine-5-carboxamide (Intermediate 131) (0.18 g, 0.3 mmol, 1.0 eq.), NaOtBu (0.1 g, 0.5 mmol, 3.0 eq.) dissolved in 1,4-dioxane (4 mL). The reaction mixture was stirred at rt overnight. Purification by FCC (MeOH gradient in CH$_2$Cl$_2$) afforded 3-(3-aminoquinolin-6-yl)-N-(pyridin-3-ylmethyl)-1H-pyrrolo[2,3-b]pyridine-5-carboxamide (0.08 g; yield: 62%; HPLC purity: 94%).

Intermediate 132

N-(6-Bromoquinolin-3-yl)acetamide

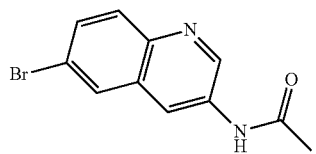

A solution of 6-bromoquinolin-3-amine (0.33 g, 1.5 mmol, 1.0 eq.) in acetic anhydride (5 mL) was heated at 90° C. for 1 h. After cooling to rt water was added and the occurred white precipitate was collected by filtration. N-(6-bromoquinolin-3-yl)acetamide was used in consecutive step without further purification (UPLC purity: 97%).

Intermediate 133

(3-Acetamidoquinolin-6-yl)boronic acid

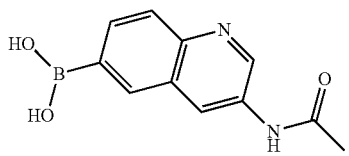 [SMILES: CC(=O)Nc1cnc2ccc(B(O)O)cc2c1]

The title compound was prepared according to General Procedure 1 with N-(6-bromoquinolin-3-yl)acetamide (Intermediate 132) (0.3 g, 1.2 mmol, 1.0 eq.), bis(pinacolato)diboron (0.3 g, 1.3 mmol, 1.1 eq.), potassium acetate (0.2 g, 2.0 mmol, 2.0 eq.), Pd(dppf)$_2$Cl$_2$*CH$_2$Cl$_2$ (0.05 g, 0.06 mmol, 0.05 eq.) and 1,4-dioxane (5 mL). The reaction mixture was stirred at 80° C. for 5 h. Purification by FCC (MeOH gradient in CH$_2$Cl$_2$) provided (3-acetamidoquinolin-6-yl)boronic acid (0.23 g; yield: 63%; UPLC purity: 83%).

Intermediate 134

3-(3-Acetamidoquinolin-6-yl)-1-(4-methylbenzenesulfonyl)-N-(pyridin-3-ylmethyl)-1H-pyrrolo[2,3-b]pyridine-5-carboxamide

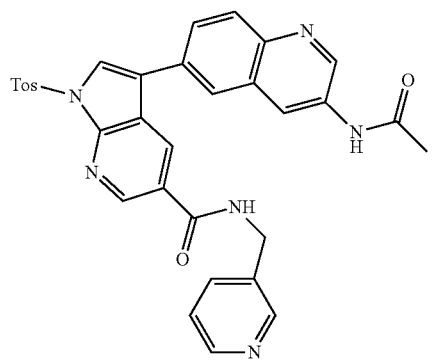

The title compound was prepared according to General Procedure 2 with 3-iodo-1-(4-methylbenzenesulfonyl)-N-(pyridin-3-ylmethyl)-1H-pyrrolo[2,3-b]pyridine-5-carboxamide (Intermediate 91) (0.4 g, 0.7 mmol, 1.0 eq.), (3-acetamidoquinolin-6-yl)boronic acid (Intermediate 133) (0.23 g, 0.7 mmol, 1.0 eq.), K$_2$CO$_3$ (0.21 g, 1.5 mmol, 2.0 eq.), Pd(dppf)$_2$Cl$_2$*CH$_2$Cl$_2$ (0.09 g, 0.1 mmol, 0.15 eq.) in a mixture of 1,4-dioxane/water 2/1 (6 mL). The reaction mixture was stirred at 80° C. for 3 h. Purification by FCC (MeOH gradient in CH$_2$Cl$_2$) afforded 3-(3-acetamidoquinolin-6-yl)-1-(4-methylbenzenesulfonyl)-N-(pyridin-3-ylmethyl)-1H-pyrrolo[2,3-b]pyridine-5-carboxamide (0.31 g; yield: 76%; UPLC purity: 98%).

Example 62

3-(3-Acetamidoquinolin-6-yl)-N-(pyridin-3-ylmethyl)-1H-pyrrolo[2,3-b]pyridine-5-carboxamide

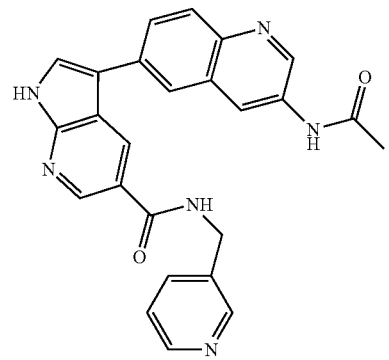 [SMILES: CC(=O)Nc1cnc2ccc(-c3c[nH]c4ncc(C(=O)NCc5cccnc5)cc34)cc2c1]

The title compound was prepared according to General Procedure 3 with 3-(3-acetamidoquinolin-6-yl)-1-(4-methylbenzenesulfonyl)-N-(pyridin-3-ylmethyl)-1H-pyrrolo[2,3-b]pyridine-5-carboxamide (Intermediate 134) (0.31 g, 0.5 mmol, 1.0 eq.), NaOtBu (0.165 g, 1.7 mmol, 3.4 eq.) dissolved in 1,4-dioxane (4 mL). The reaction mixture was stirred at rt for 5 days. Purification by FCC (MeOH gradient in CH$_2$Cl$_2$; column neutralized with 0.1% Et$_3$N in CH$_2$Cl$_2$ then washed with CH$_2$Cl$_2$ before purification) afforded 3-(3-acetamidoquinolin-6-yl)-N-(pyridin-3-ylmethyl)-1H-pyrrolo[2,3-b]pyridine-5-carboxamide as a beige solid (0.02 g; yield: 12%; HPLC purity: 97%).

Intermediate 135

6-Bromo-N-(oxan-4-ylmethyl)quinolin-3-amine

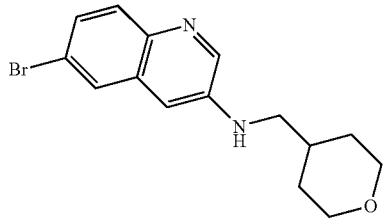 [SMILES: Brc1ccc2ncc(NCC3CCOCC3)cc2c1]

The title compound was prepared according to General Procedure 6 with 6-bromoquinolin-3-amine (0.2 g, 0.9 mmol, 1.0 eq.), tetrahydropyran-4-carbaldehyde (0.26 g, 2.2 mmol, 2.5 eq.), AcOH (0.5 mL), sodium cyanoborohydride (0.11 g, 1.7 mmol, 2.0 eq.) in MeOH (5 mL). The reaction mixture was stirred at rt overnight. Purification by FCC (EtOAc gradient in hexane) gave 6-bromo-N-(oxan-4-ylmethyl)quinolin-3-amine (0.23 g; yield: 80%; UPLC purity: 90%).

Intermediate 136

{3-[(Oxan-4-ylmethyl)amino]quinolin-6-yl}boronic acid

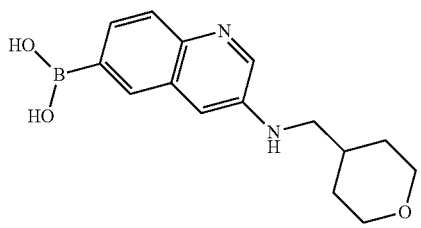 [SMILES: OB(O)c1ccc2ncc(NCC3CCOCC3)cc2c1]

The title compound was prepared according to General Procedure 1 with 6-bromo-N-(oxan-4-ylmethyl)quinolin-3-amine (Intermediate 135) (0.23 g, 0.7 mmol, 1.0 eq.), bis(pinacolato)diboron (0.2 g, 0.8 mmol, 1.1 eq.), potassium acetate (0.14 g, 1.4 mmol, 2.0 eq.), Pd(dppf)$_2$Cl$_2$*CH$_2$Cl$_2$ (0.03 g, 0.03 mmol, 0.05 eq.) and 1,4-dioxane (15 mL). The reaction mixture was stirred at 80° C. overnight. Obtained {3-[(oxan-4-ylmethyl)amino]quinolin-6-yl}boronic acid was used in consecutive step without further purification (UPLC purity: 61%).

Intermediate 137

1-(4-Methylbenzenesulfonyl)-3-{3-[(oxan-4-ylmethyl)amino]quinolin-6-yl}-N-(pyridin-3-ylmethyl)-1H-pyrrolo[2,3-b]pyridine-5-carboxamide

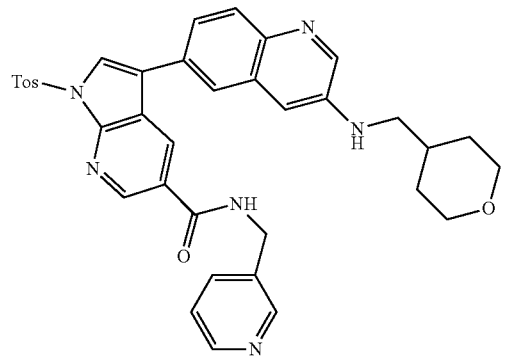

The title compound was prepared according to General Procedure 2 with 3-iodo-1-(4-methylbenzenesulfonyl)-N-(pyridin-3-ylmethyl)-1H-pyrrolo[2,3-b]pyridine-5-carboxamide (Intermediate 91) (0.09 g, 0.2 mmol, 1.0 eq.), {3-[(oxan-4-ylmethyl)amino]quinolin-6-yl}boronic acid (Intermediate 136) (0.1 g, 0.3 mmol, 1.5 eq.), K$_2$CO$_3$ (0.05 g, 0.3 mmol, 2.0 eq.), Pd(dppf)$_2$Cl$_2$*CH$_2$Cl$_2$ (0.01 g, 0.02 mmol, 0.1 eq.) in a mixture of 1,4-dioxane/water 2/1 (6 mL). The reaction mixture was stirred at 80° C. for 3 h. Purification by FCC (MeOH gradient in CH$_2$Cl$_2$) afforded 1-(4-methylbenzenesulfonyl)-3-{3-[(oxan-4-ylmethyl)amino]quinolin-6-yl}-N-(pyridin-3-ylmethyl)-1H-pyrrolo[2,3-b]pyridine-5-carboxamide (0.07 g; yield: 59%; UPLC purity: 100%).

Example 63

3-{3-[(Oxan-4-ylmethyl)amino]quinolin-6-yl}-N-(pyridin-3-ylmethyl)-1H-pyrrolo[2,3-b]pyridine-5-carboxamide

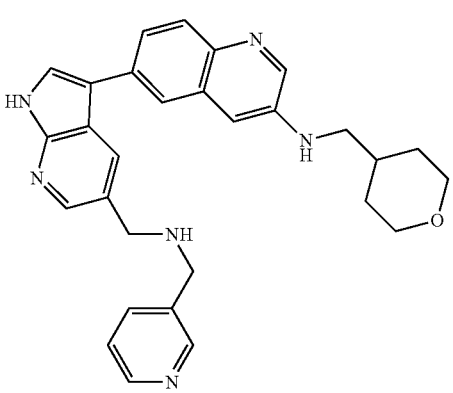 [SMILES: c1cncc(CNCc2cnc3[nH]cc(-c4ccc5ncc(NCC6CCOCC6)cc5c4)c3c2)c1]

The title compound was prepared according to General Procedure 3 with 1-(4-methylbenzenesulfonyl)-3-{3-[(oxan-4-ylmethyl)amino]quinolin-6-yl}-N-(pyridin-3-ylmethyl)-1H-pyrrolo[2,3-b]pyridine-5-carboxamide (Intermediate 137) (0.07 g, 0.1 mmol, 1.0 eq.), NaOtBu (0.03 g, 0.3 mmol, 3.0 eq.) dissolved in 1,4-dioxane (4 mL). The reaction mixture was stirred at rt for 3 days. Purification by FCC (MeOH gradient in CH$_2$Cl$_2$) afforded 3-{3-[(oxan-4-ylmethyl)amino]quinolin-6-yl}-N-(pyridin-3-ylmethyl)-1H-pyrrolo[2,3-b]pyridine-5-carboxamide as a beige solid (0.03 g; yield: 67%; HPLC purity: 94%).

Intermediate 138

6-Bromo-4-[(1-methylpiperidin-4-yl)amino]quinoline-3-carbonitrile

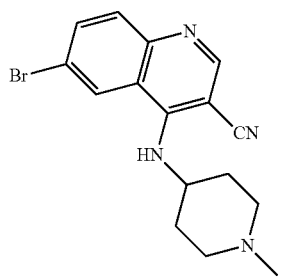 [SMILES: CN1CCC(Nc2c(C#N)cnc3ccc(Br)cc23)CC1]

The title compound was prepared according to General Procedure 4 with 6-bromo-4-chloroquinoline-3-carbonitryle (0.2 g, 0.7 mmol, 1.0 eq.), 1-methylpiperidin-4-amine (0.24 g, 2.1 mmol, 3.0 eq.), DIPEA (0.27 g, 2.1 mmol, 3.0 eq.) in i-PrOH (3 mL). The reaction mixture was irradiated in microwave at 100° C. for 30 min. The reaction mixture was portioned between CH$_2$Cl$_2$ and water. The water phase was extracted with CH$_2$Cl$_2$. Combined organic phases were washed with brine, dried over Na$_2$SO$_4$ and concentrated to afford 6-bromo-4-[(1-methylpiperidin-4-yl)amino]quinoline-3-carbonitrile as a pale orange solid (0.24 g; yield: 99%; UPLC purity: 97%).

Intermediate 139

{3-Cyano-4-[(1-methylpiperidin-4-yl)amino]quinolin-6-yl}boronic acid

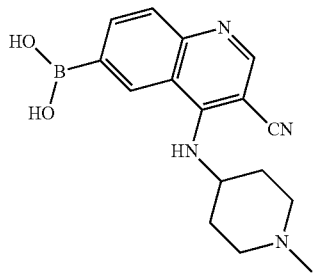 [SMILES: CN1CCC(Nc2c(C#N)cnc3ccc(B(O)O)cc23)CC1]

The title compound was prepared according to General Procedure 1 with 6-bromo-4-[(1-methylpiperidin-4-yl)amino]quinoline-3-carbonitrile (Intermediate 138) (0.24 g, 0.7 mmol, 1.0 eq.), bis(pinacolato)diboron (0.26 g, 1.0 mmol, 1.5 eq.), K$_3$PO$_4$ (0.2 g, 2.1 mmol, 3.0 eq.), Pd(dppf)$_2$Cl$_2$*CH$_2$Cl$_2$ (0.04 g, 0.05 mmol, 0.07 eq.) and 1,4-dioxane (5 mL). The reaction mixture was stirred at 100° C. for 20 h. UPLC-MS showed 60% of starting material and additional portion of bis(pinacolato)diboron (0.5 eq.) and 10% mol catalyst was added. The reaction mixture was heated at 100° C. for 3 days. After work up {3-cyano-4-[(1-methylpiperidin-4-yl)amino]quinolin-6-yl}boronic acid was used in consecutive step without further purification (UPLC purity: 79%).

Intermediate 140

6-[1-(4-Methylbenzenesulfonyl)-1H-pyrrolo[2,3-b]pyridin-3-yl]-4-[(1-methylpiperidin-4-yl)amino]quinoline-3-carbonitrile

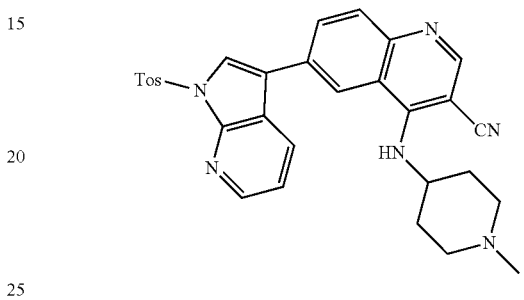

The title compound was prepared according to General Procedure 2 with 3-bromo-1-(4-methylbenzenesulfonyl)-1H-pyrrolo[2,3-b]pyridine (Intermediate 1b) (0.2 g, 0.5 mmol, 1.0 eq.), {3-cyano-4-[(1-methylpiperidin-4-yl)amino]quinolin-6-yl}boronic acid (Intermediate 139) (0.17 g, 0.6 mmol, 1.1 eq.), K$_2$CO$_3$ (0.13 g, 1.0 mmol, 2.0 eq.), Pd(dppf)$_2$Cl$_2$*CH$_2$Cl$_2$ (0.04 g, 0.05 mmol, 0.1 eq.) in a mixture of 1,4-dioxane/water 3/1 (4.0 mL) and heated at 80° C. for 20 h. Purification by FCC (EtOAc gradient in hexane) provided 6-[1-(4-methylbenzenesulfonyl)-1H-pyrrolo[2,3-b]pyridin-3-yl]-4-[(1-methylpiperidin-4-yl)amino]quinoline-3-carbonitrile (0.06 g; yield: 22%; UPLC purity: 78%).

Example 64

4-[(1-Methylpiperidin-4-yl)amino]-6-{1H-pyrrolo[2,3-b]pyridin-3-yl}quinoline-3-carbonitrile

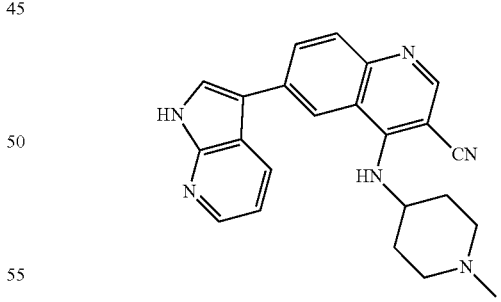

The title compound was prepared according to General Procedure 3 with 6-[1-(4-methylbenzenesulfonyl)-1H-pyrrolo[2,3-b]pyridin-3-yl]-4-[(1-methylpiperidin-4-yl)amino]quinoline-3-carbonitrile (Intermediate 140) (0.06 g, 0.1 mmol, 1.0 eq.), NaOtBu (0.01 g, 0.2 mmol, 1.5 eq.) dissolved in 1,4-dioxane (6 mL). The reaction mixture was stirred at rt overnight. UPLC-MS showed ca. 30% of starting material, additional portion of NaOtBu (0.1 eq.) was added and stirring was continued overnight. Purification by FCC (MeOH gradient in EtOAc) afforded 4-[(1-methylpiperidin- 4-yl)amino]-6-{1H-pyrrolo[2,3-b]pyridin-3-yl}quinoline-3-carbonitrile as an yellowish solid (0.02 g; yield: 56%; HPLC purity: 97%).

Intermediate 141

6-Bromo-N-methyl-N-(1-methylpiperidin-4-yl)-3-nitroquinolin-4-amine

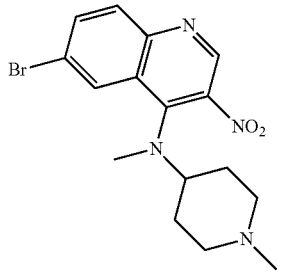 [SMILES: CN1CCC(N(C)c2c([N+](=O)[O-])cnc3ccc(Br)cc23)CC1]

The title compound was prepared according to General Procedure 4 with 6-bromo-4-chloro-3-nitroquinoline (0.3 g, 1.0 mmol, 1.0 eq.), 1-methyl-4-(methylamino)piperidine (0.16 g, 1.2 mmol, 1.2 eq.), DIPEA (0.40 g, 3.1 mmol, 3.0 eq.) in i-PrOH (2 mL). The reaction mixture was stirred at rt for 2 h and then concentrated. Purification by FCC (MeOH gradient in $CH_2Cl_2$) afforded 6-bromo-N-methyl-N-(1-methylpiperidin-4-yl)-3-nitroquinolin-4-amine (0.28 g; yield: 70%; UPLC purity: 100%).

Intermediate 142

{4-[Methyl(1-methylpiperidin-4-yl)amino]-3-nitroquinolin-6-yl}boronic acid

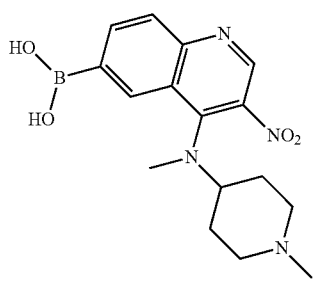 [SMILES: CN1CCC(N(C)c2c([N+](=O)[O-])cnc3ccc(B(O)O)cc23)CC1]

The title compound was prepared according to General Procedure 1 with 6-bromo-N-methyl-N-(1-methylpiperidin-4-yl)-3-nitroquinolin-4-amine (Intermediate 141) (0.28 g, 0.7 mmol, 1.0 eq.), bis(pinacolato)diboron (0.20 g, 0.8 mmol, 1.1 eq.), potassium acetate (0.14 g, 1.4 mmol, 2.0 eq.), $Pd(dppf)_2Cl_2 \cdot CH_2Cl_2$ (0.03 g, 0.04 mmol, 0.05 eq.) and 1,4-dioxane (3 mL). The reaction mixture was stirred at 80° C. for 5 h. UPLC-MS showed 30% of starting material and additional portion of $Pd(dppf)_2Cl_2 \cdot CH_2Cl_2$ (0.05 eq.) was added. The reaction mixture was heated at 80° C. for 3 h. After work up {4-[methyl(1-methylpiperidin-4-yl)amino]-3-nitroquinolin-6-yl}boronic acid was used in consecutive step without further purification (UPLC purity: 70%).

Intermediate 143

N-Methyl-6-[1-(4-methylbenzenesulfonyl)-1H-pyrrolo[2,3-b]pyridin-3-yl]-N-(1-methylpiperidin-4-yl)-3-nitroquinolin-4-amine

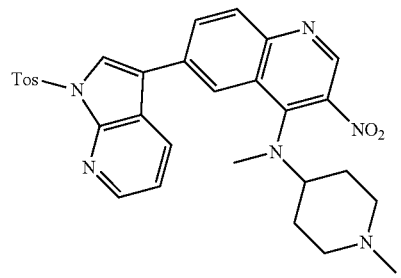

The title compound was prepared according to General Procedure 2 with 3-bromo-1-(4-methylbenzenesulfonyl)-1H-pyrrolo[2,3-b]pyridine (Intermediate 1b) (0.06 g, 0.3 mmol, 1.0 eq.), {4-[methyl(1-methylpiperidin-4-yl)amino]-3-nitroquinolin-6-yl}boronic acid (Intermediate 142) (0.08 g, 0.2 mmol, 1.3 eq.), $K_2CO_3$ (0.05 g, 0.3 mmol, 2.0 eq.), $Pd(dppf)_2Cl_2 \cdot CH_2Cl_2$ (0.03 g, 0.03 mmol, 0.2 eq.) in a mixture of 1,4-dioxane/water 2/1 (6.0 mL) and heated at 80° C. for 3 h. After work up N-methyl-6-[1-(4-methylbenzenesulfonyl)-1H-pyrrolo[2,3-b]pyridin-3-yl]-N-(1-methylpiperidin-4-yl)-3-nitroquinolin-4-amine was used in consecutive step without further purification (UPLC purity: 80%).

Example 65

N-Methyl-N-(1-methylpiperidin-4-yl)-3-nitro-6-{1H-pyrrolo[2,3-b]pyridin-3-yl}quinolin-4-amine

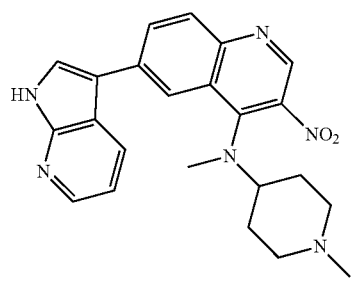 [SMILES: CN1CCC(N(C)c2c([N+](=O)[O-])cnc3ccc(-c4c[nH]c5ncccc45)cc23)CC1]

The title compound was prepared according to General Procedure 3 with N-methyl-6-[1-(4-methylbenzenesulfonyl)-1H-pyrrolo[2,3-b]pyridin-3-yl]-N-(1-methylpiperidin-4-yl)-3-nitroquinolin-4-amine (Intermediate 143) (0.05 g, 0.1 mmol, 1.0 eq.), NaOtBu (0.01 g, 0.2 mmol, 1.5 eq.) dissolved in 1,4-dioxane (2 mL). The reaction mixture was stirred at rt overnight. Purification by FCC (MeOH gradient in $CH_2Cl_2$) afforded N-methyl-N-(1-methylpiperidin-4-yl)-3-nitro-6-{1H-pyrrolo[2,3-b]pyridin-3-yl}quinolin-4-amine as an yellowish solid (0.008 g; yield: 22%; HPLC purity: 95%).

Intermediate 144

1-{4-[(6-Bromo-3-nitroquinolin-4-yl)amino]piperidin-1-yl}ethan-1-one

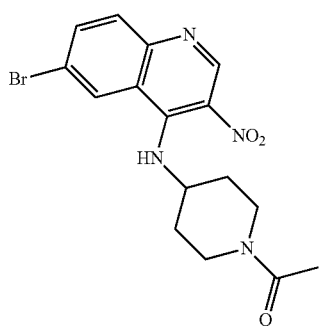 [SMILES: CC(=O)N1CCC(Nc2c([N+](=O)[O-])cnc3ccc(Br)cc23)CC1]

The title compound was prepared according to General Procedure 4 with 6-bromo-4-chloro-3-nitroquinoline (0.3 g, 1.0 mmol, 1.0 eq.), 1-acetyl-4-aminopiperidine (0.17 g, 1.2 mmol, 1.2 eq.), DIPEA (0.40 g, 3.1 mmol, 3.0 eq.) in i-PrOH (2 mL). The reaction mixture was stirred at rt overnight and then concentrated. Purification by FCC (MeOH gradient in $CH_2Cl_2$) afforded 1-{4-[(6-bromo-3-nitroquinolin-4-yl)amino]piperidin-1-yl}ethan-1-one (0.21 g; yield: 52%; UPLC purity: 96%).

Intermediate 145

{4-[1-Acetylpiperidin-4-yl)amino]-3-nitroquinolin-6-yl}boronic acid

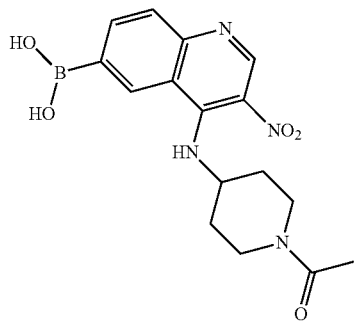 [SMILES: CC(=O)N1CCC(Nc2c([N+](=O)[O-])cnc3ccc(B(O)O)cc23)CC1]

The title compound was prepared according to General Procedure 1 with 1-{4-[(6-bromo-3-nitroquinolin-4-yl)amino]piperidin-1-yl}ethan-1-one (Intermediate 144) (0.1 g, 0.3 mmol, 1.0 eq.), bis(pinacolato)diboron (0.07 g, 0.3 mmol, 1.1 eq.), potassium acetate (0.05 g, 0.5 mmol, 2.0 eq.), $Pd(dppf)_2Cl_2$*$CH_2Cl_2$ (0.009 g, 0.01 mmol, 0.05 eq.) and 1,4-dioxane (2 mL). The reaction mixture was stirred at 80° C. for 5 h. Purification by FCC (MeOH gradient in EtOAc) provided {4-[(1-acetylpiperidin-4-yl)amino]-3-nitroquinolin-6-yl}boronic acid (0.1 g; yield: 95%; UPLC purity: 64%).

Intermediate 146

1-[4-({6-[1-(4-Methylbenzenesulfonyl)-1H-pyrrolo[2,3-b]pyridin-3-yl]-3-nitroquinolin-4-yl}amino)piperidin-1-yl]ethan-1-one

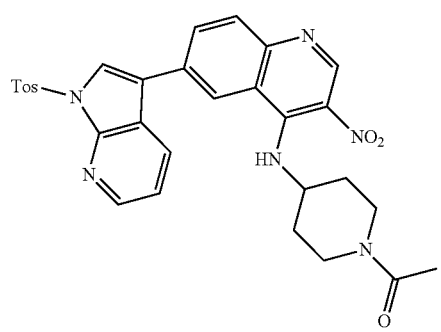

The title compound was prepared according to General Procedure 2 with 3-bromo-1-(4-methylbenzenesulfonyl)-1H-pyrrolo[2,3-b]pyridine (Intermediate 1b) (0.08 g, 0.2 mmol, 1.0 eq.), {4-[(1-acetylpiperidin-4-yl)amino]-3-nitroquinolin-6-yl}boronic acid (Intermediate 145) (0.1 g, 0.3 mmol, 1.3 eq.), $K_2CO_3$ (0.06 g, 0.5 mmol, 2.0 eq.), $Pd(dppf)_2Cl_2$*$CH_2Cl_2$ (0.04 g, 0.05 mmol, 0.2 eq.) in a mixture of 1,4-dioxane/water 2/1 (6.0 mL) and heated at 80° C. for 3 h. Purification by FCC (EtOAc gradient in hexane) afforded 1-[4-({6-[1-(4-methylbenzenesulfonyl)-1H-pyrrolo[2,3-b]pyridin-3-yl]-3-nitroquinolin-4-yl}amino)piperidin-1-yl]ethan-1-one (0.13 g; yield: 99%; UPLC purity: 77%).

Intermediate 147

1-[4-({3-Amino-6-[1-(4-methylbenzenesulfonyl)-1H-pyrrolo[2,3-b]pyridin-3-yl]quinolin-4-yl}amino)piperidin-1-yl]ethan-1-one

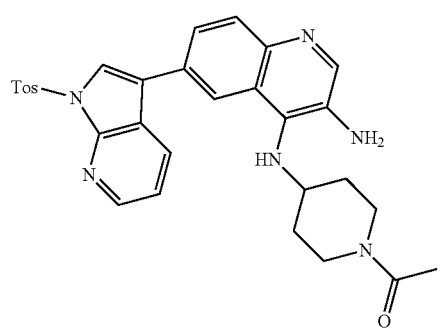

The title compound was prepared according to General Procedure 10 with 1-[4-({6-[1-(4-methylbenzenesulfonyl)-1H-pyrrolo[2,3-b]pyridin-3-yl]-3-nitroquinolin-4-yl}amino)piperidin-1-yl]ethan-1-one (Intermediate 146) (0.13 g, 0.2 mmol, 1.0 eq.), Raney-Nickel (0.5 g) in THF (4 mL) under balloon with hydrogen. Purification by FCC (EtOAc gradient in hexane) provided 1-[4-({3-amino-6-[1-(4-methylbenzenesulfonyl)-1H-pyrrolo[2,3-b]pyridin-3-yl]quinolin-4-yl}amino)piperidin-1-yl]ethan-1-one (0.025 g, yield: 20%; UPLC purity: 92%).

Example 66

1-{4-[(3-Amino-6-{1H-pyrrolo[2,3-b]pyridin-3-yl}quinolin-4-yl)amino]piperidin-1-yl}ethan-1-one

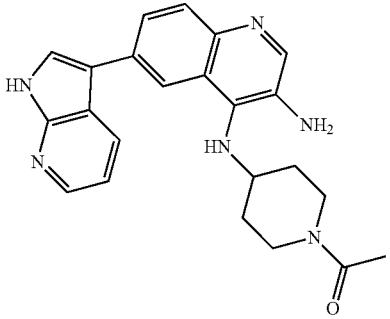 [SMILES: CC(=O)N1CCC(Nc2c(N)cnc3ccc(-c4c[nH]c5ncccc45)cc23)CC1]

The title compound was prepared according to General Procedure 3 with 1-[4-({3-amino-6-[1-(4-methylbenzenesulfonyl)-1H-pyrrolo[2,3-b]pyridin-3-yl]quinolin-4-yl}amino)piperidin-1-yl]ethan-1-one (Intermediate 147) (0.025 g, 0.05 mmol, 1.0 eq.), NaOtBu (0.018 g, 0.07 mmol, 1.5 eq.) dissolved in 1,4-dioxane (1 mL). The reaction mixture was stirred at rt for 7 days. Purification by FCC (MeOH gradient in $CH_2Cl_2$) afforded 1-{4-[(3-amino-6-{1H-pyrrolo[2,3-b]pyridin-3-yl}quinolin-4-yl)amino]piperidin-1-yl}ethan-1-one as a red solid (0.004 g; yield: 22%; HPLC purity: 92%).

Analytical data of compounds according to the examples described hereinabove are provided in the following Table 4.

TABLE 4

| Ex. No. | MW | IUPAC name | Analitical method/purity/ LC-MS | $^1$H-NMR (400 MHz, DMSO-$d_6$) |
|---|---|---|---|---|
| 2 | 245.28 | 6-{1H-pyrrolo[2,3-b]pyridin-3-yl}quinoline | B 97% (M + H)$^+$ = 246.0 | δ 12.06 (s, 1H), 8.84 (s, 1H), 8.54 (s, 1H), 8.45 (s, 1H), 8.32 (s, 2H), 8.18 (s, 1H), 8.11 (d, J = 2.7 Hz, 1H), 8.06 (s, 1H), 7.51 (s, 1H), 7.22 (s, 1H) |
| 3 | 343.43 | (3S)-1-(6-{1H-pyrrolo[2,3-b]pyridin-3-yl}quinolin-4-yl)piperidin-3-amine | B 95% (M + H)$^+$ = 344.2 | δ 12.52 (s, 1H), 8.79-8.23 (m, 9H), 7.32 (s, 2H), 4.25 (d, J = 10.8 Hz, 1H), 3.93 (d, J = 11.1 Hz, 1H), 3.78-3.62 (m, 2H), 3.61-3.46 (m, 1H), 2.22-2.02 (m, 2H), 1.85 (s, 2H) |
| 6 | 322.37 | 4-(pyridin-3-yl)-6-{1H-pyrrolo[2,3-b]pyridin-3-yl}quinoline | B 99% (M + H)$^+$ = 323.3 | δ 12.56 (s, 1H), 9.22 (dd, J = 15.3, 3.4 Hz, 2H), 9.03 (dd, J = 5.3, 1.3 Hz, 1H), 8.66 (d, J = 8.0 Hz, 1H), 8.52 (dt, J = 17.9, 5.3 Hz, 2H), 8.41-8.31 (m, 2H), 8.23 (d, J = 2.5 Hz, 1H), 8.16 (d, J = 1.6 Hz, 1H), 8.07 (dd, J = 7.9, 5.4 Hz, 1H), 8.00 (d, J = 5.1 Hz, 1H), 7.30 (dd, J = 8.0, 4.9 Hz, 1H) |
| 7 | 322.37 | 4-(pyridin-4-yl)-6-{1H-pyrrolo[2,3-b]pyridin-3-yl}quinoline | R 100% (M + H)$^+$ = 323.2 | δ 12.64 (s, 1H), 9.26-9.11 (m, 3H), 8.54-8.42 (m, 3H), 8.41 (d, J = 8.0 Hz, 2H), 8.33 (d, J = 5.2 Hz, 2H), 8.28-8.20 (m, 1H), 8.13 (d, J = 1.6 Hz, 1H), 7.92 (d, J = 4.6 Hz, 1H), 7.34 (dd, J = 7.8, 4.8 Hz, 1H) |
| 8 | 321.38 | 4-phenyl-6-{1H-pyrrolo[2,3-b]pyridin-3-yl}quinoline | R 98% (M + H)$^+$ = 322.2 | δ 12.07 (s, 1H), 8.90 (d, J = 4.4 Hz, 1H), 8.29 (dd, J = 4.6, 1.5 Hz, 1H), 8.22-8.12 (m, 3H), 8.09 (dd, J = 8.0, 1.5 Hz, 1H), 8.03 (d, J = 2.5 Hz, 1H), 7.72-7.63 (m, 4H), 7.62-7.56 (m, 1H), 7.49 (d, J = 4.4 Hz, 1H), 7.15 (dd, J = 8.0, 4.6 Hz, 1H) |
| 10 | 357.46 | N-(1-methylpiperidin-4-yl)-6-{1H-pyrrolo[2,3-b]pyridin-3-yl}quinolin-4-amine | KR 92% (M + H)$^+$ = 358.4 | δ 11.99 (s, 1H), 8.48 (d, J = 1.5 Hz, 1H), 8.40 (dd, J = 8.0, 1.5 Hz, 1H), 8.35 (d, J = 5.4 Hz, 1H), 8.31 (dd, J = 4.6, 1.4 Hz, 1H), 8.03-7.98 (m, 2H), 7.83 (d, J = 8.7 Hz, 1H), 7.21 (dd, J = 8.0, 4.6 Hz, 1H), 6.83 (d, J = 7.5 Hz, 1H), 6.52 (d, J = 5.5 Hz, 1H), 3.51 (td, J = 11.8, 7.4 Hz, 1H), 2.85 (d, J = 11.6 Hz, 2H), 2.22 (s, 3H), 2.12-1.95 (m, 4H), 1.69 (qd, J = 12.1, 3.5 Hz, 2H) |

TABLE 4-continued

| Ex. No. | MW | IUPAC name | Analitical method/purity/ LC-MS | ¹H-NMR (400 MHz, DMSO-$d_6$) |
|---|---|---|---|---|
| 12 | 259.31 | 8-methyl-6-{1H-pyrrolo[2,3-b]pyridin-3-yl}quinoline hydrochloride | R 99% (M + H)⁺ = 260.0 | δ 12.29 (s, 1H), 8.99 (d, J = 4.7 Hz, 1H), 8.83 (s, 1H), 8.66 (d, J = 8.0 Hz, 1H), 8.43-8.32 (m, 2H), 8.33-8.18 (m, 2H), 7.83 (d, J = 7.0 Hz, 1H), 7.29 (dd, J = 8.0, 4.7 Hz, 1H), 2.84 (s, 3H) |
| 13 | 263.27 | 8-fluoro-6-{1H-pyrrolo[2,3-b]pyridin-3-yl}quinoline | R 100% (M + H)⁺ = 264.0 | δ 12.15 (s, 1H), 8.88 (dd, J = 4.2, 1.6 Hz, 1H), 8.59 (d, J = 8.1, 1.5 Hz, 1H), 8.53 (dt, J = 8.5, 1.7 Hz, 1H), 8.34 (dd, J = 4.6, 1.5 Hz, 1H), 8.21 (d, J = 2.7 Hz, 2H), 8.06 (dd, J = 12.7, 1.9 Hz, 1H), 7.63 (dd, J = 8.4, 4.2 Hz, 1H), 7.25 (dd, J = 8.0, 4.6 Hz, 1H) |
| 15 | 275.31 | 8-methoxy-6-{1H-pyrrolo[2,3-b]pyridin-3-yl}quinoline | R 98% (M + H)⁺ = 276.1 | δ 12.07 (s, 1H), 8.77 (dd, J = 4.1, 1.7 Hz, 1H), 8.54 (dd, J = 8.0, 1.5 Hz, 1H), 8.42-8.29 (m, 2H), 8.17 (d, J = 2.7 Hz, 1H), 7.87 (d, J = 1.7 Hz, 1H), 7.60-7.49 (m, 2H), 7.23 (dd, J = 8.0, 4.6 Hz, 1H), 4.08 (s, 3H) |
| 16 | 340.39 | N-(furan-3-ylmethyl)-6-{1H-pyrrolo[2,3-b]pyridin-3-yl}quinolin-3-amine | KR 95% (M + H)⁺ = 341.3 | δ 11.97 (s, 1H), 8.46 (dd, J = 8.7, 1.9 Hz, 2H), 8.31 (dd, J = 4.6, 1.5 Hz, 1H), 8.01 (dd, J = 4.3, 2.3 Hz, 2H), 7.81 (d, J = 8.6 Hz, 1H), 7.75 (d, J = 1.9 Hz, 1H), 7.75-7.73 (m, 1H), 7.64 (t, J = 1.7 Hz, 1H), 7.24-7.18 (m, 2H), 6.61-6.56 (m, 2H), 4.22 (d, J = 5.6 Hz, 2H) |
| 17 | 335.41 | 8-methyl-4-phenyl-6-{1H-pyrrolo[2,3-b]pyridin-3-yl}quinoline | R 100% (M + H)⁺ = 336.3 | δ 12.02 (s, 1H), 8.91 (d, J = 4.3 Hz, 1H), 8.27 (dd, J = 4.7, 1.5 Hz, 1H), 8.09-8.04 (m, 2H), 8.00 (d, J = 2.7 Hz, 1H), 7.98-7.95 (m, 1H), 7.68-7.61 (m, 4H), 7.60-7.54 (m, 1H), 7.47 (d, J = 4.3 Hz, 1H), 7.13 (dd, J = 8.0, 4.6 Hz, 1H), 2.84 (s, 3H) |
| 18 | 336.40 | 8-methyl-4-(pyridin-3-yl)-6-{1H-pyrrolo[2,3-b]pyridin-3-yl}quinoline | KR 94% (M + H)⁺ = 337.2 | δ 12.05 (s, 1H), 8.96 (d, J = 4.4 Hz, 1H), 8.86 (d, J = 2.1 Hz, 1H), 8.78 (d, J = 4.5 Hz, 1H), 8.28 (dd, J = 4.6, 1.5 Hz, 1H), 8.15 (dt, J = 7.9, 1.9 Hz, 1H), 8.11 (dd, J = 2.1, 1.1 Hz, 1H), 8.07 (dd, J = 8.0, 1.5 Hz, 1H), 8.02 (d, J = 2.4 Hz, 1H), 7.87 (d, J = 1.9 Hz, 1H), 7.68 (dd, J = 7.8, 4.7 Hz, 1H), 7.55 (d, J = 4.4 Hz, 1H), 7.14 (dd, J = 8.0, 4.6 Hz, 1H), 2.86 (s, 3H) |
| 19 | 340.36 | 8-fluoro-4-(pyridin-3-yl)-6-{1H-pyrrolo[2,3-b]pyridin-3-yl}quinoline | KR 98% (M + H)⁺ = 341.1 | δ 12.16 (s, 1H), 8.98 (d, J = 4.4 Hz, 1H), 8.92-8.86 (m, 1H), 8.80 (dd, J = 4.8, 1.6 Hz, 1H), 8.29 (dd, J = 4.6, 1.4 Hz, 1H), 8.24-8.03 (m, 4H), 7.86 (d, J = 1.4 Hz, 1H), 7.72-7.62 (m, 2H), 7.16 (dd, J = 8.0, 4.7 Hz, 1H) |
| 20 | 376.84 | 3-(4-chloroquinolin-6-yl)-N-methyl-N-(prop-2-en-1-yl)-1H-pyrrolo[2,3-b]pyridine-5-carboxamide | R 91% (M + H)⁺ = 377.9 | δ 12.44 (s, 1H), 8.80 (d, J = 4.7 Hz, 1H), 8.47-8.37 (m, 3H), 8.30 (dd, J = 7.7, 2.0 Hz, 2H), 8.16 (d, J = 8.8 Hz, 1H), 7.82-7.76 (m, 1H), 5.97-5.84 (m, 1H), 5.33-5.23 (m, 2H), 4.22-3.80 (m, 2H), 3.01 (s, 3H) |

TABLE 4-continued

| Ex. No. | MW | IUPAC name | Analitical method/purity/ LC-MS | $^1$H-NMR (400 MHz, DMSO-$d_6$) |
|---|---|---|---|---|
| 21 | 396.54 | methyl({3-[4-(pent-4-en-1-yl)quinolin-6-yl]-1H-pyrrolo[2,3-b]pyridin-5-yl}methyl)(prop-2-en-1-yl)amine | B 98% (M + H)$^+$ = 397.5 | δ 12.05 (s, 1H), 8.72 (d, J = 4.3 Hz, 1H), 8.31 (d, J = 1.9 Hz, 1H), 8.26 (dd, J = 9.4, 1.9 Hz, 2H), 8.16-8.04 (m, 3H), 7.38 (d, J = 4.4 Hz, 1H), 5.97-5.82 (m, 2H), 5.26-4.96 (m, 4H), 3.64 (br s, 2H), 3.19-3.12 (m, 2H), 3.04 (dt, J = 6.3, 1.4 Hz, 2H), 2.21 (q, J = 7.2 Hz, 2H), 2.14 (s, 3H), 1.87 (p, J = 7.5 Hz, 2H) |
| 22 | 379.42 | N-methyl-3-[4-(pyridin-3-yl)quinolin-6-yl]-1H-pyrrolo[2,3-b]pyridine-5-carboxamide | KR 96% (M + H)$^+$ = 380.2 | δ 12.31 (s, 1H), 8.96 (d, J = 4.4 Hz, 1H), 8.90-8.87 (m, 1H), 8.78 (dd, J = 4.8, 1.6 Hz, 1H), 8.76 (d, J = 2.0 Hz, 1H), 8.64 (d, J = 2.0 Hz, 1H), 8.56-8.41 (m, 1H), 8.30-8.20 (m, 3H), 8.11 (dd, J = 6.1, 2.2 Hz, 2H), 7.68 (ddd, J = 7.9, 4.9, 0.9 Hz, 1H), 7.59 (d, J = 4.4 Hz, 1H), 2.89 (d, J = 4.5 Hz, 3H) |
| 23 | 387.44 | N-methyl-3-[4-(morpholin-4-yl)quinolin-6-yl]-1H-pyrrolo[2,3-b]pyridine-5-carboxamide | KR 99% (M + H)$^+$ = 388.4 | δ 12.34 (s, 1H), 8.81 (q, J = 2.1 Hz, 2H), 8.68 (d, J = 4.9 Hz, 1H), 8.59 (d, J = 4.6 Hz, 1H), 8.33 (d, J = 2.0 Hz, 1H), 8.20 (d, J = 2.6 Hz, 1H), 8.15 (dd, J = 8.8, 2.0 Hz, 1H), 8.04 (d, J = 8.7 Hz, 1H), 7.04 (d, J = 5.0 Hz, 1H), 3.95 (t, J = 4.5 Hz, 4H), 3.27 (t, J = 4.5 Hz, 4H), 2.85 (d, J = 4.5 Hz, 3H) |
| 24 | 336.78 | 3-(4-chloroquinolin-6-yl)-N-methyl-1H-pyrrolo[2,3-b]pyridine-5-carboxamide | KR 98% (M + H)$^+$ = 337.1 | δ 12.43 (d, J = 2.4 Hz, 1H), 8.86-8.80 (m, 3H), 8.62 (d, J = 4.6 Hz, 1H), 8.45 (d, J = 1.9 Hz, 1H), 8.34 (dd, J = 8.8, 2.0 Hz, 1H), 8.28 (d, J = 2.5 Hz, 1H), 8.20 (d, J = 8.8 Hz, 1H), 7.83-7.78 (m, 1H), 2.85 (d, J = 4.5 Hz, 3H) |
| 25 | 302.34 | N-methyl-3-(quinolin-6-yl)-1H-pyrrolo[2,3-b]pyridine-5-carboxamide | KR 99% (M + H)$^+$ = 303.2 | δ 12.32 (s, 1H) 8.91-8.85 (m, 2H), 8.81 (d, J = 2.0 Hz, 1H), 8.62 (d, J = 4.4 Hz, 1H), 8.45 (d, J = 8.4 Hz, 1H), 8.35 (d, J = 1.9 Hz, 1H), 8.22 (dd, J = 8.8, 2.0 Hz, 1H), 8.18 (s, 1H), 8.10 (d, J = 8.7 Hz, 1H), 7.57 (dd, J = 8.3, 4.2 Hz, 1H), 2.87 (d, J = 4.5 Hz, 3H) |
| 27 | 360.39 | 3-(8-fluoroquinolin-6-yl)-N-methyl-N-(prop-2-en-1-yl)-1H-pyrrolo[2,3-b]pyridine-5-carboxamide | R 98% (M + H)$^+$ = 361.5 | δ 12.38 (s, 1H), 8.88 (dd, J = 4.2, 1.6 Hz, 1H), 8.60 (s, 1H), 8.58-8.50 (m, 1H), 8.38 (br s, 1H), 8.32-8.26 (m, 1H), 8.18 (s, 1H), 8.05 (dd, J = 12.5, 1.8 Hz, 1H), 7.63 (dd, J = 8.4, 4.2 Hz, 1H), 5.91 (ddt, J = 17.1, 10.3, 5.2 Hz, 1H), 5.36-5.21 (m, 2H), 4.22-3.86 (m, 2H), 2.99 (s, 3H) |
| 28 | 376.84 | 3-(8-chloroquinolin-6-yl)-N-methyl-N-(prop-2-en-1-yl)-1H-pyrrolo[2,3-b]pyridine-5-carboxamide | H 97% | δ 12.39 (d, J = 2.7 Hz, 1H), 8.95 (dd, J = 4.2, 1.7 Hz, 1H), 8.62-8.50 (m, 2H), 8.39 (d, J = 1.9 Hz, 2H), 8.33 (d, J = 2.7 Hz, 2H), 7.65 (dd, J = 8.3, 4.2 Hz, 1H), 5.92 (ddt, J = 15.2, 10.1, 5.0 Hz, 1H), 5.34-5.21 (m, 2H), 4.20-3.88 (m, 2H), 2.99 (s, 3H) |

TABLE 4-continued

| Ex. No. | MW | IUPAC name | Analitical method/purity/ LC-MS | $^1$H-NMR (400 MHz, DMSO-$d_6$) |
|---|---|---|---|---|
| 29 | 332.36 | 3-(8-methoxyquinolin-6-yl)-N-methyl-1H-pyrrolo[2,3-b]pyridine-5-carboxamide | R 86% (M + H)$^+$ = 333.3 | δ 12.32 (s, 1H), 8.88 (d, J = 2.0 Hz, 1H), 8.82-8.77 (m, 2H), 8.61 (d, J = 4.7 Hz, 1H), 8.39 (dd, J = 8.4, 1.7 Hz, 1H), 8.23 (d, J = 2.6 Hz, 1H), 7.88 (d, J = 1.7 Hz, 1H), 7.55 (dd, J = 8.3, 4.1 Hz, 1H), 7.52 (d, J = 1.8 Hz, 1H), 4.08 (s, 3H), 2.85 (d, J = 4.5 Hz, 3H) |
| 30 | 320.33 | 3-(8-fluoroquinolin-6-yl)-N-methyl-1H-pyrrolo[2,3-b]pyridine-5-carboxamide | R 97% (M + H)$^+$ = 321.3 | δ 12.39 (s, 1H), 8.91 (dd, J = 4.3, 1.5 Hz, 2H), 8.81 (d, J = 1.9 Hz, 1H), 8.64 (d, J = 4.6 Hz, 1H), 8.53 (d, J = 8.4 Hz, 1H), 8.24 (dd, J = 12.4, 2.0 Hz, 2H), 8.08 (dd, J = 12.5, 1.7 Hz, 1H), 7.66 (dd, J = 8.4, 4.2 Hz, 1H), 2.87 (d, J = 4.5 Hz, 3H) |
| 31 | 396.43 | N-benzyl-3-(8-fluoroquinolin-6-yl)-1H-pyrrolo[2,3-b]pyridine-5-carboxamide | H 96% | δ 12.42 (s, 1H), 9.24 (t, J = 6.0 Hz, 1H), 8.97 (d, J = 2.0 Hz, 1H), 8.91 (dd, J = 4.2, 1.6 Hz, 1H), 8.88 (d, J = 2.0 Hz, 1H), 8.51 (dt, J = 8.5, 1.6 Hz, 1H), 8.29-8.21 (m, 2H), 8.09 (dd, J = 12.5, 1.8 Hz, 1H), 7.65 (dd, J = 8.4, 4.2 Hz, 1H), 7.41-7.32 (m, 4H), 7.29-7.23 (m, 1H), 4.58 (d, J = 5.9 Hz, 2H) |
| 32 | 412.88 | N-benzyl-3-(8-chloroquinolin-6-yl)-1H-pyrrolo[2,3-b]pyridine-5-carboxamide | KB 100% (M + H)$^+$ = 413.2 | δ 12.44 (s, 1H), 9.24 (t, J = 6.0 Hz, 1H), 8.99-8.94 (m, 2H), 8.88 (d, J = 2.0 Hz, 1H), 8.53 (dd, J = 8.4, 1.7 Hz, 1H), 8.41 (d, J = 1.9 Hz, 1H), 8.37 (d, J = 2.0 Hz, 1H), 8.31 (s, 1H), 7.67 (dd, J = 8.3, 4.2 Hz, 1H), 7.43-7.30 (m, 4H), 7.29-7.20 (m, 1H), 4.57 (d, J = 5.8 Hz, 2H) |
| 33 | 306.30 | 3-(8-fluoroquinolin-6-yl)-1H-pyrrolo[2,3-b]pyridine-5-carboxamide | KR 95% (M + H)$^+$ = 307.1 | δ 12.39 (d, J = 2.8 Hz, 1H), 8.95 (d, J = 2.0 Hz, 1H), 8.91 (dd, J = 4.1, 1.6 Hz, 1H), 8.86 (d, J = 2.0 Hz, 1H), 8.52 (dt, J = 8.4, 1.6 Hz, 1H), 8.27 (d, J = 2.7 Hz, 1H), 8.25-8.19 (m, 2H), 8.09 (dd, J = 12.5, 1.8 Hz, 1H), 7.66 (dd, J = 8.4, 4.2 Hz, 1H), 7.47 (s, 1H) |
| 34 | 379.85 | N-(3-aminopropyl)-3-(8-chloroquinolin-6-yl)-1H-pyrrolo[2,3-b]pyridine-5-carboxamide hydrochloride | KR 98% (M + H)$^+$ = 380.4 | δ 12.44 (d, J = 2.7 Hz, 1H), 9.08-8.94 (m, 2H), 8.84 (d, J = 2.0 Hz, 1H), 8.73-8.63 (m, 1H), 8.53-8.46 (m, 1H), 8.43 (d, J = 1.9 Hz, 1H), 8.33 (d, J = 2.7 Hz, 1H), 7.85 (s, 2H), 3.49-3.37 (m, 2H), 2.97-2.83 (m, 2H), 1.88 (p, J = 6.9 Hz, 2H). |
| 36 | 473.51 | N-benzyl-3-[8-fluoro-4-(pyridin-3-yl)quinolin-6-yl]-1H-pyrrolo[2,3-b]pyridine-5-carboxamide | KR 92% (M + H)$^+$ = 474.4 | δ 12.41 (d, J = 2.7 Hz, 1H), 9.12 (t, J = 6.0 Hz, 1H), 8.99 (d, J = 4.4 Hz, 1H), 8.87 (d, J = 2.2 Hz, 1H), 8.83 (d, J = 2.0 Hz, 1H), 8.69 (dd, J = 5.3, 1.7 Hz, 2H), 8.24 (dt, J = 7.9, 2.0 Hz, 1H), 8.20 (d, J = 2.4 Hz, 1H), 8.15 (dd, J = 12.0, 1.8 Hz, 1H), 7.92 (d, J = 1.7 Hz, 1H), 7.68 (d, J = 4.4 Hz, 1H), 7.56 (dd, J = 7.8, 4.8 Hz, 1H), 7.42-7.34 (m, 5H), 7.31-7.25 (m, 1H), 4.59 (d, J = 5.9 Hz, 2H) |

TABLE 4-continued

| Ex. No. | MW | IUPAC name | Analitical method/purity/ LC-MS | $^1$H-NMR (400 MHz, DMSO-$d_6$) |
|---|---|---|---|---|
| 37 | 440.48 | N-(3-aminopropyl)-3-[8-fluoro-4-(pyridin-3-yl)quinolin-6-yl]-1H-pyrrolo[2,3-b]pyridine-5-carboxamide hydrochloride | KR 98% (M + H)$^+$ = 441.4 | δ 12.52 (s, 1H), 9.22 (s, 1H), 9.13 (br s, 1H), 9.05 (d, J = 4.3 Hz, 1H), 8.86 (t, J = 5.5 Hz, 2H), 8.81 (d, J = 1.9 Hz, 1H), 8.67 (d, J = 1.9 Hz, 1H), 8.28 (d, J = 2.5 Hz, 1H), 8.23 (dd, J = 12.0, 1.6 Hz, 1H), 8.20-8.06 (m, 4H), 7.91 (d, J = 1.6 Hz, 1H), 7.78 (d, J = 4.3 Hz, 1H), 3.50-3.37 (m, 2H), 2.96-2.83 (m, 2H), 1.96-1.83 (m, 2H) |
| 39 | 397.41 | 3-[8-fluoro-4-(pyridin-3-yl)quinolin-6-yl]-N-methyl-1H-pyrrolo[2,3-b]pyridine-5-carboxamide | KR 99% (M + H)$^+$ = 398.4 | δ 12.47 (d, J = 2.7 Hz, 1H), 9.18 (s, 1H), 9.04 (d, J = 4.5 Hz, 2H), 8.79 (d, J = 8.0 Hz, 1H), 8.76 (d, J = 1.9 Hz, 1H), 8.62 (d, J = 1.9 Hz, 1H), 8.56 (d, J = 4.9 Hz, 1H), 8.27 (d, J = 2.6 Hz, 1H), 8.22 (dd, J = 12.1, 1.7 Hz, 1H), 8.11 (dd, J = 8.0, 5.3 Hz, 1H), 7.92 (d, J = 1.7 Hz, 1H), 7.77 (d, J = 4.4 Hz, 1H), 2.88 (d, J = 4.3 Hz, 3H) |
| 40 | 424.48 | 3-[8-fluoro-4-(2-phenylethyl)quinolin-6-yl]-N-methyl-1H-pyrrolo[2,3-b]pyridine-5-carboxamide | KB 94% (M + H)$^+$ = 425.2 | δ 12.39 (s, 1H), 8.89 (d, J = 2.0 Hz, 1H), 8.81 (d, J = 2.0 Hz, 1H), 8.78 (d, J = 4.4 Hz, 1H), 8.62 (t, J = 4.6 Hz, 1H), 8.30-8.23 (m, 2H), 8.06 (dd, J = 12.0, 1.7 Hz, 1H), 7.48 (d, J = 4.4 Hz, 1H), 7.33 (d, J = 7.0 Hz, 2H), 7.27 (t, J = 7.4 Hz, 2H), 7.21-7.16 (m, 1H), 3.50 (dd, J = 9.5, 6.5 Hz, 2H), 3.10 (dd, J = 9.4, 6.6 Hz, 2H), 2.83 (d, J = 4.4 Hz, 3H) |
| 41 | 418.48 | 3-{4-[(3R)-3-aminopiperidin-1-yl]-8-fluoroquinolin-6-yl}-N-methyl-1H-pyrrolo[2,3-b]pyridine-5-carboxamide hydrochloride | KR 100% (M + H)$^+$ = 419.2 | δ 12.41 (s, 1H), 8.84 (d, J = 2.0 Hz, 1H), 8.80 (d, J = 1.9 Hz, 1H), 8.69 (d, J = 4.9 Hz, 1H), 8.64 (q, J = 4.5 Hz, 1H), 8.24 (s, 1H), 8.14 (d, J = 1.8 Hz, 1H), 8.00 (dd, J = 12.1, 1.7 Hz, 1H), 7.09 (d, J = 5.0 Hz, 1H), 3.62-3.52 (m, 1H), 3.41-3.28 (m, 2H), 3.12-3.00 (m, 1H), 2.93-2.85 (m, 1H), 2.85 (d, J = 4.4 Hz, 3H), 2.54 (s, 1H), 2.01 (d, J = 10.7 Hz, 2H), 1.93-1.79 (m, 1H), 1.58-1.43 (m, 1H) |
| 42 | 393.45 | N-methyl-3-[8-methyl-4-(pyridin-3-yl)quinolin-6-yl]-1H-pyrrolo[2,3-b]pyridine-5-carboxamide | KR 98% (M + H)$^+$ = 394.2 | δ 12.28 (d, J = 2.6 Hz, 1H), 8.97 (d, J = 4.4 Hz, 1H), 8.86 (d, J = 2.2 Hz, 1H), 8.77 (dd, J = 4.8, 1.6 Hz, 1H), 8.74 (d, J = 2.0 Hz, 1H), 8.59 (d, J = 2.0 Hz, 1H), 8.49 (t, J = 4.5 Hz, 1H), 8.22 (dt, J = 7.8, 2.0 Hz, 1H), 8.13 (s, 1H), 8.10 (d, J = 2.6 Hz, 1H), 7.93 (d, J = 1.9 Hz, 1H), 7.66 (dd, J = 7.8, 4.8 Hz, 1H), 7.58 (d, J = 4.3 Hz, 1H), 2.88 (d, J = 5.0 Hz, 3H), 2.87 (s, 3H) |
| 43 | 418.48 | 3-{4-[(3S)-3-aminopiperidin-1-yl]-8-fluoroquinolin-6-yl}-N-methyl-1H-pyrrolo[2,3-b]pyridine-5-carboxamide hydrochloride | KR 94% (M + H)$^+$ = 419.2 | δ 12.56 (s, 1H), 8.87 (s, 1H), 8.83 (s, 1H), 8.74 (d, J = 6.0 Hz, 1H), 8.69 (dd, J = 6.4, 2.4 Hz, 1H), 8.41-8.31 (m, 2H), 8.21 (s, 1H), 7.32 (d, J = 4.6 Hz, 1H), 4.24-4.13 (m, 1H), 3.93-3.85 (m, 1H), 3.74-3.65 (m, 1H), 2.85 (d, J = 4.3 Hz, 3H), 2.14 (d, J = 10.6 Hz, 2H), 1.94-1.76 (m, 2H) |

TABLE 4-continued

| Ex. No. | MW | IUPAC name | Analytical method/purity/ LC-MS | ¹H-NMR (400 MHz, DMSO-$d_6$) |
|---|---|---|---|---|
| 44 | 411.44 | 3-[8-fluoro-4-(4-methylpyridin-3-yl)quinolin-6-yl]-N-methyl-1H-pyrrolo[2,3-b]pyridine-5-carboxamide | KR 96% (M + H)⁺ = 412.2 | δ 12.36 (s, 1H), 9.01 (d, J = 4.3 Hz, 1H), 8.74 (d, J = 1.9 Hz, 1H), 8.63 (d, J = 5.1 Hz, 1H), 8.52 (s, 1H), 8.43 (t, J = 3.6 Hz, 2H), 8.16-8.11 (m, 2H), 7.61 (d, J = 4.3 Hz, 1H), 7.52 (d, J = 5.1 Hz, 1H), 7.46 (d, J = 1.7 Hz, 1H), 2.88 (d, J = 4.5 Hz, 3H), 2.16 (s, 3H) |
| 45 | 395.42 | 3-[8-methoxy-4-(pyridin-3-yl)quinolin-6-yl]-1H-pyrrolo[2,3-b]pyridine-5-carboxamide | KR 99% (M + H)⁺ = 396.2 | δ 12.36 (s, 1H), 8.88 (d, J = 4.3 Hz, 1H), 8.84 (d, J = 2.2 Hz, 1H), 8.80 (d, J = 2.0 Hz, 1H), 8.75 (dd, J = 4.9, 1.6 Hz, 1H), 8.67 (d, J = 2.0 Hz, 1H), 8.26 (dt, J = 7.9, 2.0 Hz, 1H), 8.19 (s, 1H), 8.05 (s, 1H), 7.68 (dd, J = 7.9, 4.8 Hz, 1H), 7.64 (d, J = 1.7 Hz, 1H), 7.61-7.57 (m, 2H), 7.43 (s, 1H), 4.12 (s, 3H) |
| 46 | 397.41 | N-{3-[8-fluoro-4-(pyridin-3-yl)quinolin-6-yl]-1H-pyrrolo[2,3-b]pyridin-5-yl}acetamide | KR 95% (M + H)⁺ = 398.1 | δ 12.08 (d, J = 3.1 Hz, 1H), 10.06 (s, 1H), 8.98 (d, J = 4.4 Hz, 1H), 8.81 (dd, J = 2.3, 0.9 Hz, 1H), 8.77 (dd, J = 4.8, 1.6 Hz, 1H), 8.58 (d, J = 2.2 Hz, 1H), 8.27 (d, J = 2.2 Hz, 1H), 8.20 (ddd, J = 7.9, 2.4, 1.6 Hz, 1H), 8.08 (d, J = 2.8 Hz, 1H), 8.04 (dd, J = 12.1, 1.7 Hz, 1H), 7.83 (d, J = 1.7 Hz, 1H), 7.69 (ddd, J = 7.8, 4.8, 0.8 Hz, 1H), 7.66 (d, J = 4.4 Hz, 1H), 2.14 (s, 3H) |
| 47 | 474.50 | 3-[8-fluoro-4-(pyridin-3-yl)quinolin-6-yl]-N-(pyridin-3-ylmethyl)-1H-pyrrolo[2,3-b]pyridine-5-carboxamide | KR 91% (M + H)⁺ = 475.2 | δ 12.42 (s, 1H), 9.17 (t, J = 5.7 Hz, 1H), 9.00 (d, J = 4.3 Hz, 1H), 8.88 (d, J = 2.4 Hz, 1H), 8.82 (d, J = 2.0 Hz, 1H), 8.71 (dd, J = 4.9, 1.6 Hz, 1H), 8.68 (d, J = 2.0 Hz, 1H), 8.64 (s, 1H), 8.51 (dd, J = 4.8, 1.7 Hz, 1H), 8.26-8.20 (m, 2H), 8.15 (dd, J = 11.9, 1.9 Hz, 1H), 7.92 (d, J = 1.7 Hz, 1H), 7.80 (d, J = 8.1 Hz, 1H), 7.69 (d, J = 4.3 Hz, 1H), 7.41 (dd, J = 8.0, 4.7 Hz, 1H), 4.60 (d, J = 5.8 Hz, 2H) |
| 50 | 459.53 | benzyl({3-[8-fluoro-4-(pyridin-3-yl)quinolin-6-yl]-1H-pyrrolo[2,3-b]pyridin-5-yl}methyl)amine | KB 99% (M + H)⁺ = 460.4 | δ 12.09 (d, J = 2.6 Hz, 1H), 8.96 (d, J = 4.4 Hz, 1H), 8.88 (d, J = 2.2 Hz, 1H), 8.68 (dd, J = 4.8, 1.6 Hz, 1H), 8.27 (d, J = 1.8 Hz, 1H), 8.19 (dt, J = 7.9, 2.0 Hz, 1H), 8.16-8.10 (m, 2H), 8.04 (d, J = 1.9 Hz, 1H), 7.89 (d, J = 1.7 Hz, 1H), 7.66 (d, J = 4.4 Hz, 1H), 7.56 (ddd, J = 7.8, 4.8, 0.9 Hz, 1H), 7.39-7.30 (m, 4H), 7.28-7.21 (m, 1H), 3.80 (s, 2H) |
| 51 | 480.59 | (3R)-1-(6-{5-[(benzylamino)methyl]-1H-pyrrolo[2,3-b]pyridin-3-yl}-8-fluoroquinolin-4-yl)piperidin-3-amine | KR 91% (M + H)⁺ = 481.2 | δ 12.06 (s, 1H), 8.65 (d, J = 5.0 Hz, 1H), 8.37 (d, J = 1.9 Hz, 1H), 8.29 (d, J = 1.8 Hz, 1H), 8.14 (s, 1H), 8.12 (d, J = 1.8 Hz, 1H), 7.96 (dd, J = 12.4, 1.8 Hz, 1H), 7.39-7.28 (m, 4H), 7.25-7.20 (m, 1H), 7.05 (d, J = 5.0 Hz, 1H), 3.86 (s, 2H), 3.74 (s, 2H), 3.59-3.40 (m, 3H), 3.06 (s, 1H), 2.86 (t, J = 10.9 Hz, 1H), 2.62 (t, J = 10.3 Hz, 1H), 1.85 (dt, J = 28.4, 11.3 Hz, 4H), 1.23 (d, J = 9.1 Hz, 1H) |

TABLE 4-continued

| Ex. No. | MW | IUPAC name | Analitical method/purity/ LC-MS | $^1$H-NMR (400 MHz, DMSO-$d_6$) |
|---|---|---|---|---|
| 52 | 423.50 | ({3-[8-fluoro-4-(pyridin-3-yl)quinolin-6-yl]-1H-pyrrolo[2,3-b]pyridin-5-yl}methyl)(methyl)(prop-2-en-1-yl)amine | KR 95% $(M + H)^+ = 424.4$ | δ 12.13 (d, J = 2.7 Hz, 1H), 8.96 (d, J = 4.4 Hz, 1H), 8.87 (dd, J = 2.3, 0.9 Hz, 1H), 8.81 (dd, J = 4.8, 1.6 Hz, 1H), 8.21-8.16 (m, 3H), 8.13 (dd, J = 12.3, 1.8 Hz, 1H), 7.89 (dd, J = 7.7, 1.8 Hz, 2H), 7.69-7.66 (m, 1H), 7.65 (d, J = 4.3 Hz, 1H), 5.90-5.80 (m, J = 1H), 5.24-5.12 (m, 2H), 3.53 (s, 2H), 3.00 (d, J = 6.4 Hz, 2H), 2.07 (s, 3H) |
| 53 | 445.48 | 3-{4-[(3S)-3-aminopiperidin-1-yl]-3-nitroquinolin-6-yl}-N-methyl-1H-pyrrolo[2,3-b]pyridine-5-carboxamide hydrochloride | KR 91% $(M + H)^+ = 446.3$ | δ 12.54 (d, J = 2.6 Hz, 1H), 9.08 (s, 1H), 8.90 (d, J = 1.9 Hz, 1H), 8.86 (d, J = 1.9 Hz, 1H), 8.70 (q, J = 4.5 Hz, 1H), 8.43-8.37 (m, 2H), 8.37-8.31 (m, 3H), 8.21 (d, J = 8.6 Hz, 1H), 3.65-3.53 (m, 3H), 3.34-3.23 (m, 1H), 3.12 (dd, J = 11.8, 9.2 Hz, 1H), 2.86 (d, J = 4.2 Hz, 3H), 2.26-2.14 (m, 1H), 2.11-1.96 (m, 2H), 1.77-1.63 (m, 1H) |
| 54 | 415.50 | 3-{3-amino-4-[(3S)-3-aminopiperidin-1-yl]quinolin-6-yl}-N-methyl-1H-pyrrolo[2,3-b]pyridine-5-carboxamide hydrochloride | KR 98% $(M + H)^+ = 416.3$ | δ 12.56 (d, J = 2.8 Hz, 1H), 8.89 (d, J = 2.0 Hz, 1H), 8.86 (d, J = 1.9 Hz, 1H), 8.74 (d, J = 5.1 Hz, 1H), 8.68 (s, 1H), 8.48-8.38 (m, 2H), 8.36-8.29 (m, 2H), 8.26-8.17 (m, 2H), 3.86 (d, J = 8.3 Hz, 1H), 3.56 (s, 2H), 3.52-3.39 (m, 2H), 2.86 (d, J = 4.2 Hz, 3H), 2.16 (s, 1H), 2.04 (s, 1H), 1.92 (s, 1H), 1.76 (d, J = 7.5 Hz, 1H) |
| 55 | 540.07 | 3-{4-[(3S)-3-aminopiperidin-1-yl]-3-{[(3-chlorophenyl)methyl]amino}quinolin-6-yl}-N-methyl-1H-pyrrolo[2,3-b]pyridine-5-carboxamide hydrochloride | KR 95% $(M + H)^+ = 540.2$ | δ 12.56 (s, 1H), 8.88 (d, J = 15.9 Hz, 2H), 8.73 (d, J = 5.1 Hz, 1H), 8.56-8.49 (m, 2H), 8.39-8.31 (m, 2H), 8.23 (q, J = 8.8 Hz, 2H), 7.55 (s, 1H), 7.44-7.31 (m, 2H), 4.80-4.61 (m, 2H), 3.68-3.60 (m, 2H), 3.54-3.38 (m, 3H), 2.86 (d, J = 4.1 Hz, 3H), 2.27-2.09 (m, 2H), 2.05-1.89 (m, 1H), 1.89-1.74 (m, 1H) |
| 56 | 527.03 | 3-(3-{[(3-chloro-phenyl)methyl]amino}-4-(morpholin-4-yl)quinolin-6-yl)-N-methyl-1H-pyrrolo[2,3-b]pyridine-5-carboxamide | KR 99% $(M + H)^+ = 527.2$ | δ 12.29 (s, 1H), 8.86 (d, J = 2.1 Hz, 1H), 8.81 (d, J = 2.0 Hz, 1H), 8.54 (q, J = 4.4 Hz, 1H), 8.42 (s, 1H), 8.29 (d, J = 1.9 Hz, 1H), 8.10 (s, 1H), 7.87 (d, J = 8.6 Hz, 1H), 7.78 (dd, J = 8.7, 1.8 Hz, 1H), 7.49 (s, 1H), 7.37 (s, 1H), 7.37-7.33 (m, 1H), 7.28 (dt, J = 6.6, 2.2 Hz, 1H), 6.34 (t, J = 6.8 Hz, 1H), 4.66 (d, J = 6.7 Hz, 2H), 3.97-3.87 (m, 4H), 3.43 (br s, 4H), 2.84 (d, J = 4.5 Hz, 3H) |
| 57 | 444.50 | 3-[3-acetamido-4-(morpholin-4-yl)quinolin-6-yl]-N-methyl-1H-pyrrolo[2,3-b]pyridine-5-carboxamide | KR 92% $(M + H)^+ = 445.2$ | δ 12.41 (s, 1H), 9.86 (s, 1H), 8.88-8.82 (m, 2H), 8.62 (s, 1H), 8.59 (d, J = 4.6 Hz, 1H), 8.40 (d, J = 2.0 Hz, 1H), 8.27-8.20 (m, 2H), 8.08 (d, J = 8.7 Hz, 1H), 3.94-3.84 (m, 4H), 3.50 (d, J = 8.2 Hz, 4H), 2.85 (d, J = 4.4 Hz, 3H), 2.18 (s, 3H) |

TABLE 4-continued

| Ex. No. | MW | IUPAC name | Analitical method/purity/ LC-MS | ¹H-NMR (400 MHz, DMSO-$d_6$) |
|---|---|---|---|---|
| 58 | 500.60 | N-methyl-3-[4-(morpholin-4-yl)-3-[(oxan-4-ylmethyl)amino]quinolin-6-yl]-1H-pyrrolo[2,3-b]pyridine-5-carboxamide hydrochloride | KR 95% $(M + H)^+ = 501.2$ | δ 8.85 (d, J = 2.0 Hz, 1H), 8.80 (d, J = 1.9 Hz, 1H), 8.62 (s, 1H), 8.25 (d, J = 1.9 Hz, 1H), 8.10 (d, J = 2.5 Hz, 1H), 7.93 (d, J = 8.7 Hz, 1H), 7.77 (dd, J = 8.6, 1.8 Hz, 1H), 5.56 (t, J = 6.5 Hz, 1H), 3.93-3.78 (m, 6H), 3.29 (q, J = 5.6, 4.6 Hz, 6H), 2.84 (d, J = 4.4 Hz, 3H), 2.55 (s, 1H), 1.68 (d, J = 12.7 Hz, 2H), 1.29 (ddd, J = 25.3, 12.5, 4.7 Hz, 2H) |
| 60 | 604.76 | 3-{4-[(4-aminocyclohexyl)amino]-3-[(oxan-4-ylmethyl)amino]quinolin-6-yl}-N-(pyridin-3-ylmethyl)-1H-pyrrolo[2,3-b]pyridine-5-carboxamide hydrochloride | KR 90% $(M + H)^+ = 605.4$ | δ 12.52 (d, J = 2.7 Hz, 1H), 9.66 (t, J = 5.9 Hz, 1H), 8.99 (d, J = 2.0 Hz, 1H), 8.92 (dd, J = 10.3, 2.0 Hz, 1H), 8.81 (d, J = 5.8 Hz, 1H), 8.56 (s, 1H), 8.49 (d, J = 8.2 Hz, 1H), 8.29-8.23 (m, 2H), 8.14-8.07 (m, 1H), 8.04-7.97 (m, 2H), 7.49 (br s, 1H), 4.72 (d, J = 5.7 Hz, 2H), 3.92 (dd, J = 11.0, 4.2 Hz, 2H), 3.34 (t, J = 11.3 Hz, 2H), 3.07 (d, J = 6.7 Hz, 2H), 2.02 (dd, J = 37.4, 12.2 Hz, 4H), 1.77 (d, J = 13.0 Hz, 3H), 1.34 (q, J = 12.5, 11.9 Hz, 4H) |
| 61 | 394.44 | 3-(3-aminoquinolin-6-yl)-N-(pyridin-3-ylmethyl)-1H-pyrrolo[2,3-b]pyridine-5-carboxamide | KR 94% $(M + H)^+ = 395.1$ | δ 12.29 (s, 1H), 9.37 (d, J = 5.4 Hz, 1H), 8.91 (d, J = 2.1 Hz, 1H), 8.86 (d, J = 2.0 Hz, 1H), 8.61 (d, J = 2.0 Hz, 1H), 8.50-8.44 (m, 1H), 8.40 (d, J = 2.6 Hz, 1H), 8.08 (d, J = 1.9 Hz, 1H), 7.98 (d, J = 1.9 Hz, 1H), 7.86-7.73 (m, 3H), 7.38 (dd, J = 7.9, 4.7 Hz, 1H), 7.24 (d, J = 2.7 Hz, 1H), 5.70 (s, 2H), 4.58 (d, J = 5.8 Hz, 2H) |
| 62 | 436.48 | 3-(3-acetamidoquinolin-6-yl)-N-(pyridin-3-ylmethyl)-1H-pyrrolo[2,3-b]pyridine-5-carboxamide | KR 97% $(M + H)^+ = 437.2$ | δ 12.34 (d, J = 2.7 Hz, 1H), 10.44 (s, 1H), 9.31 (t, J = 6.0 Hz, 1H), 8.94 (d, J = 2.1 Hz, 1H), 8.90-8.76 (m, 3H), 8.62 (d, J = 2.3 Hz, 1H), 8.48 (dd, J = 4.7, 1.7 Hz, 1H), 8.29 (d, J = 2.0 Hz, 1H), 8.19 (d, J = 2.6 Hz, 1H), 8.09 (dd, J = 8.7, 2.1 Hz, 1H), 8.01 (d, J = 8.7 Hz, 1H), 7.79 (dd, J = 7.7, 2.1 Hz, 1H), 7.38 (dd, J = 7.9, 4.7 Hz, 1H), 4.59 (d, J = 5.8 Hz, 2H), 2.17 (s, 3H) |
| 63 | 492.58 | 3-{3-[(oxan-4-ylmethyl)amino]quinolin-6-yl}-N-(pyridin-3-ylmethyl)-1H-pyrrolo[2,3-b]pyridine-5-carboxamide | KR 94% $(M + H)^+ = 493.2$ | δ 12.31 (d, J = 2.6 Hz, 1H), 9.30 (t, J = 5.9 Hz, 1H), 8.88 (dd, J = 16.4, 2.0 Hz, 2H), 8.67 (d, J = 2.2 Hz, 1H), 8.51 (dd, J = 16.0, 3.8 Hz, 2H), 8.09 (dd, J = 13.4, 2.3 Hz, 2H), 7.94-7.77 (m, 3H), 7.48 (dd, J = 7.9, 4.9 Hz, 1H), 7.25 (d, J = 2.7 Hz, 1H), 6.49 (s, 1H), 4.60 (d, J = 5.7 Hz, 2H), 3.90 (dd, J = 10.6, 4.1 Hz, 2H), 3.37-3.26 (m, 2H), 3.07 (d, J = 6.7 Hz, 2H), 1.96-1.87 (m, 1H), 1.75 (d, J = 12.9 Hz, 2H), 1.39-1.25 (m, 2H) |

TABLE 4-continued

| Ex. No. | MW | IUPAC name | Analitical method/purity/ LC-MS | $^1$H-NMR (400 MHz, DMSO-$d_6$) |
|---|---|---|---|---|
| 64 | 382.47 | 4-[(1-methylpiperidin-4-yl)amino]-6-{1H-pyrrolo[2,3-b]pyridin-3-yl}quinoline-3-carbonitrile | KR 97% (M + H)$^+$ = 383.2 | δ 12.10 (s, 1H), 8.62 (d, J = 1.8 Hz, 1H), 8.45 (s, 1H), 8.39 (dd, J = 8.0, 1.5 Hz, 1H), 8.32 (dd, J = 4.7, 1.5 Hz, 1H), 8.17 (dd, J = 8.6, 1.7 Hz, 1H), 8.08 (d, J = 2.7 Hz, 1H), 7.89 (d, J = 8.6 Hz, 1H), 7.68 (d, J = 8.4 Hz, 1H), 7.22 (dd, J = 8.0, 4.7 Hz, 1H), 4.38-4.25 (m, 1H), 2.88 (d, J = 11.0 Hz, 2H), 2.22 (s, 3H), 2.04 (d, J = 11.9 Hz, 4H), 1.94-1.77 (m, 2H) |
| 65 | 416.49 | N-methyl-N-(1-methylpiperidin-4-yl)-3-nitro-6-{1H-pyrrolo[2,3-b]pyridin-3-yl}quinolin-4-amine | KR 95% (M + H)$^+$ = 417.3 | δ 12.19 (s, 1H), 8.97 (s, 1H), 8.43-8.33 (m, 3H), 8.32-8.24 (m, 1H), 8.16-8.06 (m, 2H), 7.24 (dd, J = 7.6, 4.8 Hz, 1H), 3.68 (s, 1H), 2.90 (s, 3H), 2.82 (s, 2H), 2.14 (s, 2H), 2.02-1.83 (m, 6H) |
| 66 | 400.49 | 1-{4-[(3-amino-6-{1H-pyrrolo[2,3-b]pyridin-3-yl}quinolin-4-yl)amino]piperidin-1-yl}ethan-1-one | KR 92% (M + H)$^+$ = 401.3 | δ 12.00-11.95 (m, 1H), 8.41-8.35 (m, 2H), 8.31 (dd, J = 4.6, 1.3 Hz, 1H), 8.22 (d, J = 1.5 Hz, 1H), 7.98 (d, J = 2.6 Hz, 1H), 7.80 (d, J = 8.6 Hz, 1H), 7.72 (dd, J = 8.6, 1.7 Hz, 1H), 7.20 (dd, J = 7.9, 4.7 Hz, 1H), 5.13 (s, 2H), 4.65 (d, J = 10.4 Hz, 1H), 4.35 (d, J = 13.2 Hz, 1H), 3.82 (d, J = 14.4 Hz, 1H), 3.52-3.41 (m, 1H), 3.01 (t, J = 11.9 Hz, 1H), 2.62-2.52 (m, 1H), 2.00 (s, 3H), 1.93-1.79 (m, 2H), 1.64-1.40 (m, 2H) |

Determination of the Inhibitory Activity In Vitro

The compounds of the present invention were tested for their inhibitory activity against DYRK1A and DYRK1B kinases once or several times. When tested more than once, the data are reported herein as average value, wherein the average value, also referred to as the mean value, represents the sum of obtained values divided by the number of times tested.

DYRK-inhibitory activity of the compounds of the present invention was tested using the ADP-Glo™ assay as described in the following paragraphs. The procedure for determining the IC$_{50}$ values with the ADP-Glo™ assay in in vitro kinase assays consists of two parts:

1. Kinase reaction performed under optimized conditions;
2. Detection of ADP as a product of the reaction using ADP-Glo™ system (Promega).

The tested compounds indicated in Table 5 below were dissolved in DMSO, then transferred to the V-bottom PP plate to perform nine serial dilutions (in order to obtain dose-response curves) in 25% DMSO, as indicated in Table 5 below.

The optimized conditions for performing DYRK1A in vitro kinase assay were as follows:

| Reagent/condition | Final concentration |
|---|---|
| Buffer | 50 mM TRIS, pH 7.5 |
| MgCl$_2$ | 10 mM |
| NaCl | 25 mM |
| DTT | 0,1 mM |
| ATP (Km) (ultrapure, from ADP-Glo ™ kit) | 70 µM |
| Substrate (Km): RRRFRPASPLRGPPK (Lipopharm) | 3 µM |
| Enzyme - DYRK1A (Carna Bioscence) catalog no. 04-130 | 2 nM or 0.7 nM |
| Time of reaction | 30 min |
| Temperature of reaction | rt |

The optimized conditions for performing DYRK1B in vitro kinase assay were as follows:

| Reagent/condition | Final concentration |
|---|---|
| Buffer | 5 mM MOPS, pH 7.5 |
| MgCl$_2$ | 5 mM |
| EDTA | 0.4 mM |
| DTT | 1 mM |
| ATP (Km) (ultrapure, from ADP-Glo ™ kit) | 15 µM |
| Substrate (Km): RRRFRPASPLRGPPK (Lipopharm) | 7 µM |
| Enzyme - DYRK1B (Carna Bioscence) catalog no. 04-131 | 1 nM or 0.3 nM |
| Time of reaction | 1 h |
| Temperature of reaction | rt |

For compound testing, the following protocol was used: two mixes were prepared on ice, Mix 1 containing substrate, ATP and reaction buffer and Mix 2 containing reaction buffer and the kinase. 15 µL per well of Mix 1 was transferred to wells of a 96-well plate. Next, 2.5 μL of the pre-diluted compound to be tested was added to Mix 1, followed by the addition of 12.5 μL of Mix 2. Total reaction volume was 30 μL per well. The experiment was performed in duplicate for each data point being examined. Dose response curve for the positive control was carried out on each assay plate by adding the reference inhibitory compound staurosporine. For each test, three controls were also included: (i) 30 μL of the reaction mixture containing: reaction buffer, ATP, kinase, DMSO without substrate (quasi-positive control); (ii) 30 μL of the reaction mixture containing reaction buffer, substrate, ATP, DMSO without kinase (background control); (iii) 30 μL of the reaction mixture containing reaction buffer, substrate, kinase, ATP, DMSO (vehicle control). Final concentration of DMSO in the reaction was 2%. To detect the ADP amount produced during the kinase reaction, the commercially available kit ADP-Glo™ Kinase Assay (Promega, cat. No # V9103) was used. The protocol used for the detection was based on the Technical Bulletin of the ADP-Glo™ Kinase Assay (Promega) and was adapted to 96-well plate containing 30 μL reaction mixture as explained below.

30 μL of ADP-Glo™ Reagent was added to each well of a 96 well plate containing 30 μL of reaction mixture to terminate the kinase reaction and deplete the remaining ATP. The plate was incubated for 60 minutes on a shaker at rt. 60 μL of Kinase Detection Solution was then added to each well of 96-well plate containing 60 μL of the solution to convert ADP to ATP and to allow the newly synthesized ATP to be measured using a luciferase/luciferin reaction (ratio of kinase reaction volume to ADP Glo™ Reagent volume to Kinase Detection Solution volume was maintained at 1:1:2). The plate was incubated for 40 minutes on a shaker at rt, protected from light. Luminescence was measured in the plate reader, wherein the luminescent signal is proportional to the ADP concentration produced and thus correlates with kinase activity.

After data normalization to controls (complete reaction mix and no-substrate control) and transforming X values (test compound concentrations) using: X=log(X), $IC_{50}$ values were determined, using the GraphPad Prism 6.0 [log (agonist) vs. normalized response—Variable slope].

In Table 5, A represents a calculated $IC_{50}$ value of less than 10 nM; B represents a calculated $IC_{50}$ value of greater than or equal to 10 nM and less than 100 nM; C represents a calculated $IC_{50}$ value of greater than or equal to 100 nM.

TABLE 5

| Example No. | DYRK1B | DYRK1A |
|---|---|---|
| 1 | NA | B |
| 2 | A | A |
| 3 | A | A |
| 4 | NA | C |
| 5 | NA | A |
| 6 | A | A |
| 7 | A | A |
| 8 | A | A |
| 9 | A | A |
| 10 | B | B |
| 11 | A | A |
| 12 | B | C |
| 13 | A | A |
| 14 | B | C |
| 15 | B | C |
| 16 | A | A |
| 17 | C | C |
| 18 | B | B |
| 19 | A | A |

TABLE 5-continued

| Example No. | DYRK1B | DYRK1A |
|---|---|---|
| 20 | A | B |
| 21 | A | B |
| 22 | A | A |
| 23 | A | A |
| 24 | A | A |
| 25 | A | A |
| 26 | C | C |
| 27 | A | A |
| 28 | A | B |
| 29 | B | C |
| 30 | A | A |
| 31 | A | A |
| 32 | A | B |
| 33 | A | A |
| 34 | A | A |
| 35 | A | A |
| 36 | A | B |
| 37 | A | A |
| 38 | A | B |
| 39 | A | A |
| 40 | A | A |
| 41 | A | A |
| 42 | B | C |
| 43 | A | A |
| 44 | A | A |
| 45 | B | C |
| 46 | A | A |
| 47 | A | A |
| 48 | A | A |
| 49 | A | A |
| 50 | A | A |
| 51 | A | A |
| 52 | A | B |
| 53 | A | B |
| 54 | A | A |
| 55 | A | B |
| 56 | A | B |
| 57 | A | A |
| 58 | A | B |
| 59 | B | B |
| 60 | A | B |
| 61 | A | A |
| 62 | A | A |
| 63 | A | A |
| 64 | B | B |
| 65 | B | B |
| 66 | A | A |

NA - not analyzed

The invention claimed is:
1. A compound of formula (I)

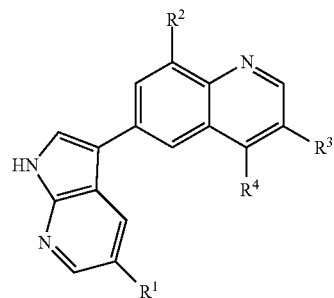

or a salt, stereoisomer, tautomer or N-oxide thereof, wherein $R^1$, $R^3$ are independently selected from the group consisting of
   (i) H, CN, $NO_2$, $C_1$-$C_6$-alkyl, $C_2$-$C_6$-alkenyl, $C_2$-$C_6$-alkynyl;

wherein each substitutable carbon atom in the aforementioned moieties is independently unsubstituted or substituted with one or more, same or different substituents $R^7$;

(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$;

(iii) a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^2$ is selected from the group consisting of H, halogen, CN, $NO_2$, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy and $C_1$-$C_6$-haloalkoxy;

$R^4$ is independently selected from the group consisting of
(i) H, CN, $NO_2$, $C_1$-$C_6$-alkyl, $C_2$-$C_6$-alkenyl, $C_2$-$C_6$-alkynyl;
wherein each substitutable carbon atom in the aforementioned moieties is independently unsubstituted or substituted with one or more, same or different substituents $R^7$;

(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$;

(iii) a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

$R^5$, $R^6$, $R^{6a}$, $R^{6b}$ are independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties is independently unsubstituted or substituted with one or more, same or different substituents $R^9$; and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the afore- mentioned cyclic moieties is independently unsubstituted or substituted with one or more, same or different substituents $R^{10}$;

$R^7$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$; and a 3- to 9-membered saturated, partially unsaturated or fully unsaturated carbocyclic or heterocyclic ring and a 6- to 14-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or hetero-atom in the aforementioned cyclic or bicyclic moieties is unsubstituted or substituted with one or more, same or different substituents $R^8$;

$R^8$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{6a})(R^{6b})$, $OR^6$ and $S(=O)_nR^6$;

$R^9$ is selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

and a 3- to 9-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is unsubstituted or substituted with one or more, same or different substituents $R^{10}$;

$R^{10}$ is selected from halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $N(R^{11a})(R^{11b})$, $OR^{11}$ and $S(=O)_nR^{11}$;

$R^{11}$, $R^{11a}$, $R^{11b}$ are independently selected from the group consisting of H, $C_1$-$C_6$-alkyl, $C_2$-$C_6$-alkenyl and $C_2$-$C_6$-alkynyl;

and wherein
n is 0, 1 or 2.

2. The compound according to claim 1, wherein $R^1$ is selected from the group consisting of
(i) H, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl;
wherein each substitutable carbon atom in the aforementioned moieties is independently unsubstituted or substituted with one or more, same or different substituents $R^7$;

(ii) $C(=O)R^5$, $C(=O)OR^6$, $C(=O)SR^6$, $C(=O)N(R^{6a})(R^{6b})$, $OR^6$, $S(=O)_nR^6$, $S(=O)_nN(R^{6a})(R^{6b})$, $S(=O)_nOR^6$, $N(R^{6a})(R^{6b})$, $N(R^6)C(=O)R^5$, $N(R^6)C(=O)OR^6$, $N(R^6)C(=O)N(R^{6a})(R^{6b})$, $N(R^6)S(=O)_nR^6$, $N(R^6)S(=O)_nN(R^{6a})(R^{6b})$, $N(R^6)S(=O)_nOR^6$;

(iii) $C_1$-$C_3$-alkyl, $C_2$-$C_3$-alkenyl, and $C_2$-$C_3$;

wherein each substitutable carbon atom in the aforementioned moieties is independently unsubstituted or substituted with one or more, same or different substituents $R^7$;

wherein each substitutable carbon atom in the aforementioned moieties is independently unsubstituted or substituted with one or more, same or different substituents $R^7$;

and wherein all other substituents have the meaning as defined in claim 1.

3. The compound according to claim 1, wherein $R^2$ is selected from the group consisting of H, halogen, CN, $NO_2$, $C_1$-$C_2$-alkyl, vinyl, $C_1$-$C_2$-alkoxy and $C_1$-$C_2$-haloalkoxy;

and wherein all other substituents have the meaning as defined in claim 1.

4. The compound according to claim 1, wherein $R^3$ is selected from the group consisting of
(i) H, halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl;
  wherein each substitutable carbon atom in the aforementioned moieties is independently unsubstituted or substituted with one or more, same or different substituents $R^7$;
(ii) C(=O)$R^5$, C(=O)O$R^6$, C(=O)S$R^6$, C(=O)N($R^{6a}$)($R^{6b}$), O$R^6$, S(=O)$_n$$R^6$, S(=O)$_n$N($R^{6a}$)($R^{6b}$), S(=O)$_n$O$R^6$, N($R^{6a}$)($R^{6b}$), N($R^6$)C(=O)$R^5$, N($R^6$)C(=O)O$R^6$, N($R^6$)C(=O)N($R^{6a}$)($R^{6b}$), N($R^6$)S(=O)$_n$$R^6$, N($R^6$)S(=O)$_n$N($R^{6a}$)($R^{6b}$), N($R^6$)S(=O)$_n$O$R^6$;

and wherein all other substituents have the meaning as defined in claim 1.

5. The compound according to claim 1, wherein $R^4$ is selected from the group consisting of H, halogen, $C_1$-$C_6$-alkyl, $C_2$-$C_6$-alkenyl, $C_2$-$C_6$-alkynyl, wherein each substitutable carbon atom in the aforementioned moieties is independently unsubstituted or substituted with one or more, same or different $R^7$;

and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$;

and wherein all other substituents have the meaning as defined in claim 1.

6. The compound according to claim 1, wherein $R^5$, $R^6$, $R^{6a}$ and $R^{6b}$ are independently from each other selected from the group consisting of H, $C_1$-$C_5$-alkyl, $C_2$-$C_5$-alkenyl, $C_2$-$C_5$-alkynyl, wherein each substitutable carbon atom in the aforementioned moieties is independently unsubstituted or substituted with one or more, same or different substituents $R^9$; and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moieties is independently unsubstituted or substituted with one or more, same or different substituents $R^{10}$.

7. The compound according to claim 1, wherein $R^7$ is selected from the group consisting of halogen, CN, $NO_2$, $C_1$-$C_5$-alkyl, $C_1$-$C_5$-haloalkyl, $C_2$-$C_5$-alkenyl, $C_2$-$C_5$-haloalkenyl, $C_2$-$C_5$-alkynyl, $C_2$-$C_5$-haloalkynyl, O$R^6$, N($R^{6a}$)($R^{6b}$); and a 5- to 6-membered saturated, partially unsaturated or fully unsaturated carbocyclic or heterocyclic ring and a 8- to 9-membered saturated, partially unsaturated or fully unsaturated carbobicyclic or heterobicyclic ring, wherein said heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic or bicyclic moieties is independently unsubstituted or substituted with one or more, same or different substituents $R^8$.

8. The compound according to claim 1, wherein $R^8$ is selected from the group consisting of $C_1$-$C_3$-alkyl, $C_2$-$C_3$-alkenyl, $C_1$-$C_3$-alkylcarbonyl, $C_2$-$C_3$-alkynyl and N($R^{6a}$)($R^{6b}$).

9. The compound according to claim 1, wherein $R^9$ is selected from the group consisting of halogen, $C_1$-$C_4$-alkyl, $C_2$-$C_4$-alkenyl, $C_2$-$C_4$-alkynyl, N($R^{11a}$)($R^{11b}$) and a 5- to 6-membered saturated, partially unsaturated or fully unsaturated carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic moiety is independently unsubstituted or substituted with one or more, same or different substituents $R^{10}$.

10. The compound according to claim 1, wherein $R^{10}$ is selected from the group consisting of halogen, $C_1$-$C_3$-alkyl, $C_2$-$C_3$-alkenyl, $C_1$-$C_3$-alkylcarbonyl, $C_2$-$C_3$-alkynyl and N($R^{11a}$)($R^{11b}$).

11. The compound according to claim 1, wherein $R^{11}$, $R^{11a}$ and $R^{11b}$ are independently selected from the group consisting of H, $C_1$-$C_3$-alkyl, $C_2$-$C_3$-alkenyl and $C_2$-$C_3$-alkynyl.

12. The compound according to claim 1, wherein said compound is selected from the group consisting of 4-chloro-6-{1H-pyrrolo[2,3-b]pyridin-3-yl}quinoline; 6-{1H-pyrrolo[2,3-b]pyridin-3-yl}quinoline; (3S)-1-(6-{1H-pyrrolo[2,3-b]pyridin-3-yl}quinolin-4-yl)piperidin-3-amine; 1-N-(6-{1H-pyrrolo[2,3-b]pyridin-3-yl}quinolin-4-yl)cyclohexane-1,4-diamine; (3S)-1-(6-{1H-pyrrolo[2,3-b]pyridin-3-yl}quinolin-4-yl)pyrrolidin-3-amine; 4-(pyridin-3-yl)-6-{1H-pyrrolo[2,3-b]pyridin-3-yl}quinoline; 4-(pyridin-4-yl)-6-{1H-pyrrolo[2,3-b]pyridin-3-yl}quinoline; 4-phenyl-6-{1H-pyrrolo[2,3-b]pyridin-3-yl}quinoline; {5-ethenyl-1-azabicyclo[2.2.2]octan-2-yl}(6-{1H-pyrrolo[2,3-b]pyridin-3-yl})quinolin-4-yl)methanol; N-(1-methylpiperidin-4-yl)-6-{1H-pyrrolo[2,3-b]pyridin-3-yl}quinolin-4-amine; 8-chloro-6-{1H-pyrrolo[2,3-b]pyridin-3-yl}quinoline hydrochloride; 8-methyl-6-{1H-pyrrolo[2,3-b]pyridin-3-yl}quinoline hydrochloride; 8-fluoro-6-{1H-pyrrolo[2,3-b]pyridin-3-yl}quinoline; 6-{1H-pyrrolo[2,3-b]pyridin-3-yl}-8-(trifluoromethoxy)quinoline; 8-methoxy-6-{1H-pyrrolo[2,3-b]pyridin-3-yl}quinoline; N-(furan-3-ylmethyl)-6-{1H-pyrrolo[2,3-b]pyridin-3-yl}quinolin-3-amine; 8-methyl-4-phenyl-6-{1H-pyrrolo[2,3-b]pyridin-3-yl}quinoline; 8-methyl-4-(pyridin-3-yl)-6-{1H-pyrrolo[2,3-b]pyridin-3-yl}quinoline; 8-fluoro-4-(pyridin-3-yl)-6-{1H-pyrrolo[2,3-b]pyridin-3-yl}quinoline; 3-(4-chloroquinolin-6-yl)-N-methyl-N-(prop-2-en-1-yl)-1H-pyrrolo[2,3-b]pyridine-5-carboxamide; methyl({3-[4-(pent-4-en-1-yl)quinolin-6-yl]-1H-pyrrolo[2,3-b]pyridin-5-yl}methyl)(prop-2-en-1-yl)amine; N-methyl-3-[4-(pyridin-3-yl)quinolin-6-yl]-1H-pyrrolo[2,3-b]pyridine-5-carboxamide; N-methyl-3-[4-(morpholin-4-yl)quinolin-6-yl]-1H-pyrrolo[2,3-b]pyridine-5-carboxamide; 3-(4-chloroquinolin-6-yl)-N-methyl-1H-pyrrolo[2,3-b]pyridine-5-carboxamide;

N-methyl-3-(quinolin-6-yl)-1H-pyrrolo[2,3-b]pyridine-5-carboxamide; 3-(8-methoxyquinolin-6-yl)-N-methyl-N-(prop-2-en-1-yl)-1H-pyrrolo[2,3-b]pyridine-5-carboxamide; 3-(8-fluoroquinolin-6-yl)-N-methyl-N-(prop-2-en-1-yl)-1H-pyrrolo[2,3-b]pyridine-5-carboxamide; 3-(8-chloroquinolin-6-yl)-N-methyl-N-(prop-2-en-1-yl)-1H-pyrrolo[2,3-b]pyridine-5-carboxamide; 3-(8-methoxyquinolin-6-yl)-N-methyl-1H-pyrrolo[2,3-b]pyridine-5-carboxamide; 3-(8-fluoroquinolin-6-yl)-N-methyl-1H-pyrrolo[2,3-b]pyridine-5-carboxamide; N-benzyl-3-(8-fluoroquinolin-6-yl)-1H-pyrrolo[2,3-b]pyridine-5-carboxamide; N-benzyl-3-(8-chloroquinolin-6-yl)-1H-pyrrolo[2,3-b]pyridine-5-carboxamide; 3-(8-fluoroquinolin-6-yl)-1H-pyrrolo[2,3-b]pyridine-5-carboxamide; N-(3-aminopropyl)-3-(8-chloroquinolin-6-yl)-1H-pyrrolo[2,3-b]pyridine-5-carboxamide hydrochloride; N-benzyl-3-[8-fluoro-4-(pyridin-3-yl)quinolin-6-yl]-1H-pyrrolo[2,3-b]pyridine-5-carboxamide; N-(3-aminopropyl)-3-[8-fluoro-4-(pyridin-3-yl)quinolin-6-yl]-1H-pyrrolo[2,3-b]pyridine-5-carboxamide hydrochloride; 3-[8-fluoro-4-(pyridin-3-yl)quinolin-6-yl]-N-methyl-N-(prop-2-en-1-yl)-1H-pyrrolo[2,3-b]pyridine-5-carboxamide; 3-[8-fluoro-4-(pyridin-3-yl)quinolin-6-yl]-N-methyl-1H-pyrrolo[2,3-b]pyridine-5-carboxamide; 3-[8-fluoro-4-(2-phenylethyl)quinolin-6-yl]-N-methyl-1H-pyrrolo[2,3-b]pyridine-5-carboxamide; 3-{4-[(3R)-3-aminopiperidin-1-yl]-8-fluoroquinolin-6-yl}-N-methyl-1H-pyrrolo[2,3-b]pyridine-5-carboxamide hydrochloride; N-methyl-3-[8-methyl-4-(pyridin-3-yl)quinolin-6-yl]-1H-pyrrolo[2,3-b]pyridine-5-carboxamide; 3-{4-[(3S)-3-aminopiperidin-1-yl]-8-fluoroquinolin-6-yl}-N-methyl-1H-pyrrolo[2,3-b]pyridine-5-carboxamide hydrochloride; N-methyl-3-[8-fluoro-4-(4-methylpyridin-3-yl)quinolin-6-yl]-1H-pyrrolo[2,3-b]pyridine-5-carboxamide; 3-[8-methoxy-4-(pyridin-3-yl)quinolin-6-yl]-1H-pyrrolo[2,3-b]pyridine-5-carboxamide; N-{3-[8-fluoro-4-(pyridin-3-yl)quinolin-6-yl]-1H-pyrrolo[2,3-b]pyridin-5-yl}acetamide; 3-[8-fluoro-4-(pyridin-3-yl)quinolin-6-yl]-N-(pyridin-3-ylmethyl)-1H-pyrrolo[2,3-b]pyridine-5-carboxamide; 3-{4-[(3R)-3-aminopiperidin-1-yl]-8-fluoroquinolin-6-yl}-N-(pyridin-3-ylmethyl)-1H-pyrrolo[2,3-b]pyridine-5-carboxamide hydrochloride; 3-{4-[(3R)-3-aminopiperidin-1-yl]-8-fluoroquinolin-6-yl}-N-(pyrimidin-5-ylmethyl)-1H-pyrrolo[2,3-b]pyridine-5-carboxamide hydrochloride; benzyl({3-[8-fluoro-4-(pyridin-3-yl)quinolin-6-yl]-1H-pyrrolo[2,3-b]pyridin-5-yl}methyl)amine; (3R)-1-(6-{5-[(benzylamino)methyl]-1H-pyrrolo[2,3-b]pyridin-3-yl}-8-fluoroquinolin-4-yl)piperidin-3-amine; ({3-[8-fluoro-4-(pyridin-3-yl)quinolin-6-yl]-1H-pyrrolo[2,3-b]pyridin-5-yl}methyl)(methyl)(prop-2-en-1-yl)amine; 3-{4-[(3S)-3-aminopiperidin-1-yl]-3-nitroquinolin-6-yl}-N-methyl-1H-pyrrolo[2,3-b]pyridine-5-carboxamide hydrochloride; 3-{3-amino-4-[(3S)-3-aminopiperidin-1-yl]quinolin-6-yl)}-N-methyl-1H-pyrrolo[2,3-b]pyridine-5-carboxamide hydrochloride; 3-{4-[(3S)-3-aminopiperidin-1-yl]-3-{[(3-chlorophenyl)methyl]amino}quinolin-6-yl}-N-methyl-1H-pyrrolo[2,3-b]pyridine-5-carboxamide hydrochloride; 3-(3-{[(3-chlorophenyl)methyl]amino}-4-(morpholin-4-yl)quinolin-6-yl)-N-methyl-1H-pyrrolo[2,3-b]pyridine-5-carboxamide; 3-[3-acetamido-4-(morpholin-4-yl)quinolin-6-yl]-N-methyl-1H-pyrrolo[2,3-b]pyridine-5-carboxamide; N-methyl-3-[4-(morpholin-4-yl)-3-[(oxan-4-ylmethyl)amino]quinolin-6-yl]-1H-pyrrolo[2,3-b]pyridine-5-carboxamide; 3-{4-[(4-aminocyclohexyl)amino]-3-nitroquinolin-6-yl}-N-(pyridin-3-ylmethyl)-1H-pyrrolo[2,3-b]pyridine-5-carboxamide hydrochloride; 3-{4-[(4-aminocyclohexyl)amino]-3-[(oxan-4-ylmethyl)amino]quinolin-6-yl}-N-(pyridin-3-ylmethyl)-1H-pyrrolo[2,3-b]pyridine-5-carboxamide hydrochloride; 3-(3-aminoquinolin-6-yl)-N-(pyridin-3-ylmethyl)-1H-pyrrolo[2,3-b]pyridine-5-carboxamide; 3-{3-[(oxan-4-ylmethyl)amino]quinolin-6-yl}-N-(pyridin-3-ylmethyl)-1H-pyrrolo[2,3-b]pyridine-5-carboxamide; 4-[(1-methylpiperidin-4-yl)amino]-6-{1H-pyrrolo[2,3-b]pyridin-3-yl}quinoline-3-carbonitrile; N-methyl-N-(1-methylpiperidin-4-yl)-3-nitro-6-{1H-pyrrolo[2,3-b]pyridin-3-yl}quinolin-4-amine; 1-{4-[(3-amino-6-{1H-pyrrolo[2,3-b]pyridin-3-yl})quinolin-4-yl)amino]piperidin-1-yl}ethan-1-one; N-(3-aminopropyl)-3-(8-fluoroquinolin-6-yl)-1H-pyrrolo[2,3-b]pyridine-5-carboxamide hydrochloride and 3-(3-acetamidoquinolin-6-yl)-N-(pyridin-3-ylmethyl)-1H-pyrrolo[2,3-b]pyridine-5-carboxamide.

13. A pharmaceutical composition comprising a pharmaceutically effective amount of the compound of claim 1, optionally further comprising a pharmaceutically acceptable carrier, diluent or excipient.

14. The compound of claim 1, wherein $R^4$ is $N(R^{6a})(R^{6b})$, and wherein when $R^4$ is $N(R^{6a})(R^{6b})$, $R^{6a}$ is independently selected from the group consisting of $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties of C1-C6-alkyl, C1-C6-haloalkyl, C2-C6-alkenyl, C2-C6-alkynyl, C1-C6-alkylcarbonyl is independently unsubstituted or substituted with one or more, same or different substituents $R^9$, and $R^{6b}$ is independently selected from the group consisting of H, $C_1$-$C_6$-alkyl, $C_1$-$C_6$-haloalkyl, $C_2$-$C_6$-alkenyl, $C_2$-$C_6$-alkynyl, $C_1$-$C_6$-alkylcarbonyl, wherein each substitutable carbon atom in the aforementioned moieties of C1-C6-alkyl, C1-C6-haloalkyl, C2-C6-alkenyl, C2-C6-alkynyl, C1-C6-alkylcarbonyl is independently unsubstituted or substituted with one or more, same or different substituents $R^9$.

* * * * *

UNITED STATES PATENT AND TRADEMARK OFFICE
CERTIFICATE OF CORRECTION

PATENT NO. : 10,577,365 B2
APPLICATION NO. : 15/848786
DATED : March 3, 2020
INVENTOR(S) : Agnieszka Dreas et al.

It is certified that error appears in the above-identified patent and that said Letters Patent is hereby corrected as shown below:

In the Claims

At Column 182, Line 67, in Claim 2, change "(iii) $C_1$-$C_3$-alkyl, $C_2$-$C_3$-alkenyl, and $C_2$-$C_3$;" to "(iii) $C_1$-$C_3$-alkyl, $C_2$-$C_3$-alkenyl, and $C_2$-$C_3$-alkynyl;"

At Column 185, Line 10, in Claim 12, change "methyl-1H-pyrrolo[2,3-b]pyridine-5-carb oxamide;" to "methyl-1H-pyrrolo[2,3-b]pyridine-5-carboxamide;"

At Column 186, Line 1, Claim 12, change "amino-4-[(3S)-3-aminopiperidin-1-yl]quinolin-6-yl)}-N-" to "amino-4-[(3S)-3-aminopiperidin-1-yl]quinolin-6-yl}-N-"

At Column 186, Line 25, Claim 12, change "6-{1H-pyrrolo[2,3-b]pyridin-3-yl)} quinolin-4-yl)amino]pi-" to "6-{1H-pyrrolo[2,3-b]pyridin-3-yl}quinolin-4-yl)amino]pi-"

Signed and Sealed this
Eighth Day of September, 2020

Andrei Iancu
*Director of the United States Patent and Trademark Office*